US008497376B2

(12) United States Patent
Illig et al.

(10) Patent No.: US 8,497,376 B2
(45) Date of Patent: Jul. 30, 2013

(54) INHIBITORS OF C-FMS KINASE

(75) Inventors: Carl R. Illig, Phoenixville, PA (US);
Jinsheng Chen, Exton, PA (US); Sanath K. Meegalia, Boothwyn, PA (US);
Mark J. Wall, Flourtown, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 707 days.

(21) Appl. No.: 12/252,439

(22) Filed: Oct. 16, 2008

(65) Prior Publication Data

US 2009/0105296 A1    Apr. 23, 2009

Related U.S. Application Data

(60) Provisional application No. 60/980,623, filed on Oct. 17, 2007.

(51) Int. Cl.
C07D 405/14 (2006.01)
C07D 471/04 (2006.01)
C07D 493/08 (2006.01)

(52) U.S. Cl.
USPC .............. 546/112; 546/274.7; 548/311.4

(58) Field of Classification Search
None
See application file for complete search history.

(56) References Cited

U.S. PATENT DOCUMENTS

| | | | |
|---|---|---|---|
| 2,466,420 A | 4/1949 | Hagemeyer et al. | |
| 3,226,394 A | 12/1965 | Schipper | |
| 4,551,540 A | 11/1985 | Hechenbleikner et al. | |
| 5,190,541 A | 3/1993 | Abele et al. | |
| 5,474,765 A | 12/1995 | Thorpe | |
| 5,762,918 A | 6/1998 | Thorpe | |
| 5,855,866 A | 1/1999 | Thorpe et al. | |
| 5,874,442 A | 2/1999 | Doll et al. | |
| 5,944,718 A | 8/1999 | Austin et al. | |
| 5,968,952 A | 10/1999 | Venet et al. | |
| 6,037,350 A | 3/2000 | Venet et al. | |
| 6,100,254 A | 8/2000 | Budde et al. | |
| 6,117,432 A | 9/2000 | Ganne et al. | |
| 6,169,096 B1 | 1/2001 | Venet et al. | |
| 6,187,786 B1 | 2/2001 | Venet et al. | |
| 6,235,746 B1 | 5/2001 | Davis et al. | |
| 6,342,219 B1 | 1/2002 | Thorpe et al. | |
| 6,346,625 B1 | 2/2002 | Karabelas et al. | |
| 6,383,790 B1 | 5/2002 | Shokat | |
| 6,420,387 B1 | 7/2002 | Venet et al. | |
| 6,458,800 B1 | 10/2002 | Angibaud et al. | |
| 6,596,746 B1 | 7/2003 | Das et al. | |
| 6,692,491 B1 | 2/2004 | Phan | |
| 7,157,456 B2 | 1/2007 | Straub et al. | |
| 7,208,493 B2 | 4/2007 | Wrasidlo et al. | |
| 7,427,683 B2 | 9/2008 | Player et al. | |
| 7,429,603 B2 | 9/2008 | Player et al. | |
| 7,645,755 B2 | 1/2010 | Illig et al. | |
| 7,662,837 B2 | 2/2010 | Illig et al. | |
| 7,790,724 B2 | 9/2010 | Player et al. | |
| 7,795,279 B2 | 9/2010 | Ballentine et al. | |
| 7,973,035 B2 | 7/2011 | Illig et al. | |
| 2002/0016625 A1 | 2/2002 | Falotico et al. | |
| 2002/0019414 A1 | 2/2002 | Altmann et al. | |
| 2003/0153610 A1 | 8/2003 | Straub et al. | |
| 2004/0049032 A1 | 3/2004 | Charrier et al. | |
| 2005/0113566 A1 | 5/2005 | Player et al. | |
| 2005/0131022 A1 | 6/2005 | Player et al. | |
| 2006/0040995 A1 | 2/2006 | Bacque et al. | |
| 2006/0100619 A1 | 5/2006 | McClurken et al. | |
| 2006/0122181 A1 | 6/2006 | Ikemoto et al. | |
| 2006/0148812 A1 | 7/2006 | Illig et al. | |
| 2006/0189623 A1 | 8/2006 | Illig et al. | |
| 2006/0258724 A1 | 11/2006 | Straub et al. | |

(Continued)

FOREIGN PATENT DOCUMENTS

EP    1566379 A1    8/2005
GB    1189719       4/1970

(Continued)

OTHER PUBLICATIONS

Vippagunta et al., Crystalline solids, 48 Adv. Drug Delivery Rev. 3-26 (2001).*

(Continued)

*Primary Examiner* — Janet Andres
*Assistant Examiner* — Timothy R. Rozof

(57) ABSTRACT

The invention is directed to compounds of Formula I:

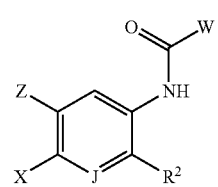

wherein Z, X, J, $R^2$ and W are set forth in the specification, as well as solvates, hydrates, tautomers and pharmaceutically acceptable salts thereof, that inhibit protein tyrosine kinases, especially c-fms kinase. Methods of treating autoimmune diseases; and diseases with an inflammatory component; treating metastasis from ovarian cancer, uterine cancer, breast cancer, prostate cancer, lung cancer, colon cancer, stomach cancer, hairy cell leukemia; and treating pain, including skeletal pain caused by tumor metastasis or osteoarthritis, or visceral, inflammatory, and neurogenic pain; as well as osteoporosis, Paget's disease, and other diseases in which bone resorption mediates morbidity including rheumatoid arthritis, and other forms of inflammatory arthritis, osteoarthritis, prosthesis failure, osteolytic sarcoma, myeloma, and tumor metastasis to bone with the compounds of Formula I, are also provided.

16 Claims, 4 Drawing Sheets

U.S. PATENT DOCUMENTS

| | | | |
|---|---|---|---|
| 2006/0281788 | A1 | 12/2006 | Baumann et al. |
| 2007/0249593 | A1 | 10/2007 | Illig et al. |
| 2007/0249608 | A1 | 10/2007 | Illig et al. |
| 2007/0249649 | A1 | 10/2007 | Illig et al. |
| 2007/0249680 | A1 | 10/2007 | Illig et al. |
| 2007/0249685 | A1 | 10/2007 | Illig et al. |
| 2008/0051402 | A1 | 2/2008 | Illig et al. |
| 2009/0197913 | A1 | 8/2009 | Baumann et al. |
| 2011/0195960 | A1 | 8/2011 | Illig et al. |

FOREIGN PATENT DOCUMENTS

| | | |
|---|---|---|
| WO | 94/10138 | 5/1994 |
| WO | 96/11932 | 4/1996 |
| WO | 96/21452 | 7/1996 |
| WO | 96/32907 | 10/1996 |
| WO | 97/16443 | 5/1997 |
| WO | 97/21701 | 6/1997 |
| WO | 97/30992 | 8/1997 |
| WO | 98/06700 | 2/1998 |
| WO | 98/28264 | 7/1998 |
| WO | 98/28303 | 7/1998 |
| WO | 98/40383 | 9/1998 |
| WO | 98/49157 | 11/1998 |
| WO | 98/54174 | 12/1998 |
| WO | 99/45712 | 9/1999 |
| WO | 99/45912 | 9/1999 |
| WO | 00/01691 | 1/2000 |
| WO | 00/02871 | 1/2000 |
| WO | 00/12498 | 3/2000 |
| WO | 00/12499 | 3/2000 |
| WO | WO 00/27820 | 5/2000 |
| WO | 00/39082 | 7/2000 |
| WO | 01/47919 | 7/2001 |
| WO | WO 01/47897 | 7/2001 |
| WO | WO 01/49667 | 7/2001 |
| WO | 02/32861 A2 | 4/2002 |
| WO | WO 02/068406 | 9/2002 |
| WO | 02/092599 A1 | 11/2002 |
| WO | 03/024931 A1 | 3/2003 |
| WO | 03/024969 A1 | 3/2003 |
| WO | 03/035009 A2 | 5/2003 |
| WO | 03/037347 A1 | 5/2003 |
| WO | 03/057690 A1 | 7/2003 |
| WO | 03/099771 A2 | 12/2003 |
| WO | 03/099796 | 12/2003 |
| WO | 2004/005281 A1 | 1/2004 |
| WO | 2004/016597 A2 | 2/2004 |
| WO | 2004/018419 A2 | 3/2004 |
| WO | WO 2004/022525 | 3/2004 |
| WO | 2004/039782 A1 | 5/2004 |
| WO | 2004/043389 A2 | 5/2004 |
| WO | 2004/046120 A2 | 6/2004 |
| WO | 2004/058749 A1 | 7/2004 |
| WO | 2004/085388 | 10/2004 |
| WO | WO 2004/096795 | 11/2004 |
| WO | 2005/012220 | 2/2005 |
| WO | 2005/040139 | 5/2005 |
| WO | 2005/047273 | 5/2005 |
| WO | 2005/073225 | 8/2005 |
| WO | WO 2006/047277 | 5/2006 |
| WO | WO 2006/047504 | 5/2006 |
| WO | 2006/135630 | 12/2006 |
| WO | 2006/135636 | 12/2006 |
| WO | 2006/135713 | 12/2006 |
| WO | 2006/135718 | 12/2006 |
| WO | 2006/138155 A1 | 12/2006 |
| WO | 2007/048088 | 4/2007 |
| WO | WO 2009/058968 | 5/2009 |

OTHER PUBLICATIONS

Wilson et al., Reducing Ion Channel Activity in a Series of 4-Heterocyclic Arylamide FMS Inhibitors, 20 Bioorg. & Med. Chem. Letts. 3925-3929 (2010).*
Abarbri et al., J. Org. Chem. (2000), 65, 4618-4634.
Barkenbus et al., Journal of Organic Chemistry (1951), 16, 232-8.
Brown et al., J. Chem. Soc., Perkin Trans. 2, 1039-1051 (2002).
Byrn et al., Solid-State Chemistry of Drugs, Second Edition, 1999, pp. 233-247.
Crandall et al., J. Am. Chem. Soc. (1968), 90, 6251-6253.
Eastwood, P., Tetrahedron Lett. (2000), 41, 3705-8.
Gavezzotti, "Are Crystal Structures Predictable?" Accounts of Chemical Research, vol. 27, pp. 309-314 (1994).
Guillory (in Brittain ed.) Polymorphism, etc., NY: Marcel Dekker, Inc., 1999, 1-2, 183-226.
Harmata et al., Org. Lett. (2000), 2, 2703-2705.
Hess et al., J. Am. Chem. Soc. (1998), 120, 12310.
Hogermeier et al., Chem. Eur. J., 2007, 13, 2410.
Johnson et al., J. Org. Chem. (1970), 35(3), 584-592.
Kim et al., European Journal of Organic Chemistry (2000), 12, 2195-2201.
Larock, R.C., Comprehensive Organic Transformations, $2^{nd}$ Ed., Wiley-VCH, NY, (1999), pp. 996-1003.
Lee, K. and Cha, J. K., J. Amer. Chem. Soc., 123: 5590-5591 (2001).
Lipshutz et al., Tetrahedron Lett. (1988), 29, 3411-3414.
McBee et al., Journal of the American Chemical Society (1957), 79, 2323-5.
Meltzer et al., Bioorganic & Medicinal Chemistry (2002), 10(11) and 3583-3591.
Noyori et al., Org. React., 1983, 29, 163.
Regan et al., J. Med. Chem., 46: 4676-86 (2003).
Reinecke et al., Chemistry-A European Journal (1995), 1(6), 368-73.
Sasaki et al., Tett. Lett. (1982), 23, 1693.
Sato et al., Bulletin of the Chemical Society of Japan (1983), 56(9), 2680-99.
Sato et al., Bulletin of the Chemical Society of Japan (1984), 57(9), 2515-25.
Schmid et al., Helv. Chim. Acta. (1974), 57, 1883 [see English summary provided].
Sendelbach, et al, Journal of Organic Chemistry (1999), 64(10), 3398-3408.
Stille, J. K., Angew. Chem, Int. Ed. Engl., 25: 508-524 (1986).
Sundermeier, U., Doebler, C. and Beller, M., Modern Oxidation Methods, Baeckvall, J. (Ed.)., 1-20, Wiley-Verlag (2004) Weinheim, Germany (2004).
Takahashi, K., et al, Chem. Lett. (2000), 126-7.
Takaya et al., J Amer Chem Soc, (1978), 100(6), 1765-77.
West et al., J. Org. Chem (1993), 58, 6795-6803.
Wroblewski et al., Journal of the American Chemical Society (1996), 118, 10168-10174.
Abdel-Magid et al, "Reductive Amination of Aldehydes and Ketones with Sodium Triacetoxyborohydride.Studies on Direct and Indirect Reductive Amination Procedures", J Org. Chem., vol. 61 pp. 3849-3862 (1996).
Aboutaleb et al., International Sem in Surgical Oncol 6(17): 1-3, 2006.
Acute myeloid leukemia: MedlinePlus Medical Encyclopedia. Retrieved on Dec. 28, 2010. Electronic Resource: http://www.nlm.nih.gov/medlineplus/ency/article/000542.htm].
Advani, A., Curr Hematologic Malignancy Reports 1:101-107,2006.
Ansari-Lari, A. et al., "FLT3 mutations in myeloid sarcoma" British Journal of Haematology. Sep. 2004 126(6):785-91.
Armstrong, S.A. et al., (2004) "FLT3 mutations in childhood acute lymphoblastic leukemia." Blood. 103: 3544-6.
Arnon et al., "Monoclonal Antibodies for Immunotargeting of Drugs in Cancer Therapy", in Monoclonal Antibodies and Cancer Therapy, Reisfeld et al. (eds.), pp. 243-256 (Alan R. Liss, Inc. 1985).
Auewarakul et al., Ann Hematol, 85:108-112, 2006.
Baumann CA, Zeng L, Donatelli RR, Maroney AC. Development of a quantitative, high-throughput cell-based enzyme-linked immunosorbent assay for detection of colony-stimulating factor-1 receptor tyrosine kinase inhibitors. J Biochem Biophys Methods. 2004; 60:69-79.
Beller et al., Applied Homogeneous Catalysis with Organometallic Compounds, Cornils, B. and Herrmann, W. A. (Eds.), 2, 1009-1024, VCH, Weinheim, Germany (1996).
Berenbaum et al. What is synergy? Pharmacological Reviews, 1989.
Berge, S., et al, "Pharmaceutical Salts", J. Pharm. Sci., Jan. 1997, 66(1): 1-19.

Bodansky, M. et al., "The Practice of Peptide Synthesis", Springer-Verlag, NY (1984).
British Journal of Haematology, "Flt3 mutations and leukaemia", 2003,122(4):523-38.
Buchner T., W. Hiddemann, et al. (2002). "Acute myeloid leukemia: treatment over 60." Rev Clin Exp Hematol. 6(1):46-59.
Buchwald, E.L. et al., Top. Curr. Chem., 219:131-209 (2001).
Burnett, A. K. (2002). "Acute myeloid leukemia: treatment of adults under 60 years." Rev Clin Exp Hematol 6(1): 26-45.
Canibano, V. et al., Synthesis 14, 2175 (2001).
ChemBlink. Tipifarnib. Electronic Resource. Retrived on Dec. 18, 2010: [http://www.chemblink.com/products/192185-72-1.htm].
Chou TC, Talalay P. (1984) "Quantitative analysis of dose-effect relationships: the combined effects of multiple drugs or enzyme inhibitors." Adv Enzyme Regul. 22:27-55.
Coll. Czech. Chem. Commun.: 31(11), 4432-41, (1966), Palecek, J.
Comprehensive Organic Transformations: Larock, R.S.; Wiley and Sons Inc., USA 1999.
Cortes. Farnesyltransferase inhibitors in acute myeloid leukemia and myelodysplastic syndromes. Clinical Lymphoma, vol. 4, Suppl. 1, S30-S35, 2003.
Cummins et al., Tetrahedron (1988), 44(16), 5151.
Drexler, H. G. et al. (2004), "FLT3: receptor and ligand"; Growth Factors 22(2):71-3.
Drexler, H.G., "The Leukemia-Lymphoma Cell Line Factsbook", Academic Pres:SanDiego, CA, 2000.
Ferrara et al., "Prognostic factors and therapeutic options for relapsed or refractory acute myeloid leukemia." Haematologica. Aug. 2004, vol. 89, No. 8, Aug. 2004; pp. 998-1008.
Gilliland, G., et.al, "The roles of FLT3 in mematopoiesis and leukemia", Blood. 2002; 100:1532-42.
Gotlib, J (2005) "Farnesyltransferase inhibitor therapy in acute myelogenous leukemia." Curr. Hematol. Rep.;4(1):77-84.
Gould, P., "Salt selection for basic drugs", Ref. International J. Pharm. 1986, 33, 201-217.
Gray, M. et al., Tetrahedron Lett., 41:6237-40 (2000).
Griswold, I. J. et al., "Effects of MLN518, A Dual FLT3 and KIT inhibitor, on Normal and Malignant Hematopoiesis" Blood, Jul. 2004 [Epub ahead of print].
Haluska P., G.K. Dy, A.A. Adjei. (2002) "Farnesyl transferase inhibitors as anticancer agents." Eur J Cancer. 38(13):1685-700.
Han, J., Advances in Characterization of Pharmaceutical Hydrates, Trends in Bio/PharmaceuticalIndustry, pp. 25-29. Mar. 2006.
Hartwig, J.F., "Organopalladium Chemistry for Organic Synthesis," Wiley Interscience, NY (2002).
Hellstrom et al., "Antibodies for Drug Delivery", in Controlled Drug Delivery (2nd Ed.), Robinson et al. (eds.), pp. 623-53 (Marcel Dekker, Inc. 1987).
Hengartner, Mo. (2000) "The biochemistry of apoptosis." Nature 407:770-76.
Hill et al., J. Am. Chem. Soc. (1973), 95, 1338.
Iddon. B. et al., J. Chem. Soc. Perkin Trans. 1., 1370, (1980).
Ishikubo et al (Jpn J Clin Oncol 36:494-498, 2006).
Johnson et al., Brit J Cancer, 84:1424-1431 (2001).
Lyon et al., J. Med. Chem., 29: 630-634 (1986).
Romeo et al., J. Med. Chem., 46: 2877 (2003).
Kamwakami J., et al. "A Convenient Synthesis of 4(5)-Alkylacyl-1H-imidazoles from 4(5)-Imidazolecarboxaldehyde" Synthesis, No. 5, pp. 677-680 (2003).
Katritsky, A. et al., "para-Formylation of Nitroarenes via Vicarious Nucleophilic Substitution of Hydrogen with Tris(benzotriazol-1-yl)methane", Tetrahedron Lett., 37:347-50 (1996).
Kolder, C.R., et al, "Synthesis and Reactivity of 5-Chloro-2,4-Dihydrosypyridine", x Recl. Tray. Chim. Pays-Bas; 285 (1953).
Lancet J.E., J.D. Rosenblatt, J.E. Karp. (2003) "Farnesyltransferase inhibitors and myeloid malignancies: phase I evidence of Zarnestra activity in high-risk leukemias." Semin Hematol. 39(3 Suppl 2):31-5.
Levis, M. et al. 2001, "A FLT3 tyrosine kinase inhibitor is selectively cytotoxic to acute myeloid leukemia blasts harboring FLT3 internal tandem duplication mutations", Blood 98(3):885-7.
Levis, M. et al., "Novel FLT3 tyrosine kinase inhibitors" Expert Opin. Investing. Drugs (2003) 12 (12) 1951-1962.

Levis, M. et al., "Small Molecule FLT3 Tyrosine Kinase Inhibitors" Current Pharmaceutical Design, 2004, 10, 1183-1193.
Levis, M., et al. (2004) "In vitro studies of a FLT3 inhibitor combined with chemotherapy: sequence of administration is important to achieve synergistic cytotoxic effects." Blood. 104(4):1145-50.
Lewis, et al. "Diacetoxypiperidinium Analogs of Acetylcholine", Junal of Medicinal Chemistry, 1973, vol. 16, No. 2 pp. 156-159.
Loader, C., et al., "Pyrrole chemistry. XXIII. The cyanation of substituted pyrroles with chlorosulfonyl isocyanate (CSI). New syntheses of pyrrole-3-carbonitriles.", Can. J. Chem, 59, 2673 (1981).
Lovborg H, Gullbo J, Larsson R. (2005) "Screening for apoptosis-classical and emerging techniques." Anticancer Drugs 16:593-9.
Lyon, R. , et al., "Synthesis and Evaluation of Phenyl-and Benzoylpiperazines as Potential Serotonergic Agents", J. Med. Chem., 29: 630-4 (1986).
Major, R., et al. "1-Alkoxy-4-phenyl-4-propionoxypiperdines and Their 3-Methyl Homologs as New Analgesics", vol. 26, pp. 1867-1847, (1961).
McKenna, H.J. et al., "Mice lacking flt3 ligand having deficient hematopoiesis affecting hematopoietic progenitor cells, dendritic cells and natural killer cells", Blood Jun. 2000; 95:3489-3497.
Miyaura, N. et al., "Palladium-Catalyzed Cross-Coupling Reactions of Organoboron Compounds", Chem. Rev. 95:2457 (1995).
Modern Amination Methods: Ricci, A., Ed., Wiley-VCH: Weinheim, 2000.
Muci, et al., "Practical Palladium Catalysts for C—N. and C—O Bond Formation", Top. Curr., Chem. 219-131-209 (2001.
Murata, K. et al., "Selective cytotoxic mechanism of GTP-14564, a novel tyrosine kinase inhibitor in leukemia cells expressing a constitutively active Fms-like tyrosine kinase 3 (FLT3)" J Biol Chem. Aug. 29, 2003; 278(35):32892-8.
Murata, K. et al., "Synthesis of Alkenylboronates via Palladium-Catalyzed Borylation of Alkenyl Triflates (or Iodindes) with Pinacolborane" Synthesis, 2000, No. 6, pp. 778-780.
Nicolai, E., et al., "New Process for the Synthesis of Imidazo[4-5-b]pyridine Derivatives as Potent Orally Active Thromboxane $A_2$ Receptor Antagonists", J. Heterocyclic Chemistry, 31, (73) (1994).
Nunez G, Benedict MA, Hu Y, Inohara N. (1998) "Caspases: the proteases of the apoptotic pathway." Oncogene 17:3237-45.
O'Farrell, A.M. et al. "SU11248 is a novel FLT3 tyrosine kinase inhibitor with potent activity in vitro and in vivo" Blood, May 2003; 101:3597-3605.
Olah, G.A. et al., "Formylating Agents", Chemical Reviews, vol. 87, No. 4, 1987.
Prendergast et al., (2001) "Farnesyl Transferase Inhibtors: Mechanism and Applications" Expert Opin Investig Drugs. 10(12):2105-16).
Protecting Groups, P, Kocienski Thieme Medical Publishers, 2000.
Pure Appl. Chem., 1976, 45:13-30.
Quentmeier H, et al. FLT3 mutations in acute myeloid leukemia cell lines. Leukemia. Jan. 2003;17:120-124.
Romeo, G., et al, "New Pyrimido [5,4-b_indoles as Ligands for *1-Adrenoceptor Subtypes", J. Med. Chem., 46: 2877-2894 (2003).
Sadick, M. et al., Analysis of Heregulin-Induced ErbB2 Phosphorylation with a High-Throughput Kinase Receptor Activation Enzyme-Linked Immunosorbent Assay, Analytical Biochemistry. 1996; 235:207-214.
Scheijen, B. et al. (2002), "Tyrosine kinase oncogenes innormal hematopoiesis and hematological disease", Oncogene 21(21):3314-33.
Shih L. Y. et al., (2004) "Internal tandem duplication of fms-like tyrosine kinase 3 is associated with poor outcome in patients with myelodysplastic syndrome." Cancer, 101; 989-98.
Simpson WG, The calcium channel blocker verapamil and cancer chemotherapy. Cell Calcium. Dec. 1985;6(6):449-67.
Smith, B. D. et al., "Single-agent CEP-701, a novel FLT3 inhibitor, shows biologic and clinical activity in patients with relapsed or refractory acute myeloid leukemia" Blood, May 2004; 103:3669-3676.
Smith, P, "The Curtius Reaction", Organic Reactions 3:337 (1947).
Stirewalt, D.L. et al. (2003), "The role of FLT3 in haematopoietic malignancies", NatRev Cancer 3(9):650-65.

Stone, R.M. et al. "PKC 412 FLT3 inhibitor therapy in AML: results of a phase II trial" An Hematol 2004; 83 Suppl 1:S89-90.
Suzuki, A., "Metal-Catalyzed Coupling Reactions" F. Deiderich, P. Stang, Eds., Wiley-VCH, Weinheim (1998).
Takada, Y., et al. (2004). "Protein farnesyltransferase inhibitor (SCH 66336) abolishes NF-kappaB activation induced by various carcinogens and inflammatory stimuli leading to suppression of NF-kappaB-regulated gene expression and up-regulation of apoptosis."J Biol Chem 279, 26287-99.
Thalhammer et al. Duration of second complete remission in patients with acute myeloid leukemia treated with chemotherapy: a retrospective single-center study. Ann. Hematology, 1996, 72: 216-222.
Thompson et al., Journal of Industrial and Engineering Chemistry (Washington, D. C.) (1952), 44,1659-62.
Thorpe, "Antibody Carriers of Cytotoxic Agents in Cancer Therapy: A Review", in Monoclonal Antibodies '84: Biological and Clinical Applications, Pinchera et al. (eds.), pp. 475-506 (1985).
Tse, K.F. et al., "Inhibition of FLT3-mediated transformation by use of a tyrosine kinase inhibitor" Leukemia, Jul. 2001 15(7):1001-10.
van Engeland M., L.J. Nieland , et al. (1998) "Annexin V-affinity assay: a review on an apoptosis detection system based on phosphatidylserine exposure." Cytometry. 31(1):1-9.
Walker et al (Dermatol 212:70-72, 2006; (Abstract Only).
Wustrow, et al, "Coupling of Arylboronic Acids with a Partially Reduced Pyridine Derivative" Synthesis, 993 (1991).
www.cancer.org (accessed online Mar. 2, 2010), "Can Acute Myeloid Luchemia (AML) Be Prevented?".
Yee et al. Synergistic effect of SU11248 with cytarabine or daunorubicin on FLT3 ITD-positive leukemic cells. Blood, 2004, 104: 4202-4209. Published online Aug. 10, 2004.
Yee, K.W.H. et al., "SU5416 and SU5614 inhibit kinase activity of wild-type and mutant FLT3 receptor tyrosine kinase" Blood, Sep. 2002; 100:2941-294.
Zhu et al. Farnesyltransferase inhibitor R115777 (Zarnestra, Tipifarnib) synergizes with paclitaxel to induce apoptosis and mitotic arrest and to inhibit tumor growth of multiple myeloma cells. Blood, vol. 105, No. 12, 4759-4766, Published online Feb. 22, 2005.
International Search Report re: PCT/US2008/080081 dated Mar. 18, 2009.
Beletskaya et al., *Chem. Rev.*, 100:3009 (2000).
Brase et al., *Angew. Chemie Int. Ed.*, 44(33), 5188-5240, (2005).
Brase et al., Metal-Catalyzed Cross-Coupling Reactions (2nd Edition), p. 217-315, A. de Meijere, F. Diederich, Eds., Wiley-VCH, Weinheim (2004).
Corey et al., *Tetrahedron Lett.*, 29, 995 (1988).

Couturier et al., *Organic Process Research & Development*, 2002, 6, 42-48.
Dirlam et al., *J. Heterocyclic Chem*, 17, 409, (1980).
Dolan, S., et al., *J. Chem., Soc., Chem. Commun.*, 1588-9 (1985).
Fohlisch et al, *Liebigs Annalen der Chemie*, (1), 1-5 (1987) [English Abstract provided].
Galemmo et al., *J. Med. Chem.*, 33(10), 2828-41; (1990).
Guanti et al., *Tetrahedron*, 46 (20), 7081, (1990).
Guanti et al., *Tetrahedron: Asymmetry* 8(13), 2175-2187, (1997).
Hayakawa et al., *Bioorg. Med. Chem. Lett.*, 14(2): 455-8 (2004).
Hulkenberg et al., *Tetrahedron Lett.*, 23(14), 1505-08; (1982).
Itsuno et al., *Synthesis*, 12, 995-6, (1988).
Khanapure et al, *J. Med. Chem.*, 48(11): 3930-34 (2005).
Koutek, et al, *Synth. Commun.*, 6 (4), 305-8 (1976).
Leonard et al., *J. Org. Chem.*, 28, 3021, (1963).
Liu et al., *J. Am. Chem. Soc.* 2004, 126, 5182.
Martinez_Teipel et al., *QSAR & Combinatorial Science*, 23(10), 854-858 (2004).
Mock et al., *J. Phys. Org. Chem.*, 16(3), 175-182 (2003).
Myles et al., *J. Org. Chem.*, 55, 1636 (1990).
Nguyen et al., *Tetrahedron*, 62(4), 647-651; (2006).
Nose et al., *Chem. Pharm. Bull.*, 38(8), 2097-101, (1990).
Quintard et al., *J. Org. Chem.*, 48: 1559-60 (1983).
Reed et al., *Synthetic Communications*, 20(4), 563-71, (1990).
Roush, W., *J. Am. Chem. Soc.* 102, 1390 (1980).
Tohma et al., *Adv. Syn. Catalysis*, 346, 111-124 (2004).
Wustrow et al., *Tetrahedron Lett.*, 35, 61-4 (1994).
Suzuki, A. In *Metal-Catalyzed Cross Coupling Reactions*; Diederich, F., Stang, P. J., Eds.; Wiley-VCH: Weinheim, Germany, 1998; Chapter 2, pp. 49-89.
International Search Report re: PCT/US2005/037868 dated Sep. 17, 2008.
Chemcats RN 93730-20-2, Nov. 28, 1988.
Chemcats RN 443895-82-7 Apr. 24, 2003.
Chemcats RN 701272-70-0, Jan. 1, 2004.
Chemcats RN 712290-43, Jan. 1, 2004.
Jonas, Nilsson W. et al., "Solid-Phase Synthesis of Libraries Generated from a 4-Phenyl-2-carboxy-piperazine Scaffold", J. Comb. Chem., 2001, 3, 546-553.
Moffett, Robert Bruce et al., "Antiulcer Agents. p-Aminobenzamido Aromatic Compounds", Journal of Medicinal Chemistry, 1971, vol. 14, No. 10, pp. 963-968.
Nilsson et al., J. Comb. Chem., vol. 3, pp. 546-553 (2001).
Rastelli et al. J. Med. Chem., 2003, 46, 2834-2845.

* cited by examiner

XPRD of 4-Cyano-1H-imidazole-2-carboxylic acid [2-(4,4-dimethyl-cyclohex-1-enyl)-6-(2,2,6,6-tetramethyl-tetrahydro-pyran-4-yl)-pyridin-3-yl]-amide sulfate salt XPRD of 4-Cyano-1H-imidazole-2-carboxylic acid [2-(4,4-dimethyl-cyclohex-1-enyl)-6-(2,2,6,6-tetramethyl-tetrahydro-pyran-4-yl)-pyridin-3-yl]-amide sulfate salt (Form A)

XPRD of 4-Cyano-1H-imidazole-2-carboxylic acid [2-(4,4-dimethyl-cyclohex-1-enyl)-6-(2,2,6,6-tetramethyl-tetrahydro-pyran-4-yl)-pyridin-3-yl]-amide sulfate salt (Form B)

Compound A reversed the ankle and paw swelling during the chronic phase of SCW-induced arthritis and enhanced weight gain.

INHIBITORS OF C-FMS KINASE

CROSS REFERENCE TO RELATED APPLICATION

This application claims priority from U.S. Provisional Applications Ser. No. 60/980,623, filed on Oct. 17, 2007, the contents of which are hereby incorporated by reference in their entirety.

BACKGROUND OF THE INVENTION

The invention relates to novel compounds that function as protein tyrosine kinase inhibitors. More particularly, the invention relates to novel compounds that function as inhibitors of c-fms kinase.

Protein kinases are enzymes that serve as key components of signal transduction pathways by catalyzing the transfer of the terminal phosphate from adenosine 5'-triphosphate (ATP) to the hydroxy group of tyrosine, serine and threonine residues of proteins. As a consequence, protein kinase inhibitors and substrates are valuable tools for assessing the physiological consequences of protein kinase activation. The overexpression or inappropriate expression of normal or mutant protein kinases in mammals has been demonstrated to play significant roles in the development of many diseases, including cancer and diabetes.

Protein kinases can be divided into two classes: those which preferentially phosphorylate tyrosine residues (protein tyrosine kinases) and those which preferentially phosphorylate serine and/or threonine residues (protein serine/threonine kinases). Protein tyrosine kinases perform diverse functions ranging from stimulation of cell growth and differentiation to arrest of cell proliferation. They can be classified as either receptor protein tyrosine kinases or intracellular protein tyrosine kinases. The receptor protein tyrosine kinases, which possess an extracellular ligand binding domain and an intracellular catalytic domain with intrinsic tyrosine kinase activity, are distributed among 20 subfamilies.

Receptor tyrosine kinases of the epidermal growth factor ("EGF") family, which includes HER-1, HER-2/neu and HER-3 receptors, contain an extracellular binding domain, a transmembrane domain and an intracellular cytoplasmic catalytic domain. Receptor binding leads to the initiation of multiple intracellular tyrosine kinase dependent phosphorylation processes, which ultimately results in oncogene transcription. Breast, colorectal and prostate cancers have been linked to this family of receptors.

Insulin receptor ("IR") and insulin-like growth factor I receptor ("IGF-1R") are structurally and functionally related but exert distinct biological effects. IGF-1R over-expression has been associated with breast cancer.

Platelet derived growth factor ("PDGF") receptors mediate cellular responses that include proliferation, migration and survival and include PDGFR, the stem cell factor receptor (c-kit) and c-fms. These receptors have been linked to diseases such as atherosclerosis, fibrosis and proliferative vitreoretinopathy.

Fibroblast growth factor ("FGR") receptors consist of four receptors which are responsible for the production of blood vessels, for limb outgrowth, and for the growth and differentiation of numerous cell types.

Vascular endothelial growth factor ("VEGF"), a potent mitogen of endothelial cells, is produced in elevated amounts by many tumors, including ovarian carcinomas. The known receptors for VEGF are designated as VEGFR-1 (Flt-1), VEGFR-2 (KDR), VEGFR-3 (Flt-4). A related group of receptors, tie-1 and tie-2 kinases, have been identified in vascular endothelium and hematopoietic cells. VEGF receptors have been linked to vasculogenesis and angiogenesis.

Intracellular protein tyrosine kinases are also known as non-receptor protein tyrosine kinases. Over 24 such kinases have been identified and have been classified into 11 subfamilies. The serine/threonine protein kinases, like the cellular protein tyrosine kinases, are predominantly intracellular.

Diabetes, angiogenesis, psoriasis, restenosis, ocular diseases, schizophrenia, rheumatoid arthritis, cardiovascular disease and cancer are exemplary of pathogenic conditions that have been linked with abnormal protein tyrosine kinase activity. Thus, a need exists for selective and potent small-molecule protein tyrosine kinase inhibitors. U.S. Pat. Nos. 6,383,790; 6,346,625; 6,235,746; 6,100,254 and PCT International Applications WO 01/47897, WO 00/27820 and WO 02/068406 are indicative of recent attempts to synthesize such inhibitors.

SUMMARY OF THE INVENTION

The invention addresses the current need for selective and potent protein tyrosine kinase inhibitors by providing potent inhibitors of c-fms kinase. The invention is directed to the novel compounds of Formula I:

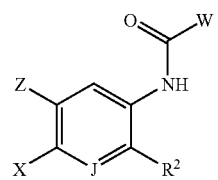

or a solvate, hydrate, tautomer or pharmaceutically acceptable salt thereof, wherein:

W is

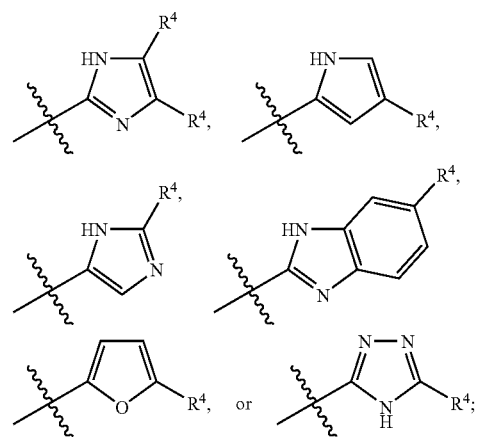

wherein each $R^4$ is independently H, F, Cl, Br, I, OH, $OCH_3$, $OCH_2CH_3$, $SC_{(1-4)}$alkyl, $SOC_{(1-4)}$alkyl, $SO_2C_{(1-4)}$alkyl, —$C_{(1-3)}$alkyl, $CO_2R^d$, $CONR^eR^f$, $C\equiv CR^g$, or CN;

wherein $R^d$ is H, or —$C_{(1-3)}$alkyl;

$R^e$ is H, or —$C_{(1-3)}$alkyl;

$R^f$ is H, or —$C_{(1-3)}$alkyl; and $R^g$ is H, —$CH_2OH$, or —$CH_2CH_2OH$;

$R^2$ is cycloalkyl, spiro-substituted cycloalkenyl, thiophenyl, dihydrosulfonopyranyl, phenyl, furanyl, tetrahydropyridyl, or dihydropyranyl, any of which may be independently substituted with one or two of each of the following: chloro, fluoro, hydroxy, $C_{(1-3)}$alkyl, and $C_{(1-4)}$alkyl;
Z is H, F, Cl, or $CH_3$;
J is CH, or N;
X is
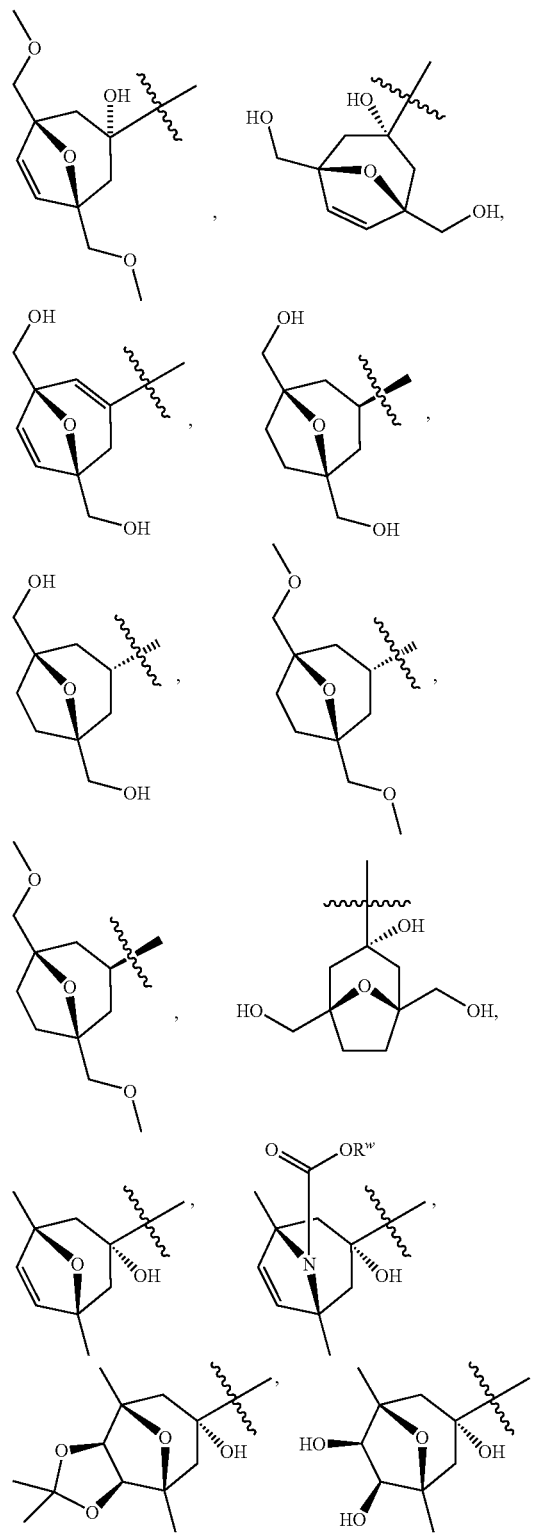
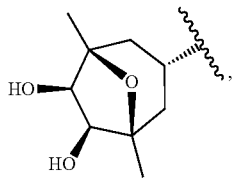
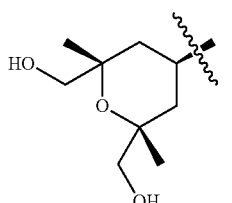
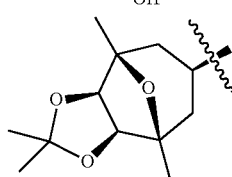
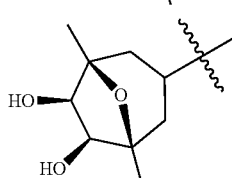
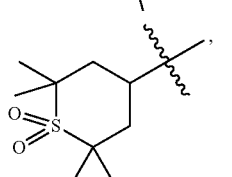
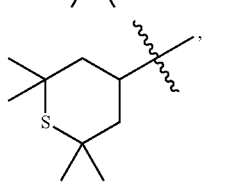
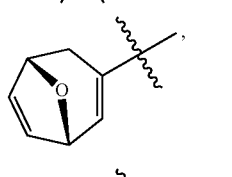
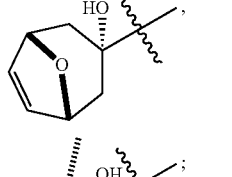
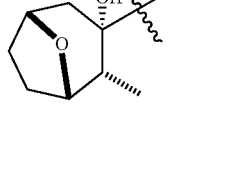
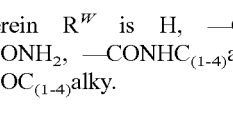
wherein $R^W$ is H, —$C_{(1-4)}$alkyl, —$CO_2C_{(1-4)}$alkyl, —$CONH_2$, —$CONHC_{(1-4)}$alkyl, —$CON(C_{(1-4)}alkyl)_2$, or —$COC_{(1-4)}$alky.

DETAILED DESCRIPTION OF THE INVENTION

Figure 1:
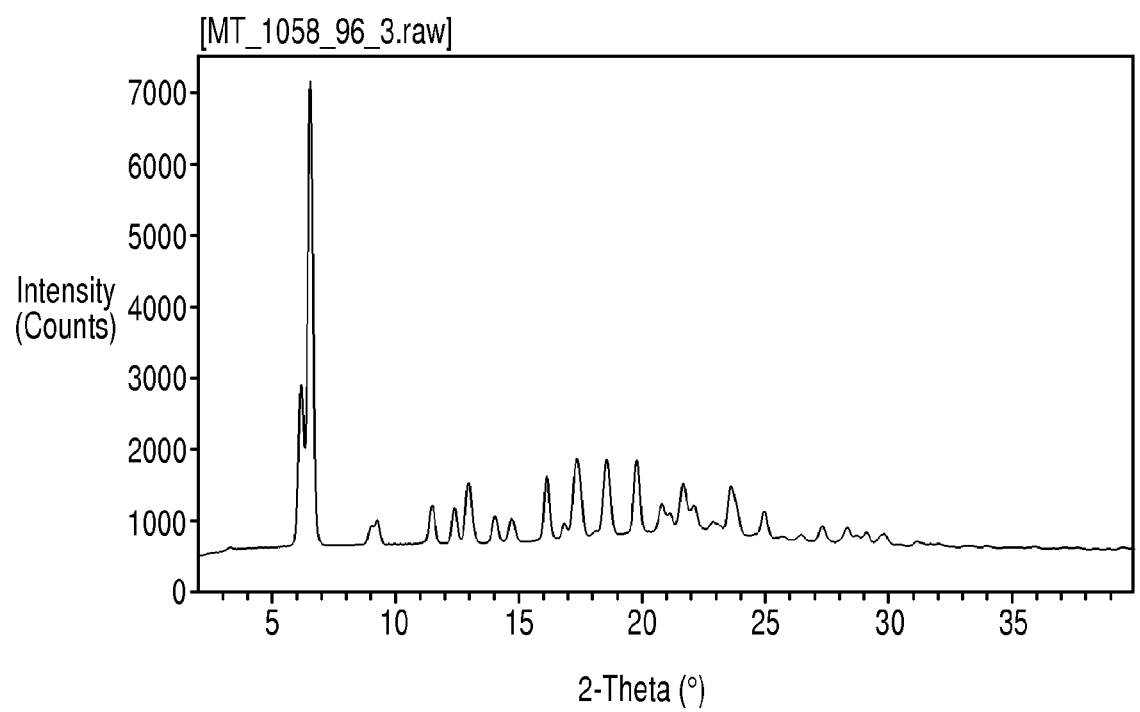
FIG. 1 is an X-ray powder diffraction pattern of the compound of Example 31 expressed in terms of °2θ.

The invention addresses the current need for selective and potent protein tyrosine kinase inhibitors by providing potent inhibitors of c-fms kinase. The invention is directed to the novel compounds of Formula I:

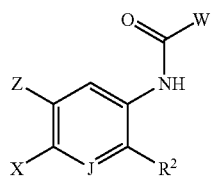

or a solvate, hydrate, tautomer or pharmaceutically acceptable salt thereof, wherein:

W is

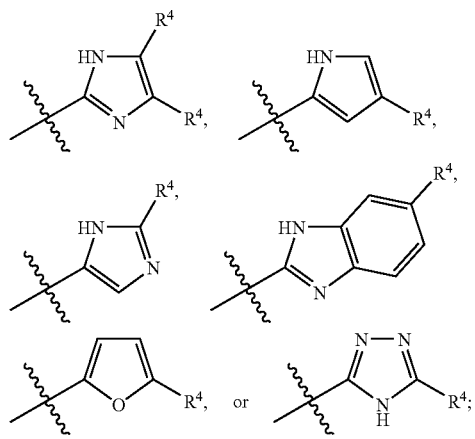

wherein each $R^4$ is independently H, F, Cl, Br, I, OH, $OCH_3$, $OCH_2CH_3$, $SC_{(1-4)}$alkyl, $SOC_{(1-4)}$alkyl, $SO_2C_{(1-4)}$alkyl, —$C_{(1-3)}$alkyl, $CO_2R^d$, $CONR^eR^f$, C≡$CR^g$, or CN;

wherein $R^d$ is H, or —$C_{(1-3)}$alkyl;

$R^e$ is H, or —$C_{(1-3)}$alkyl;

$R^f$ is H, or —$C_{(1-3)}$alkyl; and $R^g$ is H, —$CH_2OH$, or —$CH_2CH_2OH$;

$R^2$ is cycloalkyl, spiro-substituted cycloalkenyl, thiophenyl, dihydrosulfonopyranyl, phenyl, furanyl, tetrahydropyridyl, or dihydropyranyl, any of which may be independently substituted with one or two of each of the following: chloro, fluoro, hydroxy, $C_{(1-3)}$alkyl, and $C_{(1-4)}$alkyl;

Z is H, F, Cl, or $CH_3$;

J is CH, or N;

X is

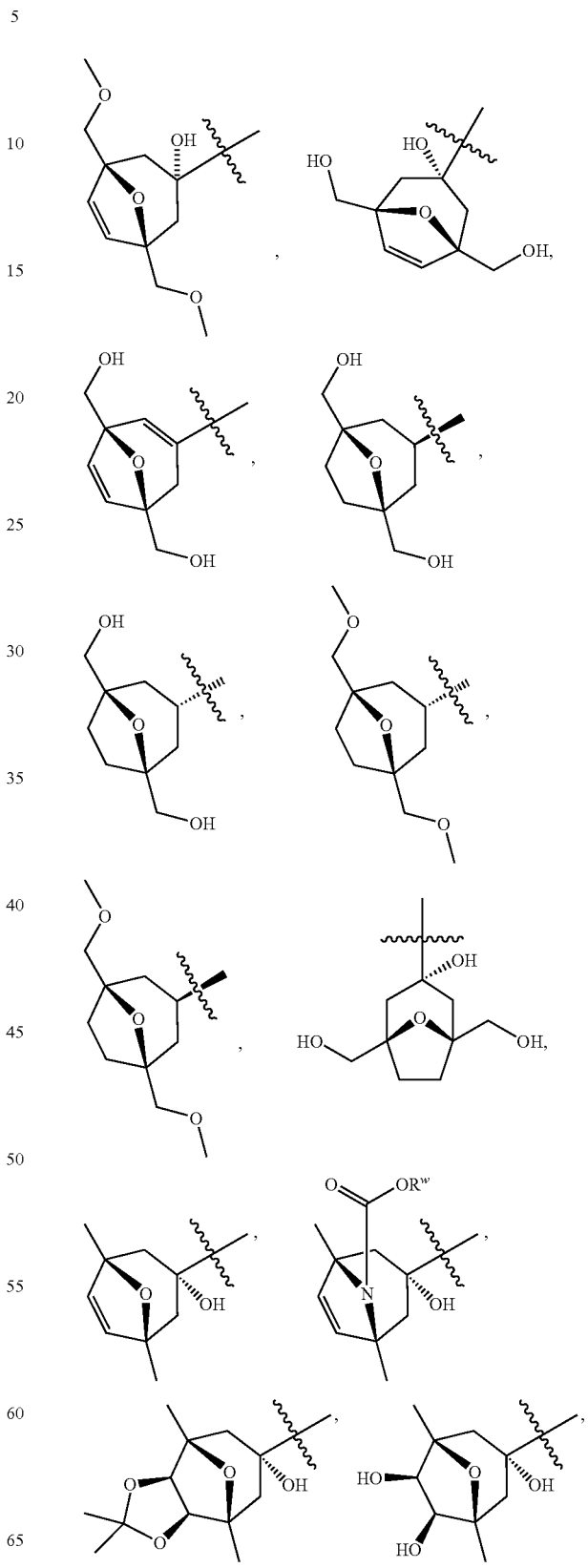

-continued
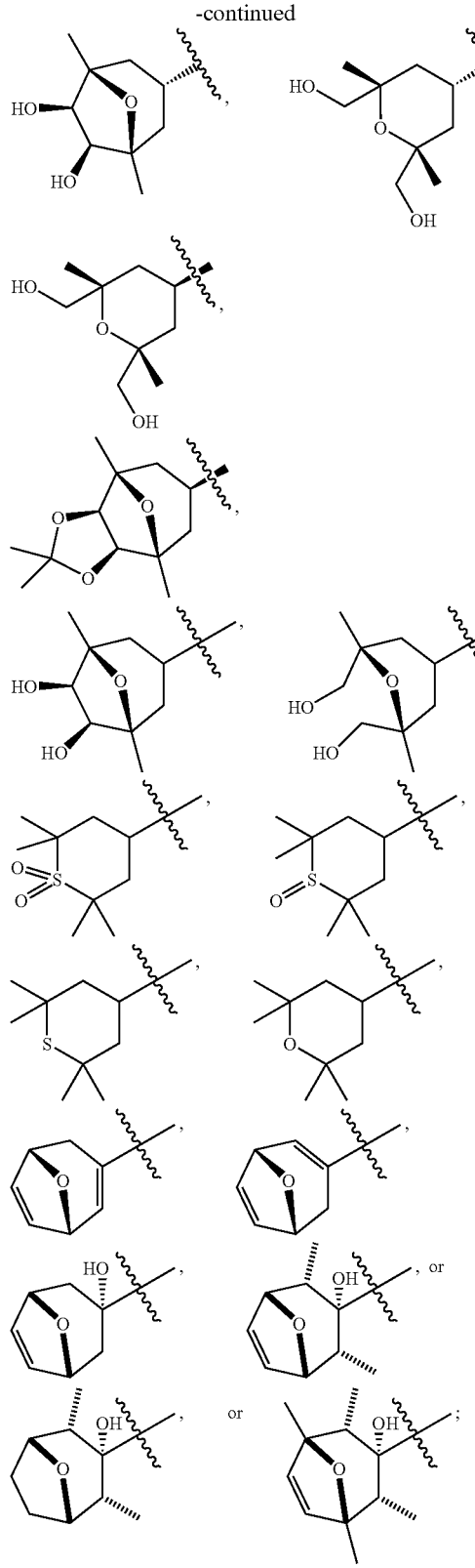
wherein $R^W$ is H, —$C_{(1-4)}$alkyl, —$CO_2C_{(1-4)}$alkyl, —$CONH_2$, —$CONHC_{(1-4)}$alkyl, —$CON(C_{(1-4)}alkyl)_2$, or —$COC_{(1-4)}$alkyl.
Another embodiment of the invention is a compound of Formula I, wherein:
W is
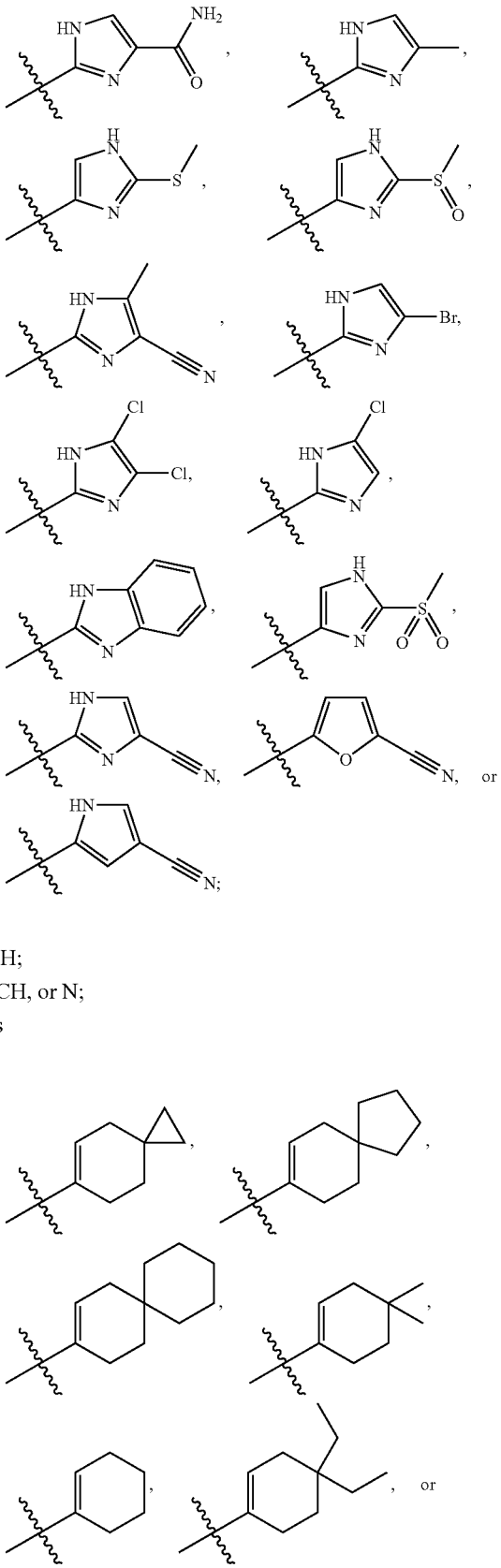
Z is H;
J is CH, or N;
$R^2$ is

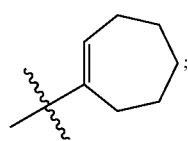
X is
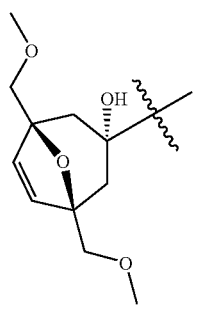 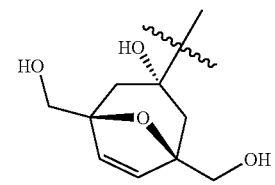
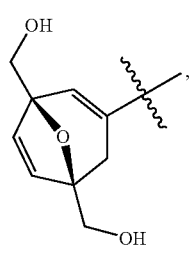 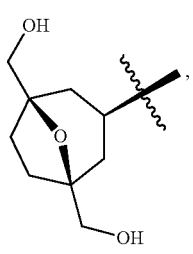
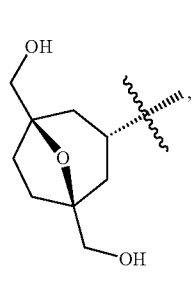 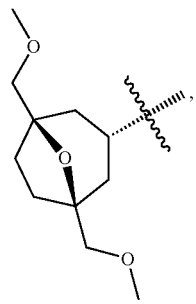
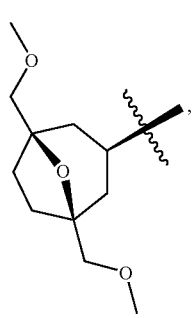 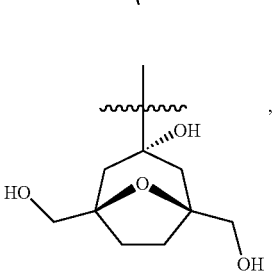
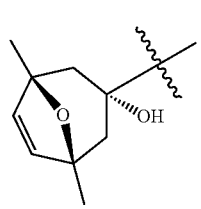 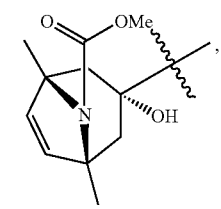
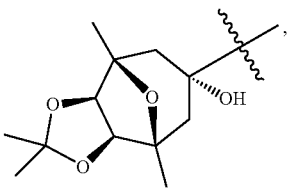
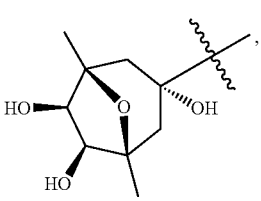
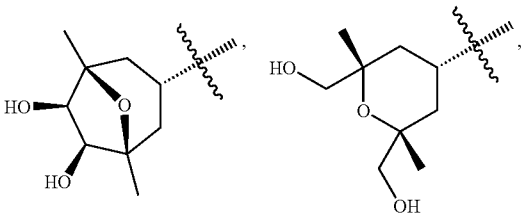
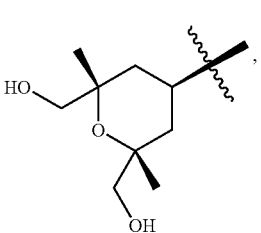
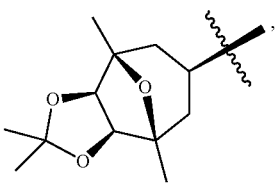
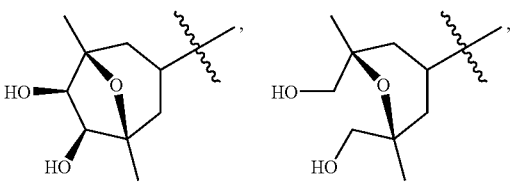
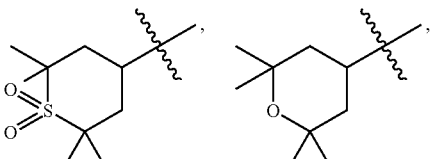
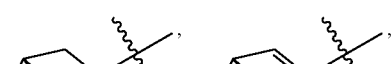
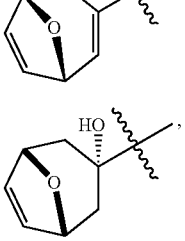 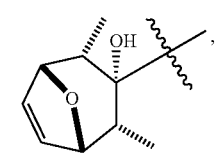

-continued
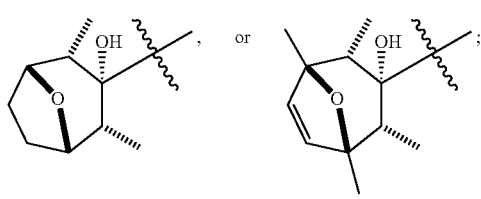 [SMILES: *[C@@]1(O)[C@H](C)[C@@H]2CC[C@@H](O2)[C@@H]1C ; *[C@]1(O)[C@@H](C)[C@@]2(C)C=C[C@](C)(O2)[C@H]1C]
and solvates, hydrates, tautomers and pharmaceutically acceptable salts thereof.
Another embodiment of the invention is a compound of Formula I, wherein:
W is
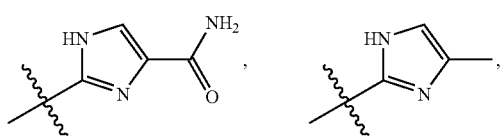
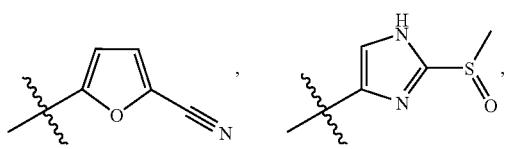
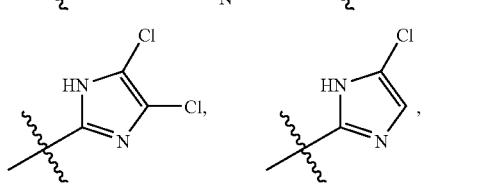
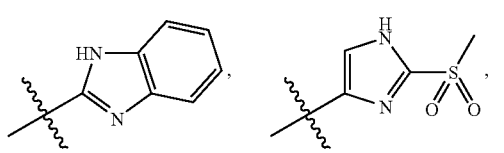
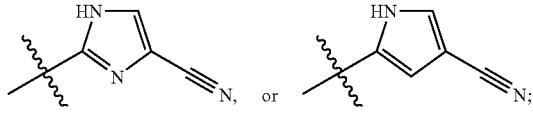
Z is H;
J is CH, or N;
R² is
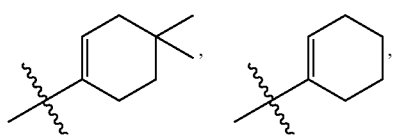
-continued
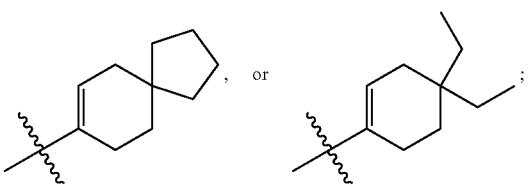
X is
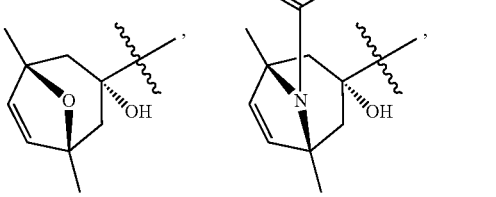

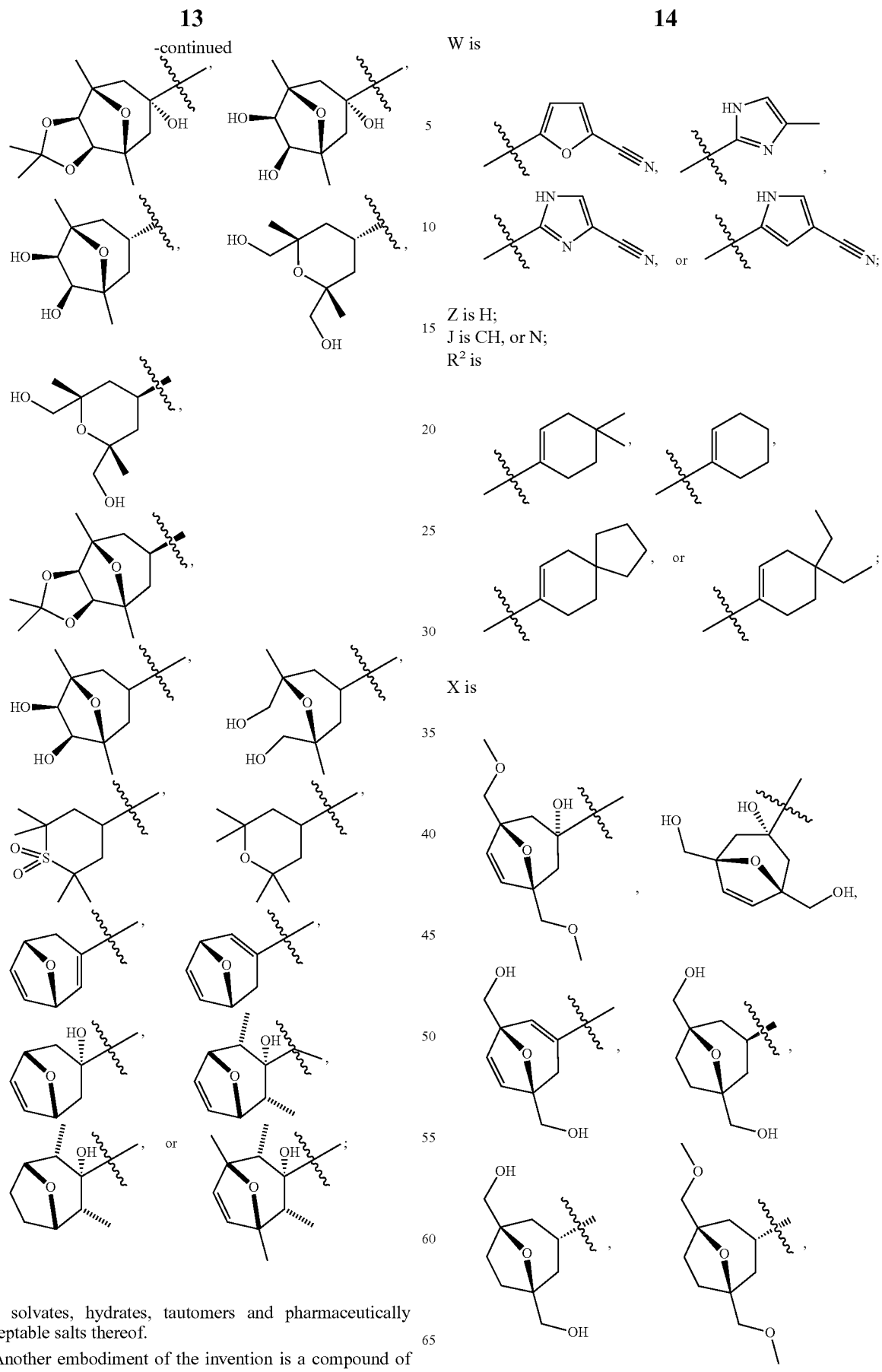
and solvates, hydrates, tautomers and pharmaceutically acceptable salts thereof.
Another embodiment of the invention is a compound of Formula I, wherein:

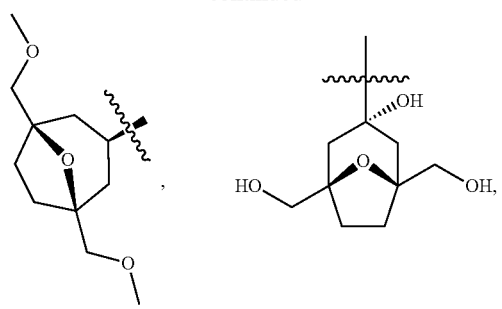
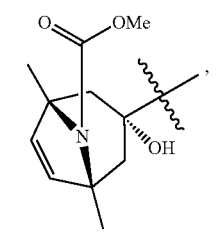
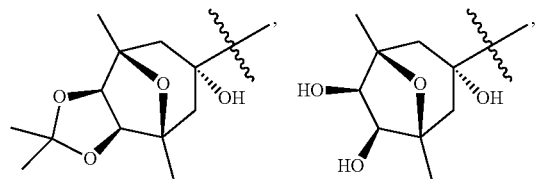
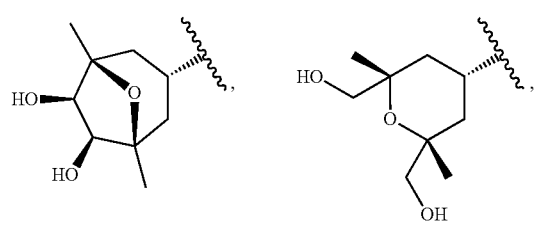
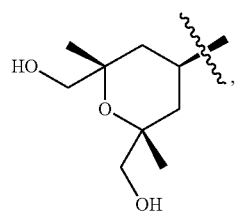
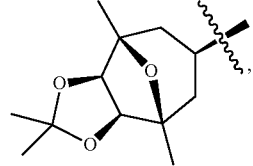
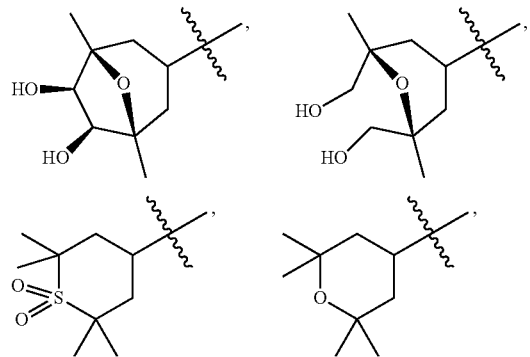
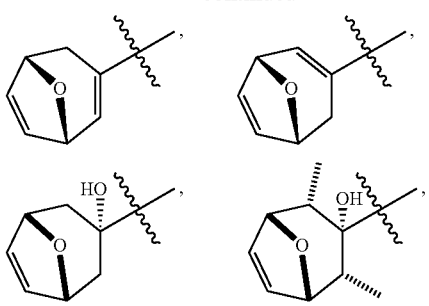
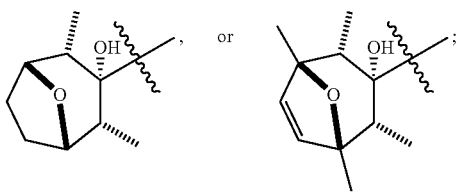
and solvates, hydrates, tautomers and pharmaceutically acceptable salts thereof.
Another embodiment of the invention is a compound of Formula I, wherein:
W is
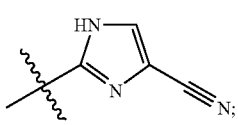
Z is H;
J is CH, or N;
$R^2$ is
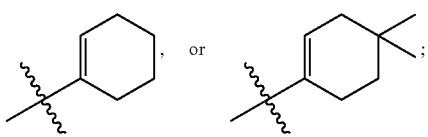
X is
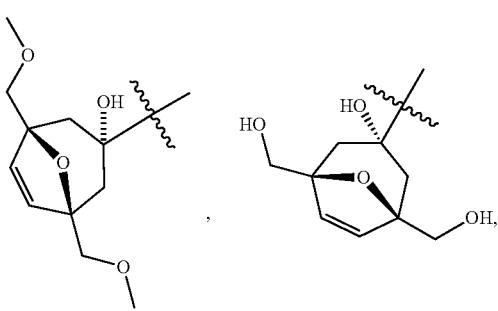

-continued
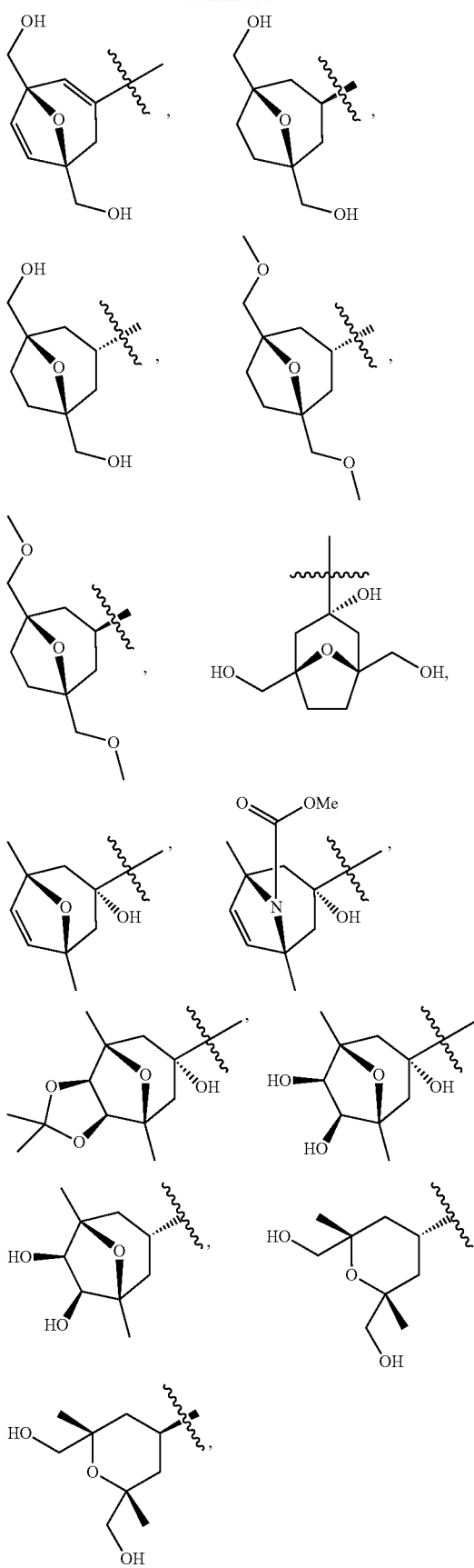
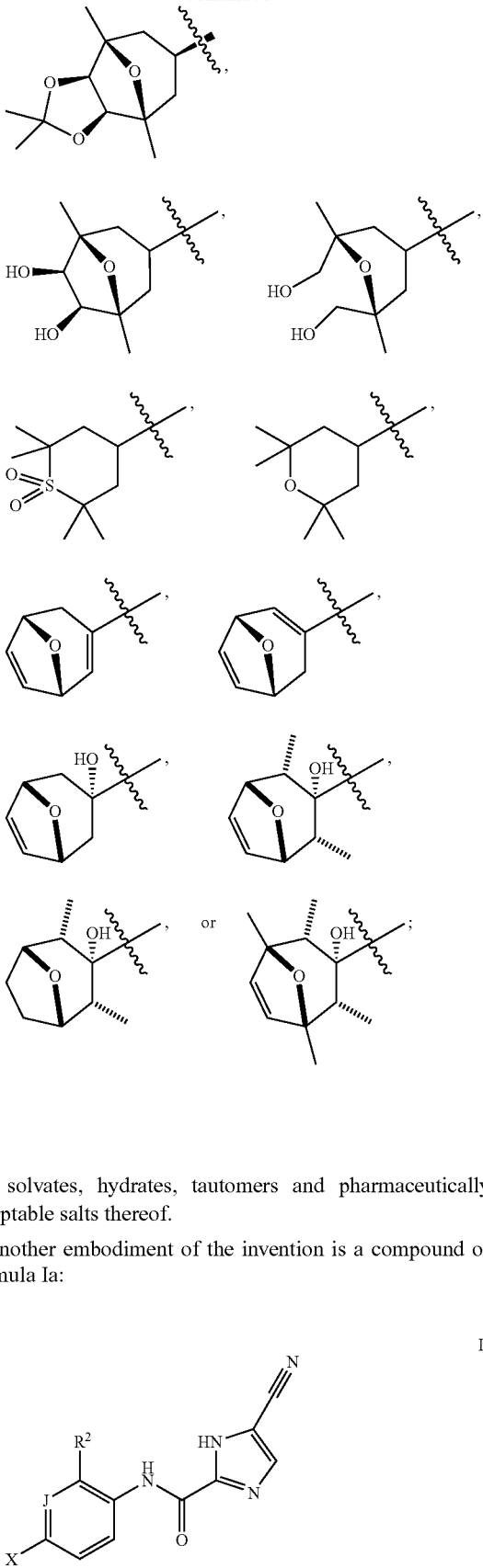
and solvates, hydrates, tautomers and pharmaceutically acceptable salts thereof.
Another embodiment of the invention is a compound of Formula Ia:
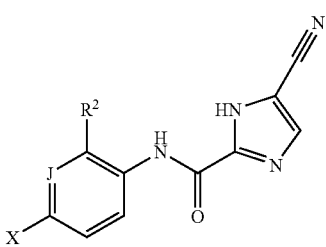
Ia wherein:
R² is
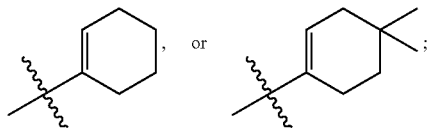
J is CH, or N; and
X is
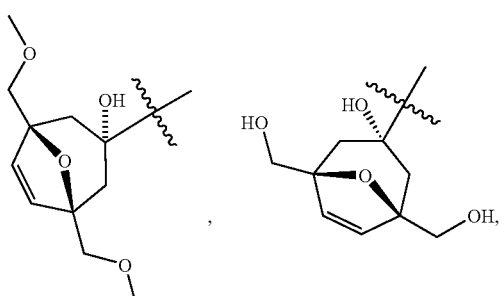
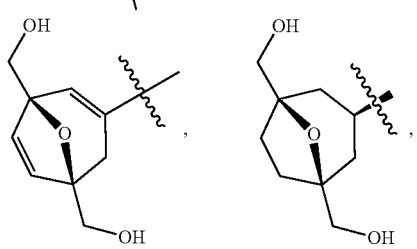
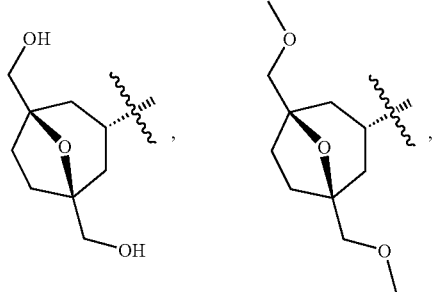
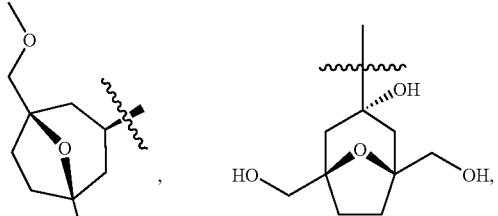
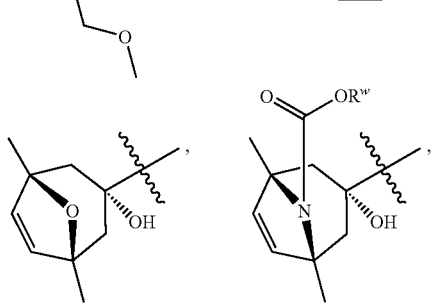
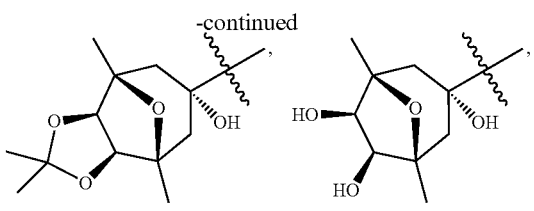
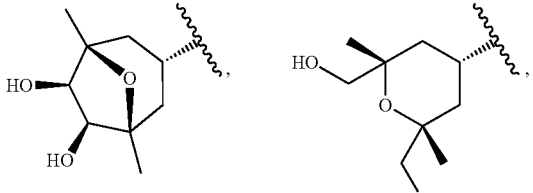
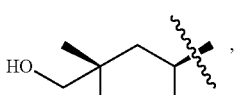
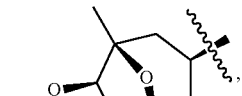
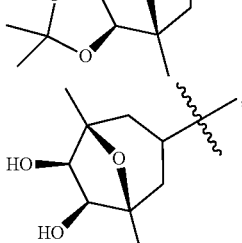
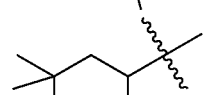
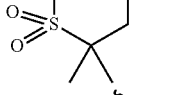
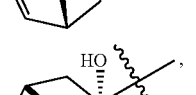
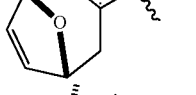
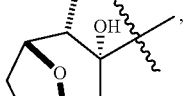
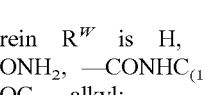
wherein $R^W$ is H, —$C_{(1-4)}$alkyl, —$CO_2C_{(1-4)}$alkyl, —$CONH_2$, —$CONHC_{(1-4)}$alkyl, —$CON(C_{(1-4)}alkyl)_2$, or —$COC_{(1-4)}$alkyl;
and solvates, hydrates, tautomers and pharmaceutically acceptable salts thereof.

Another embodiment of the invention is a compound of Formula Ia wherein
R² is
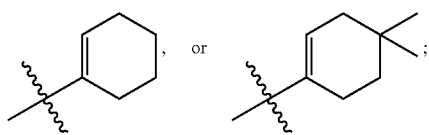
J is CH, or N;
X is
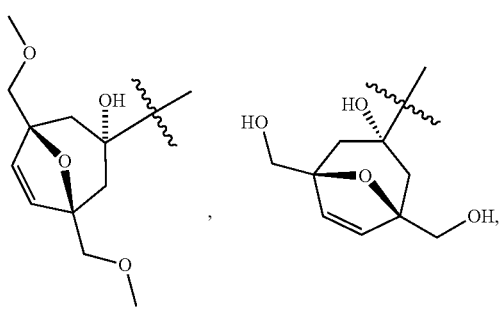
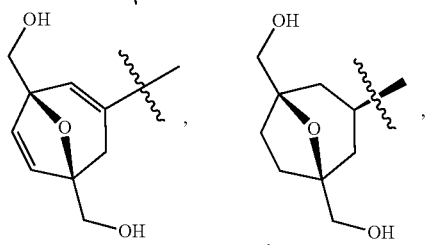
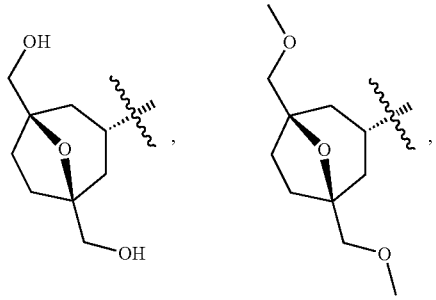
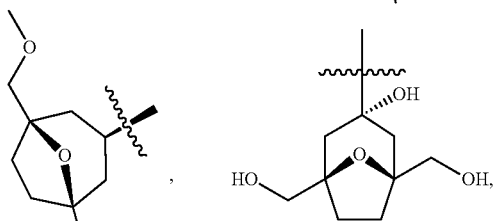
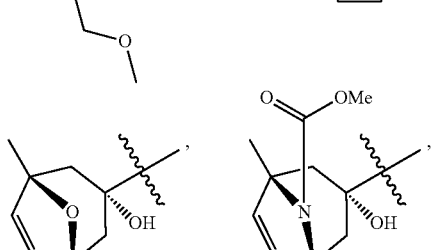
-continued
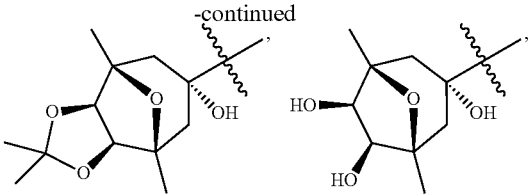
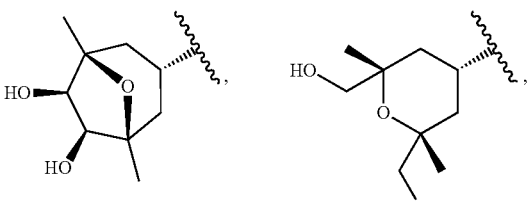
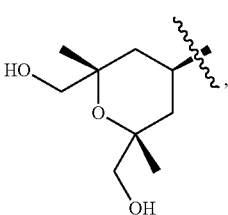
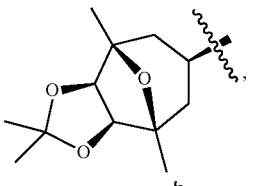
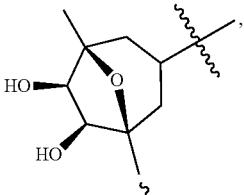
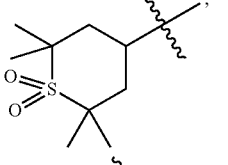
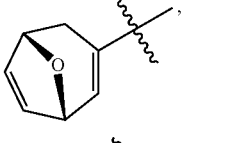
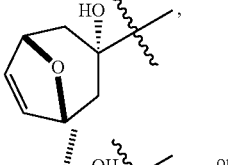
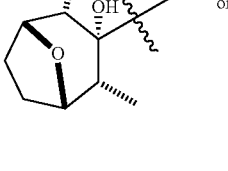
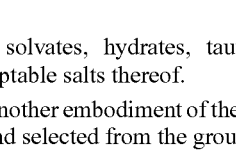
and solvates, hydrates, tautomers and pharmaceutically acceptable salts thereof.
Another embodiment of the invention is any example compound selected from the group consisting of:

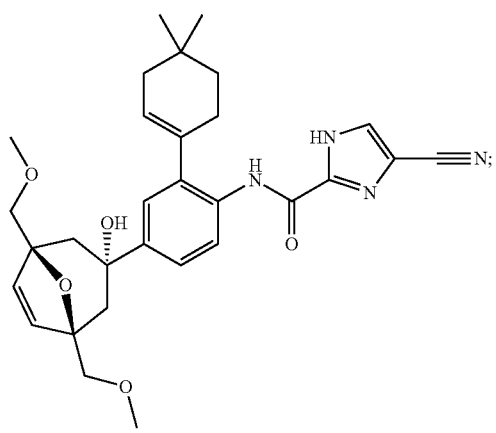
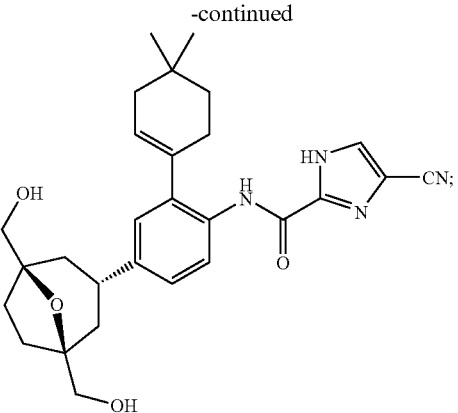
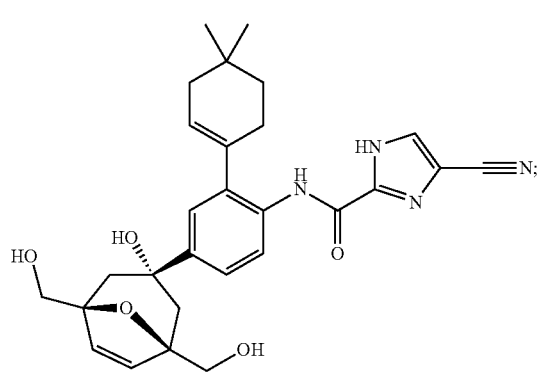
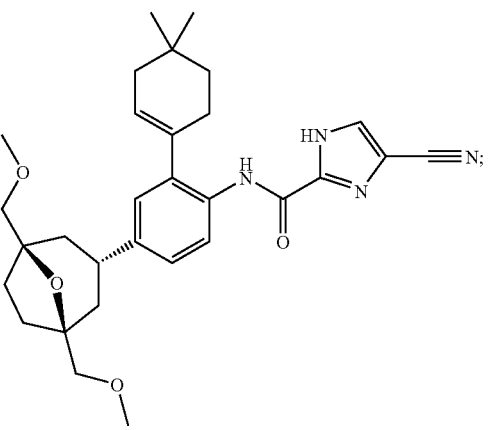
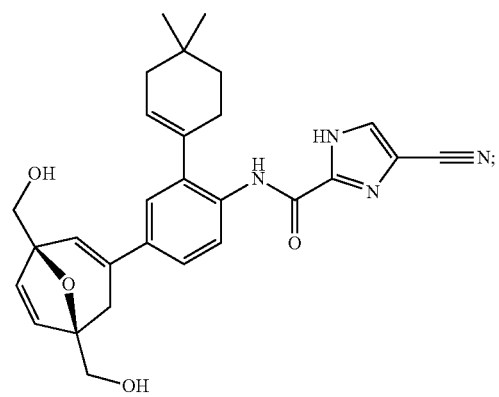
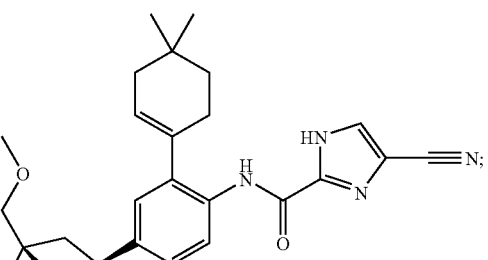
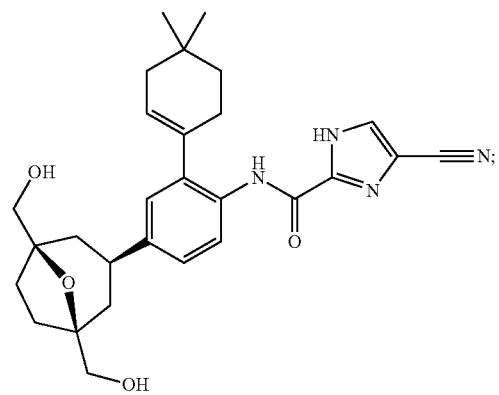
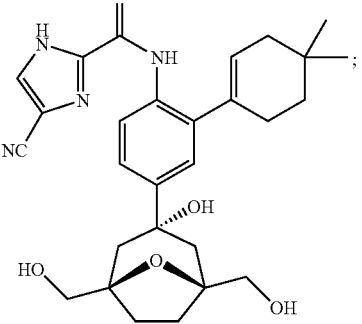

-continued
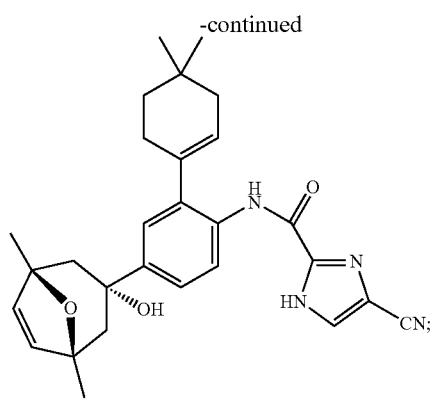
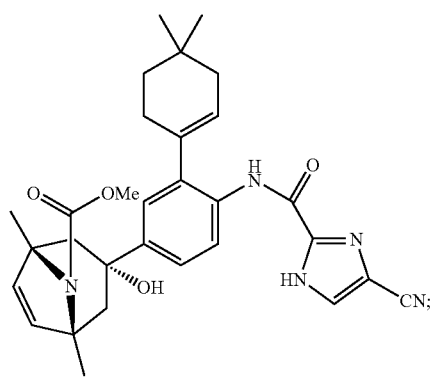
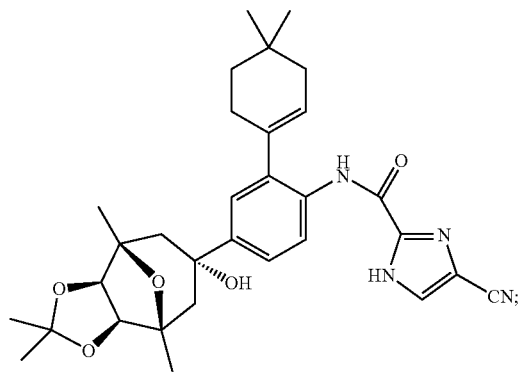
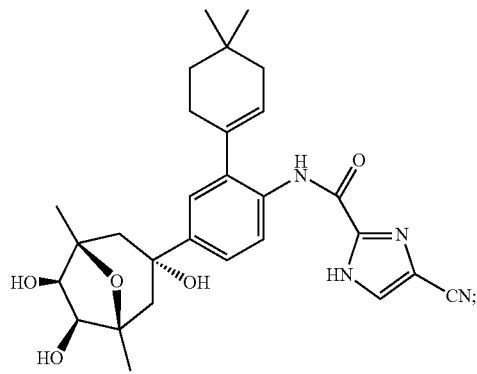
-continued
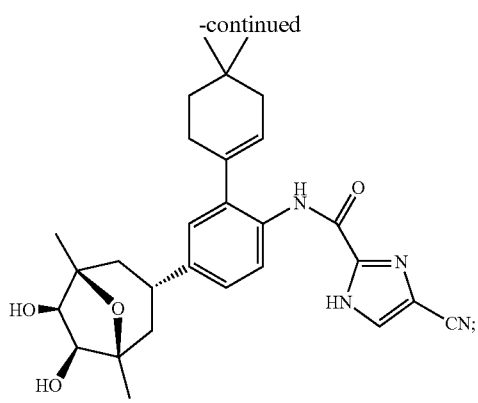
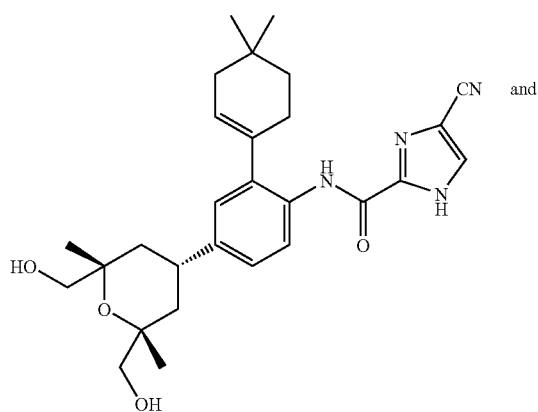
and
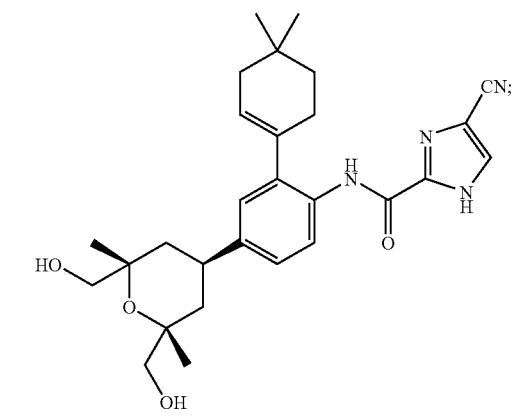
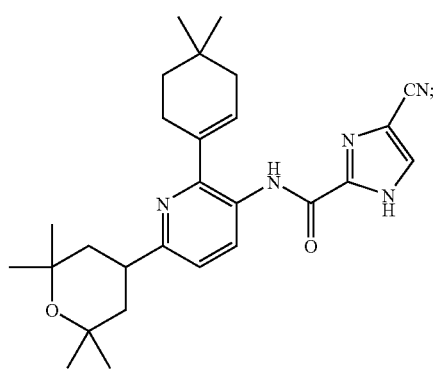 [SMILES: CC1(C)CC=C(c2nc(C3CC(C)(C)OC(C)(C)C3)ccc2NC(=O)c2nc(C#N)c[nH]2)CC1]

27
-continued
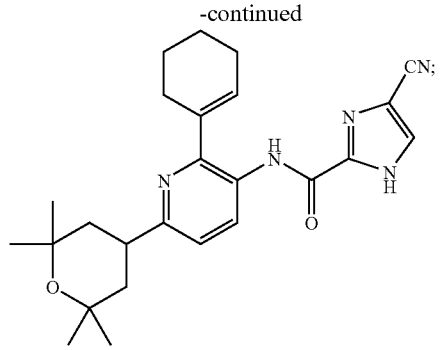
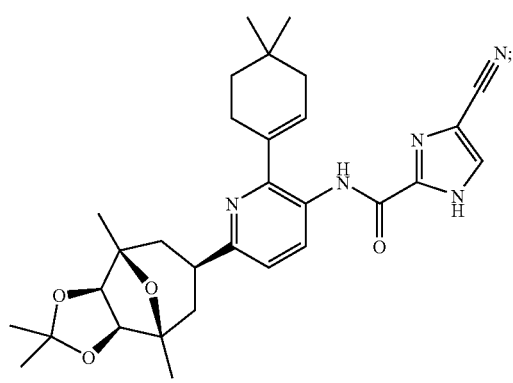
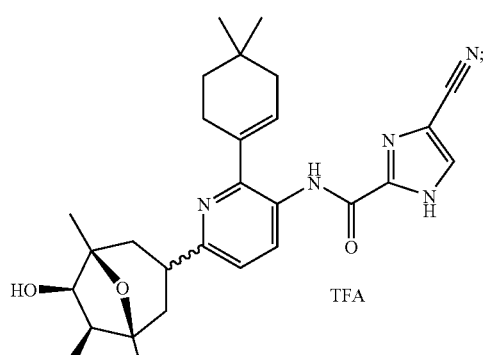
TFA
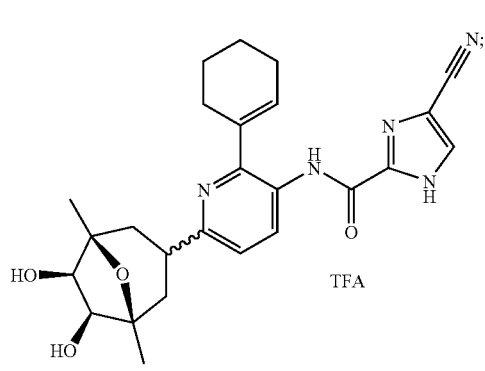
TFA
28
-continued
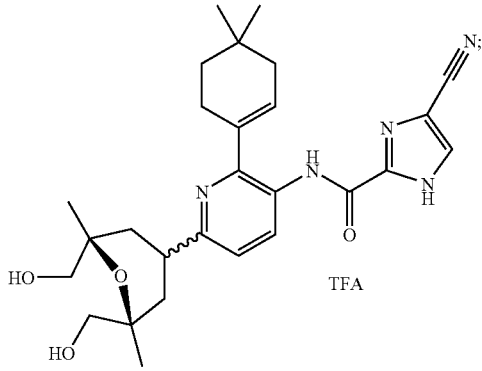
TFA
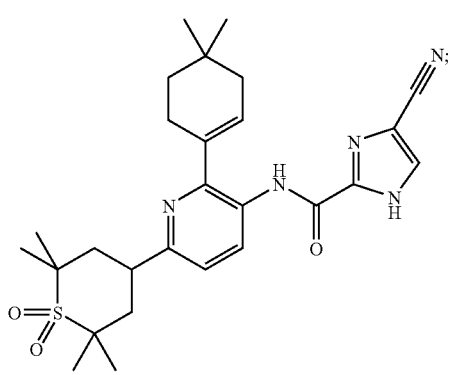
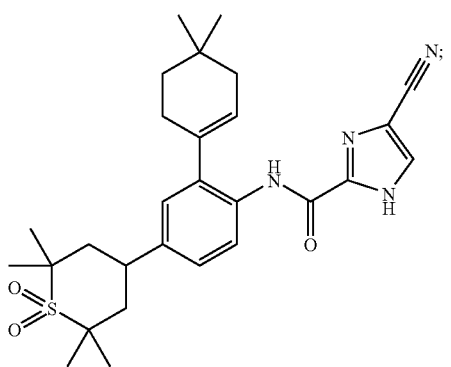
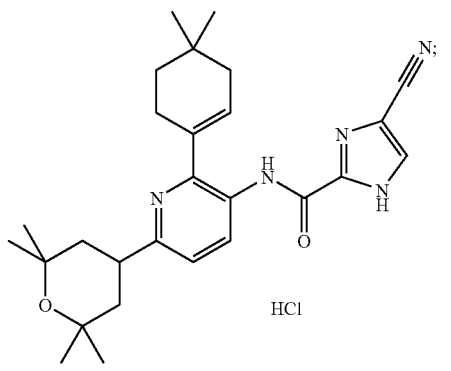
HCl

29
-continued
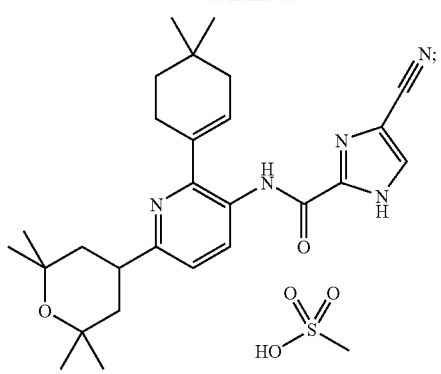
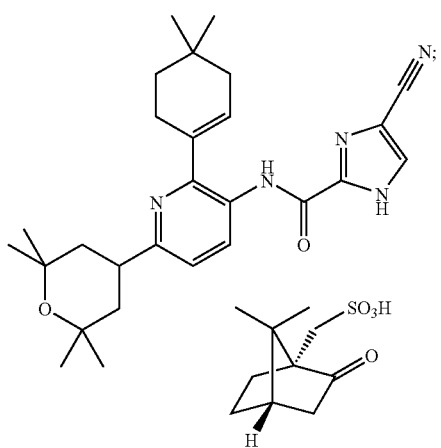
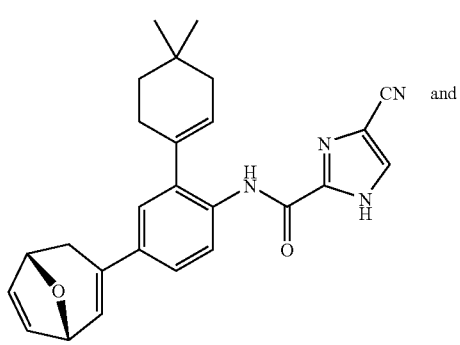
and
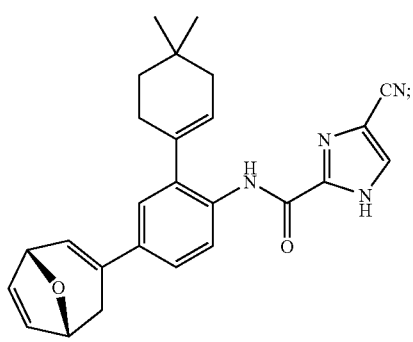
30
-continued
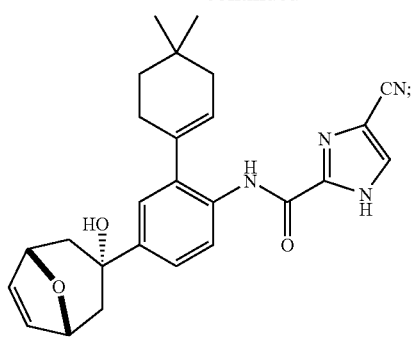
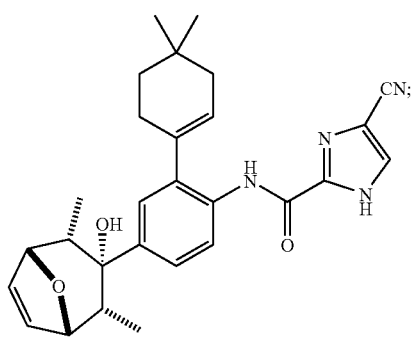
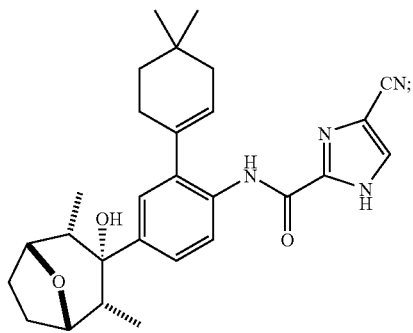
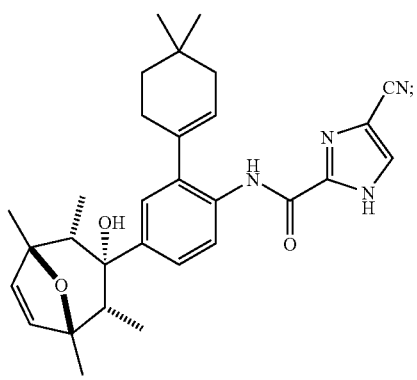
and solvates hydrates, tautomers, and pharmaceutically acceptable salts thereof.
Further embodying the invention is a compound of the formula

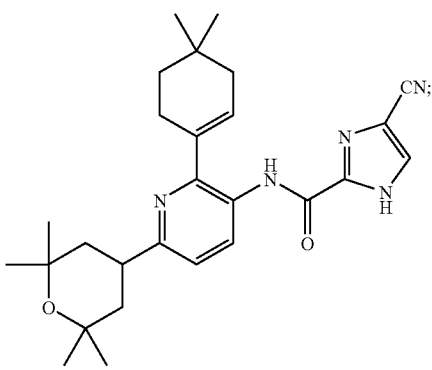

and solvates hydrates, tautomers, and pharmaceutically acceptable salts thereof.

Preferably, the compound is selected from the group consisting of:

4-Cyano-1H-imidazole-2-carboxylic acid[2-cyclohex-1-enyl-6-(2,2,6,6-tetramethyl-tetrahydro-pyran-4-yl)-pyridin-3-yl]-amide;

4-Cyano-1H-imidazole-2-carboxylic acid[2-(4,4-dimethyl-cyclohex-1-enyl)-6-(2,2,6,6-tetramethyl-tetrahydro-pyran-4-yl)-pyridin-3-yl]-amide hydrochloride salt;4-Cyano-1H-imidazole-2-carboxylic acid[2-(4,4-dimethyl-cyclohex-1-enyl)-6-(2,2,6,6-tetramethyl-tetrahydro-pyran-4-yl)-pyridin-3-yl]-amide methanesulfonic acid salt; and 4-Cyano-1H-imidazole-2-carboxylic acid[2-(4,4-dimethyl-cyclohex-1-enyl)-6-(2,2,6,6-tetramethyl-tetrahydro-pyran-4-yl)-pyridin-3-yl]-amide(1S)-(+)-10-camphorsulfonic acid salt. Most preferably, the compound is 4-Cyano-1H-imidazole-2-carboxylic acid[2-(4,4-dimethyl-cyclohex-1-enyl)-6-(2,2,6,6-tetramethyl-tetrahydro-pyran-4-yl)-pyridin-3-yl]-amide hydrochloride salt.

In another embodiment of the invention is a product made by any of the processes of Examples 1-30.

Another embodiment of the invention is a pharmaceutical composition, comprising a compound of Formula I and a pharmaceutically acceptable carrier.

Another embodiment of the invention is a pharmaceutical composition, comprising a compound of Formula Ia and a pharmaceutically acceptable carrier.

Another embodiment of the invention is a pharmaceutical composition, comprising a compound listed in the Examples section of this specification and a pharmaceutically acceptable carrier.

Another embodiment of the invention is a method of treating a disease selected from the group consisting of osteoporosis, Paget's disease, rheumatoid arthritis and other forms of inflammatory arthritis, osteoarthritis, prosthesis failure, osteolytic sarcoma, myeloma, and tumor metastasis to bone comprising administering to a mammal in need of such treatment a therapeutically effective amount of at least one compound of Formula I.

Another embodiment of the invention is a method of treating a disease selected from the group consisting of glomerulonephritis, inflammatory bowel disease, prosthesis failure, sarcoidosis, congestive obstructive pulmonary disease, idiopathic pulmonary fibrosis, asthma, pancreatitis, HIV infection, psoriasis, diabetes, tumor related angiogenesis, age-related macular degeneration, diabetic retinopathy, restenosis, schizophrenia and Alzheimer's dementia comprising administering to a mammal in need of such treatment a therapeutically effective amount of at least one compound of Formula I.

Another embodiment of the invention is a method of treating pain, including skeletal pain caused by tumor metastasis or osteoarthritis, or visceral, inflammatory, or neurogenic pain in a mammal comprising administering to the mammal in need of such treatment a therapeutically effective amount of at least one compound of Formula I.

Another embodiment of the invention is a method of treating a disease selected from the group consisting of ovarian cancer, uterine cancer, breast cancer, prostate cancer, lung cancer, colon cancer, stomach cancer, or hairy cell leukemia comprising administering to the mammal in need of such treatment a therapeutically effective amount of at least one compound of Formula I.

Another embodiment of the invention is a method of treating or preventing metastasis from: ovarian cancer, uterine cancer, breast cancer, prostate cancer, lung cancer, colon cancer, stomach cancer, or hairy cell leukemia comprising administering to the mammal in need of such treatment a therapeutically effective amount of at least one compound of Formula I.

Another embodiment of the invention is a method of treating an autoimmune disease selected from the group consisting of systemic lupus erythematosus, rheumatoid arthritis and other forms of inflammatory arthritis, psoriasis, Sjogren's syndrome, multiple sclerosis, or uveitis comprising administering to the mammal in need of such treatment a therapeutically effective amount of at least one compound of Formula I.

Another embodiment of the invention is a method of treating a disease selected from the group consisting of osteoporosis, Paget's disease, rheumatoid arthritis and other forms of inflammatory arthritis, osteoarthritis, prosthesis failure, osteolytic sarcoma, myeloma, and tumor metastasis to bone comprising administering to a mammal in need of such treatment a therapeutically effective amount of at least one compound listed in the Examples section of this specification.

Another embodiment of the invention is a method of treating a disease selected from the group consisting of glomerulonephritis, inflammatory bowel disease, prosthesis failure, sarcoidosis, congestive obstructive pulmonary disease, idiopathic pulmonary fibrosis, asthma, pancreatitis, HIV infection, psoriasis, diabetes, tumor related angiogenesis, age-related macular degeneration, diabetic retinopathy, restenosis, schizophrenia and Alzheimer's dementia comprising administering to a mammal in need of such treatment a therapeutically effective amount of at least one compound listed in the Examples section of this specification.

Another embodiment of the invention is a method of treating pain, including skeletal pain caused by tumor metastasis or osteoarthritis, or visceral, inflammatory, or neurogenic pain in a mammal comprising administering to the mammal in need of such treatment a therapeutically effective amount of at least one compound listed in the Examples section of this specification.

Another embodiment of the invention is a method of treating a disease selected from the group consisting of ovarian cancer, uterine cancer, breast cancer, prostate cancer, lung cancer, colon cancer, stomach cancer, or hairy cell leukemia comprising administering to the mammal in need of such treatment a therapeutically effective amount of at least one compound listed in the Examples section of this specification.

Another embodiment of the invention is a method of treating or preventing metastasis from: ovarian cancer, uterine cancer, breast cancer, prostate cancer, lung cancer, colon cancer, stomach cancer, or hairy cell leukemia comprising administering to the mammal in need of such treatment a therapeutically effective amount of at least one compound listed in the Examples section of this specification.

Another embodiment of the invention is a method of treating an autoimmune disease selected from the group consisting of systemic lupus erythematosus, rheumatoid arthritis and other forms of inflammatory arthritis, psoriasis, Sjogren's syndrome, multiple sclerosis, or uveitis comprising administering to the mammal in need of such treatment a therapeutically effective amount of at least one compound listed in the Examples section of this specification.

Another embodiment of the invention is a method of treating a disease selected from the group consisting of osteoporosis, Paget's disease, rheumatoid arthritis and other forms of inflammatory arthritis, osteoarthritis, prosthesis failure, osteolytic sarcoma, myeloma, and tumor metastasis to bone comprising administering to the mammal in need of such treatment a therapeutically effective amount of at least one compound listed in the Examples section of this specification.

The invention also relates to methods of inhibiting protein tyrosine kinase activity in a mammal by administration of a therapeutically effective amount of at least one compound of Formula I. A preferred tyrosine kinase is c-fms.

The invention is considered to include the enantiomeric, diastereomeric and tautomeric forms of all compounds of Formula I as well as their racemic mixtures. In addition, some of the compounds represented by Formulae I and Ia may be prodrugs, i.e., derivatives of an acting drug that possess superior delivery capabilities and therapeutic value as compared to the acting drug. Prodrugs are transformed into active drugs by in vivo enzymatic or chemical processes.

I. Definitions

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "cycloalkyl" refers to a saturated or partially unsaturated ring composed of from 3 to 8 carbon atoms. Up to four alkyl substituents may optionally be present on the ring. Examples include cyclopropyl, 1,1-dimethyl cyclobutyl, 1,2,3-trimethylcyclopentyl, cyclohexyl, cyclopentenyl, cyclohexenyl, and 4,4-dimethyl cyclohexenyl.

The term "alkylamino" refers to an amino with one alkyl substituent, wherein the amino group is the point of attachment to the rest of the molecule.

The term "heteroaryl" refers to 5- to 7-membered mono- or 8- to 10-membered bicyclic aromatic ring systems, any ring of which may consist of from one to four heteroatoms selected from N, O or S where the nitrogen and sulfur atoms can exist in any allowed oxidation state. Examples include benzimidazolyl, benzothiazolyl, benzothienyl, benzoxazolyl, furyl, imidazolyl, isothiazolyl, isoxazolyl, oxazolyl, pyrazinyl, pyrazolyl, pyridyl, pyrimidinyl, pyrrolyl, quinolinyl, thiazolyl and thienyl.

The term "heteroatom" refers to a nitrogen atom, an oxygen atom or a sulfur atom wherein the nitrogen and sulfur atoms can exist in any allowed oxidation states.

The term "alkoxy" refers to straight or branched chain radicals of up to 12 carbon atoms, unless otherwise indicated, bonded to an oxygen atom. Examples include methoxy, ethoxy, propoxy, isopropoxy and butoxy.

The term "spiro-substituted cycloalkenyl" refers to a pair of cycloalkyl rings that share a single carbon atom and wherein at least one of the rings is partially unsaturated, for example:

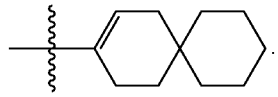 [SMILES: *C1=CCC2(CCCCC2)CC1]

II. Therapeutic Uses

The compounds of Formula I represent novel potent inhibitors of protein tyrosine kinases, such as c-fms, and may be useful in the prevention and treatment of disorders resulting from actions of these kinases.

The invention also provides methods of inhibiting a protein tyrosine kinase comprising contacting the protein tyrosine kinase with an effective inhibitory amount of at least one of the compounds of Formula I. A preferred tyrosine kinase is c-fms. The compounds of the present invention are also inhibitors of FLT3 tyrosine kinase activity. In one embodiment of inhibiting a protein tyrosine kinase, at least one of the compounds of Formula I is combined with a known tyrosine kinase inhibitor.

In various embodiments of the invention, the protein tyrosine kinases inhibited by the compounds of Formula I are located in cells, in a mammal or in vitro. In the case of mammals, which includes humans, a therapeutically effective amount of a pharmaceutically acceptable form of at least one of the compounds of Formula I is administered.

The invention further provides methods of treating cancer in mammals, including humans, by administration of a therapeutically effective amount of a pharmaceutically acceptable composition of least one compound of Formula I. Exemplary cancers include, but are not limited to, acute myeloid leukemia, acute lymphocytic leukemia, ovarian cancer, uterine cancer, prostate cancer, lung cancer, breast cancer, colon cancer, stomach cancer, and hairy cell leukemia. The invention also provides methods of treating certain precancerous lesions including myelofibrosis. In one embodiment of the invention, an effective amount of at least one compound of Formula I is administered in combination with an effective amount of a chemotherapeutic agent.

The invention further provides methods of treating and of preventing metastasis arising from cancers that include, but are not limited to, ovarian cancer, uterine cancer, prostate cancer, lung cancer, breast cancer, colon cancer, stomach cancer, and hairy cell leukemia.

The invention further provides methods for the treatment osteoporosis, Paget's disease, and other diseases in which bone resorption mediates morbidity including rheumatoid arthritis and other forms of inflammatory arthritis, osteoarthritis, prosthesis failure, osteolytic sarcoma, myeloma, and tumor metastasis to bone as occurs frequently in cancers including, but not limited to, breast cancer, prostate cancer, and colon cancer.

The invention also provides methods of treating pain, in particular skeletal pain caused by tumor metastasis or osteoarthritis, as well as visceral, inflammatory, and neurogenic pain.

The invention also provides methods of treating cardiovascular, inflammatory, and autoimmune diseases in mammals, including humans, by administration of a therapeutically effective amount of a pharmaceutically acceptable form of at least one of the compounds of Formula I. Examples of diseases with an inflammatory component include glomerulonephritis, inflammatory bowel disease, prosthesis failure, sarcoidosis, congestive obstructive pulmonary disease, idiopathic pulmonary fibrosis, asthma, pancreatitis, HIV infection, psoriasis, diabetes, tumor related angiogenesis, age-related macular degeneration, diabetic retinopathy, restenosis, schizophrenia or Alzheimer's dementia. These may be effectively treated with compounds of this invention. Other diseases that may be effectively treated include, but are not limited to atherosclerosis and cardiac hypertrophy.

Autoimmune diseases such as systemic lupus erythematosus, rheumatoid arthritis, and other forms of inflammatory arthritis, psoriasis, Sjogren's syndrome, multiple sclerosis, or uveitis, can also be treated with compounds of this invention.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation, prevention, treatment, or the delay of the onset or progression of the symptoms of the disease or disorder being treated.

When employed as protein tyrosine kinase inhibitors, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention. As used herein, the term "composition" is intended to encompass a product comprising the specified ingredients in the specified amounts, as well as any product which results, directly or indirectly, from combinations of the specified ingredients in the specified amounts.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope solvates of the compounds of the present invention. Thus, in the methods of treatment of the present invention, the term "administering" shall encompass the means for treating, ameliorating or preventing a syndrome, disorder or disease described herein with the compounds of the present invention or a solvate thereof, which would obviously be included within the scope of the invention albeit not specifically disclosed.

In another embodiment, the invention relates to a compound as described in the Examples, Formula I, or Formula Ia for use as a medicament.

In another embodiment, the invention relates to the use of a compound as described in the Examples, Formula I, or Formula Ia for the preparation of a medicament for the treatment of a disease associated with an elevated level of c-FMS production.

In another embodiment, the invention relates to the use of a compound according to the Examples, Formula I, or Formula Ia for the preparation of a medicament for the treatment of a disease selected from the group consisting of osteoporosis, Paget's disease, rheumatoid arthritis and other forms of inflammatory arthritis, osteoarthritis, prosthesis failure, osteolytic sarcoma, myeloma, and tumor metastasis to bone.

In another embodiment, the invention relates to the use of a compound according to the Examples, Formula I, or Formula Ia for the preparation of a medicament for the treatment of an autoimmune disease selected from the group consisting of systemic lupus erythematosus, rheumatoid arthritis and other forms of inflammatory arthritis, psoriasis, Sjogren's syndrome, multiple sclerosis, or uveitis.

In another embodiment, the invention relates to the use of a compound according to the Examples, Formula I, or Formula Ia for the preparation of a medicament for the treatment of a disease selected from the group consisting of glomerulonephritis, inflammatory bowel disease, prosthesis failure, sarcoidosis, congestive obstructive pulmonary disease, idiopathic pulmonary fibrosis, asthma, pancreatitis, HIV infection, psoriasis, diabetes, tumor related angiogenesis, age-related macular degeneration, diabetic retinopathy, restenosis, schizophrenia and Alzheimer's dementia.

In another embodiment, the invention relates to the use of a compound according to the Examples, Formula I, or Formula Ia for the preparation of a medicament for the treatment of pain, including skeletal pain caused by tumor metastasis or osteoarthritis, or visceral, inflammatory, or neurogenic pain in a mammal.

In another embodiment, the invention relates to the use of a compound according to the Examples, Formula I, or Formula Ia for the preparation of a medicament for the treatment of ovarian cancer, uterine cancer, breast cancer, prostate cancer, lung cancer, colon cancer, stomach cancer, or hairy cell leukemia.

Methods of Preparation

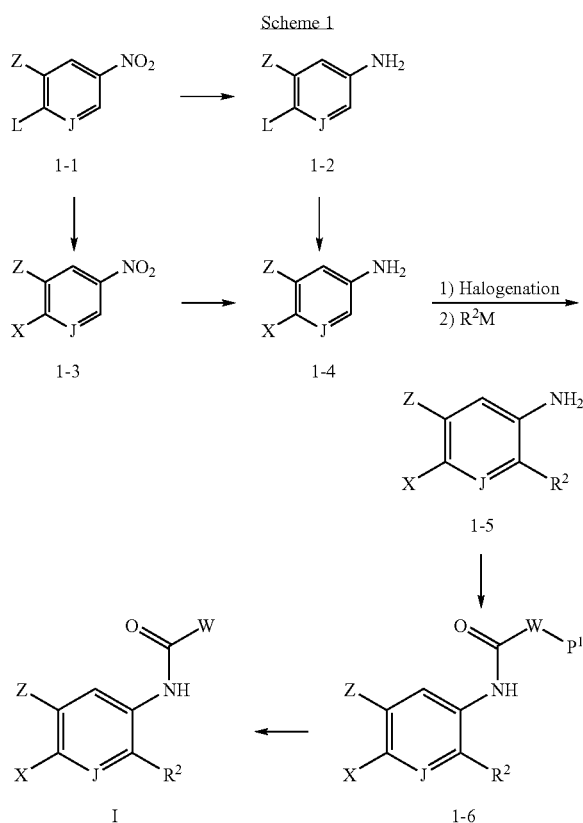

Scheme 1

Scheme 1 illustrates general methodology for the preparation of compounds of Formula I. To illustrate the methodology of this scheme, reagents and conditions for the compounds where J is CH are defined. Those skilled in the art will recognize that where J is N, minor modifications of the reaction conditions and preferred reagents may or may not be required.

Compounds of Formula 1-3 can be obtained from nitro compounds of Formula 1-1 where L is a leaving group or reactive group such as a halogen, trialkyl tin, dihydroxyboron, dialkoxyboron, or polyfluorinated alkylsulfonyloxy by means of metal-catalyzed coupling reactions with appropriate coupling partners to introduce X. Suitable coupling partners are: polyfluorinated alkylsulfonate esters of enols when L is trialkyl tin, dihydroxyboron, or dialkoxyboron; and cycloalkenyl boronate esters and boronic acids when L is bromo, iodo, or polyfluorinated alkylsulfonyloxy. The preferred coupling method is the Suzuki-Miyaura reaction (for references, see: N. Miyaura and A. Suzuki, *Chem. Rev.*, 95:2457 (1995); A. Suzuki in "Metal-Catalyzed Coupling Reactions," F. Deiderich, P. Stang, Eds., Wiley-VCH, Weinheim (1988)) of compounds of Formula 1-1 where L is bromo or iodo. The preferred conditions for the Suzuki-Miyaura reaction are a palladium catalyst such as tetrakis(triphenylphosphine)-palladium(0) ($Pd(PPh_3)_4$), an aqueous base such as aq. $Na_2CO_3$, and a suitable solvent such as toluene, ethanol, 1,4-dioxane, dimethoxyethane (DME), or DMF. The synthesis of the coupling partners is described in later schemes.

Amines of Formula 1-4 may be obtained from nitro compounds of Formula 1-3 by reduction using standard synthetic methodology (see Reductions in Organic Chemistry, M. Hudlicky, Wiley, New York, 1984). The preferred conditions are catalytic hydrogenation using a palladium catalyst in a suitable solvent such as methanol or ethanol. When X contains an alkene it will be reduced to an alkane. For compounds where X contains an alkene to be retained in the final compound, nitro reductions may be performed selectively using iron or zinc in a suitable solvent such as acetic acid, or by using iron and ammonium chloride in ethanol and water.

Alternately, the compounds of Formula 1-4 can be obtained from amines of Formula 1-2 by the methods to replace L with X described above. For compounds of Formula 1-4 where X contains an alkene, it can be reduced to an alkane by the methods described above if desired. Compounds of Formula 1-2 that are not commercially available may be obtained from compounds of Formula 1-1 by nitro reduction using iron or zinc in a suitable solvent such as acetic acid, or by using iron and ammonium chloride in ethanol and water.

Compounds of Formula 1-5 can be obtained by ortho-halogenation, preferably bromination, of amino compounds of Formula 1-4 followed by metal-catalyzed coupling reactions with boronic acids or boronate esters (Suzuki-Miyaura reactions, where $R^2M$ is $R^2B(OH)_2$ or a boronic ester, see references above) or tin reagents (Stille reactions, where $R^2M$ is $R^2Sn(alkyl)_3$, see J. K. Stille, *Angew. Chem, Int. Ed. Engl.*, 25: 508-524 (1986)) on the intermediate halo compound. Preferred conditions for the bromination of 1-4 are N-bromosuccinimide (NBS) in a suitable solvent such as N,N-dimethylformamide (DMF), tetrachloromethane or preferably dichloromethane (DCM) or acetonitrile. Metal-catalyzed couplings, preferably Suzuki-Miyaura reactions, can then be performed according to standard methodology as described and referenced above.

Compounds of Formula 1-6 can be obtained from compounds of Formula 1-5 by reaction of the amino group with a heterocyclic acid $P^1$—WCOOH (or a corresponding salt thereof $P^1$—WCOO$M^2$, where $M^2$ is Li, Na or K) where $P^1$ is an optional protecting group (for example 2-(trimethylsilyl)ethoxymethyl (SEM) such as when W is imidazole, triazole, pyrrole, or benzimidazole) or where $P^1$ is not present such as when W is furan. (For a list of suitable protecting groups for W, see Theodora W. Greene and Peter G. M. Wuts, Protective Groups in Organic Synthesis, John Wiley and Sons, Inc., NY (1991)). The coupling can be carried out according to standard procedures for amide bond formation (for a review, see: M. Bodansky and A. Bodansky, The Practice of Peptide Synthesis, Springer-Verlag, NY (1984)) or by reaction with acid chlorides P$^1$—WCOCl or activated esters P$^1$—WCO$_2$R$^q$ (where R$^q$ is a leaving group such as pentafluorophenyl or N-succinimide) to form compounds of Formula 1-6. The preferred reaction conditions for coupling with P$^1$—WCOOH or P$^1$—WCOOM$^2$ are: when W is a furan (optional protecting group p1 not present), oxalyl chloride in dichloromethane (DCM) with DMF as a catalyst to form the acid chloride WCOCl and then coupling in the presence of a trialkylamine such as N,N-diisopropylethylamine (DIEA); when W is a pyrrole (optional protecting group P$^1$ not present), 1-(3-dimethylaminopropyl)-3-ethylcarbodiimide hydrochloride (EDCI) and 1-hydroxybenzotriazole (HOBt); and when W is an imidazole, triazole, pyrrole or benzimidazole (optional P$^1$ present) the preferred conditions are bromotripyrrolidinophosphonium hexafluorophosphate (Py-BroP) and DIEA in a solvent such as DCM or DMF.

When W in compounds of Formula 1-6 contain an optional protecting group P$^1$ as mentioned previously, it can be removed at this point to give compounds of Formula I. For example, when W is imidazole protected on nitrogen with a SEM group, the SEM group can be removed with either acidic reagents such as trifluoroacetic acid (TFA) or fluoride sources such as tetrabutylammonium fluoride (TBAF) (see Greene and Wuts, above). When compounds of Formula 1-6 do not contain a protecting group then they are also compounds of Formula I Finally it is understood that compounds of Formula I may be further derivatized. Examples of further derivatization, include, but are not limited to: when compounds of Formula I contain a cyano group, this group may be hydrolyzed to amides or acids under acidic or basic conditions; when compounds of Formula I contain an ester, the ester may be hydrolysed to the acid, and the acid may be converted to amides by the methods described above for amide bond formation. Acids may be reduced to alcohols. The preferred conditions for the reduction of a carboxylic acid in the presence of a cyano group include sodium borohydride and ethyl chloroformate in THF. Olefins may be reduced by catalytic hydrogenation. Olefins can also be dihydroxylated to give diols using a number of methods including reaction with N-methylmorpholine N-oxide catalyzed by osmium tetroxide (for reviews, see: Sundermeier, U., Doebler, C. and Beller, M., Modern Oxidation Methods, Baeckvall, J. (Ed.)., 1-20, Wiley-Verlag (2004) Weinheim, Germany (2004), and, Beller, M. and Sharpless, K. B., Applied Homogeneous Catalysis with Organometallic Compounds, Cornils, B. and Herrmann, W. A. (Eds.), 2, 1009-1024, VCH, Weinheim, Germany (1996)). When compounds of Formula I contain a sulfide, either acyclic or cyclic, the sulfide can be further oxidized to the corresponding sulfoxides or sulfones. Sulfoxides can be obtained by oxidation using an appropriate oxidant such as one equivalent of meta-chloroperbenzoic acid (MCPBA) or by treatment with NaIO$_4$ (see, for example, *J. Med. Chem.*, 46: 4676-86 (2003)) and sulfones can be obtained using two equivalents of MCPBA or by treatment with 4-methylmorpholine N-oxide and catalytic osmium tetroxide (see, for example, PCT application WO 01/47919). Also, both sulfoxides and sulfones can be prepared by using one equivalent and two equivalents of H$_2$O$_2$ respectively, in the presence of titanium (IV) isopropoxide (see, for example, *J. Chem. Soc., Perkin Trans.* 2, 1039-1051 (2002)).

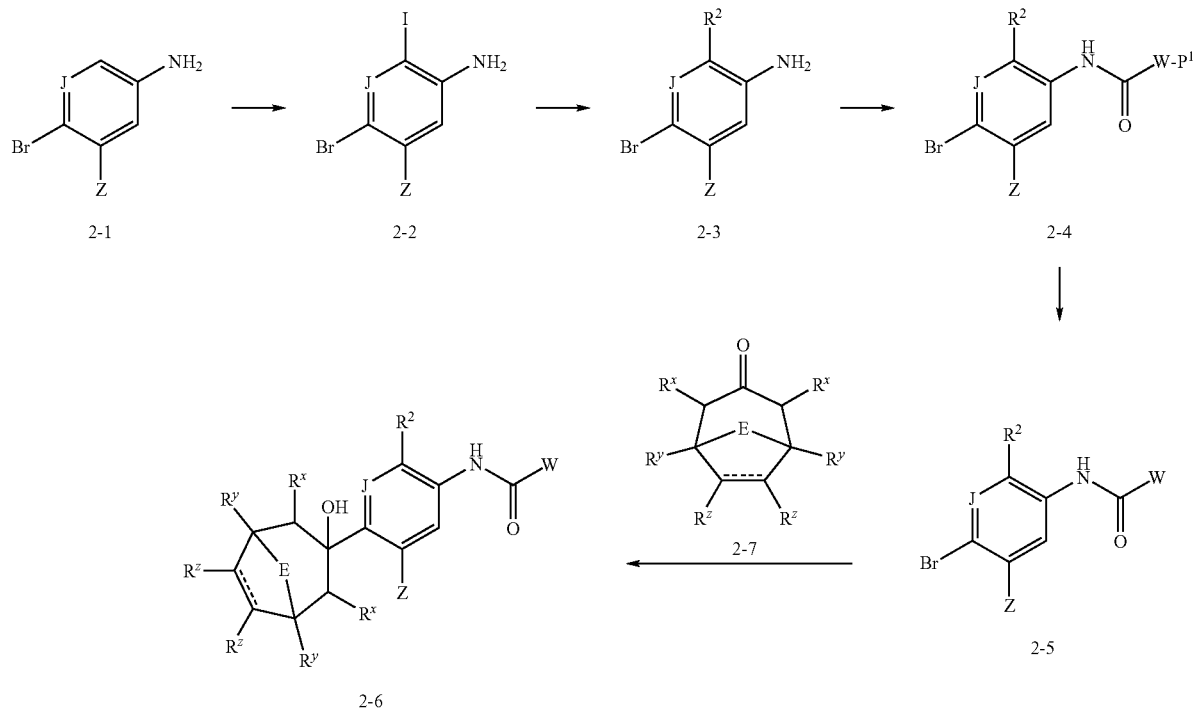

Scheme 2

Scheme 2 describes the synthesis of compounds of Formula I where X is

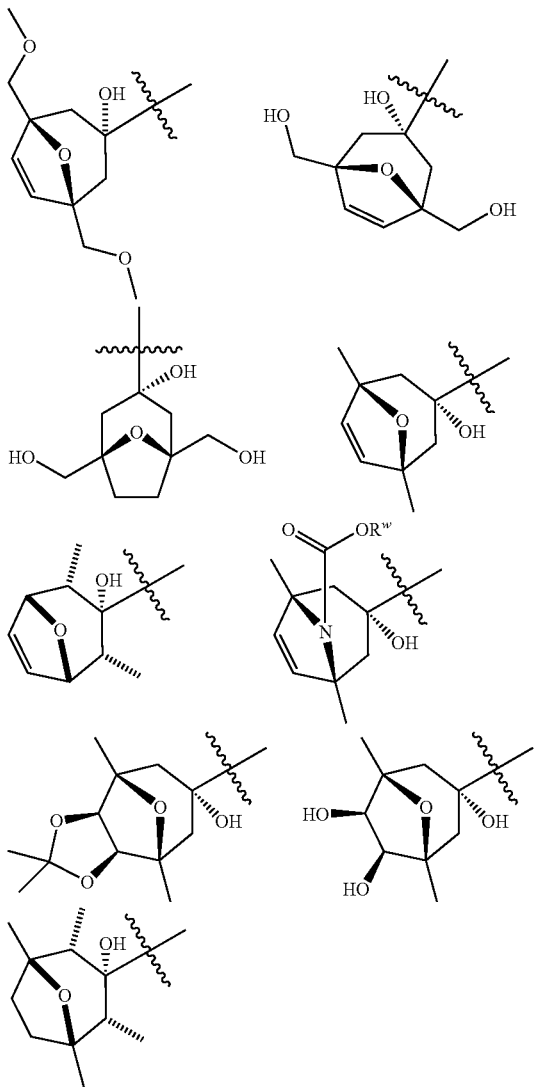

For the purpose of illustrating the methodology, reagents and conditions are defined in this scheme for the substrates where X is

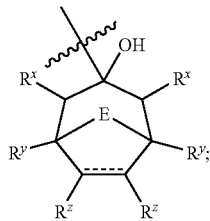

E is O, or $NCO_2R^w$; $R^x$ is H, or Me; $R^y$ is H, or $CH_2R^v$ where $R^v$ is H, OMe or OPG where PG is a suitable protecting group that is stable to the conditions of the transformation of this scheme and can be removed later to reveal $R^v$ is OH; and $R^z$ is H or OH where the two OH groups can be suitably protected by appropriate ketal or silyl protecting groups which can be either removed or retained in the final products. Those skilled in the art will recognize that the chemistry is applicable to all X, $R^x$, $R^y$, and $R^z$ referenced above and can be utilized with minor modifications to the reagents and conditions.

The starting material 2-1 is converted to iodinated compound 2-2 by reaction with $I_2$, or NIS or preferably by $I_2/Ag_2SO_4$ in a suitable solvent such as methyl alcohol, isopropyl alcohol or preferably ethyl alcohol. Compounds of Formula 2-3 where $R^2$ is cycloalkenyl and cycloalkyl can be obtained from 2-2 by selective metal-catalyzed coupling reactions with boronic acids or boronate esters as described in Scheme 1. The amino group in compounds of Formula 2-3 can then be coupled with a heterocyclic acid $P^1$—WCOOH to form compounds of Formula 2-4 as described in Scheme 1. When W in compounds of Formula 2-4 contains an optional protecting group $P^1$, it can be removed at this point as described in Scheme 1 to give compound 2-5. Finally the bromo compound 2-5 is converted to alcohol 2-6 by initial deprotonation of acidic protons with a suitable base, such as isopropylmagnesium chloride (i-PrMgCl) in a solvent such as ethyl ether, DME or preferably THF, followed by lithium-halogen exchange with an appropriate lithium reagent such as n-butyllithium, sec-butyllithium or preferably tert-butyllithium at a temperature of –100° C. to –40° C., preferably –78° C., and then trapping of the organolithium intermediate with an appropriate ketone 2-7. Synthesis of ketones of Formula 2-7 is described in schemes 6 and 7. Those skilled in the art will recognize that compounds of the present invention may be further modified at this point. For instance, if the compund 2-6 has an acid group on W, then that acid group may be esterified; likewise an amide on W may be dehydrated to form a nitrile.

Scheme 3

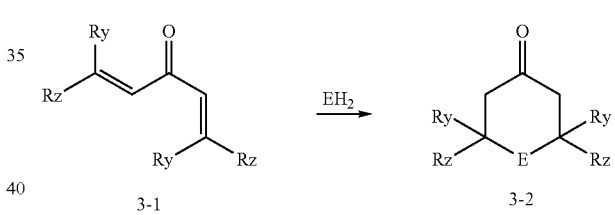

3-1    3-2

Scheme 3 illustrates general methodology for the preparation of heterocyclic ketones of Formula 3-2 where E is O, S, SO, or $SO_2$ and $R^y$ is $R^z$ is $CH_3$. These ketones are useful for preparation of compounds Formula I where X is

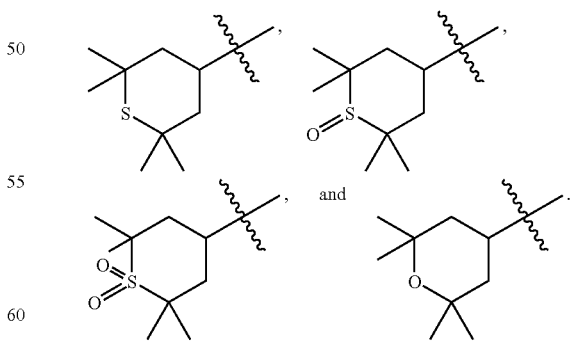

These heterocyclic ketones can be prepared by either acid- or base-catalyzed double Michael addition reactions of appropriate nucleophiles to dienones of Formula 3-1 at temperatures from 0-100° C. When water is employed as the nucleophile ($EH_2$ is $OH_2$), the preferred conditions for this transformation include the reaction of dienones of Formula 3-1 at, for example, 40-50° C. for 4 days with excess 1-4 N aqueous HCl to afford compounds of Formula 3-2 where E is O (WO 2005012220). Similarly, when $H_2S$ is employed as a nucleophile, compounds of Formula 3-2 where E is S can be obtained in the presence of inorganic bases such as KOH with or without a catalytic amount of an organic amine such as piperidine in protic solvents such as EtOH under reflux conditions with continuous slow bubbling of $H_2S$ (*Journal of Industrial and Engineering Chemistry* (Washington, D.C.) (1952), 44,1659-62). It should be clear to those skilled in the art, that sulfur-containing ketones of Formula 3-2 where E is S can be oxidized with one or two equivalents of an appropriate oxidant, such as m-chloroperbenzoic acid, to obtain the compounds of Formula 3-2 where E is SO or $SO_2$, respectively.

$CH_2Rv$ where $R^v$ is H, OMe or OPG where PG is a suitable protecting group that is stable to the conditions of the transformation of this scheme and can be removed later to reveal $R^v$ is OH, and $R^z$ is Me or both $R^z$ taken together are $CH_2$—$CH_2$ or CHisCH such that the resulting ketone 3-2 is bicyclic.

These can be made by intramolecular Dieckmann-type cyclization of appropriate precursors of Formula 5-1 ($R^t$ is Me or Et) under acidic or basic conditions followed by the removal of the α-alkoxycarbonyl substituent $CO_2R^t$ as shown in Scheme 5. The preferred methodology of this synthetic sequence involves the base-induced cyclization of diesters of Formula 5-1 at temperatures from −78° C. to RT to obtain the β-ketoesters of Formula 5-2 followed by the acid-catalyzed hydrolysis and decarboxylation at temperatures ranging from 20 to 200° C. It is understood that, following hydrolysis of the ester, the decarboxylation of intermediate 5-2 can be carried Scheme 4

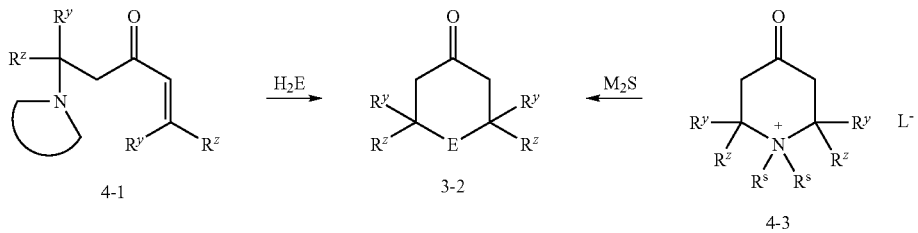

Two other synthetic routes for the preparation of the compounds of Formula 3-2 are shown in Scheme 4 where E is S and Ry is H, Me, and $CH_2R^v$ where $R^v$ is H, OMe or OPG where PG is a suitable protecting group that is stable to the conditions of the transformation of this scheme and can be removed later to reveal $R^v$ is OH. The unsaturated aminoketones of Formula 4-1 and quaternary ammonium salts of piperidones of Formula 4-3 (preferably substituted N,N-dimethylpiperidonium halides ($R^s$ is Me) formed by treatment of the appropriately substituted piperidone with a halomethane such as iodomethane (L is I)), can be converted to the compounds of Formula 3-2 where E is S by the actions of $H_2S$ or by metal sulfides ($M_2S$), preferably alkali metal sulfides such as $Na_2S$, respectively (*Khimiya Geterotsiklicheskikh Soedinenii, Sbornik* (1970) (2), 174-80 and *Izvestiya Akademii Nauk Kazakhskoi SSR, Seriya Khimicheskaya* (1986) (3), 92-3, respectively).

Scheme 5

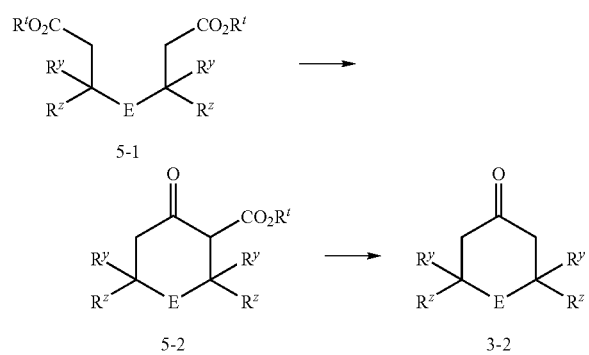

Scheme 5 shows another approach to synthesis of heterocyclic ketones of Formula 3-2 where E is O, S, $R^y$ is Me and out with or without the isolation of the corresponding carboxylic acid to obtain the compounds of Formula 3-2. The preferred bases for the first step include, but are not limited to, strong bases such as alkali metal alkoxides and hydroxides such as sodium methoxide, sodium ethoxide, potassium tert-butoxide and lithium hydroxide, and, alkali metal salts of secondary organic amines such as lithium diisopropylamide and lithium hexamethyldisilazide. The preferred conditions for hydrolysis and decarboxylation include, but are not limited to, heating the compounds of Formula 5-2 with dilute mineral acids such as 1 M aqueous HCl with or without a suitable solvent such as THF. Hydrolysis of the ester of Formula 5-2 may also be performed by treatment with aqueous base such as sodium hydroxide, potassium hydroxide or potassium carbonate in a suitable solvent mixture such as water and an organic solvent such as THF, methanol, ethanol or isopropanol. Using this base-catalyzed procedure for hydrolysis, the resulting carboxylic acid salt would then be treated with a mineral acid such as 0.01-12 M aqueous HCl or $H_2SO_4$ with or without a suitable organic solvent such as THF or dioxane to produce the corresponding carboxylic acid. It is clear to those skilled in the art that the corresponding carboxylic acids of compounds of Formula 5-2 thus produced either by acid-catalyzed hydrolysis, or by base-catalyzed hydrolysis followed by acidification, may spontaneously decarboxylate with or without the presence of any external acid or base reagent and with or without heating. In addition, it is understood that the compounds of Formula 5-1 can be prepared utilizing known methodologies or simple modification or extension of known methodologies. (For examples of diesters of Formula 5-1 and corresponding diacids see: *Journal of the American Chemical Society* (1996), 118, 10168-10174; U.S. Pat. No. 2,466,420; *Journal of the American Chemical Society* (1957), 79, 2323-5 and *Journal of Organic Chemistry* (1951), 16, 232-8.)

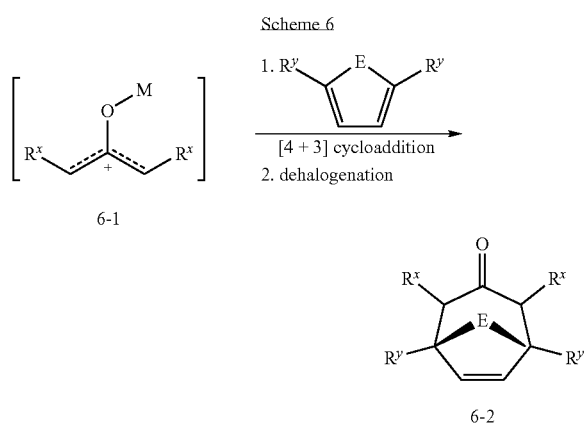

Scheme 6

Scheme 6 illustrates the synthesis of hetero-bicyclic ketones of Formula 6-2 which are used as intermediates for coupling reactions in Scheme 2. The general synthetic route is comprised of a [4+3] cycloaddition of an in-situ generated oxyallyl cation of Formula 6-1 with a suitable diene followed by subsequent dehalogenation, if necessary, of the resulting product. The preferable precursors for the generation of oxyallyl cations include poly α-halo ketones, 2-oxygen substituted allyl ethers and acroleins which can be converted to oxyallyl cation and trapped in-situ with an appropriate diene under reductive, basic or Lewis acidic conditions. The required oxyallyl cation can also be generated by disrotatory ring opening of cyclopropanones or conrotatory isomerization of allene oxides (J. Am. Chem. Soc. (1998), 120, 12310). The dehalogenation of poly α-haloketones can be achieved with reagents such as Cu/NaI (M is Na), Zn/Cu or Zn/Ag (M is Zn), Zn/Cu/TMSCl (M is TMS) or Zn/(EtO)$_3$B (M is B (OEt)$_2$), Et$_2$Zn (M is Zn) and Fe$_2$(CO)$_9$ (M is Fe)(for a review see Org. React., 1983, 29, 163, J. Org. Chem. (1999), 64, 3398)) to generate oxyallyl cations. The basic reagents for dehalogenation of α-halo ketones to generate oxyallyl cations of Formula 6-1 include reagents such as Et$_3$N/CF$_3$CH$_2$OH, sodium alkoxides of 2,2,3,3-tetrafluoropropanol and 2,2,2-trifluoroethanol (J. Chem. Res., Synop, (1986), 424. J. Chem. Res., Synop. (1981), 246., J. Chem. Res., Synop. (1983), 166.) and LiClO$_4$/Et$_3$N (J. Org. Chem. (1999), 64, 3398). Lewis acids such as AgO$_2$CCF$_3$ can be used for dehalogenation to obtain oxyallyl cations from 2-methoxyallyl halides (J. Am. Chem. Soc. (1973), 95, 1338) while AgBF$_4$ can be used for 2-amino substituted allyl halides (Helv. Chim. Acta. (1974), 57, 1883). Other Lewis acids such as SnCl$_4$, Sc(OTf)$_2$ and TiCl$_4$ can be used to generate oxyallyl cations from 2-O-silyloxy-acroleins (Tett. Lett. (1982), 23, 1693; Org. Lett. (2000), 2, 2703). One methodology for generation of oxyallyl cations is the treatment of α-haloketones, for example tetrabromoacetone, with Zn/Cu couple in a suitable organic solvent such as THF. A second methodology for generation of oxyallyl cations is the treatment of α-haloketones, for example trichloroacetone or pentachloroacetone, with sodium 2,2,2-trifluoroethoxide or triethylammonium 2,2,2-trifluoroethoxide in 2,2,2-trifluoroethanol as solvent (Lee, K. and Cha, J. K., J. Am. Chem. Soc. (2001), 123, 5590-91; and Sendelbach, et al, Journal of Organic Chemistry (1999), 64(10), 3398-3408). In addition, photochemical conditions can be used to generate oxyallyl cations from divinylketones (J. Org. Chem (1993), 58, 6795 and J. Am. Chem. Soc. (1968), 90, 6251).

The diene trapping agents are aromatic heterocycles such as suitably substituted pyrroles and furans which are either commercially available or can be prepared by established literature procedures. The initial [4+3] cycloaddition product thus obtained can be dehalogenated by known methods preferably by reductive dehalogenation using Zn or Zn/Cu couple.

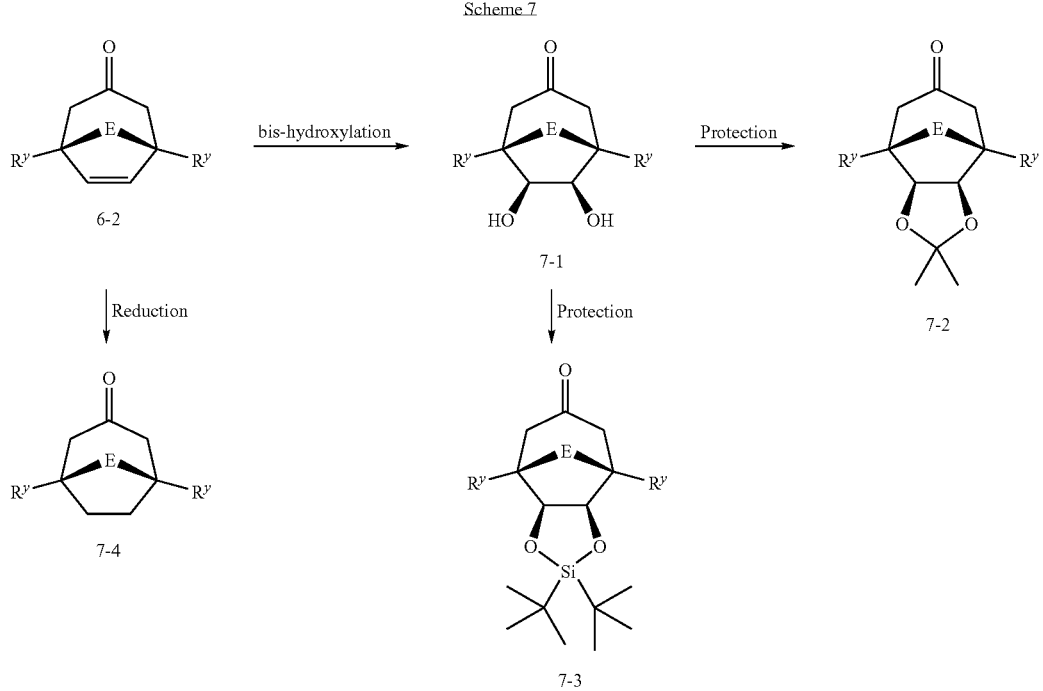

It is understood the double bond in the oxabicyclo adducts of Formula 6-2 can be further functionalized using appropriate reaction conditions. As shown in Scheme 7, for example, the compounds of Formula 6-2 can be bis-hydroxylated using known literature protocols (for a list of reagents and references see, Larock, R. C. *Comprehensive Organic Transformations*, 2nd Ed., Wiley-VCH, NY, (1999), pp 996-1003) to obtain cis-diols of Formula 7-1 which can then be protected to obtain compounds of Formulas 7-2 and 7-3. The preferred conditions for bis-hydroxylation include, but are not limited to, the treatment of the compounds of Formula 6-2 with a catalytic amount of $OsO_4$ and tert-BuOOH as the reoxidant in the presence of $Et_4NOH$ (*Bulletin of the Chemical Society of Japan* (1984), 57(9), 2515-25). The diols of Formula 7-1 can be protected to obtain compounds of Formula 7-2 and 7-3. The examples of suitable diol-protecting groups can be found in "Protective Groups in Organic Synthesis", by Theodora W. Greene and Peter G. M. Wuts, John Wiley & Sons. Inc, NY, (1999). The preferred protecting groups are isopropylidine ketal (*Bulletin of the Chemical Society of Japan* (1984), 57(9), 2515-25) and di-tert-butylsilylene using (tert-$Bu)_2SiCl_2$ as the silylating agent in chlorinated solvents such as DCM or DCE and imidazole at the temperatures from −78° C. to RT, preferably at 0° C. The olefinic functionalities of the compounds of Formula 6-2 can also be saturated to obtain the compounds of Formula 7-4. The preferred conditions for this transformation are catalytic hydrogenation (For example, see: *Journal of Organic Chemistry* (1999), 64(10), 3398-3408.)

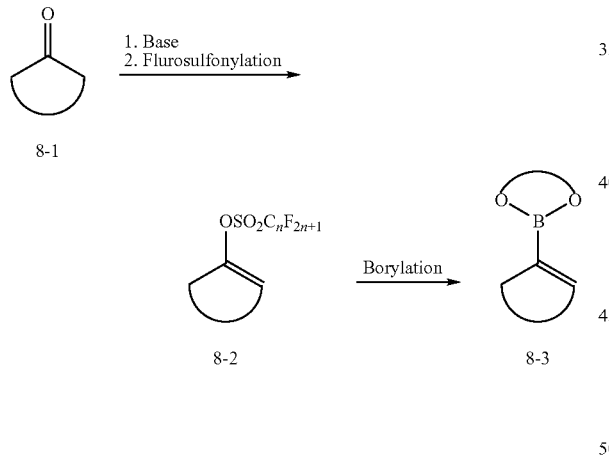

Scheme 8 illustrates the use of heterocyclic ketones of Formula 3-2, 6-2, 7-2, 7-3 and 7-4 which are all represented by Formula 8-1 for the purposes of Scheme 8. These ketones of Formula 8-1 can be converted to the corresponding enol polyfluorinated alkylsulfonate esters, preferably enol trifluoromethanesulfonates and enol nonafluorobutanesulfonates, by known literature methods. (For examples see: *Bioorganic & Medicinal Chemistry* (2002), 10(11) and 3583-3591, *Chem. Eur. J.*, 2007, 13, 2410, respectively). The preferred conditions for this transformation include, but are not limited to, the treatment of heterocyclic ketones of Formula 8-1 with strong bases such as lithium diisopropylamide or lithium hexamethyldisilazide at temperatures from −78° C. to RT, preferably −78° C., followed by the addition of fluorosulfonylating agents such as nonafluorobutanesulfonyl fluoride, 2-[N,N-bis(trifluoromethanesulfonyl)amino]pyridine or N-phenyl-bis(trifluoromethane-sulfonimide). The compounds of Formula 8-2 can be directly employed in metal-catalyzed couplings described previously in Scheme 1. In addition, the compounds of Formula 8-2 can be converted to the corresponding boronate esters of Formula 8-3 prior to use in Suzuki-Miyaura coupling procedures described in Scheme 1. (For representative procedures, see: Eastwood, P., *Tetrahedron Lett.* (2000), 41, 3705-8 and Takahashi, K., et al, *Chem. Lett.* (2000), 126-7.) Finally, when a compound of Formula 8-2 or 8-3 contains a protecting group, it can be removed in an intermediate or final step using the appropriate conditions. For example, when a cis-diol is present protected as the isopropylidine ketal, the protecting group can be removed with acidic aqueous conditions at elevated temperature, preferably at 100° C., and when it is protected as a di-tert-butylsilylene diether, the protecting group can be removed under acidic conditions or preferably with fluoride sources such as TBAF (see: "Protective Groups in Organic Synthesis" by Theodora W. Greene and Peter G. M. Wuts, John Wiley & Sons. Inc, NY, (1999).

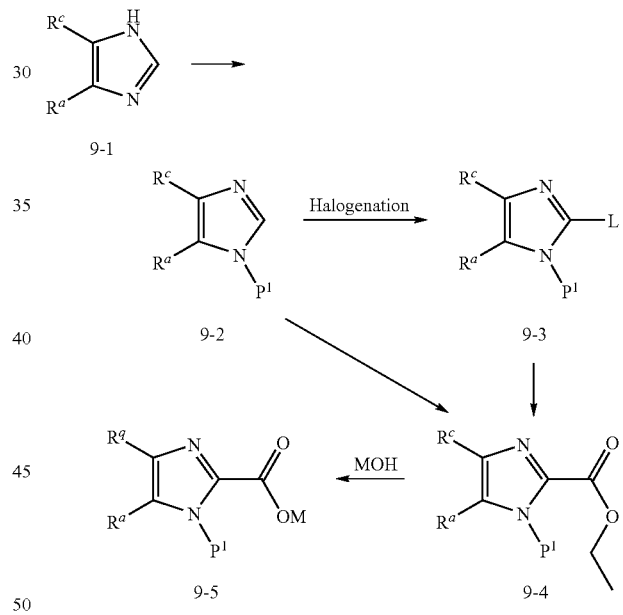

Scheme 9 illustrates a route to the preparation of 2-imidazolecarboxylates of Formula 9-5 where $R^a$ is H or $C_{(1-4)}$alkyl, and $R^q$ is H, alkyl, —CN, or —$CONH_2$ that are used as intermediates in the synthesis of compounds of Formula I where W is imidazole.

Imidazoles of Formula 9-1 where $R^a$ is H or $C_{(1-4)}$alkyl, and $R^c$ is H, $C_{(1-4)}$alkyl or —CN are either commercially available or, in the case where $R^c$ is —CN, are readily available from commercially available aldehydes (9-1 where $R^c$ is CHO) by reaction with hydroxylamines followed by dehydration with a suitable reagent such as phosphorus oxychloride or acetic anhydride (*Synthesis*, (2003), 677). Imidazoles of Formula 9-1 can be protected with a suitable group ($P^1$)

such as a methoxymethylamine (MOM), or preferably a SEM group to give compounds of Formula 9-2 (see Theodora W. Greene and Peter G. M. Wuts, Protective Groups in Organic Synthesis, John Wiley and Sons, Inc., NY (1991)).

Imidazoles of Formula 9-2, where $R^c$ is —CN, can be halogenated with a suitable reagent such as N-bromosuccinimide or N-iodosuccinimide under either electrophilic conditions in a solvent such as DCM or $CH_3CN$ or under radical conditions in the presence of an initiator such as azobis(isobutyronitrile) (AIBN) in a solvent such as $CCl_4$ to give compounds of Formula 9-3 where L is a leaving group (preferably bromo or iodo). Halogen-magnesium exchange on compounds of Formula 9-3 can provide the organomagnesium species, which can then reacted with a suitable electrophile to provide compounds of Formula 9-4. The preferred conditions for halogen-magnesium exchange are using an alkyl-magnesium reagent, preferably isopropylmagnesium chloride in a suitable solvent such as THF at temperatures between −78° C.-to 0° C. The preferred electrophiles are ethyl chloroformate or ethyl cyanoformate. (For examples of halogen-magnesium exchange on cyanoimidazoles, see: *J. Org. Chem.* (2000), 65, 4618).

For imidazoles of Formula 9-2, where $R^c$ is not —CN, these may be converted directly to imidazoles of Formula 9-4 by deprotonation with a suitable base such as an alkyllithium followed by reaction with an electrophile as described above for the organomagnesium species. The preferred conditions are treating the imidazole with n-butyllithium in THF at −78° C. and quenching the resulting organolithium species with ethyl chloroformate. (For examples, see: *Tetrahedron Lett.* (1988), 29, 3411-3414.)

The esters of Formula 9-4 may then be hydrolyzed to carboxylic acids (M is H) or carboxylate salts (M is Li, Na, or K,) of Formula 9-5 using one equivalent of an aqueous metal hydroxide (MOH) solution, preferably potassium hydroxide in a suitable solvent such as ethanol or methanol. Synthesis of compounds of Formula 9-5 where $R^q$ is —$CONH_2$ is accomplished by first treating compounds of Formula 9-4 where $R^c$ is —CN with an appropriate alkoxide such as potassium ethoxide to convert the cyano group to an imidate group (Pinner reaction) followed by hydrolysis of both the ester and imidate groups with two equivalents of an aqueous metal hydroxide solution.

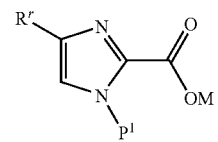

10-3

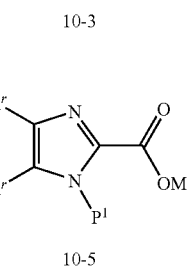

10-5

Scheme 10 illustrates a route to 2-imidazolecarboxylates of Formula 10-3 or 10-5 where $R^r$ is chloro or bromo, and M is H, Li, K, or Na that are used as intermediates in the synthesis of compounds of Formula I where W is imidazole.

Compounds of Formula 10-1 can be first prepared by protection of commercially available ethyl imidazolecarboxylate according to the methods outlined in Scheme 9, preferably with a SEM group.

Compounds of Formula 10-2 can be prepared by reaction of compounds of Formula 10-1 with one equivalent of an appropriate halogenating reagent, such as NBS or NCS in a suitable solvent such as $CH_3CN$, DCM or DMF at 25° C. Compounds of Formula 10-4 can be prepared by reaction of compounds of Formula 10-1 with two equivalents of an appropriate halogenating reagent, such as NBS or NCS in a suitable solvent such as $CH_3CN$ or DMF at temperatures between 30° C. and 80° C. Imidazoles of Formula 10-3 and 10-5 can then be obtained from the respective esters by hydrolysis as described in Scheme 9.

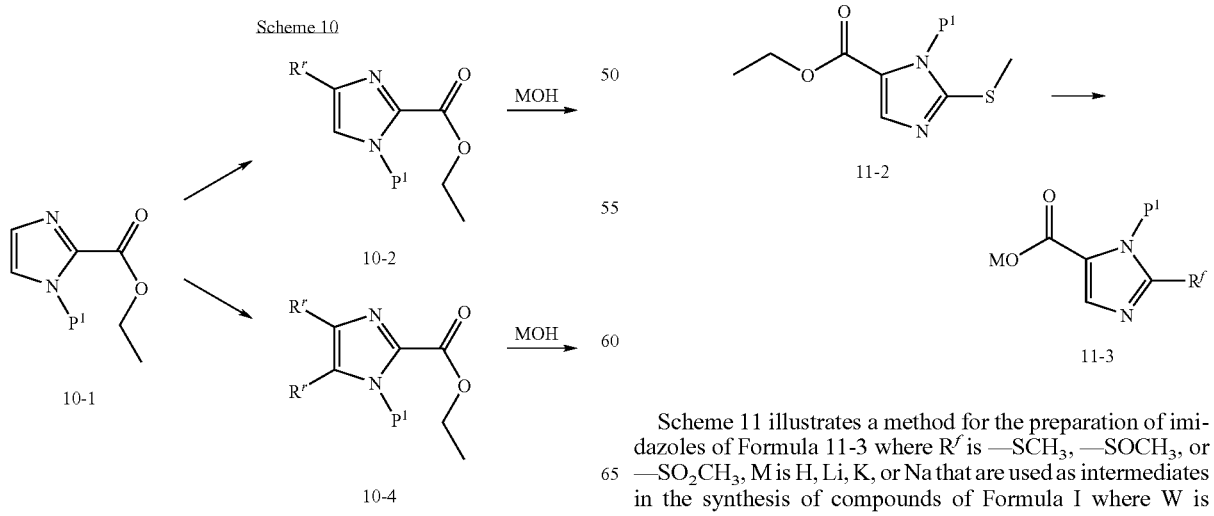

Scheme 11 illustrates a method for the preparation of imidazoles of Formula 11-3 where $R^f$ is —$SCH_3$, —$SOCH_3$, or —$SO_2CH_3$, M is H, Li, K, or Na that are used as intermediates in the synthesis of compounds of Formula I where W is imidazole.

Imidazole 11-1 (WO 1996011932) is protected according to the methods described in Scheme 9, preferably with a SEM protecting group to give compounds of Formula 11-2. Ester hydrolysis according to the procedure in Scheme 9 gives compounds of Formula 11-3 where $R^f$ is —$SCH_3$. Oxidation of 2-methylthioimidazoles of Formula 11-2 with one equivalent of an appropriate oxidant, followed by ester hydrolysis according to the procedure in Scheme 9 gives compounds of Formula 11-3 where $R^f$ is —$SOCH_3$. Oxidation with two equivalents of an appropriate oxidant, followed by ester hydrolysis according to the procedure in Scheme 9 gives compounds of Formula 11-3 where $R^f$ is —$SO_2CH_3$. The preferred reagent for oxidation is MCPBA in DCM. References for the conversion of sulfides to sulfoxides and sulfones are given in Scheme 1.

EXAMPLES

Example 1

4-Cyano-1H-imidazole-2-carboxylic acid[2-(4,4-dimethyl-cyclohex-1-enyl)-4-[(3-exo)-3-hydroxy-1,5-bis-methoxymethyl-8-oxa-bicyclo[3.2.1]oct-6-en-3-yl]-phenyl]-amide

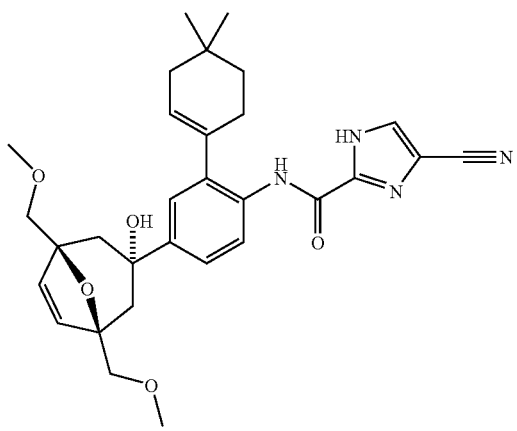 [SMILES: COC[C@@]12C=C[C@@](COC)(C[C@](O)(c3ccc(NC(=O)c4nc(C#N)c[nH]4)c(C4=CCC(C)(C)CC4)c3)C1)O2]

a) 4-Bromo-2-(4,4-dimethyl-cyclohex-1-enyl)-phenylamine

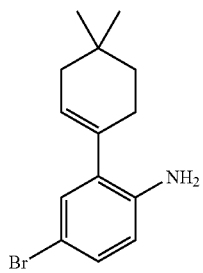 [SMILES: CC1(C)CC=C(c2cc(Br)ccc2N)CC1]

A mixture of 4-bromo-2-iodo-phenylamine (873 mg, 2.93 mmol), 4,4-dimethylcyclohexen-1-ylboronic acid (496 mg, 3.22 mmol), $Pd(PPh_3)_4$ (169 mg, 0.147 mmol) and 2.0 M aq $Na_2CO_3$ (11.7 mL, 23.4 mmol) in 20 mL of 1,4-dioxane was stirred at 80° C. for 12 h under Ar. After cooling to RT, the reaction was treated with EtOAc (50 mL) and washed with $H_2O$ (25 mL) and brine (20 mL). The organic layer was dried ($Na_2SO_4$) and concentrated in vacuo. The residue was purified by flash chromatography on silica gel (5% EtOAc/hexane) to afford 770 mg (91%) of the title compound as a colorless oil. Mass spectrum (ESI, m/z): Calcd. for $C_{14}H_{18}BrN$, 280.1 (M+H), found 280.1.

b) 4-Cyano-1-(2-trimethylsilanyl-ethoxymethyl)-1H-imidazole-2-carboxylic acid[4-bromo-2-(4,4-dimethyl-cyclohex-1-enyl)-phenyl]-amide

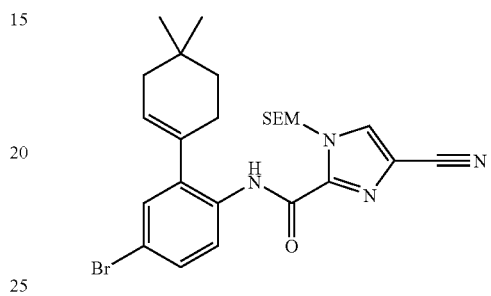

To a mixture of 4-bromo-2-(4,4-dimethyl-cyclohex-1-enyl)-phenylamine (as prepared in the previous step, 770 mg, 2.75 mmol), potassium 4-cyano-1-(2-trimethylsilanyl-ethoxymethyl)-1H-imidazole-2-carboxylate (US Pat Applic 2006189623 A1, 840 mg, 2.75 mmol) and PyBroP (1.28 g, 2.75 mmol) in 20 mL of DMF was added DIEA (1.44 mL, 8.25 mmol). The resulting mixture was stirred at RT for 16 h under Ar. Treated with 80 mL of EtOAc, the mixture was washed with $H_2O$ (2×20 mL), brine (20 mL) and dried ($Na_2SO_4$). Removal of the solvent under reduced pressure followed by flash chromatography of the residue on silica gel (5-10% EtOAc/hexane) gave 1.28 g (88%) of the title compound as a white solid. Mass spectrum (ESI, m/z): Calcd. for $C_{25}H_{33}BrN_4O_2Si$, 529.2 (M+H), found 528.9.

c) 4-Cyano-1H-imidazole-2-carboxylic acid[4-bromo-2-(4,4-dimethyl-cyclohex-1-enyl)-phenyl]-amide

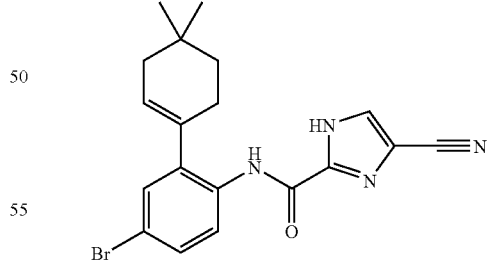

To a solution of 4-cyano-1-(2-trimethylsilanyl-ethoxymethyl)-1H-imidazole-2-carboxylic acid[4-bromo-2-(4,4-dimethyl-cyclohex-1-enyl)-phenyl]-amide (as prepared in the previous step, 350 mg, 0.661 mmol) in 5 mL of DCM ($CH_2Cl_2$) was added 0.15 mL of EtOH followed by 2.5 mL of TFA. After stirring at RT for 3 h, the mixture was treated with 10 mL of n-propanol and concentrated in vacuo. The residue was triturated with DCM to afford 253 mg (96%) of the title compound as a white solid. $^1$H-NMR (DMSO-$d_6$; 400 MHz):

δ 14.3 (s, 1H), 9.78 (s, 1H), 8.31 (s, 1H), 7.95 (d, 2H, J=8.6 Hz), 7.50 (dd, 2H, J=8.6, 2.3 Hz), 7.41 (d, 1H, J=2.3 Hz), 5.71 (m, 1H), 2.24 (m, 2H), 1.95 (m, 2H), 1.47 (m, 2H), 0.98 (s, 6H). Mass spectrum (ESI, m/z): Calcd. for $C_{19}H_{19}BrN_4O$, 399.1 (M+H), found 399.1.

d) 2,5-Bis-methoxymethyl-furan

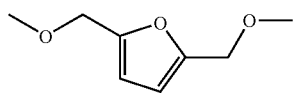

To a suspension of sodium hydride (dry, 314 mg, 13.1 mmol) in 2 mL of anh THF under Ar was carefully added a solution of 2,5-bis-hydroxymethylfuran (Pat Applic WO 2006122772 A1) in 10 mL of anh THF. After stirring at RT for 20 min, methyl iodide (672 µL, 10.8 mmol) was added and the mixture stirred for an additional 14 h. Water (15 mL) was added very carefully and the mixture concentrated in vacuo to remove the THF. The remaining aqueous mixture was saturated with solid NaCl and extracted with $Et_2O$ (5×15 mL). The combined organic layers were dried over $Na_2SO_4$ and concentrated in vacuo to a yellow oil which was purified by silica gel chromatography (5-30% EtOAc/hexane) to give the title compound (688 mg, 94%) as a colorless oil. $^1$H-NMR ($CDCl_3$; 400 MHz): δ 6.28 (s, 2 H) 4.39 (s, 4 H) 3.37 (s, 6 H).

e) 1,5-Bis-methoxymethyl-8-oxa-bicyclo[3.2.1]oct-6-en-3-one

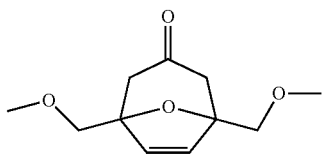

To a suspension of zinc (nanopowder, Aldrich Chemical Co., 602 mg, 9.20 mmol) in a solution of 2,5-bis-methoxymethylfuran (as prepared in the previous step, 958 mg, 6.13 mmol) in 1.0 mL anh THF under Ar was added a solution of 1,1,3,3-tetrabromoacetone (3.44 g, 9.20 mmol) and triethyl borate (2.20 mL, 12.9 mmol) in 2.8 mL of THF dropwise over 15 min. The flask was covered in aluminum foil to exclude light and the mixture was stirred at RT for 18 h. Water (10 mL) was added and, after stirring for 15 min, the mixture was filtered (Celite) washing with EtOAc (2×10 mL). The layers were separated, the aqueous layer was extracted with EtOAc (3×25 mL) and the combined organic layers were washed with water (50 mL), dried ($Na_2SO_4$), and concentrated to a dark oil. This residue in 5 mL of MeOH was added dropwise to a suspension of zinc dust (<10 µm, 2.09 g, 31.9 mmol), copper (I) chloride (316 mg, 3.19 mmol) and ammonium chloride (2.29 g, 42.9 mmol) in 5 mL MeOH and stirred at RT for 16 h. The mixture was filtered (Celite) washing with MeOH (10 mL) and EtOAc (10 mL) and the filtrate concentrated to a dark oil. The residue was partitioned between $Et_2O$-hexane (3:1, 50 mL) and water (25 mL). Precipitated solids were dissolved by addition of 1M HCl (ca. 10 mL) and the aqueous layer was extracted with $Et_2O$-hexane (3:1, 3×50 mL). The combined organic layers were washed with satd aq $NaHCO_3$ (100 mL) and brine (100 mL), dried ($Na_2SO_4$), and concentrated to 1.21 g of a yellow oil. Chromatography on a 20-g silica gel SPE column (2% EtOAc-DCM) afforded 278 mg (29%) unreacted 2,5-bis-methoxymethylfuran. Subsequent elution with 2-15% EtOAc-DCM afforded the title compound (667 mg, 51%, 72% based on recovered starting material) as a colorless oil. $^1$H-NMR ($CDCl_3$; 400 MHz): δ 6.10 (s, 2H) 3.63 (d, 4H, J=1.77 Hz) 3.44 (s, 6H) 2.69 (d, 2H, J=16.9 Hz) 2.34 (d, 2H, J=16.9 Hz). Mass spectrum (ESI, m/z): Calcd. for $C_{11}H_{16}O_4$, 213.1 (M+H), found 212.8.

f) 4-Cyano-1H-imidazole-2-carboxylic acid[2-(4,4-dimethyl-cyclohex-1-enyl)-4-[(3-exo)-3-hydroxy-1,5-bis-methoxymethyl-8-oxa-bicyclo[3.2.1]oct-6-en-3-yl]-phenyl]-amide To a solution of 4-cyano-1H-imidazole-2-carboxylic acid [4-bromo-2-(4,4-dimethyl-cyclohex-1-enyl)-phenyl]-amide (as prepared in this Example, step (c), 204 mg, 0.511 mmol) in 7 mL of anh THF at −78° C. under Ar was added a solution of isopropylmagnesium chloride (2.0 M in THF, 321 µL, 0.641 mmol). The reaction was warmed to RT and stirred for 75 min and then cooled again to −78° C. A solution of tert-butyllithium (1.7 M in pentane, 900 µL, 1.53 mmol) was added and, after stirring for 20 min, a solution of 1,5-bis-methoxymethyl-8-oxa-bicyclo[3.2.1]oct-6-en-3-one (as prepared in the previous step, 141 mg, 0.664 mmol) in 3.5 mL of THF was added over 1.5 min. The mixture was stirred at −78° C. for 30 min and then at RT for 16 h. The reaction was quenched with 4 mL of satd aq. $NH_4Cl$, poured into EtOAc (50 mL), washed with water (10 mL) and brine (10 mL), dried ($Na_2SO_4$), and concentrated to give 292 mg of a solid. This residue was suspended in 4 mL of MeCN and filtered, washing with MeCN (2×1 mL), and the filtrate concentrated to afford 230 mg of a solid. Chromatography on a 20-g silica gel SPE column (10-60% EtOAc-DCM) gave a glass which, after concentration from EtOAc-hexane (1:1), afforded the title compound (32.4 mg, 12%) as a white solid. $^1$H-NMR ($CDCl_3$; 400 MHz): δ 9.62 (s, 1H), 8.37 (d, 1H, J=8.6 Hz), 7.69 (s, 1H), 7.53 (dd, 1H, J=8.6, 2.3 Hz), 7.35 (d, 1H, J=2.3 Hz), 6.43 (s, 2H), 5.74-5.78 (m, 1H), 2.59 (s, 4H), 3.40 (s, 6H), 2.40 (d, 2H, J=14.7 Hz), 2.25-2.33 (m, 2H), 2.08-2.11 (m, 2H), 1.96 (d, 2H, J=14.7 Hz), 1.58 (t, 2H, J=6.2 Hz), 1.10 (s, 6H). Mass spectrum (ESI, m/z): Calcd. for $C_{30}H_{36}N_4O_5$, 515.3 (M−$H_2O$+H), found 515.0.

Assignment of relative stereochemistry was made using 1D $^1$H-NMR and 2D $^1$H-NMR (NOESY).

Example 2

4-Cyano-1H-imidazole-2-carboxylic acid[2-(4,4-dimethyl-cyclohex-1-enyl)-4-((3-exo)-3-hydroxy-1,5-bis-hydroxymethyl-8-oxa-bicyclo[3.2.1]oct-6-en-3-yl)-phenyl]-amide

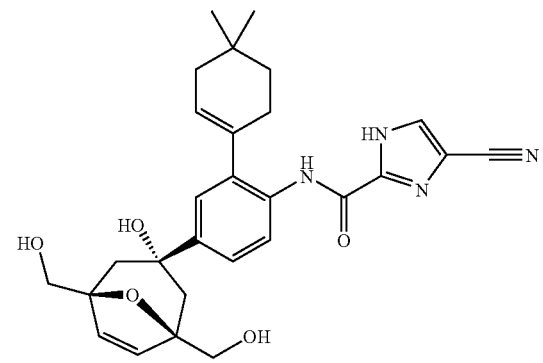 [SMILES: CC1(C)CC=C(c2cc([C@]3(O)C[C@@]4(CO)C=C[C@@](CO)(C3)O4)ccc2NC(=O)c2nc(C#N)c[nH]2)CC1]

a) 4-Cyano-1H-imidazole-2-carboxylic acid[4-[(3-exo)-3-hydroxy-1,5-bis-(tert-butyl-dimethyl-silanyloxymethyl)-8-oxa-bicyclo[3.2.1]oct-6-en-3-yl]-2-(4,4-dimethyl-cyclohex-1-enyl)-phenyl]-amide

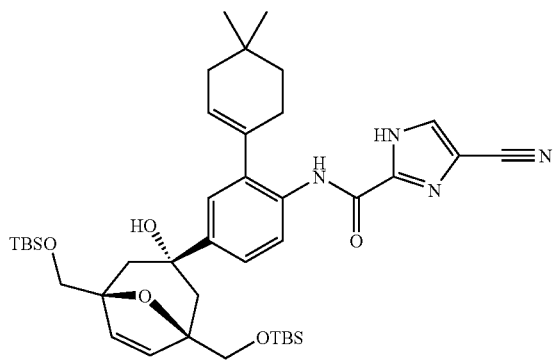 [SMILES: CC1(C)CC=C(c2cc([C@]3(O)C[C@@]4(CO[Si](C)(C)C(C)(C)C)C=C[C@@](CO[Si](C)(C)C(C)(C)C)(C3)O4)ccc2NC(=O)c2nc(C#N)c[nH]2)CC1]

The title compound was prepared by the procedure of Example 1, step (f) using 4-cyano-1H-imidazole-2-carboxylic acid[4-bromo-2-(4,4-dimethyl-cyclohex-1-enyl)-phenyl]-amide (as prepared in the example 1, step (c), 299 mg, 0.749 mmol) and 1,5-bis-(tert-butyl-dimethyl-silanyloxymethyl)-8-oxa-bicyclo[3.2.1]oct-6-en-3-one (Lee, K. and Cha, J. K., *J. Amer. Chem. Soc.*, 123: 5590-5591 (2001), 309 mg, 0.749 mmol). Silica gel chromatography (1-3% EtOAc/DCM) afforded the title compound (154 mg, 28%) as a white solid. Mass spectrum (ESI, m/z). Calcd. for $C_{40}H_{60}N_4O_5Si_2$, 715.4 (M–$H_2O$+H), found 715.0.

b) 4-Cyano-1H-imidazole-2-carboxylic acid[2-(4,4-dimethyl-cyclohex-1-enyl)-4-((3-exo)-3-hydroxy-1,5-bis-hydroxymethyl-8-oxa-bicyclo[3.2.1]oct-6-en-3-yl)-phenyl]-amide A mixture of 4-cyano-1H-imidazole-2-carboxylic acid[4-[(3-endo)-3-hydroxy-1,5-bis-(tert-butyl-dimethyl-silanyloxymethyl)-8-oxa-bicyclo[3.2.1]oct-6-en-3-yl]-2-(4,4-dimethyl-cyclohex-1-enyl)-phenyl]-amide (as prepared in the previous step, 125 mg, 0.171 mmol) and tetrabutylammonium fluoride monohydrate (TBAF.$H_2O$) (357 mg, 1.36 mmol) in 3 mL of THF was stirred at 60° C. for 1 h. After cooling to RT, the mixture was treated with EtOAc (50 mL) and washed with $H_2O$ (10 mL), aqueous saturated $NH_4Cl$ (2×10 mL) and brine (10 mL). The organic layer was dried over $Na_2SO_4$ and concentrated in vacuo. The residue was triturated with DCM to give the title compound (72 mg, 84%) as a white solid. $^1$H-NMR (CD$_3$OD; 400 MHz): δ 8.15 (d, 1H, J=8.6 Hz), 7.99 (s, 1H), 7.38 (dd, 1H, J=8.6, 2.3 Hz), 7.31 (d, 1H, J=2.3 Hz), 6.18 (s, 2H), 5.73 (m, 1H), 3.68 (s, 4H), 2.31 (m, 2H), 2.12 (d, 2H, J=14.7 Hz), 2.07 (m, 2H), 1.79 (d, 2H, J=14.7 Hz), 1.59 (t, 2H, J=6.3 Hz), 1.09 (s, 6H).

Assignment of relative stereochemistry was made based on analogy to 4-cyano-1H-imidazole-2-carboxylic acid[2-(4,4-dimethyl-cyclohex-1-enyl)-4-[(3-exo)-3-hydroxy-1,5-bis-methoxymethyl-8-oxa-bicyclo[3.2.1]oct-6-en-3-yl]-phenyl]-amide (as prepared in Example 1, step (f)).

Example 3

4-Cyano-1H-imidazole-2-carboxylic acid[4-(1,5-bis-hydroxymethyl-8-oxa-bicyclo[3.2.1]octa-2, 6-dien-3-yl)-2-(4,4-dimethyl-cyclohex-1-enyl)-phenyl]-amide

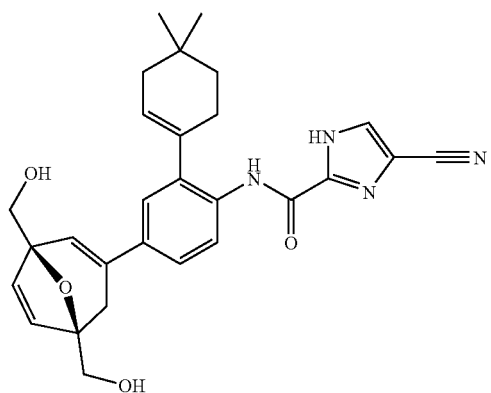 [SMILES: CC1(C)CC=C(c2cc(C3=C[C@@]4(CO)C=C[C@@](CO)(C3)O4)ccc2NC(=O)c2nc(C#N)c[nH]2)CC1]

To a mixture of 4-cyano-1H-imidazole-2-carboxylic acid [2-(4,4-dimethyl-cyclohex-1-enyl)-4-[(3-endo)-3-hydroxy-1,5-bis-hydroxymethyl-8-oxa-bicyclo[3.2.1]oct-6-en-3-yl]-phenyl]-amide (as prepared in example 2, step (b), 40.0 mg, 0.0793 mmol) in 1 mL of DCM at 0° C. was added trifluoroacetic acid (50 µL) dropwise. The resulting mixture was stirred at RT for 2 h. The solvent was removed in vacuo and the residue was purified by silica gel chromatography (2-5% MeOH/DCM) to give the title compound (37 mg, 95%) as white solid. $^1$H-NMR (CD$_3$OD; 400 MHz): δ 8.18 (d, 1H, J=8.6 Hz), 7.98 (s, 1H), 7.32 (dd, 1H, J=8.6, 2.3 Hz), 7.21 (d, 1H, J=2.3 Hz), 6.51 (br s, 1H), 6.41 (d, 1H, J=5.8 Hz), 5.96 (d, 1H, J=5.8 Hz), 5.73 (m, 1H), 3.77-3.88 (m, 4H), 2.69 (dd, 1H, J=17.7, 2.0 Hz), 2.30 (m, 2H), 2.17 (dd, 2H, J=17.7, 1.7 Hz), 2.07 (m, 2H), 1.59 (t, 2H), J=6.3 Hz), 1.09 (s, 6H). Mass spectrum (ESI, m/z): Calcd. for $C_{28}H_{30}N_4O_4$, 487.3 (M+H), found 487.1.

Example 4

4-Cyano-1H-imidazole-2-carboxylic acid[4-[(3-exo)-1,5-bis-hydroxymethyl-8-oxa-bicyclo[3.2.1]oct-3-yl]-2-(4,4-dimethyl-cyclohex-1-enyl)-phenyl]-amide

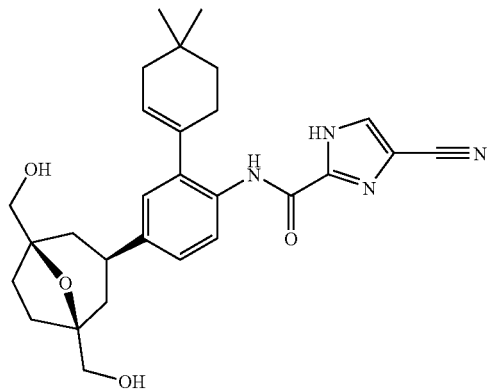 [SMILES: CC1(C)CC=C(c2cc([C@H]3C[C@]4(CO)CC[C@](CO)(C3)O4)ccc2NC(=O)c2nc(C#N)c[nH]2)CC1]

a) Trifluoro-methanesulfonic acid 1,5-bis-(tert-butyl-dimethyl-silanyloxymethyl)-8-oxa-bicyclo[3.2.1]octa-2,6-dien-3-yl ester

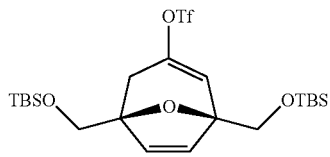 [SMILES: CC(C)(C)[Si](C)(C)OC[C@]12C=C[C@](CO[Si](C)(C)C(C)(C)C)(CC(OS(=O)(=O)C(F)(F)F)=C1)O2]

A solution of 1,5-bis-(tert-butyl-dimethyl-silanyloxymethyl)-8-oxa-bicyclo[3.2.1]oct-6-en-3-one (Lee, K. and Cha, J. K., *J. Amer. Chem. Soc.*, 123: 5590-5591 (2001), 929 mg, 2.25 mmol) in 10 ml of THF was added to a solution of LHMDS (1.0 M in THF, 2.48 mL, 2.48 mmol) in 20 ml of THF at −78° C. under Ar. The mixture was warmed to RT and stirred for 0.5 h, then cooled to −78° C. again. A solution of 2-[N,N-bis(trifluoromethanesulfonyl)amino]pyridine (888 mg, 2.48 mmol) in 10 ml of THF was added. The resulting mixture was warmed to RT and stirred for 2 h under Ar. Treated with 10 mL of saturated aqueous NH$_4$Cl followed by 100 ml of EtOAc, the mixture was washed with aqueous saturated citric acid (3×20 mL), H$_2$O (20 mL), brine (10 mL) and dried (Na$_2$SO$_4$). Removal of the solvent under reduced pressure gave 1.22 g of the title compound as light yellow oil. $^1$H-NMR (CDCl$_3$; 400 MHz): δ 6.42 (d, 1H, J=5.8 Hz), 6.29 (br s, 1H), 5.91 (d, 1H, J=5.8 Hz), 3.80 (s, 1H), 2.81 (dd, 2H, J=17.7, 1.9 Hz), 2.13 (dd, 1H, J=17.7, 1.3 Hz), 0.91 (s, 18H), 0.08 (s, 12H).

The product was used for the next step without further purification.

b. 4-[1,5-Bis-(tert-butyl-dimethyl-silanyloxymethyl)-8-oxa-bicyclo[3.2.1]octa-2,6-dien-3-yl]-phenylamine

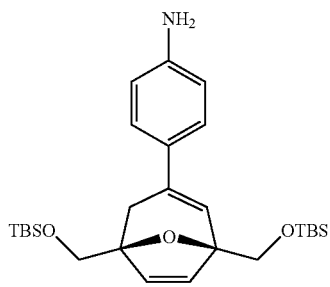 [SMILES: CC(C)(C)[Si](C)(C)OC[C@]12C=C[C@](CO[Si](C)(C)C(C)(C)C)(CC(c3ccc(N)cc3)=C1)O2]

To a mixture of trifluoromethanesulfonic acid 1,5-bis-(tert-butyl-dimethyl-silanyloxymethyl)-8-oxa-bicyclo[3.2.1]octa-2,6-dien-3-yl ester (as prepared in the previous step, 1.22 g, 2.24 mmol), Pd(PPh$_3$)$_4$ (259 mg, 0.224 mmol) and 4-(4,4,5,5-tetramethyl-[1,3,2]dioxaborolan-2-yl)-phenylamine (540 mg, 2.46 mmol) in 20 mL of 1,4-dioxane was added 2.0 M aqueous Na$_2$CO$_3$ solution (9.0 mL, 18 mmol). The resulting mixture was stirred at 80° C. for 2 h and then cooled to RT. Treated with 100 mL of EtOAc, the mixture was washed with H$_2$O (3×20 mL), brine (20 mL) and dried (Na$_2$SO$_4$). Removal of the solvent under reduced pressure followed by flash chromatography of the residue on silica gel (1:1 hexane/DCM-DCM) gave 802 mg (73% for two steps) of the title compound as a light brown oil. Mass spectrum (ESI, m/z): Calcd. for C$_{27}$H$_{45}$NO$_3$Si$_2$, 488.3 (M+H), found 488.4.

c) 4-[(3-Exo)-1,5-bis-(tert-butyl-dimethyl-silanyloxymethyl)-8-oxa-bicyclo[3.2.1]oct-3-yl]-phenylamine (A) and 4-[(3-Endo)-1,5-bis-(tert-butyl-dimethyl-silanyloxymethyl)-8-oxa-bicyclo[3.2.1]oct-3-yl]-phenylamine (B)

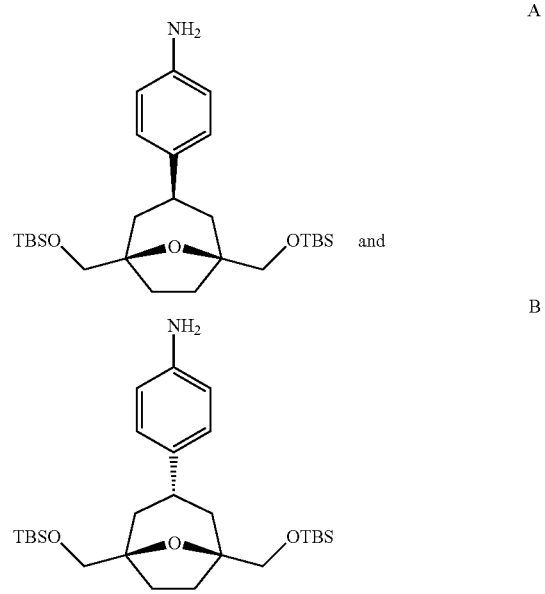

A solution of 4-[1,5-bis-(tert-butyl-dimethyl-silanyloxymethyl)-8-oxa-bicyclo[3.2.1]octa-2,6-dien-3-yl]-phenylamine (as prepared in the previous step, 500 mg, 1.03 mmol) and 5% Rh/Al$_2$O$_3$ (250 mg, 50 wt %) in 20 mL of MeOH was stirred at RT under H$_2$ (balloon pressure) for 2 h. The Rh catalyst was removed by filtration on Celite, and the filtrate was concentrated in vacuo to give 500 mg of the 4-[1,5-bis-(tert-butyl-dimethyl-silanyloxymethyl)-8-oxa-bicyclo[3.2.1]oct-2-en-3-yl]-phenylamine as a light brown oil Mass spectrum (ESI, m/z): Calcd. for C$_{27}$H$_{47}$NO$_3$Si$_2$, 490.3 (M+H), found 490.1.

A mixture of 4-[1,5-bis-(tert-butyl-dimethyl-silanyloxymethyl)-8-oxa-bicyclo[3.2.1]oct-2-en-3-yl]-phenylamine (as prepared in the above step, 500 mg, 1.02 mmol) and 10% Pd/C (250 mg, 50 wt %) in 25 mL of MeOH was stirred at RT under H$_2$ (50 psi) for 1 h. The Pd catalyst was removed by filtration on Celite, and the filtrate was concentrated to give 492 mg (98%) of the title compounds as a 2:1 (A:B) mixture as light brown oil. Mass spectrum (ESI, m/z): Calcd. for C$_{27}$H$_{49}$NO$_3$Si$_2$, 492.3 (M+H), found 492.4.

Assignment of the relative stereochemistry was made in the final step (g).

d) 4-[(3-Exo)-1,5-bis-(tert-butyl-dimethyl-silanyloxymethyl)-8-oxa-bicyclo[3.2.1]oct-3-yl]-2-bromo-phenylamine (A) and 4-[(3-endo)-1,5-Bis-(tert-butyl-dimethyl-silanyloxymethyl)-8-oxa-bicyclo[3.2.1]oct-3-yl]-2-bromo-phenylamine (B)

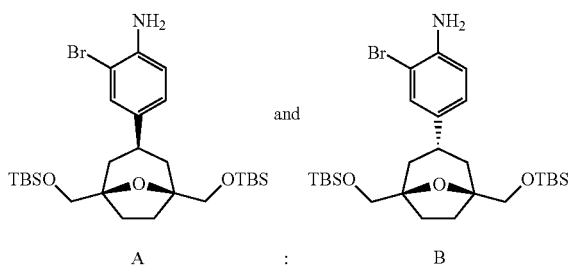

To a solution of 4-[(3-exo)-1,5-bis-(tert-butyl-dimethyl-silanyloxymethyl)-8-oxa-bicyclo[3.2.1]oct-3-yl]-phenylamine and 4-[(3-endo)-1,5-bis-(tert-butyl-dimethyl-silanyloxymethyl)-8-oxa-bicyclo[3.2.1]oct-3-yl]-phenylamine (as prepared in the previous step, 492 mg, 1.00 mmol) in 10 mL of 3:1 DCM/MeCN at 0° C. was added N-bromosuccinimide (NBS) (178 mg, 1.00 mmol) in 3 portions over 5 min. The mixture was warmed to RT and stirred for 1 h under Ar. The solvent was evaporated in vacuo and the residue was purified by flash chromatography on silica gel (1:1 hexane/DCM) to give 345 mg (60%) of the title compound A as a light brown oil and 172 mg (30%) of the title compound B as a light brown oil.

A: Mass spectrum (ESI, m/z): Calcd. for $C_{27}H_{48}BrNO_3Si_2$, 570.2 (M+H), found 570.1.

B: Mass spectrum (ESI, m/z): Calcd. for $C_{27}H_{48}BrNO_3Si_2$, 570.2 (M+H), found 570.0.

Assignment of the relative stereochemistry was made in the final step (g).

e) 4-[(3-Exo)-1,5-bis-(tert-butyl-dimethyl-silanyloxymethyl)-8-oxa-bicyclo[3.2.1]oct-3-yl]-2-(4,4-dimethyl-cyclohex-1-enyl)-phenylamine

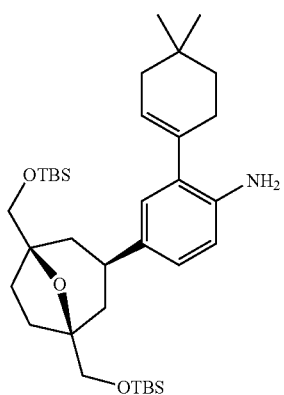 [SMILES: CC1(C)CC=C(c2cc([C@@H]3C[C@@]4(CO[Si](C)(C)C(C)(C)C)CC[C@@](CO[Si](C)(C)C(C)(C)C)(C3)O4)ccc2N)CC1]

To a mixture of 4-[(3-exo)-1,5-bis-(tert-butyl-dimethyl-silanyloxymethyl)-8-oxa-bicyclo[3.2.1]oct-3-yl]-2-bromo-phenylamine (as prepared in the previous step, 343 mg, 0.600 mmol), 4,4-dimethylcyclohexen-1-ylboronic acid (156 mg, 0.660 mmol) and Pd(PPh$_3$)$_4$ (69 mg, 0.060 mmol) in 5 mL of 1,4-dioxane was added 2.0 M aq Na$_2$CO$_3$ solution (2.4 mL, 4.8 mmol). The resulting mixture was stirred at 80° C. for 16 h under Ar, and then cooled to RT. Treated with 50 mL of EtOAc, the mixture was washed with H$_2$O (2×10 mL), brine (10 mL) and dried (Na$_2$SO$_4$). Removal of the solvent under reduced pressure followed by flash chromatography of the residue on silica gel (DCM) gave 317 mg (88%) of the title compound as a light brown solid. Mass spectrum (ESI, m/z): Calcd. for $C_{35}H_{61}NO_3Si_2$, 600.4 (M+H), found 600.5.

Assignment of the relative stereochemistry was made in the final step (g).

f) 4-Cyano-1-(2-trimethylsilanyl-ethoxymethyl)-1H-imidazole-2-carboxylic acid[4-[(3-exo)-1,5-bis-(tert-butyl-dimethyl-silanyloxymethyl)-8-oxa-bicyclo[3.2.1]oct-3-yl]-2-(4,4-dimethyl-cyclohex-1-enyl)-phenyl]-amide

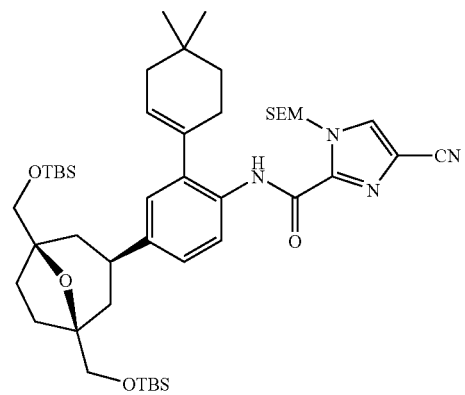 [SMILES: CC1(C)CC=C(c2cc([C@@H]3C[C@@]4(CO[Si](C)(C)C(C)(C)C)CC[C@@](CO[Si](C)(C)C(C)(C)C)(C3)O4)ccc2NC(=O)c2nc(C#N)cn2COCC[Si](C)(C)C)CC1]

To a mixture of potassium 4-cyano-1-(2-trimethylsilanyl-ethoxymethyl)-1H-imidazole-2-carboxylate (as prepared in US Pat Applic 2006189623 A1, 192 mg, 0.630 mmol) and pyridine (51.0 µL, 0.630 mmol) in 3 mL of DCM at 0° C. was added SOCl$_2$ (46.0 µL, 0.630 mmol). After stirring at 0° C. for 0.5 h under Ar, the resulting mixture was warmed to RT and added to a solution of 4-[(3-exo)-1,5-bis-(tert-butyl-dimethyl-silanyloxymethyl)-8-oxa-bicyclo[3.2.1]oct-3-yl]-2-(4,4-dimethyl-cyclohex-1-enyl)-phenylamine (as prepared in the previous step, 315 g, 0.525 mmol) in 2 mL of DCM at 0° C. After stirring at 0° C. for 2 h under Ar, the reaction was warmed to RT. Treated with 50 mL of EtOAc, the mixture was washed with H$_2$O (10 mL), 10% aqueous citric acid (10 mL), aqueous saturated NaHCO$_3$ (10 mL) and brine (20 mL). The organic layer was dried over Na$_2$SO$_4$ and concentrated in vacuo. The residue was purified by silica gel chromatography (2-5% EtOAc/hexane) to afford the title compound (401 mg, 90%) as a light brown oil. $^1$H-NMR (CDCl$_3$; 400 MHz): δ 9.72 (s, 1H), 8.29 (d, 1H, J=8.6 Hz), 7.76 (s, 1H), 7.18 (dd, 1H, J=8.6, 2.3 Hz), 7.07 (d, 1H, J=2.3 Hz), 5.96 (s, 2H), 5.76

(m, 1H), 3.59-3.68 (m, 6H), 3.02 (m, 1H), 2.29 (m, 2H), 2.09 (m, 2H), 1.76-1.88 (m, 6H), 1.66 (t, 2H, J=12.7 Hz), 1.59 (t, 2H, J=6.3 Hz), 1.11 (s, 6H), 0.97 (t, 2H, J=8.3 Hz), 0.89 (s, 18H), 0.05 (s, 12H), 0.01 (s, 9H).

Assignment of the relative stereochemistry was made in the final step (g).

g) 4-Cyano-1H-imidazole-2-carboxylic acid[4-((3-exo)-1,5-bis-hydroxymethyl-8-oxa-bicyclo[3.2.1]oct-3-yl]-2-(4,4-dimethyl-cyclohex-1-enyl)-phenyl]-amide A mixture of 4-cyano-1-(2-trimethylsilanyl-ethoxymethyl)-1H-imidazole-2-carboxylic acid[4-[(3-exo)-1,5-bis-(tert-butyl-dimethyl-silanyloxymethyl)-8-oxa-bicyclo[3.2.1]oct-3-yl]-2-(4,4-dimethyl-cyclohex-1-enyl)-phenyl]-amide (as prepared in the previous step, 400 mg, 0.471 mmol) and tetrabutylammonium fluoride monohydrate (739 mg, 2.83 mmol) in 5 mL of THF was stirred at 50° C. for 16 h. After cooling to RT, the mixture was treated with EtOAc (50 mL) and washed with $H_2O$ (10 mL), aqueous saturated $NH_4Cl$ (2×10 mL) and brine (10 mL). The organic layer was dried over $Na_2SO_4$ and concentrated in vacuo. The residue was triturated with DCM to give the title compound (203 mg, 88%) as a white solid. $^1$H-NMR ($CD_3OD$; 400 MHz): δ 8.11 (d, 1H, J=8.6Hz), 7.99 (s, 1H), 7.20 (dd, 1H, J=8.6, 2.3 Hz), 7.11 (d, 1H, J=2.3 Hz), 5.72 (m, 1H), 3.62 (d, 2H, J=11.7 Hz), 3.52 (d, 2H, J=11.7 Hz), 3.21 (m, 1H), 2.30 (m, 2H), 2.07 (m, 2H), 1.84-1.97 (m, 4H), 1.63-1.71 (m, 4H), 1.59 (t, 2H, J=6.3 Hz), 1.08 (s, 6H). Mass spectrum (ESI, m/z): Calcd. for $C_{28}H_{34}N_4O_4$, 491.3 (M+H), found 491.1.

Assignment of the relative stereochemistry was made using 1D $^1$H NMR, 2D COSY and 2D NOESY NMR.

Example 5

4-Cyano-1H-imidazole-2-carboxylic acid[4-[(3-endo)-1,5-bis-hydroxymethyl-8-oxa-bicyclo[3.2.1]oct-3-yl]-2-(4,4-dimethyl-cyclohex-1-enyl)-phenyl]-amide

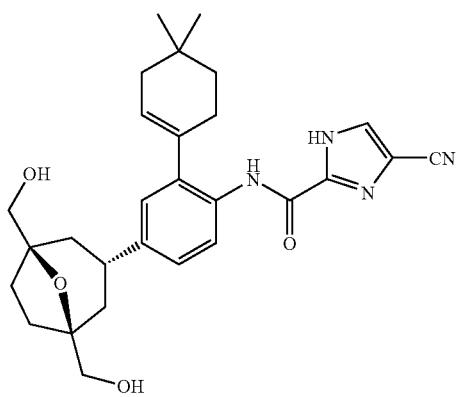 [SMILES: CC1(C)CC=C(c2cc([C@@H]3C[C@]4(CO)CC[C@](CO)(C3)O4)ccc2NC(=O)c2nc(C#N)c[nH]2)CC1]

a) 4-[(3-Endo)-1,5-bis-(tert-butyl-dimethyl-silanyloxymethyl)-8-oxa-bicyclo[3.2.1]oct-3-yl]-2-(4,4-dimethyl-cyclohex-1-enyl)-phenylamine

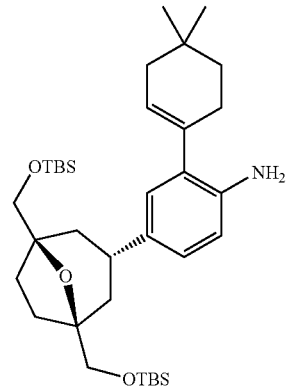 [SMILES: CC1(C)CC=C(c2cc([C@H]3C[C@@]4(CO[Si](C)(C)C(C)(C)C)CC[C@@](CO[Si](C)(C)C(C)(C)C)(C3)O4)ccc2N)CC1]

The title compound was prepared by the procedure of Example 4, step (e) using 4-[(3-endo)-1,5-bis-(tert-butyl-dimethyl-silanyloxymethyl)-8-oxa-bicyclo[3.2.1]oct-3-yl]-2-bromo-phenylamine (B) (as prepared in the example 4, step (d), 171 mg, 0.300 mmol) and 4,4-dimethylcyclohexen-1-ylboronic acid (77.9 mg, 0.330 mmol). Silica gel chromatography (DCM) afforded the title compound (165 mg, 92%) as a light brown oil. Mass spectrum (ESI, m/z): Calcd. for $C_{35}H_{61}NO_3Si_2$, 600.4 (M+H), found 600.5.

Assignment of the relative stereochemistry was made in the final step (c).

b) 4-Cyano-1-(2-trimethylsilanyl-ethoxymethyl)-1H-imidazole-2-carboxylic acid[4-[(3-endo)-1,5-bis-(tert-butyl-dimethyl-silanyloxymethyl)-8-oxa-bicyclo[3.2.1]oct-3-yl]-2-(4,4-dimethyl-cyclohex-1-enyl)-phenyl]-amide

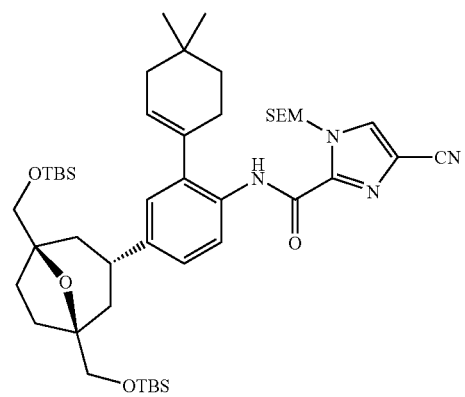 [SMILES: CC1(C)CC=C(c2cc([C@H]3C[C@@]4(CO[Si](C)(C)C(C)(C)C)CC[C@@](CO[Si](C)(C)C(C)(C)C)(C3)O4)ccc2NC(=O)c2nc(C#N)cn2COCC[Si](C)(C)C)CC1]

The title compound was prepared by the procedure of Example 4, step (f) using 4-[(3-endo)-1,5-bis-(tert-butyl-dimethyl-silanyloxymethyl)-8-oxa-bicyclo[3.2.1]oct-3-yl]-2-(4,4-dimethyl-cyclohex-1-enyl)-phenylamine (as prepared in the previous step, 150 mg, 0.250 mmol) and potassium 4-cyano-1-(2-trimethylsilanyl-ethoxymethyl)-1H-imidazole-2-carboxylate (as prepared in US Pat Applic 2006189623 A1, 92 mg, 0.300 mmol). Silica gel chromatography (2-5% EtOAc/hexane) afforded the title compound (187 mg, 88%) as a light brown oil. ¹H-NMR (CDCl₃; 400 MHz): δ 9.72 (s, 1H), 8.27 (d, 1H, J=8.6 Hz), 7.76 (s, 1H), 7.19 (dd, 1H, J=8.6, 2.3 Hz), 7.07 (d, 1H, J=2.3 Hz), 5.96 (s, 2H), 5.75 (m, 1H), 3.66 (t, 2H, J=8.3 Hz), 3.61 (s, 4H), 2.94 (m, 1H), 2.28 (m, 2H), 2.14 (dd, 1H, J=13.8, 6.7 Hz), 2.09 (m, 2H), 1.77-1.83 (m, 2H), 1.56-1.67 (m, 6H), 1.11 (s, 6H), 0.97 (t, 2H, J=8.3 Hz), 0.90 (s, 18H), 0.07 (s, 6H), 0.06 (s, 6H), 0.005 (s, 9H).

Assignment of the relative stereochemistry was made in the final step (c).

c) 4-Cyano-1H-imidazole-2-carboxylic acid[4-((3-endo)-1,5-bis-hydroxymethyl-8-oxa-bicyclo[3.2.1]oct-3-yl)-2-(4,4-dimethyl-cyclohex-1-enyl)-phenyl]-amide The title compound was prepared by the procedure of Example 4, step (g) using 4-cyano-1-(2-trimethylsilanyl-ethoxymethyl)-1H-imidazole-2-carboxylic acid[4-[(3-endo)-1,5-bis-(tert-butyl-dimethyl-silanyloxymethyl)-8-oxa-bicyclo[3.2.1]oct-3-yl]-2-(4,4-dimethyl-cyclohex-1-enyl)-phenyl]-amide (as prepared in the previous step, 185 mg, 0.218 mmol) and tetrabutyl-ammonium fluoride monohydrate (342 mg, 1.31 mmol). Silica gel chromatography (1-5% MeOH/DCM) afforded the title compound (100 mg, 93%) as a light brown oil. ¹H-NMR (CD₃OD; 400 MHz): δ 8.10 (d, 1H, J=8.6 Hz), 7.98 (s, 1H), 7.21 (dd, 1H, J=8.6, 2.0 Hz), 7.10 (d, 1H, J=2.0 Hz), 5.72 (m, 1H), 3.63 (d, 2H, J=11.6 Hz), 3.50 (d, 2H, J=11.6 Hz), 2.91 (m, 1H), 2.30 (m, 2H), 1.93-2.09 (m, 6H), 1.55-1.73 (m, 6H), 1.08 (s, 6H). Mass spectrum (ESI, m/z): Calcd. for $C_{28}H_{34}N_4O_4$, 491.3 (M+H), found 491.1.

Assignment of the relative stereochemistry was made using 1D ¹H NMR, 2D COSY and 2D NOESY NMR.

Example 6

4-Cyano-1H-imidazole-2-carboxylic acid[4-[(3-endo)-1,5-bis-methoxymethyl-8-oxa-bicyclo[3.2.1]oct-3-yl]-2-(4,4-dimethyl-cyclohex-1-enyl)-phenyl]-amide

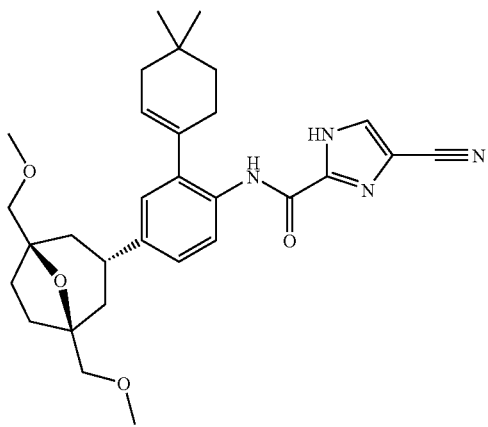 [SMILES: COC[C@@]12CC[C@@](COC)(C[C@@H](c3ccc(NC(=O)c4nc(C#N)c[nH]4)c(C4=CCC(C)(C)CC4)c3)C1)O2]

a) Trifluoromethanesulfonic acid 1,5-bis-methoxymethyl-8-oxa-bicyclo[3.2.1]octa-2,6-dien-3-yl ester

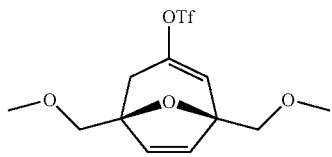

The title compound was prepared by the procedure of Example 4, step (a) using 1,5-bis-methoxymethyl-8-oxa-bicyclo[3.2.1]oct-6-en-3-one (as prepared in Example 1, step (e), 600 mg, 2.80 mmol) and 2-[N,N-bis(trifluoromethanesulfonyl)amino]pyridine (1.10 g, 3.08 mmol). The title compound (921 mg, 95%) is light brown oil. Mass spectrum (ESI, m/z): Calcd. for $C_{12}H_{15}F_3O_6S$, 345.0 (M+H), found 344.9.

b. 4-(1,5-Bis-methoxymethyl-8-oxa-bicyclo[3.2.1]octa-2,6-dien-3-yl)-phenylamine

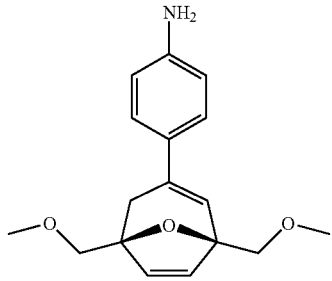

The title compound was prepared by the procedure of Example 4, step (b) using trifluoromethanesulfonic acid 1,5-bis-methoxymethyl-8-oxa-bicyclo[3.2.1]octa-2,6-dien-3-yl ester (as prepared in the previous step, 3.25 g, 9.45 mmol) and 4-(4,4,5,5-tetramethyl-[1,3,2]dioxaborolan-2-yl)-phenylamine (2.28 g, 10.4 mmol). Silica gel chromatography (5-10% EtOAc/DCM) afforded the title compound (2.19 g, 81%) as a light brown oil. Mass spectrum (ESI, m/z): Calcd. for $C_{17}H_{21}NO_3$, 288.2 (M+H), found 288.2.

c) 4-[(3-Endo)-1,5-bis-methoxymethyl-8-oxa-bicyclo[3.2.1]oct-3-yl]-phenylamine (A) and 4-[(3-Exo)-1,5-bis-methoxymethyl-8-oxa-bicyclo[3.2.1]oct-3-yl]-phenylamine (B)

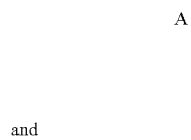

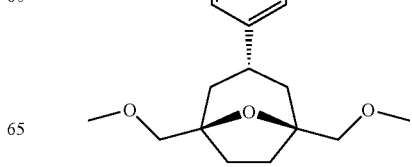

and

-continued

B

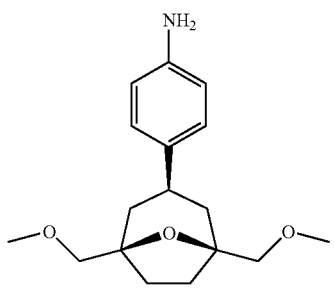

The title compound was prepared by the procedure of Example 4, step (c) using 4-(1,5-bis-methoxymethyl-8-oxa-bicyclo[3.2.1]octa-2,6-dien-3-yl)-phenylamine (as prepared in the previous step, 2.00 g, 6.96 mmol), 5% Rh/Al$_2$O$_3$ (800 mg, 40 wt %) and 10% Pd/C (800 mg, 40 wt %). Silica gel chromatography (0-1% MeOH/DCM) afforded 601 mg (44%) of the title compound A as a light brown oil and 672 mg (33%) of the title compound B as a light brown oil.

A: Mass spectrum (ESI, m/z): Calcd. for C$_{17}$H$_{25}$NO$_3$, 292.2 (M+H), found 292.2.

B: Mass spectrum (ESI, m/z): Calcd. for C$_{17}$H$_{25}$NO$_3$, 292.2 (M+H), found 292.2.

Assignment of the relative stereochemistry was made in the final step (g).

d) 4-[(3-Endo)-1,5-bis-methoxymethyl-8-oxa-bicyclo[3.2.1]oct-3-yl]-2-bromo-phenylamine

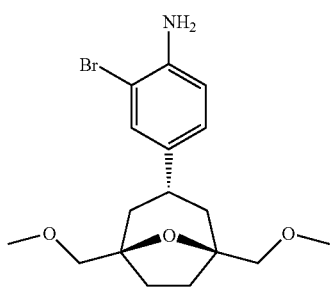

The title compound was prepared by the procedure of Example 4, step (d) using 4-[(3-endo)-1,5-bis-methoxymethyl-8-oxa-bicyclo[3.2.1]oct-3-yl]-phenylamine (as prepared in the previous step, 292 mg, 1.00 mmol), NBS (178 mg, 1.00 mmol). Silica gel chromatography (0-10% EtOAc/DCM) afforded 185 mg (50%) of the title compound as a light brown oil. Mass spectrum (ESI, m/z): Calcd. for C$_{17}$H$_{24}$BrNO$_3$, 370.1 (M+H), found 370.1.

Assignment of the relative stereochemistry was made in the final step (g).

e) 4-[(3-Endo)-1,5-bis-methoxymethyl-8-oxa-bicyclo[3.2.1]oct-3-yl]-2-(4,4-dimethylcyclohex-1-enyl)-phenylamine

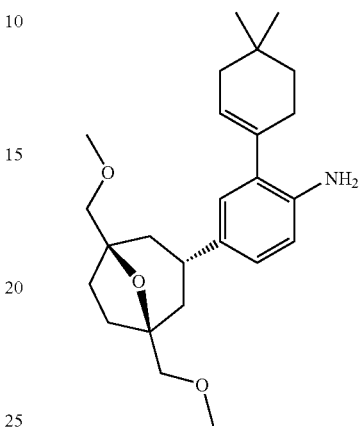

The title compound was prepared by the procedure of Example 4, step (e) using 4-[(3-endo)-1,5-bis-methoxymethyl-8-oxa-bicyclo[3.2.1]oct-3-yl]-2-bromo-phenylamine (as prepared in the previous step, 185 mg, 0.500 mmol), 4,4-dimethylcyclohexen-1-ylboronic acid (130 mg, 0.550 mmol). Silica gel chromatography (0-15% EtOAc/DCM) afforded 150 mg (75%) of the title compound as a light yellow oil. Mass spectrum (ESI, m/z): Calcd. for C$_{25}$H$_{37}$NO$_3$, 400.3 (M+H), found 400.4.

Assignment of the relative stereochemistry was made in the final step (g).

f) 4-Cyano-1-(2-trimethylsilanyl-ethoxymethyl)-1H-imidazole-2-carboxylic acid[4-[(3-endo)-1,5-bis-methoxymethyl-8-oxa-bicyclo[3.2.1]oct-3-yl]-2-(4,4-dimethyl-cyclohex-1-enyl)-phenyl]-amide

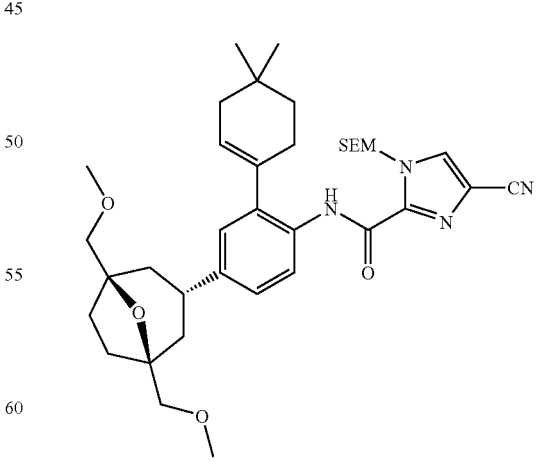

The title compound was prepared by the procedure of Example 4, step (f) using 4-[(3-endo)-1,5-bis-methoxymethyl-8-oxa-bicyclo[3.2.1]oct-3-yl]-2-(4,4-dimethyl-cyclohex-1-enyl)-phenylamine (as prepared in the previous step, 140 mg, 0.350 mmol) and potassium 4-cyano-1-(2-trimethylsilanyl-ethoxymethyl)-1H-imidazole-2-carboxylate (as prepared in US Pat Applic 2006189623 A1, 128 mg, 0.420 mmol). Silica gel chromatography (5% EtOAc/DCM) afforded 164 mg (72%) of the title compound as a light yellow oil. Mass spectrum (ESI, m/z): Calcd. for $C_{36}H_{52}N_4O_5Si$, 649.4 (M+H), found 649.1.

Assignment of the relative stereochemistry was made in the final step (g).

g) 4-Cyano-1H-imidazole-2-carboxylic acid[4-((3-endo)-1,5-bis-methoxymethyl-8-oxa-bicyclo[3.2.1]oct-3-yl)-2-(4,4-dimethyl-cyclohex-1-enyl)-phenyl]-amide The title compound was prepared by the procedure of Example 4, step (g) using 4-cyano-1-(2-trimethylsilanyl-ethoxymethyl)-1H-imidazole-2-carboxylic acid[4-[(3-endo)-1,5-bis-methoxymethyl-8-oxa-bicyclo[3.2.1]oct-3-yl]-2-(4,4-dimethyl-cyclohex-1-enyl)-phenyl]-amide (as prepared in the previous step, 150 mg, 0.231 mmol) and tetrabutyl-ammonium fluoride monohydrate (181 mg, 0.693 mmol). Silica gel chromatography (25% EtOAc/DCM) afforded the title compound (102 mg, 85%) as a white solid. Mass spectrum (ESI, m/z): Calcd. for $C_{12}H_{13}BrN_2O$, 281.0 (M+H), found 281.2. $^1$H-NMR (CD$_3$OD; 400 MHz): δ 8.11 (d, 1H, J=8.6 Hz), 7.98 (s, 1H), 7.20 (dd, 1H, J=8.6, 2.3 Hz), 7.09 (d, 1H, J=2.3 Hz), 5.71 (m, 1H), 3.46 (d, 2H, J=10.1 Hz), 3.40 (d, 2H, J=10.1 Hz), 3.40 (m, 6H), 2.90 (m, 1H), 2.29 (m, 2H), 2.17 (dd, 1H, J=13.5, 6.7 Hz), 2.06 (m, 2H), 1.80-1.89 (m, 2H), 1.67-1.76 (m, 2H), 1.58-1.64 (m, 2H), 1.58 (t, 2H, J=6.3 Hz), 1.08 (s, 6H). Mass spectrum (ESI, m/z): Calcd. for $C_{30}H_{38}N_4O_4$, 519.3 (M+H), found 519.0.

Assignment of structure was made based on analogy to 4-cyano-1H-imidazole-2-carboxylic acid[4-[(3-endo)-1,5-bis-hydroxymethyl-8-oxa-bicyclo[3.2.1]oct-3-yl]-2-(4,4-dimethyl-cyclohex-1-enyl)-phenyl]-amide (as prepared in Example 5, step (c)).

Example 7

4-Cyano-1H-imidazole-2-carboxylic acid[4-((3-exo)-1,5-bis-hydroxymethyl-8-oxa-bicyclo[3.2.1]oct-3-yl)-2-(4,4-dimethyl-cyclohex-1-enyl)-phenyl]-amide

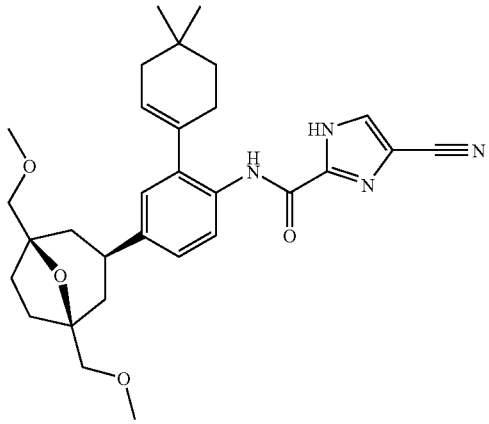 [SMILES: COC[C@@]12CC[C@@](COC)(C[C@H](c3ccc(NC(=O)c4nc(C#N)c[nH]4)c(C4=CCC(C)(C)CC4)c3)C1)O2]

a) 4-[(3-Exo)-1,5-bis-methoxymethyl-8-oxa-bicyclo[3.2.1]oct-3-yl]-2-bromo-phenylamine

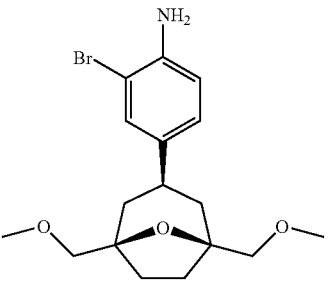

The title compound was prepared by the procedure of Example 4, step (d) using 4-((3-exo)-1,5-bis-methoxymethyl-8-oxa-bicyclo[3.2.1]oct-3-yl)-phenylamine (as prepared in Example 6, step (c), 292 mg, 1.00 mmol), NBS (178 mg, 1.00 mmol). Silica gel chromatography (0-10% EtOAc/DCM) afforded 185 mg (50%) of the title compound as light brown oil. Mass spectrum (ESI, m/z): Calcd. for $C_{17}H_{24}BrNO_3$, 370.1 (M+H), found 370.2.

Assignment of the relative stereochemistry was made in the final step (d).

b) 4-[(3-Exo)-1,5-bis-methoxymethyl-8-oxa-bicyclo[3.2.1]oct-3-yl]-2-(4,4-dimethylcyclohex-1-enyl)-phenylamine

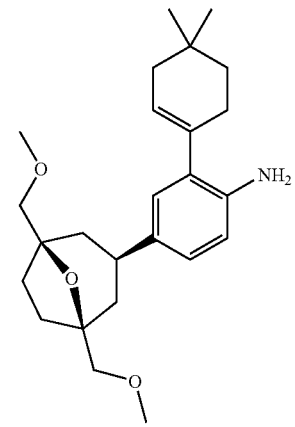 [SMILES: COC[C@@]12CC[C@@](COC)(C[C@H](c3ccc(N)c(C4=CCC(C)(C)CC4)c3)C1)O2]

The title compound was prepared by the procedure of Example 4, step (e) using 4-[(3-exo)-1,5-bis-methoxymethyl-8-oxa-bicyclo[3.2.1]oct-3-yl]-2-bromo-phenylamine (as prepared in the previous step, 185 mg, 0.500 mmol), 4,4-dimethylcyclohexen-1-ylboronic acid (130 mg, 0.550 mmol). Silica gel chromatography (0-15% EtOAc/DCM)

afforded 156 mg (78%) of the title compound as light yellow oil. Mass spectrum (ESI, m/z): Calcd. for $C_{25}H_{37}NO_3$, 400.3 (M+H), found 400.3.

Assignment of the relative stereochemistry was made in the final step (d).

c) 4-Cyano-1-(2-trimethylsilanyl-ethoxymethyl)-1H-imidazole-2-carboxylic acid[4-((3-exo)-1,5-bis-methoxymethyl-8-oxa-bicyclo[3.2.1]oct-3-yl)-2-(4,4-dimethyl-cyclohex-1-enyl)-phenyl]-amide

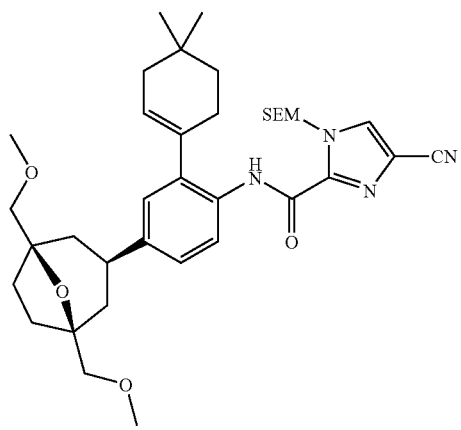 [SMILES: COC[C@@]12CC[C@@](COC)(C[C@H](c3ccc(NC(=O)c4nc(C#N)cn4COCC[Si](C)(C)C)c(C4=CCC(C)(C)CC4)c3)C1)O2]

The title compound was prepared by the procedure of Example 4, step (f) using 4-[(3-exo)-1,5-bis-methoxymethyl-8-oxa-bicyclo[3.2.1]oct-3-yl]-2-(4,4-dimethyl-cyclohex-1-enyl)-phenylamine (as prepared in the previous step, 140 mg, 0.350 mmol) and potassium 4-cyano-1-(2-trimethylsilanyl-ethoxymethyl)-1H-imidazole-2-carboxylate (as prepared in US Pat Applic 2006189623 A1, 128 mg, 0.420 mmol). Silica gel chromatography (5% EtOAc/DCM) afforded 166 mg (73%) of the title compound as a light yellow oil. Mass spectrum (ESI, m/z): Calcd. for $C_{36}H_{52}N_4O_5Si$, 649.4 (M+H), found 649.1.

Assignment of the relative stereochemistry was made in the final step (d).

d) 4-Cyano-1H-imidazole-2-carboxylic acid[4-((3-exo)-1,5-bis-methoxymethyl-8-oxa-bicyclo[3.2.1]oct-3-yl)-2-(4,4-dimethyl-cyclohex-1-enyl)-phenyl]-amide The title compound was prepared by the procedure of Example 4, step (g) using 4-cyano-1-(2-trimethylsilanyl-ethoxymethyl)-1H-imidazole-2-carboxylic acid[4-((3-exo)-1,5-bis-methoxymethyl-8-oxa-bicyclo[3.2.1]oct-3-yl)-2-(4,4-dimethyl-cyclohex-1-enyl)-phenyl]-amide (as prepared in the previous step, 150 mg, 0.231 mmol) and tetrabutylammonium fluoride monohydrate (181 mg, 0.693 mmol). Silica gel chromatography (25% EtOAc/DCM) afforded the title compound (86.4 mg, 72%) as a white solid. $^1$H-NMR (CD$_3$OD; 400 MHz): δ 8.11 (d, 1H, J=8.5 Hz), 7.98 (s, 1H), 7.19 (dd, 1H, J=8.5, 2.0 Hz), 7.09 (d, 1H, J=2.0 Hz), 5.73 (m, 1H), 3.45 (d, 2H, J=10.1 Hz), 3.41 (d, 2H, J=10.1 Hz), 3.39 (s, 6H), 3.16 (m, 1H), 2.31 (m, 2H), 2.07 (m, 2H), 1.88-1.96 (m, 2H), 1.76-1.85 (m, 2H), 1.65-1.76 (m, 4H), 1.59 (t, 2H, J=6.3 Hz), 1.08 (s, 6H). Mass spectrum (ESI, m/z): Calcd. for $C_{30}H_{38}N_4O_4$, 519.3 (M+H), found 519.1.

Assignment of structure was made based on analogy to 4-cyano-1H-imidazole-2-carboxylic acid[4-[(3-exo)-1,5-bis-hydroxymethyl-8-oxa-bicyclo[3.2.1]oct-3-yl]-2-(4,4-dimethyl-cyclohex-1-enyl)-phenyl]-amide (as prepared in Example 4, step (g)).

Example 8

4-Cyano-1H-imidazole-2-carboxylic acid[2-(4,4-dimethyl-cyclohex-1-enyl)-4-[(3-exo)-3-hydroxy-1,5-bis-hydroxymethyl-8-oxa-bicyclo[3.2.1]oct-3-yl]-phenyl]-amide

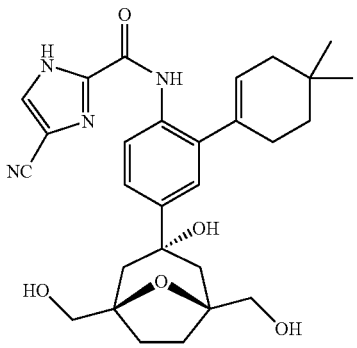

a) 1,5-Bis-(tert-butyl-dimethyl-silanyloxymethyl)-8-oxa-bicyclo[3.2.1]octan-3-one

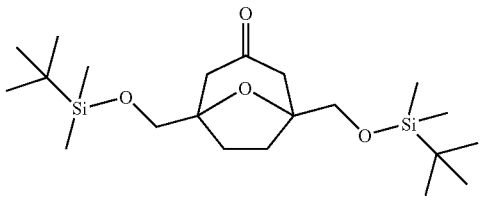 [SMILES: CC(C)(C)[Si](C)(C)OCC12CCC(CO[Si](C)(C)C(C)(C)C)(CC(=O)C1)O2]

A mixture of 1,5-bis-(tert-butyl-dimethyl-silanyloxymethyl)-8-oxa-bicyclo[3.2.1]-oct-6-en-3-one (200 mg, 4.84 mmol)(Lee, K. and Cha, J. K., *J. Amer. Chem. Soc.*, 123:5590-

5591 (2001)) and 5% Pd/C (30 mg) in 10 mL of MeOH was stirred at RT under H$_2$ (balloon pressure) for 8 h. The Pd catalyst was removed by filtration on Celite, and the filtrate was concentrated to give 200 mg (100%) of the title compound as a colorless oil. Mass spectrum (ESI, m/z): Calcd. for C$_{21}$H$_{42}$O$_4$Si$_2$, 415.2 (M+H), found 415.1.

b) 4-Cyano-1H-imidazole-2-carboxylic acid[4-[(3-exo)-1,5-bis-(tert-butyl-dimethyl-silanyloxymethyl)-3-hydroxy-8-oxa-bicyclo[3.2.1]oct-3-yl]-2-(4,4-dimethyl-cyclohex-1-enyl)-phenyl]-amide

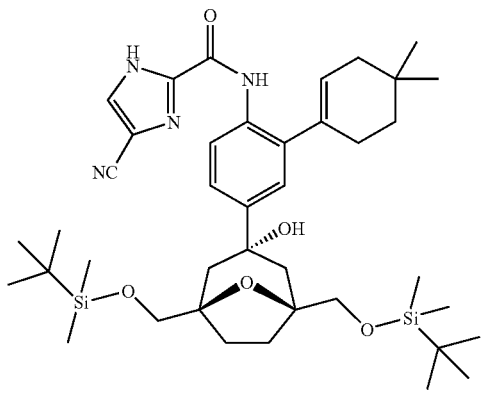

To a suspension of 4-cyano-1H-imidazole-2-carboxylic acid[4-bromo-2-(4,4-dimethyl-cyclohex-1-enyl)-phenyl]-amide (125 mg, 0.314 mmol)(prepared in Example 1, step (c)) in 2 mL of THF at −40° C. was added a solution of i-PrMgCl (2M THF, 0.392 mL, 0.785 mmol) and the mixture was allowed to attain RT. After 10 min the clear solution was cooled to −78° C. and a solution of t-BuLi (1.7M in pentane, 0.554 mL, 0.942 mmol) was added. After 15 min at −78° C. a solution of 1,5-bis-(tert-butyl-dimethyl-silanyloxymethyl)-8-oxa-bicyclo[3.2.1]octan-3-one (200 mg, 0.482 mmol) (prepared in the previous step) in THF (2 mL) was added and the mixture stirred for 30 mins at −78° C. and then allowed to attain RT and stirred for 5 more min. The reaction was quenched with saturated NH$_4$Cl (10 mL) and extracted with EtOAc (3×10 mL). The organic layer was dried (Na$_2$SO$_4$) and concentrated and the title compound was purified on silica gel eluting with 10% EtOAc/DCM to give 116 mg (51%) of a white solid. Mass spectrum (ESI, m/z): Calcd. for C$_{40}$H$_{62}$N$_4$O$_5$Si$_2$, 717.4 (M+H−H$_2$O), found 717.1.

Assignment of the relative stereochemistry was made in the final step (c).

c) 4-Cyano-1H-imidazole-2-carboxylic acid[2-(4,4-dimethyl-cyclohex-1-enyl)-4-[(3-exo)-3-hydroxy-1,5-bis-hydroxymethyl-8-oxa-bicyclo[3.2.1]oct-3-yl]-phenyl]-amide A solution of 4-cyano-1H-imidazole-2-carboxylic acid[4-[1,5-bis-(tert-butyl-dimethyl-silanyloxymethyl)-3-endo-hydroxy-8-oxa-bicyclo[3.2.1]oct-3-yl]-2-(4,4-dimethyl-cyclohex-1-enyl)-phenyl]-amide (prepared in the previous step, 110 mg, 1.49 mmol) in THF (1 mL) was treated with TBAF.H$_2$O (150 mg, 5.75 mmol) and the mixture stirred at 60° C. for 8 hr. The reaction was diluted with EtOAc (10 mL) and washed with H$_2$O (2×10 mL) and brine (10 mL) and dried over Na$_2$SO$_4$ and concentrated. The solid was triturated with Et$_2$O and filtered to give 50 mg (69%) of a white solid. $^1$H NMR (400 MHz, DMSO-d$_6$) δ ppm 14.21 (br s, 1 H), 9.73 (br s, 1 H), 8.31 (s, 1 H), 7.90 (d, J=8.6 Hz, 1 H), 7.35 (dd, J=8.6, 1.9 Hz, 1 H), 7.27 (d, J=1.9 Hz, 1 H), 5.66 (m, 1 H), 4.92 (s, 1 H), 4.61 (t, J=5.8 Hz, 2 H), 3.33-3.44 (m, 4 H), 2.22-2.29 (m, 4 H), 1.91-1.98 (m, 4 H), 1.70-1.76 (m, 2 H), 1.55-1.59 (m, 2 H), 1.47-1.52 (m, 2 H), 1.00 (s, 6 H). Mass spectrum (ESI, m/z): Calcd. for C$_{28}$H$_{34}$N$_4$O$_5$, 507.2 (M+H), found 507.1.

Assignment of relative stereochemistry was made based on analogy to 4-cyano-1H-imidazole-2-carboxylic acid[2-(4,4-dimethyl-cyclohex-1-enyl)-4-[(3-exo)-3-hydroxy-1,5-bis-methoxymethyl-8-oxa-bicyclo[3.2.1]oct-6-en-3-yl]-phenyl]-amide (as prepared in Example 1, step (f)).

Example 9

4-Cyano-1H-imidazole-2-carboxylic acid[2-(4,4-dimethyl-cyclohex-1-enyl)-4-((3-exo)-3-hydroxy-1,5-dimethyl-8-oxa-bicyclo[3.2.1]oct-6-en-3-yl)-phenyl]-amide

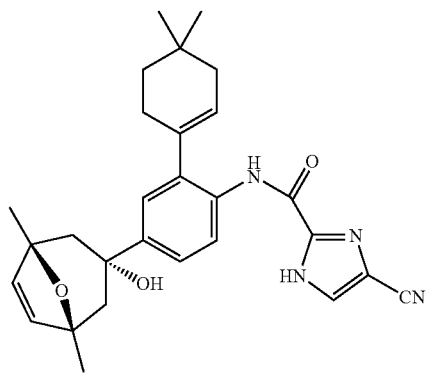 [SMILES: CC1(C)CC=C(c2cc([C@@]3(O)C[C@]4(C)C=C[C@](C)(C3)O4)ccc2NC(=O)c2nc(C#N)c[nH]2)CC1]

The title compound was prepared as described in Example 1, step (f) using 4-cyano-1H-imidazole-2-carboxylic acid[4-bromo-2-(4,4-dimethyl-cyclohex-1-enyl)-phenyl]-amide (as prepared in Example 1, step (c)) and 1,5-dimethyl-8-oxa-bicyclo[3.2.1]oct-6-en-3-one (*Chemistry—A European Journal* (1995), 1(6), 368-73). $^1$H-NMR (CDCl$_3$; 400 MHz): δ 11.85 (br s, 1H), 9.59 (s, 1H), 8.36 (d, 1H, J=8.5 Hz), 7.69 (s, 1H), 7.51 (dd, 1H, J=8.5, 2.3 Hz), 7.33 (d, 1H, J=2.3 Hz), 6.28 (s, 2H), 5.77 (br s, 1H), 3.27 (s, 1H), 2.22-2.32 (m, 4H), 1.94-2.10 (m, 4H), 1.45 (s, 6H), 1.29 (m, 2H), 1.10 (s, 6H). Mass spectrum (ESI, m/z): Calcd. for C$_{28}$H$_{32}$N$_4$O$_3$, 473.2 (M+H), found 473.1.

Assignment of relative stereochemistry was made based on analogy to 4-cyano-1H-imidazole-2-carboxylic acid[2-(4,4-dimethyl-cyclohex-1-enyl)-4-[(3-exo)-3-hydroxy-1,5-bis-methoxymethyl-8-oxa-bicyclo[3.2.1]oct-6-en-3-yl]-phenyl]-amide (as prepared in Example 1, step (f)).

Example 10

3-(3-exo)-[4-[(4-Cyano-1H-imidazole-2-carbonyl)-amino]-3-(4,4dimethyl-cyclohex-1-enyl)-phenyl]-(3-exo)-3-hydroxy-1,5-dimethyl-8-aza-bicyclo[3.2.1]oct-6-ene-8-carboxylic acid methyl ester

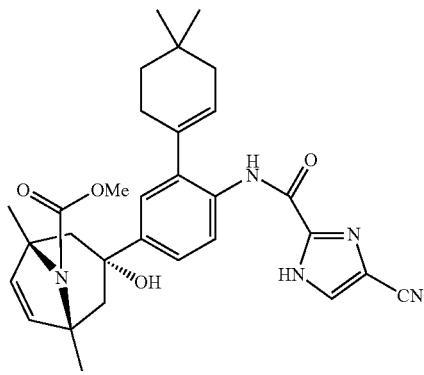 [SMILES: COC(=O)N1[C@@]2(C)C=C[C@]1(C)C[C@@](O)(c1ccc(NC(=O)c3nc(C#N)c[nH]3)c(C3=CCC(C)(C)CC3)c1)C2]

a) 1,5-Dimethyl-3-oxo-8-aza-bicyclo[3.2.1]oct-6-ene-8-carboxylic acid methyl ester

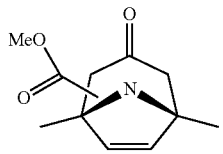

The title compound was prepared from 2,5-dimethyl-pyrrole-1-carboxylic acid methyl ester (U.S. Pat. No. 4,551,540) and 1,1,3,3-tetrabromoacetone utilizing the [4+3] cycloaddition protocol of Kim and Hoffmann (*European Journal of Organic Chemistry* (2000), (12), 2195-2201). Mass spectrum (ESI, m/z): Calcd. for $C_{11}H_{15}NO_3$, 210.1 (M+H), found 210.0.

b) 3-(3-exo)-[4-[(4-Cyano-1H-imidazole-2-carbonyl)-amino]-3-(4,4-dimethyl-cyclohex-1-enyl)-phenyl]-(3-exo)-3-hydroxy-1,5-dimethyl-8-aza-bicyclo[3.2.1]oct-6-ene-8-carboxylic acid methyl ester The title compound was prepared as described in Example 1, step (f) using 4-cyano-1H-imidazole-2-carboxylic acid[4-bromo-2-(4,4-dimethyl-cyclohex-1-enyl)-phenyl]-amide (as prepared in Example 1, step (c)) and 1,5-dimethyl-3-oxo-8-aza-bicyclo[3.2.1]oct-6-ene-8-carboxylic acid methyl ester (as prepared in the previous step). $^1$H-NMR (CDCl$_3$; 400 MHz): δ 9.60 (s, 1H), 8.16 (d, 1H, J=8.6 Hz), 7.63 (s, 1H), 7.17 (dd, 1H, J=8.6, 2.0 Hz), 7.12 (d, 1H, J=2.0 Hz), 5.98 (s, 2H), 5.68 (br s, 1H), 3.69 (s, 3H), 3.24 (br s, 1H), 2.45 (d, 2H, J=15.2 Hz), 2.20 (m, 2H), 2.00 (m, 2H), 1.81 (d, 2H, J=15.2 Hz), 1.59 (s, 6H), 1.48 (m, 2H), 1.03 (s, 6H). Mass spectrum (ESI, m/z): Calcd. for $C_{30}H_{35}N_5O_4$, 530.2 (M+H), found 530.2.

Assignment of relative stereochemistry was made based on analogy to 4-cyano-1H-imidazole-2-carboxylic acid[2-(4,4-dimethyl-cyclohex-1-enyl)-4-[(3-exo)-3-hydroxy-1,5-bis-methoxymethyl-8-oxa-bicyclo[3.2.1]oct-6-en-3-yl]-phenyl]-amide (as prepared in Example 1, step (f)).

Example 11

4-Cyano-1H-imidazole-2-carboxylic acid[2-(4,4-dimethyl-cyclohex-1-enyl)-4-[(3-exo)-3-hydroxy-1,5-dimethyl-6-exo,7-exo-(dimethylmethylenedioxy)-bicyclo[3.2.1]oct-3-yl]-phenyl]-amide

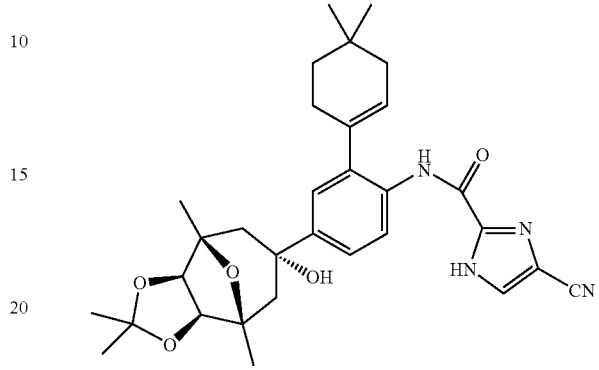

The title compound was prepared as described in Example 1, step (f) using 4-cyano-1H-imidazole-2-carboxylic acid[4-bromo-2-(4,4-dimethyl-cyclohex-1-enyl)-phenyl]-amide (as prepared in Example 1, step (c)) and 1,4,4,7-tetramethyl-3,5,11-trioxa-tricyclo[5.3.1.0$^{2,6}$]undecan-9-one (as prepared according to the procedure in *Bulletin of the Chemical Society of Japan* (1983), 56(9), 2680-99). $^1$H-NMR (CDCl$_3$; 400 MHz): δ 12.65 (s, 1H), 9.53 (s, 1H), 8.43 (d, 1H, J=8.8 Hz), 7.61 (dd, 1H, J=8.8, 2.3 Hz), 7.59 (d, 1H, J=2.5 Hz), 7.24 (d, 1H, J=2.3), 5.70 (br s, 1H), 4.93 (s, 2H), 2.22 (m, 2H), 2.03 (m, 2H), 1.82 (d, 2H, J=15.1 Hz), 1.18-1.53 (m, 17H), 1.03 (s, 6H). Mass spectrum (ESI, m/z): Calcd. for $C_{31}H_{38}N_4O_5$, 547.2 (M+H), found 547.1.

Assignment of relative stereochemistry was made based on analogy to 4-cyano-1H-imidazole-2-carboxylic acid[2-(4,4-dimethyl-cyclohex-1-enyl)-4-[(3-exo)-3-hydroxy-1,5-bis-methoxymethyl-8-oxa-bicyclo[3.2.1]oct-6-en-3-yl]-phenyl]-amide (as prepared in Example 1, step (f)).

Example 12

4-Cyano-1H-imidazole-2-carboxylic acid[2-(4,4-dimethyl-cyclohex-1-enyl)-4-(3-exo)-3,6-exo,7-exo-trihydroxy-1,5-dimethyl-8-oxa-bicyclo[3.2.1]oct-3-yl)-phenyl]-amide

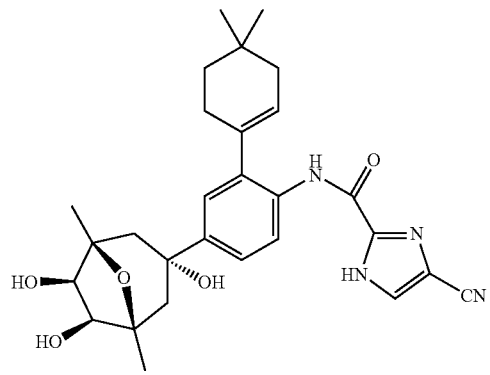 [SMILES: CC1(C)CC=C(c2cc([C@@]3(O)C[C@@]4(C)O[C@@](C)(C3)[C@H](O)[C@@H]4O)ccc2NC(=O)c2nc(C#N)c[nH]2)CC1]

a) 4,4-Di-tert-butyl-1,7-dimethyl-3,5,11-trioxa-4-sila-tricyclo[5.3.1.0$^{2,6}$]undecan-9-one

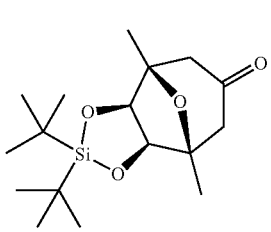 [SMILES: CC(C)(C)[Si]1(C(C)(C)C)O[C@@H]2[C@H](O1)[C@@]1(C)CC(=O)C[C@]2(C)O1]

To a solution of 6,7-dihydroxy-1,5-dimethyl-8-oxa-bicyclo[3.2.1]octan-3-one (*Bulletin of the Chemical Society of Japan* (1983), 56(9), 2680-99, 550 mg, 2.95 mmol) in DCE (20 mL) was added imidazole (2.0 g, 29 mmol) and di-tert-butyldichlorosilane (1.2 mL, 5.9 mmol). The resulting mixture was stirred under Ar for 48 h. The reaction mixture was treated with satd. NaHCO$_3$ (20 mL) and the DCE layer was separated, dried (Na$_2$SO$_4$) and concentrated and the residue obtained was purified on silica gel (5-20% EtOAc/hexane) to obtain the title compound (869 mg, 90%). $^1$H-NMR (CDCl$_3$; 400 MHz): δ 4.23 (s, 2H), 2.43 (d, 1H, J=15.6 Hz), 2.31 (d, 1H, J=15.6 Hz), 1.45 (s, 6H), 1.12 (s, 9H), 1.04 (s, 9H).

b) N'-[4-Bromo-2-(4,4dimethyl-cyclohex-1-enyl)-phenyl]-N,N-dimethyl-formamidine

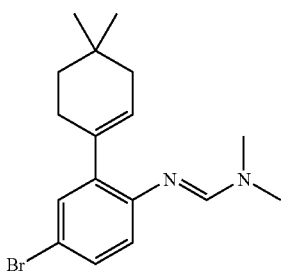 [SMILES: CN(C)/C=N/c1ccc(Br)cc1C1=CCC(C)(C)CC1]

A solution of 4-bromo-2-(4,4-dimethyl-cyclohex-1-enyl)-phenylamine (as prepared in Example 1, step (a), 3.0 g, 10 mmol) in N,N-dimethylformamide dimethyl acetal (20 mL) was heated at reflux under Ar for 48 h. The solvent was removed under reduced pressure and the residue was purified on silica gel (5-20% EtOAc/hexane) to obtain the title compound (2.6 g, 73%). $^1$H-NMR (CDCl$_3$; 400 MHz): δ 7.36 (s, 1H), 7.23-7.21 (m, 2H), 6.65 (d, 1H, J=8.0 Hz), 5.64 (m, 1H), 2.97 (s, 6H), 2.37 (m, 2H), 1.95 (m, 2H), 1.44 (m, 2H), 0.99 (s, 6H).

c) N'-[4-(9-exo)-[4,4-di-tert-butyl)-9-hydroxy-1,7-dimethyl-3,5,11-trioxa-4-sila-tricyclo[5.3.1.0$^{2,6}$]undec-9-yl]-2-(4,4-dimethyl-cyclohex-1-enyl)-phenyl]-N,N-dimethyl-formamidine

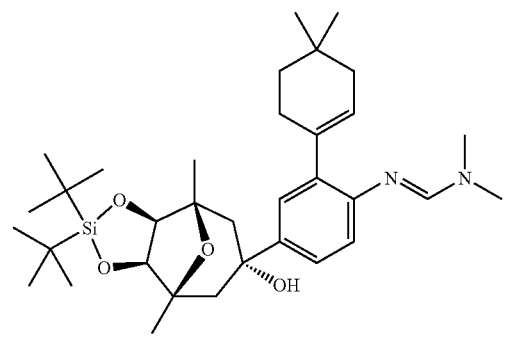 [SMILES: CN(C)/C=N/c1ccc([C@@]2(O)C[C@@]3(C)O[C@@](C)(C2)[C@@H]2O[Si](C(C)(C)C)(C(C)(C)C)O[C@@H]23)cc1C1=CCC(C)(C)CC1]

To a solution of N'-[4-bromo-2-(4,4-dimethyl-cyclohex-1-enyl)-phenyl]-N,N-dimethyl-formamidine (as prepared in the previous step, 335 mg, 1.00 mmol) in THF, BuLi (0.68 mL of 1.6 M in hexanes, 1.1 mmol) was added dropwise at −78° C. The resulting mixture was stirred at −78° C. for 45 min and treated dropwise with a solution of 4,4-di-tert-butyl-1,7-dimethyl-3,5,11-trioxa-4-sila-tricyclo[5.3.1.0$^{2,6}$]undecan-9-one (as prepared in this Example step (a), 358 mg, 1.1 mmol) in THF (5 mL). The resulting mixture was allowed to warm to RT and stirred for 1 h. The reaction mixture was then treated with satd NH$_4$Cl solution and the product was extracted with EtOAc (3×10 mL). The EtOAc layers were combined, dried (Na$_2$SO$_4$) and concentrated. The residue obtained was purified on silica gel (20% EtOAc/DCM-100% EtOAc) to obtain the title compound (197 mg, 34%). Mass spectrum (ESI, m/z): Calcd. for C$_{34}$H$_{54}$N$_2$O$_4$Si, 583.4 (M+H), found 583.5.

Assignment of relative stereochemistry was made based in the final step (f).

d) (9-exo)-[4-Amino-3-(4,4-dimethyl-cyclohex-1-enyl)-phenyl]-4,4-di-tert-butyl-1,7-dimethyl-3,5,11-trioxa-4-sila-tricyclo[5.3.1.0$^{2,6}$]undecan-9-ol

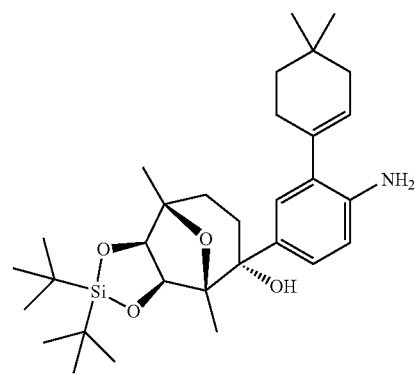 [SMILES: CC1(C)CC=C(c2cc([C@]3(O)CC[C@]4(C)O[C@@]3(C)[C@H]3O[Si](C(C)(C)C)(C(C)(C)C)O[C@H]34)ccc2N)CC1]

To a solution of N'-[4-(9-exo)-[4,4-di-tert-butyl-9-hydroxy-1,7-dimethyl-3,5,11-trioxa-4-sila-tricyclo[5.3.1.0$^{2,6}$]undec-9-yl]-2-(4,4-dimethyl-cyclohex-1-enyl)-phenyl]-N,N-dimethyl-formamidine (as prepared in previous step, 180 mg, 0.309 mmol) in isopropanol (0.5 mL), anhydrous hydrazine (0.3 mL) was added. The resulting mixture was stirred at 40° C. under Ar overnight. The reaction mixture was concentrated in vacuo and the residue obtained was treated with satd brine (10 mL) and the product was extracted with EtOAc (3×10 mL). The EtOAc layers were combined, dried (Na$_2$SO$_4$) and concentrated and the residue obtained was purified on silica gel (50% EtOAc/hexane-100% EtOAc) to obtain the title compound (110 mg, 67%). Mass spectrum (ESI, m/z): Calcd. for C$_{31}$H$_{49}$NO$_4$Si, 528.3 (M+H), found 528.2.

Assignment of relative stereochemistry was made based in the final step (f).

e) 4-Cyano-1-(2-trimethylsilanyl-ethoxymethyl)-1H-imidazole-2-carboxylic acid[4-(9-exo)-(4,4-di-tert-butyl-9-hydroxy-1,7-dimethyl-3,5,11-trioxa-4-sila-tricyclo[5.3.1.0$^{2,6}$]undec-9-yl)-2-(4,4-dimethyl-cyclohex-1-enyl)-phenyl]-amide

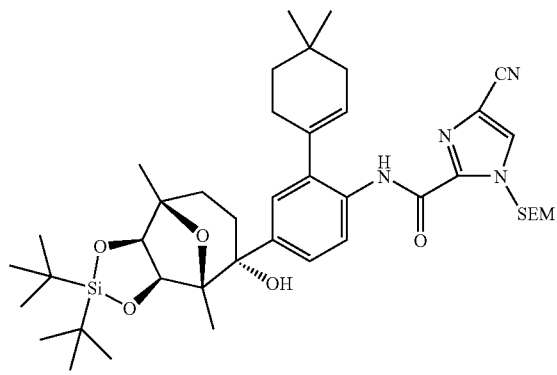 [SMILES: CC1(C)CC=C(c2cc([C@]3(O)CC[C@]4(C)O[C@@]3(C)[C@H]3O[Si](C(C)(C)C)(C(C)(C)C)O[C@H]34)ccc2NC(=O)c2nc(C#N)cn2COCC[Si](C)(C)C)CC1]

(9-exo)-[4-Amino-3-(4,4-dimethyl-cyclohex-1-enyl)-phenyl]-4,4-di-tert-butyl-1,7-dimethyl-3,5,11-trioxa-4-sila-tricyclo[5.3.1.0$^{2,6}$]undecan-9-ol (as prepared in the previous step, 148 mg, 0.28 mmol) was coupled to 4-cyano-1-(2-trimethylsilanyl-ethoxymethyl)-1H-imidazole-2-carboxylic acid, potassium salt as described in Example 1, step (b) to obtain the title compound (205 mg, 94% yield). Mass spectrum (ESI, m/z): Calcd. for C$_{42}$H$_{64}$N$_4$O$_6$Si$_2$, 777.4 (M+H), found 777.8.

Assignment of relative stereochemistry was made based in the final step (f).

f) 4-Cyano-1H-imidazole-2-carboxylic acid[2-(4,4-dimethyl-cyclohex-1-enyl)-4-((3-exo)-3,6-exo,7-exo-trihydroxy-1,5-dimethyl-8-oxa-bicyclo[3.2.1]oct-3-yl)-phenyl]-amide To a solution of 4-cyano-1-(2-trimethylsilanyl-ethoxymethyl)-1H-imidazole-2-carboxylic acid[4-(4,4-di-tert-butyl-(9-exo)-9-hydroxy-1,7-dimethyl-3,5,11-trioxa-4-sila-tricyclo[5.3.1.0$^{2,6}$]undec-9-yl)-2-(4,4-dimethyl-cyclohex-1-enyl)-phenyl]-amide (as prepared in the previous step, 250 mg, 0.321 mg) in DMF (2 mL), solid TBAF hydrate (419 mg, 1.60 mmol) was added. The resulting mixture was stirred at 50° C. overnight. The reaction mixture was allowed to cool to RT and treated with water (10 mL). The product was extracted with EtOAc (3×10 mL). The EtOAc layers were combined, dried (Na$_2$SO$_4$) and concentrated. The residue obtained was purified on silica gel (50% EtOAc/hexane-100% EtOAc) to obtain the title compound (115 mg, 55%). $^1$H-NMR (CD$_3$OD; 400 MHz): δ 8.18 (d, 1H, J=8.6 Hz), 8.01 (s, 1H), 7.37 (dd, 1H, J=8.6, 2.2 Hz), 7.30 (m, 1H), 5.75 (br s, 1H), 4.64 (s, 2H), 2.33 (m, 2H), 2.09 (m, 2H), 2.00 (d, 2H, J=14.9 Hz), 1.92 (d, 2H, J=14.9 Hz), 1.61 (t, 2H, J=6.4 Hz), 1.30 (s, 6H), 1.10 (s, 6H). Mass spectrum (APCI, m/z): Calcd. for C$_{28}$H$_{34}$N$_4$O$_5$, 507.2 (M+H), found 507.3.

Assignment of relative stereochemistry was made based on analogy to 4-cyano-1H-imidazole-2-carboxylic acid[2-(4,4-dimethyl-cyclohex-1-enyl)-4-[(3-exo)-3-hydroxy-1,5-bis-methoxymethyl-8-oxa-bicyclo[3.2.1]oct-6-en-3-yl]-phenyl]-amide (as prepared in Example 1, step (f)).

Example 13

4-Cyano-1H-imidazole-2-carboxylic acid[4-(3-endo)-(6-exo,7-exo-dihydroxy-1,5-dimethyl-8-oxa-bicyclo[3.2.1]oct-3-yl)-2-(4,4-dimethyl-cyclohex-1-enyl)-phenyl]-amide

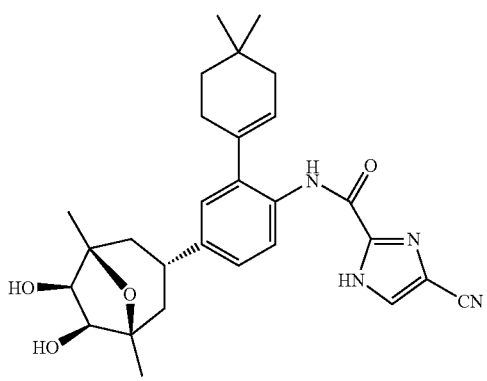 [SMILES: CC1(C)CC=C(c2cc([C@@H]3C[C@@]4(C)O[C@@](C)(C3)[C@H](O)[C@@H]4O)ccc2NC(=O)c2nc(C#N)c[nH]2)CC1]

a) 1,1,2,2,3,3,4,4,4-Nonafluoro-butane-1-sulfonic acid1,4,4,7-tetramethyl-3,5,11-trioxa-tricyclo[5.3.1.0$^{2,6}$]undec-8-en-9-yl ester

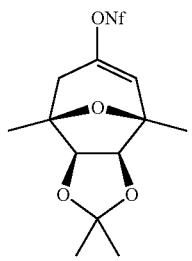

A solution of 1,4,4,7-tetramethyl-3,5,11-trioxa-tricyclo[5.3.1.0$^{2,6}$]undecan-9-one (*Bulletin of the Chemical Society of Japan* (1983), 56(9), 2680-99, 386 mg, 1.71 mmol) in THF (10 mL) was cooled to −78° C. under Ar and treated with lithium diisopropylamide (LDA) (1.00 mL of 2M in heptane/THF/ethylbenzene, 2 mmol). The resulting mixture was stirred at −78° C. for 2 h and treated dropwise with nonafluoro-1-butanesulfonylfluoride (0.60 mL, 3.4 mmol). The reaction mixture was allowed to warm to RT and stirred overnight and diluted with water (10 mL). The product was extracted with ether (4×10 mL). The organic layers were combined, dried ($Na_2SO_4$) and the product was purified on silica gel (0-2% EtOAc/hexane) to give the title compound (546 mg, 63%). $^1$H-NMR ($CDCl_3$; 400 MHz): δ 5.78 (br s, 1H), 4.37 (d, 1H, J=5.5 Hz), 4.28 (d, 1H, J=5.5 Hz), 2.52 (dd, 1H, J=17.6, 2.0 Hz), 2.04 (d, 1H, J=17.6, 1.4 Hz), 1.43 (s, 3H), 1.38 (s, 3H), 1.32 (s, 3H), 1.25 (s, 3H).

b) 1,4,4,7-Tetramethyl-9-(4-nitro-phenyl)-3,5,11-trioxa-tricyclo[5.3.1.0$^{2,6}$]undec-8-ene

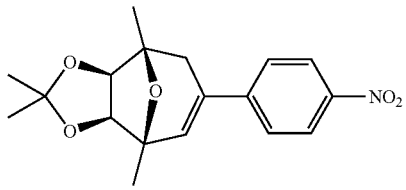 [SMILES: CC1(C)O[C@@H]2[C@H](O1)[C@@]1(C)C=C(c3ccc([N+](=O)[O-])cc3)C[C@]2(C)O1]

The title compound was then prepared according to Suzuki-Miyaura coupling procedure of Example 4, step (b) using 4-nitrophenylboronic acid (147 mg, 0.880 mmol) and 1,1,2,2,3,3,4,4,4-nonafluoro-butane-1-sulfonic acid 1,4,4,7-tetramethyl-3,5,11-trioxa-tricyclo[5.3.1.0$^{2,6}$]undec-8-en-9-yl ester (as prepared above, 326 mg, 0.641 mmol). $^1$H-NMR ($CDCl_3$; 400 MHz): δ 8.16 (d, 2H, J=8.8 Hz), 7.45 (d, 2H, J=8.8 Hz), 6.30 (br s, 1H), 4.41 (d, 1H, J=5.5 Hz), 4.32 (d, 1H, J=5.5 Hz), 2.64 (dd, 1H, J=17.0, 1.7 Hz), 2.18 (dd, 1H, J=17.0, 1.7 Hz), 1.48 (s, 3H), 1.42 (s, 3H), 1.39 (s, 3H), 1.27 (s, 3H).

c) 4-(3-exo)-[1,4,4,7-Tetramethyl-3,5,11-trioxa-tricyclo[5.3.1.0$^{2,6}$]undec-9-yl]-phenylamine and 4-(3-endo)-[1,4,4,7-tetramethyl-3,5,11-trioxa-tricyclo[5.3.1.0$^{2,6}$]undec-9-yl]-phenylamine

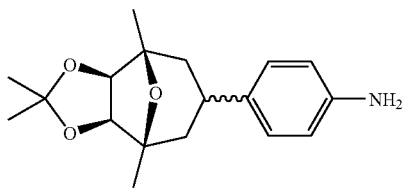 [SMILES: CC1(C)O[C@@H]2[C@H](O1)[C@@]1(C)CC(c3ccc(N)cc3)C[C@]2(C)O1]

A solution of 1,4,4,7-tetramethyl-9-(4-nitro-phenyl)-3,5,11-trioxa-tricyclo-[5.3.1.0$^{2,6}$]undec-8-ene (as prepared in previous step) (145 mg, 0.437 mmol) in EtOH (10 mL) was hydrogenated over 10% Pd/C (70 mg) at 50 psi for 1 h. The solution was filtered through a pad of Celite and concentrated to give 4-(3-endo)-(1,4,4,7-tetramethyl-3,5,11-trioxa-tricyclo[5.3.1.02,6]undec-9-yl)-phenylamine contaminated with 15% of the 4-(3-exo) isomer (118 mg, 89%), which was directly used in the next step without purification. Mass spectrum (ESI, m/z): Calcd. for $C_{18}H_{25}NO_3$, 304.1 (M+H), found 304.3.

Assignment of relative stereochemistry was made in the final step (f).

d) 2-(4,4-Dimethyl-cyclohex-1-enyl)-4-(9-endo)-(1,4,4,7-tetramethyl-3,5,11-trioxa-tricyclo[5.3.1.0$^{2,6}$]undec-9-yl)-phenylamine

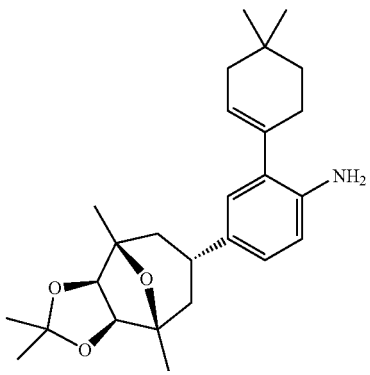 [SMILES: CC1(C)CC=C(c2cc([C@@H]3C[C@@]4(C)O[C@@](C)(C3)[C@@H]3OC(C)(C)O[C@@H]34)ccc2N)CC1]

To a solution of mixture of 4-(3-endo)-(1,4,4,7-tetramethyl-3,5,11-trioxa-tricyclo[5.3.1.0$^{2,6}$]undec-9-yl)-phenylamine containing ca. 15% of the (3-exo)-isomer (as prepared above, 350 mg, 1.06 mmol) in DCM (5 mL) was added NBS (188 mg, 1.05 mmol) in DCM (10 mL) at 0° C. and the resulting mixture was stirred at RT for 1 h. The reaction mixture was diluted with DCM (10 mL) and washed with saturated aqueous $NaHCO_3$ (10 mL) and water (10 mL). The organic layer was separated, dried ($Na_2SO_4$) and concentrated in vacuo to obtain a mixture of 2-bromo-4-[(9-endo)-1,4,4,7-tetramethyl-3,5,11-trioxa-tricyclo[5.3.1.02,6]undec-9-yl]-phenylamine contaminated with 15% of 2-bromo-4-[(9-exo)-(1,4,4,7-tetramethyl-3,5,11-trioxa-tricyclo[5.3.1.02,6]undec-9-yl)-phenylamine (404 mg, 92%) which was used in the next step without purification.

Assignment of the relative stereochemistry was made using 1D $^1$H NMR and 2D NOESY NMR.

The title compound was then prepared according to the Suzuki-Miyaura coupling procedure of Example 15, step (f) using 2-(4,4-dimethyl-cyclohex-1-enyl)-4,4,5,5-tetramethyl-[1,3,2]dioxaborolane (28.3 mg, 0.119 mmol) and 2-bromo-4-(9-endo)-(1,4,4,7-tetramethyl-3,5,11-trioxa-tricyclo[5.3.1.02,6]undec-9-yl)-phenylamine containing ca. 15% of the 9-exo isomer (as prepared above, 38.2 mg, 0.100 mmol) and purified on silica gel (20-100% EtOAc/hexanes) to afford the 9-endo isomer of the title compound (25 mg, 61%) containing ca. 15% of the 9-exo isomer. Mass spectrum, (ESI, m/z): Calcd. for $C_{26}H_{37}NO_3$, 412.3 (M+H), found 412.3.

e) 4-Cyano-1-(2-trimethylsilanyl-ethoxymethyl)-1H-imidazole-2-carboxylic acid[2-(4,4-dimethyl-cyclohex-1-enyl)-4-(9-endo)-(1,4,4,7-tetramethyl-3,5,11-trioxatricyclo[5.3.1.0$^{2,6}$]-undec-9-yl)-phenyl]-amide

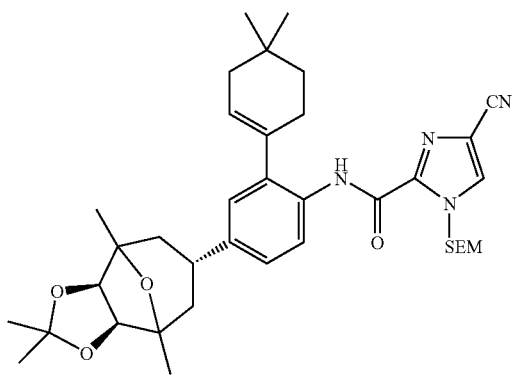 [SMILES: CC1(C)CC=C(c2cc([C@H]3CC4(C)OC(C)(C3)[C@H]3OC(C)(C)O[C@H]34)ccc2NC(=O)c2nc(C#N)cn2COCC[Si](C)(C)C)CC1]

2-(4,4-Dimethyl-cyclohex-1-enyl)-4-(9-endo)-(1,4,4,7-tetramethyl-3,5,11-trioxa-tricyclo[5.3.1.0$^{2,6}$]undec-9-yl)-phenylamine containing ca. 15% of the exo isomer (as prepared in the previous step, 439 mg, 1.06 mmol) was coupled to 4-cyano-1-(2-trimethylsilanyl-ethoxymethyl)-1H-imidazole-2-carboxylic acid, potassium salt as described in Example 1, step (b) to obtain the 9-endo isomer of the title compound containing ca. 15% of the exo isomer (514 mg, 73%) after purification on silica gel (30-70% EtOAc-hexane): Mass spectrum (ESI, m/z): Calcd. for $C_{37}H_{52}N_4O_5Si$, 661.3 (M+H), found 660.9 f) 4-Cyano-1H-imidazole-2-carboxylic acid-3-[4-(3-endo)-[6-exo,7-exo-dihydroxy-1,5-dimethyl-8-oxa-bicyclo[3.2.1]oct-3-yl]-2-(4,4-dimethyl-cyclohex-1-enyl)-phenyl]-amide To a solution of 4-cyano-1-(2-trimethylsilanyl-ethoxymethyl)-1H-imidazole-2-carboxylic acid[2-(4,4-dimethyl-cyclohex-1-enyl)-4-{(9-endo)-(1,4,4,7-tetramethyl-3,5,11-trioxatricyclo[5.3.1.0$^{2,6}$]-undec-9-yl)-phenyl)]-amide containing ca. 15% of the 9-exo isomer (330 mg, 0.500 mmol) in DCM (3 mL) and EtOH (0.1 mL) was added TFA (1 mL). After stirring for 5 h at RT, the reaction mixture was concentrated in vacuo. The residue obtained was dried and redissolved in EtOH (5 mL) and 6N HCl (10 mL). The resulting mixture was heated at reflux for 6 h and EtOH was removed in vacuo and the aqueous medium was neutralized with 6 N NaOH. The product was then extracted with DCM (3×10 mL). The organic layers were combined, dried (Na$_2$SO$_4$) and concentrated. The residue obtained was purified on silica (20-100% EtOAc/hexane) to give the 3-endo isomer (B) of the title compound (147 mg, 60%) contaminated with 15% of the 3-exo isomer (A). Endo isomer; $^1$H-NMR (CD$_3$OD; 400 MHz): 8.18 (d, 1H, J=8.3 Hz), 7.95 (s, 1H), 7.16 (dd, 1H, J=8.3, 2.3 Hz), 7.04 (d, 1H, J=2.3 Hz), 5.73 (br s, 1H), 3.96 (s, 2H), 3.02 (m, 1H), 2.28 (m, 2H), 2.08 (m, 2H), 1.97 (m, 2H), 1.60 (m, 2H), 1.58 (m, 2H) 1.30 (s, 6H), 1.08 (s, 6H); Mass spectrum (ESI, m/z): Calcd. for $C_{28}H_{34}N_4O_4$, 491.3 (M+H), found 491.1.

Assignment of the relative stereochemistry was made using 1D $^1$H NMR, $^1$H NOE NMR and 2D NOESY NMR.

Example 14

4-Cyano-1H-imidazole-2-carboxylic acid[4-cis-(2-cis,6-cis-bis-hydroxymethyl-2,6-dimethyl-tetrahydro-pyran-4-yl)-2-(4,4-dimethyl-cyclohex-1-enyl)-phenyl]-amide (A) and 4-Cyano-1H-imidazole-2-carboxylic acid[4-trans-(2-cis,6-cis-bis-hydroxymethyl-2,6-dimethyl-tetrahydro-pyran-4-yl)-2-(4,4dimethyl-cyclohex-1-enyl)-phenyl]-amide (B)

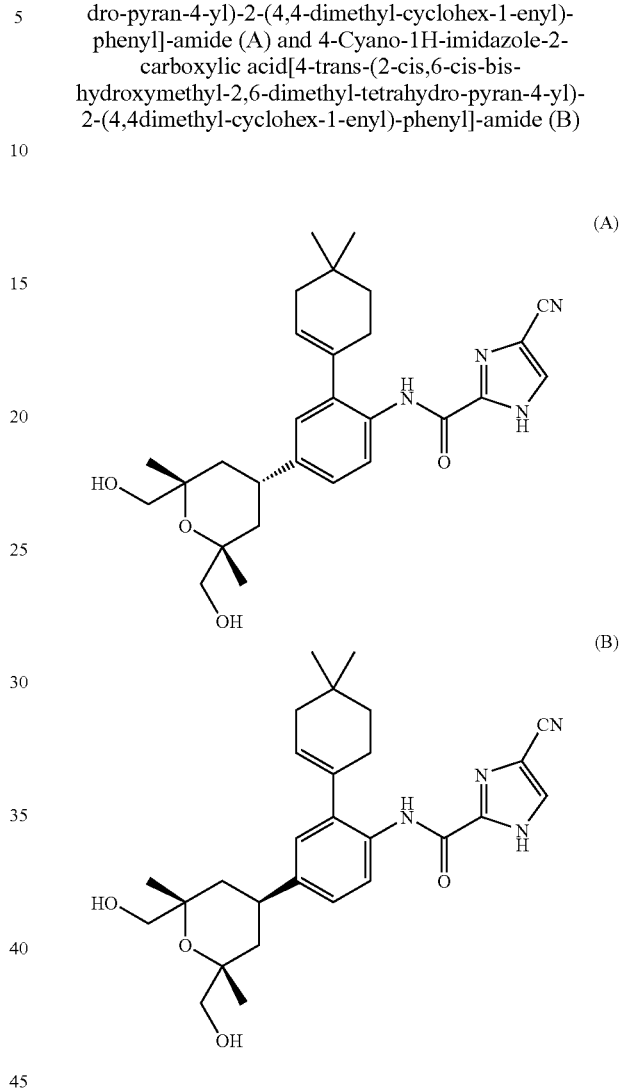

To a solution of a mixture of 4-cyano-1H-imidazole-2-carboxylic acid-3-[4-(3-endo)-[6-exo,7-exo-dihydroxy-1,5-dimethyl-8-oxa-bicyclo[3.2.1]oct-3-yl]-2-(4,4-dimethyl-cyclohex-1-enyl)-phenyl]-amide containing ca. 15% of the 3-exo isomer (as prepared in Example 13, step (f), 217 mg, 0.442 mmol) in MeOH (7 mL) and water (0.7 mL), NaIO$_4$ (140 mg, 0.654 mmol) was added. The resulting mixture was stirred at RT for 15 min after which NaBH$_4$ (41.8 mg, 1.1 mmol) in MeOH (0.2 mL) was slowly added and stirring was continued for another 30 min. The reaction mixture was concentrated and the residue obtained was partitioned between EtOAc (20 mL) and water (20 mL). The organic layer was separated, dried (Na$_2$SO$_4$) and concentrated in vacuo. The residue obtained was purified on silica (50% EtOAc/hexane-2% MeOH/EtOAc) to obtain the 4-cis isomer of the title compound (135 mg, 62% yield) containing ca. 15% of the 4-trans isomer. 4-Cis isomer: $^1$H-NMR (CD$_3$OD; 400 MHz): δ 8.00 (d, 1H, J=8.3 Hz), 7.74 (s, 1H), 7.09 (dd, 1H, J=8.3, 2.0

Hz), 6.98 (d, 1H, J=2.0 Hz), 5.61 (br s, 1H), 3.32 (m, 2H), 3.12 (m, 3H), 2.19 (m, 2H), 1.96 (m, 2H), 1.63 (m, 2H), 1.46 (m, 4H), 1.21 (s, 6H), 0.96 (s, 6H); Mass spectrum (ESI, m/z): Calcd. for $C_{28}H_{36}N_4O_4$, 493.2 (M+H), found 493.1.

Example 15

4-Cyano-1H-imidazole-2-carboxylic acid[2-(4,4-dimethyl-cyclohex-1-enyl)-6-(2,2,6,6-tetramethyl-tetrahydro-pyran-4-yl)-pyridin-3-yl]-amide

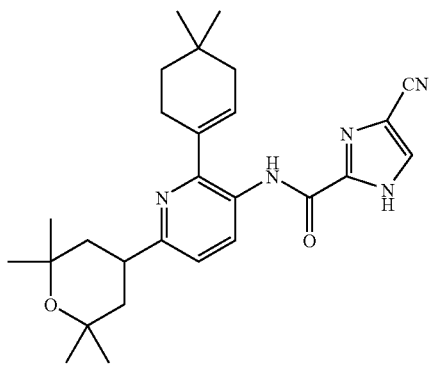 [SMILES: CC1(C)CC=C(c2nc(C3CC(C)(C)OC(C)(C)C3)ccc2NC(=O)c2nc(C#N)c[nH]2)CC1]

a) 1,1,2,2,3,3,4,4,4-Nonafluoro-butane-1-sulfonic acid 2,2,6,6-tetramethyl-3,6-dihydro-2H-pyran-4-yl ester

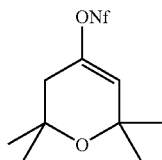

Lithium diisopropylamide (LDA) (69 mL, 0.13 mol, 2M solution in heptane/THF/ethylbenzene) was placed in a three-necked flask under Ar and cooled to −78° C. To this solution 2,2,6,6-tetramethyl-tetrahydro-pyran-4-one (Example 20 from WO 2005012220, 18 g, 0.11 mol) in THF (500 mL) was added dropwise. After the addition the reaction mixture was allowed to warm to 0° C., stirred for 1 h, cooled back to −78° C. and treated dropwise with nonafluorol-butanesulfonylfluoride (24 mL, 0.14 mmol). The mixture was warmed to RT and stirred for 12 h and treated with satd aq NaHCO₃ (200 mL). The mixture was then extracted with EtOAc (3×200 mL). The organic layers were combined, dried (Na₂SO₄) and concentrated in vacuo. The residue obtained was purified on silica gel (0-2% EtOAc/hexane to obtain the title compound (29.3 g, 68%) as a pale yellow liquid. ¹H-NMR (CDCl₃; 400 MHz): δ 5.79 (s, 1H), 2.30 (s, 2H), 1.35 (s, 6H), 1.34 (s, 6H).

b) 2,2,6,6-Tetramethyl-4-(4,4,5,5-tetramethyl-[1,3,2]dioxaborolan-2-yl)-3,6-dihydro-2H-pyran

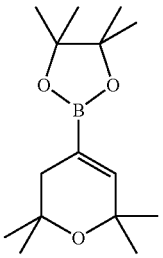

1,1,2,2,3,3,4,4,4-Nonafluoro-butane-1-sulfonic acid 2,2,6,6-tetramethyl-3,6-dihydro-2H-pyran-4-yl ester (as prepared in previous step, 43.8 g, 0.100 mol) was dissolved in anhydrous DME (500 mL) and treated with bis(pinacolato)diboron (27.9 g, 0.109 mol ), 1,1'-bis(diphenylphosphino)ferrocene (1.60 g, 2.90 mmol) and KOAc (29.4 g, 0.30 mol) and de-gassed by sonication under Ar. [1,1'-bis(diphenylphosphino)-ferrocene]-dichloropalladium(II), complex with dichloromethane (1:1) (2.19 g, 2.68 mmol) was added and heated at 80° C. overnight. The reaction mixture was allowed to cool to RT and filtered through a pad of Celite. The filtrate was concentrated and the residue obtained was chromatographed on silica gel (0-2% EtOAc/hexane) to obtain the title compound as white solid (17 g, 64%). ¹H-NMR (CDCl₃; 400 MHz): δ 6.40 (t, 1H, J=1.8 Hz), 1.97 (d, 2H, J=1.8 Hz), 1.21 (s, 12H), 1.18 (s, 6H), 1.13 (s, 6H).

c) 5-Nitro-2-(2,2,6,6-tetramethyl-3,6-dihydro-2H-pyran-4-yl)-pyridine

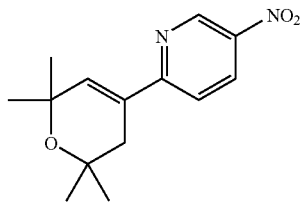 [SMILES: CC1(C)C=C(c2ccc([N+](=O)[O-])cn2)CC(C)(C)O1]

2,2,6,6-Tetramethyl-4-(4,4,5,5-tetramethyl-[1,3,2]dioxaborolan-2-yl)-3,6-dihydro-2H-pyran (as prepared in the previous step) (18.5 g, 0.069 mol) was dissolved in dimethoxyethane (DME) (350 mL). The resulting solution was treated with 2 M Na₂CO₃ (280 mL, 0.560 mol), LiCl (5.00 g, 0.110 mol) and 2-bromo-5-nitropyridine (14.0 g, 0.060 mol). The resulting mixture was degassed by sonication for 30 min under Ar and then Pd(PPh₃)₄ (8.00 g, 6.90 mmol) was added and the reaction heated at 80° C. under Ar overnight. The reaction mixture was allowed to cool to RT and extracted with EtOAc (3×150 mL). The residue was purified on silica gel with 2-10% EtOAc:hexane to obtain the title compound as a pale yellow solid (15.2 g, 83%). ¹H-NMR (CDCl₃; 400 MHz): δ 9.40 (d, 1H, J=2.8 Hz), 8.45 (dd, 1H, J=8.8, 2.8 Hz), 7.59 (d, 1H, J=8.8 Hz), 6.90 (t, 1H, J=1.6 Hz), 2.5 (d, 1H, J=1.6 Hz), 1.40 (s, 6H), 1.34 (s, 6H).

d) 6-(2,2,6,6-Tetramethyl-tetrahydro-pyran-4-yl)-pyridin-3-ylamine

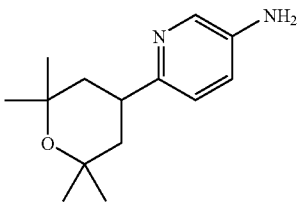 [SMILES: CC1(C)CC(c2ccc(N)cn2)CC(C)(C)O1]

To a solution of 5-nitro-2-(2,2,6,6-tetramethyl-3,6-dihydro-2H-pyran-4-yl)-pyridine (as prepared in the previous step, 15.0 g, 57.1 mmol) in EtOH (60 mL) was added 10% Pd/C (7.00 g). The resulting mixture was hydrogenated at 50 psi of hydrogen pressure for 2 h. The reaction mixture was filtered through a pad of Celite and concentrated in vacuo to obtain a beige solid (12.7 g, 95%) which was directly used in next step without further purification. $^1$H-NMR (CDCl$_3$; 400 MHz): δ 8.05 (br s, 1H), 6.98 (m, 2H), 3.59 (br s, 2H), 3.16 (m, 1H), 1.79 (m, 2H), 1.52 (m, 2H), 1.35 (s, 6H), 1.26 (s, 6H). Mass spectrum (ESI, m/z): Calcd. for $C_{14}H_{22}N_2O$, 235.2 (M+H), found 235.1.

e) 2-Bromo-6-(2,2,6,6-tetramethyl-tetrahydro-pyran-4-yl)-pyridin-3-ylamine

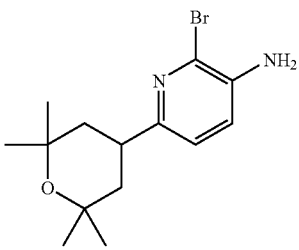 [SMILES: CC1(C)CC(c2ccc(N)c(Br)n2)CC(C)(C)O1]

To a solution of 6-(2,2,6,6-tetramethyl-tetrahydro-pyran-4-yl)-pyridin-3-ylamine (as prepared in the previous step, 13.5 g, 0.057 mol) in DCM (100 mL) was added a solution of freshly recrystallized NBS (10.2 g, 0.0570 mol) in DCM (300 mL) dropwise at 0° C. for 1 h. The reaction mixture was allowed to warm to RT, stirred for 30 min and then treated with satd aq Na$_2$CO$_3$ (300 mL). The organic phase was washed with 10% Na$_2$S$_2$O$_3$ (300 mL) and water (300 mL), dried (Na$_2$SO$_4$) and concentrated to obtain the title compound as red solid (17.1 g, 95%) which was directly used in the next step without further purification. $^1$H-NMR (CDCl$_3$; 400 MHz): δ 6.95 (d, 1H, J=8.1 Hz), 6.91 (d, 1H, j=8.1 Hz), 4.03 (br s, 2H), 3.08 (m, 1H), 1.73 (m, 2H), 1.44 (m, 2H), 1.28 (s, 6H), 1.26 (s, 6H). Mass spectrum (ESI, m/z): Calcd. for $C_{14}H_{21}BrN_2O$, 313.2 and 315.2 (M+H), found 313.2 and 315.1.

f) 2-(4,4-Dimethyl-cyclohex-1-enyl)-6-(2,2,6,6-tetramethyl-tetrahydro-pyran-4-yl)-pyridin-3-ylamine

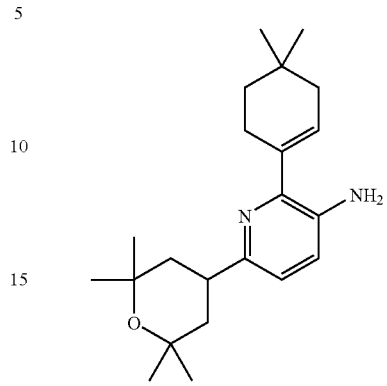

To a solution of 2-bromo-6-(2,2,6,6-tetramethyl-tetrahydro-pyran-4-yl)-pyridin-3-ylamine (as prepared in the previous step, 17.0 g, 0.054 mol ) in DME (200 mL) was added 2 M aq Na$_2$CO$_3$ (214 mL, 0.428 mol), LiCl (2.70 g, 0.0600 mol ) and 2-(4,4-dimethyl-cyclohex-1-enyl)-4,4,5,5-tetramethyl-[1,3,2]dioxaborolane (15.3 g, 0.064 mol). The resulting mixture was degassed by sonication under Ar and Pd(PPh$_3$)$_4$ (6.20 g, 5.30 mmol) was added and the reaction heated at 80° C. under Ar overnight. The reaction mixture was allowed to cool to RT and was extracted with EtOAc. After concentrating, the resulting residue was purified on silica gel with 2-20% EtOAc:hexane to give the title compound as a white solid (14.8 g, 80%). Mass spectrum (ESI, m/z): Calcd. for $C_{22}H_{34}N_2O$, 343.2 (M+H), found 343.3.

g) 4-Cyano-1-(2-trimethylsilanyl-ethoxymethyl)-1H-imidazole-2-carboxylic acid[2-(4,4-dimethyl-cyclohex-1-enyl)-6-(2,2,6,6-tetramethyl-tetrahydro-pyran-4-yl)-pyridin-3-yl]-amide

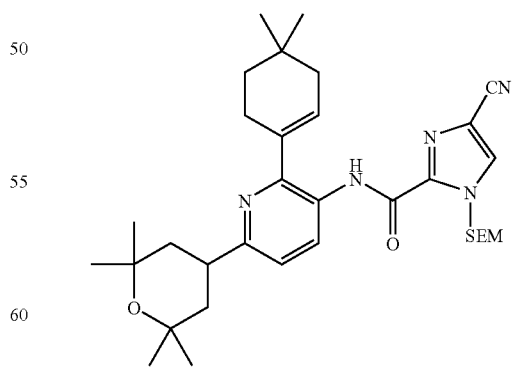

2-(4,4-Dimethyl-cyclohex-1-enyl)-6-(2,2,6,6-tetramethyl-tetrahydro-pyran-4-yl)-pyridin-3-ylamine (as prepared in the previous step, 10.0 g, 0.029 mol) was coupled to 4-cyano-1-(2-trimethylsilanyl-ethoxymethyl)-1H-imidazole-2- carboxylic acid, potassium salt as described in Example 1, step (b) to obtain the title compound (15.8 g, 92%) after purification on silica gel (30-70% EtOAc-hexane) as a white solid: Mass spectrum (ESI, m/z): Calcd. for $C_{33}H_{49}N_5O_3Si$, 592.3 (M+H), found 592.4.

h) 4-Cyano-1H-imidazole-2-carboxylic acid[2-(4,4-dimethyl-cyclohex-1-enyl)-6-(2,2,6,6-tetramethyl-tetrahydro-pyran-4-yl)-pyridin-3-yl]-amide To a solution of 4-cyano-1-(2-trimethylsilanyl-ethoxymethyl)-1H-imidazole-2-carboxylic acid[2-(4,4-dimethyl-cyclohex-1-enyl)-6-(2,2,6,6-tetramethyl-tetrahydro-pyran-4-yl)-pyridin-3-yl]-amide (as prepared in the previous example, 17.6 g, 0.0290 mol) in DMF (30 mL) was added solid TBAF hydrate (16.6 g, 0.0630 mol). The resulting mixture was heated at 70° C. overnight. The reaction mixture was allowed to cool to RT and partitioned between EtOAc (200 mL) and water (200 mL). The organic layer was separated, the aqueous layer was washed with EtOAc (3×100 mL) and the organic layers were combined, dried ($Na_2SO_4$) and concentrated. The resulting residue was dried under high vacuum to remove residual DMF. The residue was purified on silica gel (0-50% EtOAc/hexane). The resulting solid was then suspended in 25% ether/hexane and sonicated for 10 min. The product was collected by suction filtration and dried in a vacuum oven at 60° C. for 12 h to obtain the title compound as a white solid (10.2 g, 75%.) $^1$H-NMR (DMSO; 400 MHz): δ 14.26 (s, 1H), 10.02 (s, 1H), 8.32 (s, 1H), 8.12 (d, 1H, J=8.3 Hz), 7.24 (d, 1H, J=8.3 Hz), 5.86 (br s, 1H), 3.23 (m, 1H), 2.40 (m, 2H), 1.91 (m, 2H), 1.74 (dd, 2H, J=12.9, 3.3 Hz), 1.48 (m, 4H), 1.30 (s, 6H), 1.15 (s, 6H), 0.96 (s, 6H). Mass spectrum (ESI, m/z): Calcd. for $C_{27}H_{35}N_5O_2$, 462.2 (M+H), found 462.3.

Example 16

4-Cyano-1H-imidazole-2-carboxylic acid[2-cyclohex-1-enyl-6-(2,2,6,6-tetramethyl-tetrahydro-pyran-4-yl)-pyridin-3-yl]-amide

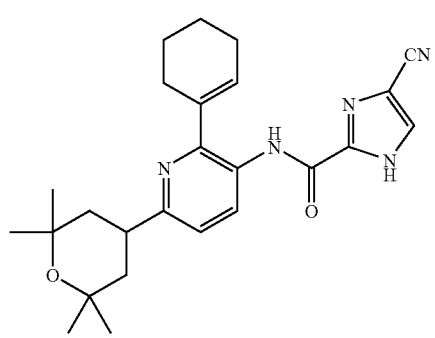 [SMILES: CC1(C)CC(c2ccc(NC(=O)c3nc(C#N)c[nH]3)c(C3=CCCCC3)n2)CC(C)(C)O1]

a) 4-Cyano-1-(2-trimethylsilanyl-ethoxymethyl)-1H-imidazole-2-carboxylic acid[2-cyclohex-1-enyl-6-(2,2,6,6-tetramethyl-tetrahydro-pyran-4-yl)-pyridin-3-yl]-amide

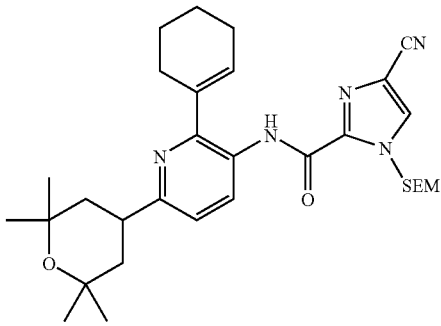 [SMILES: CC1(C)CC(c2ccc(NC(=O)c3nc(C#N)cn3COCC[Si](C)(C)C)c(C3=CCCCC3)n2)CC(C)(C)O1]

The title compound was prepared using 1-cyclohexenylboronic acid and 2-bromo-6-(2,2,6,6-tetramethyl-tetrahydro-pyran-4-yl)-pyridin-3-ylamine (as prepared in Example 15, step (e)) using the procedures of Example 15, steps (f) and (g). Mass spectrum (ESI, m/z): Calcd. for $C_{31}H_{45}N_5O_3Si$, 564.3 (M+H), found 564.3.

b) 4-Cyano-1H-imidazole-2-carboxylic acid[2-cyclohex-1-enyl-6-(2,2,6,6-tetramethyl-tetrahydro-pyran-4-yl)-pyridin-3-yl]-amide The title compound was prepared from 4-cyano-1-(2-trimethylsilanyl-ethoxymethyl)-1H-imidazole-2-carboxylic acid [2-cyclohex-1-enyl-6-(2,2,6,6-tetramethyl-tetrahydro-pyran-4-yl)-pyridin-3-yl]-amide as described in Example 15, step (h). $^1$H-NMR (CDCl$_3$; 400 MHz): δ 12.48 (br s, 1H), 9.72 (s, 1H), 8.59 (d, 1H, J=8.3 Hz), 7.74 (s, 1H), 7.12 (d, 1H, J=8.3 Hz), 6.06 (br s, 1H), 3.27 (m, 1H), 2.45 (m, 2H), 2.33 (m, 2H), 1.85 (m, 6H), 1.57 (t, 2H, J=12.8 Hz), 1.35 (s, 6H), 1.26 (s, 6H). Mass spectrum (ESI, m/z): Calcd. for $C_{25}H_{31}N_5O_2$, 434.2 (M+H), found 434.2.

Example 17

4-Cyano-1H-imidazole-2-carboxylic acid[6-[(3-exo)-6-exo,7-exo-(isopropylidinedioxy)-1,5-dimethyl-8-oxa-bicyclo[3.2.1]oct-3-yl]-2-(4,4-dimethyl-cyclohex-1-enyl)-pyridin-3-yl]-amide

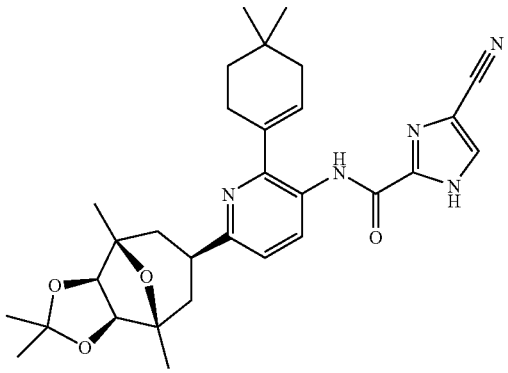 [SMILES: CC1(C)CC=C(c2nc([C@H]3C[C@@]4(C)O[C@@](C)(C3)[C@@H]3OC(C)(C)O[C@@H]34)ccc2NC(=O)c2nc(C#N)c[nH]2)CC1]

a) 1,5-Dimethyl-3-(4,4,5,5-tetramethyl-[1,3,2]dioxaborolan-2-yl)-6-exo,7-exo-(isopropylidinedioxy)-8-oxa-bicyclo[3.2.1]oct-2-ene

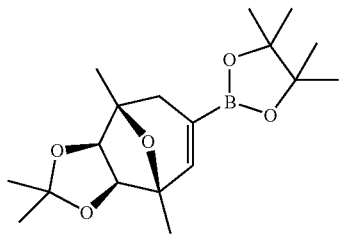

The title compound was prepared according to the procedure of Example 15, step (b) using 1,1,2,2,3,3,4,4,4-nonafluoro-butane-1-sulfonic acid 1,4,4,7-tetramethyl-3,5,11-trioxa-tricyclo[5.3.1.0$^{2,6}$]undec-8-en-9-yl ester (as prepared in Example 13, step (a)). $^1$H-NMR (CDCl$_3$; 400 MHz): δ 6.58-6.50 (m, 1H), 4.40 (d, 1H, J=5.2 Hz), 4.30 (d, 1H, J=5.2 Hz), 2.47-2.36 (m, 1H), 2.01-1.92 (m, 1H), 1.52 (s, 3H), 1.38 (s, 3H), 1.32 (s, 3H), 1.26 (s, 12 H).

b) 1,5-Dimethyl-3-(5-nitro-pyridin-2-yl)-6-exo,7-exo-(isopropylidinedioxy)-8-oxa-bicyclo[3.2.1]oct-2-ene

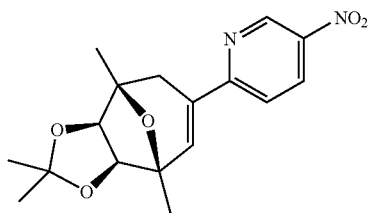 [SMILES: CC1(C)O[C@@H]2[C@H](O1)[C@@]1(C)C=C(c3ccc([N+](=O)[O-])cn3)C[C@]2(C)O1]

The title compound was prepared according to the procedure of Example 15, step (c) using 1,5-dimethyl-3-(4,4,5,5-tetramethyl-[1,3,2]dioxaborolan-2-yl)-6-exo,7-exo-(isopropylidinedioxy)-8-oxa-bicyclo[3.2.1]oct-2-ene (as prepared in the previous step) and 2-bromo-5-nitro-pyridine. Mass spectrum (APCI, m/z): Calcd. for C$_{17}$H$_{20}$N$_2$O$_5$, 333.1 (M+H), found 333.1.

c) (3-exo)-(5-Amino-pyridin-2-yl)-1,5-dimethyl-6-exo,7-exo-(isopropylidinedioxy)-8-oxa-bicyclo[3.2.1]octane

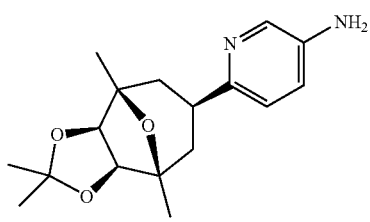 [SMILES: CC1(C)O[C@@H]2[C@H](O1)[C@@]1(C)C[C@H](c3ccc(N)cn3)C[C@]2(C)O1]

A solution of 1,5-dimethyl-3-(5-nitro-pyridin-2-yl)-6-exo,7-exo-(isopropylidinedioxy)-8-oxa-bicyclo[3.2.1]oct-2-ene (265 mg, 0.795 mmol, as prepared in the previous step) in EtOH (20 mL) was hydrogenated at 1 atm with 5% Pd/C at RT for 2.5 h. The mixture was filtered through Celite, the filter cake was washed with MeOH and the solvents were evaporated in vacuo. The residue was taken up in EtOH and hydrogenation was continued via an H-Cube apparatus under the following conditions: column temperature=40° C.; flow rate=1 mL/min; controlled H$_2$ mode, pressure=40 bar. Solvents were evaporated in vacuo to afford the title compound (189 mg, 78%) as an off-white solid. Mass spectrum (ESI, m/z): Calcd. for C$_{17}$H$_{24}$N$_2$O$_3$, 305.2 (M+H), found 305.2.

d) (3-exo)-(5-Amino-6-bromo-pyridin-2-yl)-1,5-dimethyl-6-exo,7-exo-(isopropylidinedioxy)-8-oxa-bicyclo[3.2.1]octane

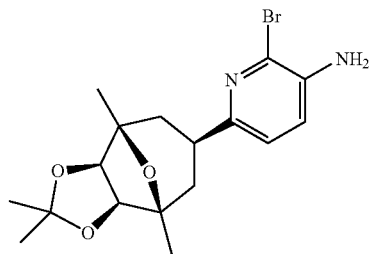 [SMILES: CC1(C)O[C@@H]2[C@H](O1)[C@@]1(C)C[C@H](c3ccc(N)c(Br)n3)C[C@]2(C)O1]

A solution of (3-exo)-(5-amino-pyridin-2-yl)-1,5-dimethyl-6-exo,7-exo-(isopropylidinedioxy)-8-oxa-bicyclo[3.2.1]octane (0.470 g, 1.54 mmol, as prepared in the previous step) in acetonitrile (10 mL) was cooled to 0° C. and treated with NBS as a solution in acetonitrile (10 mL). The mixture was concentrated in vacuo. The residue was taken up in EtOAc (50 mL) and washed with satd aq NaHCO$_3$ (1×20 mL) and the aqueous layer was extracted with EtOAc (1×20 mL). The combined organic layers were dried over MgSO$_4$ and concentrated in vacuo. The residue was purified on a 40-g Sepra Si 50 SPE column (Isco system: Flow rate=20 mL/min; Eluent=10% EtOAc-hexane for 0-5 min, then 10-40% EtOAc-hexane for 5-30 min) to afford the title compound (513 mg, 87%) as a white solid. Mass spectrum (APCI, m/z): Calcd. for C$_{17}$H$_{23}$N$_2$O$_3$Br, 385.1 (M+H), found 385.2.

e) (3-exo)-[5-Amino-6-(4,4-dimethyl-cyclohex-1-enyl)-pyridin-2-yl]-1,5-dimethyl-6-exo,7-exo-(isopropylidinedioxy)-8-oxa-bicyclo[3.2.1]octane

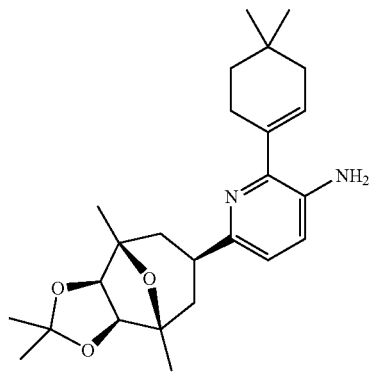 [SMILES: CC1(C)CC=C(c2nc([C@H]3C[C@@]4(C)O[C@@](C)(C3)[C@@H]3OC(C)(C)O[C@@H]34)ccc2N)CC1]

The title compound was prepared according to the procedure of Example 15, step (f) using (3-exo)-(5-amino-6- bromo-pyridin-2-yl)-1,5-dimethyl-6-exo,7-exo-(isopropylidinedioxy)-8-oxa-bicyclo[3.2.1]octane (as prepared in the previous step). Mass spectrum (ESI, m/z): Calcd. for $C_{25}H_{36}N_2O_3$, 413.3 (M+H), found 413.3.

f) 4-Cyano-1-(2-trimethylsilanyl-ethoxymethyl)-1H-imidazole-2-carboxylic acid[6-[(3-exo)-6-exo,7-exo-(isopropylidinedioxy)-1,5-dimethyl-8-oxa-bicyclo[3.2.1]oct-3-yl]-2-(4,4-dimethyl-cyclohex-1-enyl)-pyridin-3-yl]-amide

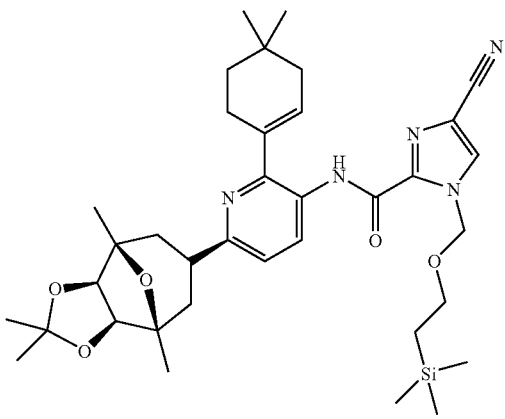

The title compound was prepared according to the procedure of Example 1, step (b), using (3-exo)-[5-amino-6-(4,4-dimethyl-cyclohex-1-enyl)-pyridin-2-yl]-1,5-dimethyl-6-exo,7-exo-(isopropylidinedioxy)-8-oxa-bicyclo[3.2.1]octane (as prepared in the previous step). Mass spectrum (ESI, m/z): Calcd. for $C_{36}H_{51}N_5O_5Si$, 662.4 (M+H), found 662.4.

g) 4-Cyano-1H-imidazole-2-carboxylic acid[6-[(3-exo)-6-exo,7-exo-(isopropylidinedioxy)-1,5-dimethyl-8-oxa-bicyclo[3.2.1]oct-3-yl]-2-(4,4-dimethyl-cyclohex-1-enyl)-pyridin-3-yl]-amide The title compound was prepared according to the procedure of Example 2, step (b), using 4-cyano-1-(2-trimethylsilanyl-ethoxymethyl)-1H-imidazole-2-carboxylic acid[6-[(3-exo)-6-exo,7-exo-(isopropylidinedioxy)-1,5-dimethyl-8-oxa-bicyclo[3.2.1]oct-3-yl]-2-(4,4-dimethyl-cyclohex-1-enyl)-pyridin-3-yl]-amide (as prepared in the previous step). $^1$H-NMR (CDCl$_3$; 400 MHz): δ 11.52 (br s, 1H), 9.75 (br s, 1H), 8.67 (d, 1H, J=8.8 Hz), 7.73 (s, 1H), 7.23 (d, 1H, J=8.8 Hz), 6.00-5.95 (m, 1H), 4.35 (s, 2H), 3.38-3.29 (m, 1H), 2.54-2.46 (m, 2H), 2.38-2.30 (m, 2H), 2.17-2.11 (m, 2H), 2.05-1.98 (m, 2H), 1.64-1.60 (m, 2H), 1.47 (s, 3H), 1.35 (s, 6H), 1.15 (s, 3H), 1.11 (s, 6H). Mass spectrum (APCI, m/z): Calcd. for $C_{30}H_{37}N_5O_4$, 532.3 (M+H), found 532.3.

Assignment of relative stereochemistry was made based on analogy to 4-cyano-1H-imidazole-2-carboxylic acid[4-((3-exo)-1,5-bis-hydroxymethyl-8-oxa-bicyclo[3.2.1]oct-3-yl)-2-(4,4-dimethyl-cyclohex-1-enyl)-phenyl]-amide (as prepared in Example 4, step (g)).

Example 18

4-Cyano-1H-imidazole-2-carboxylic acid[6-[(3-exo)-(6-exo,7-exo-dihydroxy-1,5-dimethyl-8-oxa-bicyclo[3.2.1]oct-3-yl]-2-(4,4-dimethyl-cyclohex-1-enyl)-pyridin-3-yl]-amide trifluoroacetic acid salt and 4-Cyano-1H-imidazole-2-carboxylic acid[6-[(3-endo)-(6-exo,7-exo-dihydroxy-1,5-dimethyl-8-oxa-bicyclo[3.2.1]oct-3-yl)-2-(4,4-dimethyl-cyclohex-1-enyl)-pyridin-3-yl]-amide trifluoroacetic acid salt

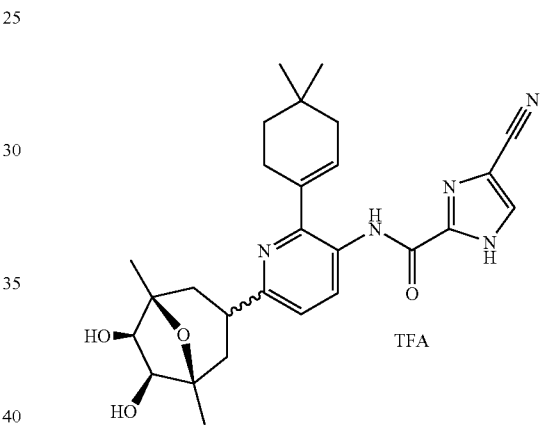

A solution of 4-cyano-1H-imidazole-2-carboxylic acid[6-[(3-exo)-6-exo,7-exo-(isopropylidinedioxy)-1,5-dimethyl-8-oxa-bicyclo[3.2.1]oct-3-yl]-2-(4,4-dimethyl-cyclohex-1-enyl)-pyridin-3-yl]-amide (76.4 mg, 0.144 mmol, as prepared in Example 17, step (g)) in isopropyl alcohol (IPA) (5 mL) was treated dropwise with 5.2 M HCl in IPA (5 mL) and heated to 60° C. for 2 h. Additional HCl in IPA (2.5 mL, 5.2 M) was added with continued heating for 3 h. The mixture was allowed to sit at RT overnight. Aqueous HCl (5 mL, 2 M) was added, and the mixture was stirred at RT for 4 h and at 45° C. for 1 h. The mixture was concentrated in vacuo. Purification of the residue by RP-HPLC (C18) with 10-80% CH$_3$CN in 0.1% TFA/H$_2$O over 25 min afforded the title compounds (28.6 mg, 40%) as a 2:1 mixture of isomers as a white solid. Major isomer: $^1$H-NMR (CD$_3$OD; 400 MHz): δ 8.94-8.92 (m, 1H), 8.06 (s, 1H), 7.71-7.62 (m, 1H), 6.20-6.13 (m, 1H), 4.14-3.96 (m, 2H), 3.43-3.19 (m, 1H), 2.55-2.42 (m, 2H), 2.21-2.11 (m, 2H), 2.11-1.84 (m, 4H), 1.69-1.61 (m, 2H), 1.37-1.29 (s, 6H), 1.12 (s, 6H). Mass spectrum (APCI, m/z): Calcd. for $C_{27}H_{33}N_5O_4$, 492.3 (M+H), found 492.2.

Example 19

4-Cyano-1H-imidazole-2-carboxylic acid[2-cyclohex-1-enyl-6-[(3-exo)-(6-exo,7-exo-dihydroxy-1,5-dimethyl-8-oxa-bicyclo[3.2.1]oct-3-yl]-pyridin-3-yl]-amide trifluoroacetic acid salt and 4-Cyano-1H-imidazole-2-carboxylic acid[2-cyclohex-1-enyl-6-[(3-endo)-(6-exo,7-exo-dihydroxy-1,5-dimethyl-8-oxa-bicyclo[3.2.1]oct-3-yl]-pyridin-3-yl]-amide trifluoroacetic acid salt

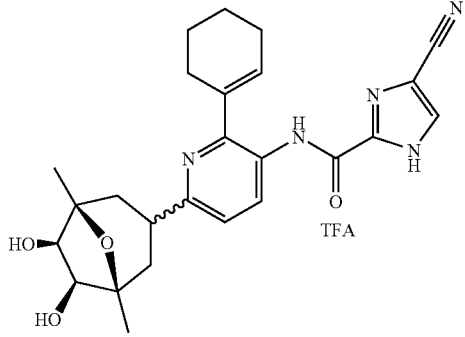 [SMILES: C[C@]12CC(c3ccc(NC(=O)c4nc(C#N)c[nH]4)c(C4=CCCCC4)n3)C[C@](C)(O1)[C@H](O)[C@@H]2O]

a) (3-exo)-[5-Amino-6-(cyclohex-1-enyl)-pyridin-2-yl]-1,5-dimethyl-6-exo,7-exo-(isopropylidinedioxy)-8-oxa-bicyclo[3.2.1]octane and (3-endo)-[5-Amino-6-(cyclohex-1-enyl)-pyridin-2-yl]-1,5-dimethyl-6-exo,7-exo-(isopropylidinedioxy)-8-oxa-bicyclo[3.2.1]octane

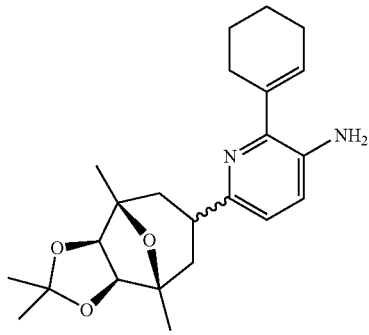 [SMILES: CC1(C)O[C@@H]2[C@H](O1)[C@@]1(C)CC(c3ccc(N)c(C4=CCCCC4)n3)C[C@]2(C)O1]

The title compounds were prepared from (3-exo)-(5-amino-6-bromo-pyridin-2-yl)-1,5-dimethyl-6-exo,7-exo-(isopropylidinedioxy)-8-oxa-bicyclo[3.2.1]octane (as prepared in Example 17, step (d)) and cyclohexen-1-ylboronic acid according to the procedure in Example 15, step (f). Mass spectrum (ESI, m/z): Calcd. for $C_{23}H_{32}N_2O_3$, 385.2 (M+H), found 385.3.

b) 4-Cyano-1-(2-trimethylsilanyl-ethoxymethyl)-1H-imidazole-2-carboxylic acid[6-[(3-exo)-6-exo,7-exo-(isopropylidinedioxy)-1,5-dimethyl-8-oxa-bicyclo[3.2.1]oct-3-yl]-2-(cyclohex-1-enyl)-pyridin-3-yl]-amide and 4-Cyano-1-(2-trimethylsilanyl-ethoxymethyl)-1H-imidazole-2-carboxylic acid[6-[(3-endo)-6-exo,7-exo-(isopropylidinedioxy)-1,5-dimethyl-8-oxa-bicyclo[3.2.1]oct-3-yl]-2-(cyclohex-1-enyl)-pyridin-3-yl]-amide

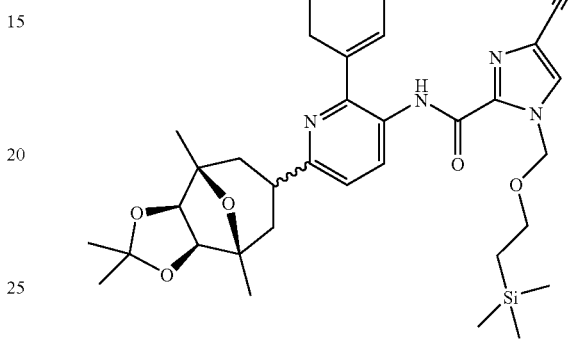

The title compounds were prepared from a mixture of (3-exo)-[5-amino-6-(cyclohex-1-enyl)-pyridin-2-yl]-1,5-dimethyl-6-exo,7-exo-(isopropylidinedioxy)-8-oxa-bicyclo[3.2.1]octane and (3-endo)-[5-amino-6-(cyclohex-1-enyl)-pyridin-2-yl]-1,5-dimethyl-6-exo,7-exo-(isopropylidinedioxy)-8-oxa-bicyclo[3.2.1]octane (as prepared in the previous step) according to the procedure of Example 1, step (b). Mass spectrum (ESI, m/z): Calcd. for $C_{34}H_{47}N_5O_5Si$, 634.3 (M+H), found 634.3.

c) 4-Cyano-1H-imidazole-2-carboxylic acid[6-[(3-exo)-6-exo,7-exo-(isopropylidinedioxy)-1,5-dimethyl-8-oxa-bicyclo[3.2.1]oct-3-yl]-2-(cyclohex-1-enyl)-pyridin-3-yl]-amide and 4-Cyano-1H-imidazole-2-carboxylic acid[6-[(3-endo)-6-exo,7-exo-(isopropylidinedioxy)-1,5-dimethyl-8-oxa-bicyclo[3.2.1]oct-3-yl]-2-(cyclohex-1-enyl)-pyridin-3-yl]-amide

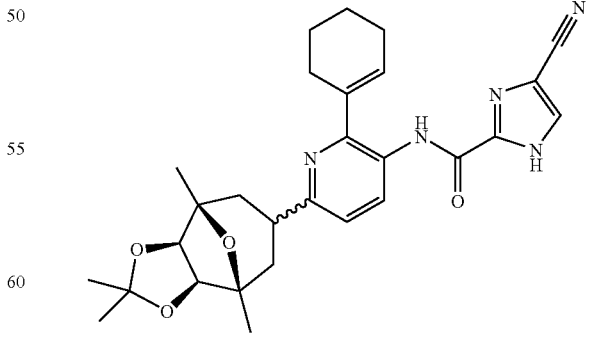

The title compounds were prepared from 4-cyano-1-(2-trimethylsilanyl-ethoxymethyl)-1H-imidazole-2-carboxylic acid[6-[(3-exo)-6-exo,7-exo-(isopropylidinedioxy)-1,5-dimethyl-8-oxa-bicyclo[3.2.1]oct-3-yl]-2-(cyclohex-1- enyl)-pyridin-3-yl]-amide and 4-cyano-1-(2-trimethylsilanyl-ethoxymethyl)-1H-imidazole-2-carboxylic acid[6-[(3-endo)-6-exo,7-exo-(isopropylidinedioxy)-1,5-dimethyl-8-oxa-bicyclo[3.2.1]oct-3-yl]-2-(cyclohex-1-enyl)-pyridin-3-yl]-amide (as prepared in the previous step) according to the procedure of Example 2, step (b), substituting DMF for THF. Mass spectrum (APCI, m/z): Calcd. for $C_{28}H_{33}N_5O_4$, 504.3 (M+H), found 504.3.

d) 4-Cyano-1H-imidazole-2-carboxylic acid[2-cyclohex-1-enyl-6-[(3-exo)-(6-exo,7-exo-dihydroxy-1,5-dimethyl-8-oxa-bicyclo[3.2.1]oct-3-yl]-pyridin-3-yl]-amide trifluoroacetic acid salt and 4-Cyano-1H-imidazole-2-carboxylic acid[2-cyclohex-1-enyl-6-[(3-endo)-(6-exo,7-exo-dihydroxy-1, 5-dimethyl-8-oxa-bicyclo[3.2.1]oct-3-yl]-pyridin-3-yl]-amide trifluoroacetic acid salt The title compounds were prepared from 4-cyano-1H-imidazole-2-carboxylic acid [6-[(3-exo)-6-exo,7-exo-(isopropylidinedioxy)-1,5-dimethyl-8-oxa-bicyclo[3.2.1]oct-3-yl]-2-(cyclohex-1-enyl)-pyridin-3-yl]-amide and 4-cyano-1H-imidazole-2-carboxylic acid[6-[(3-endo)-6-exo,7-exo-(isopropylidinedioxy)-1,5-dimethyl-8-oxa-bicyclo[3.2.1]oct-3-yl]-2-(cyclohex-1-enyl)-pyridin-3-yl]-amide (as prepared in the previous step) according to the procedure of Example 18. A 2:1 mixture of isomers was obtained. Major isomer: $^1$H-NMR (CD$_3$OD; 400 MHz): δ 8.88-8.77 (m, 1H), 8.07 (s, 1H), 7.66-7.59 (m, 1H), 6.26-6.19 (m, 1H), 4.14-3.96 (m, 2H), 3.40-3.12 (m, 1H), 2.50-2.40 (m, 2H), 2.40-2.32 (m, 2H), 2.08-1.98 (m, 2H), 1.95-1.73 (m, 6H), 1.33 (s, 6H). Mass spectrum (APCI, m/z): Calcd. for $C_{25}H_{29}N_5O_4$, 464.2 (M+H), found 464.3.

Example 20

4-Cyano-1H-imidazole-2-carboxylic acid[(4-cis)-(2-cis,6-cis-bis-hydroxymethyl-2,6-dimethyl-tetrahydro-pyran-4-yl)-2-(4,4dimethyl-cyclohex-1-enyl)-pyridin-3-yl]-amide trifluoroacetic acid salt and 4-Cyano-1H-imidazole-2-carboxylic acid[(4-trans)-(2-cis,6-cis-bis-hydroxymethyl-2,6-dimethyl-tetrahydro-pyran-4-yl)-2-(4,4-dimethyl-cyclohex-1-enyl)-pyridin-3-yl]-amide trifluoroacetic acid salt

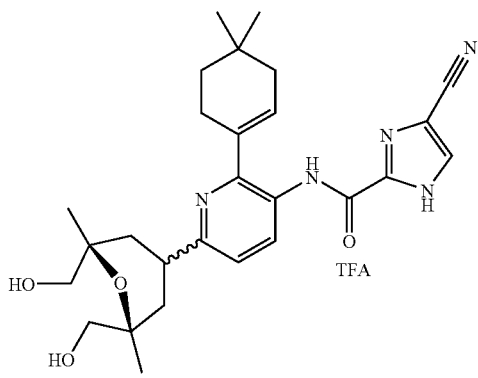

A solution of 4-cyano-1H-imidazole-2-carboxylic acid[6-(6-exo,7-exo-dihydroxy-1,5-dimethyl-8-oxa-bicyclo[3.2.1]oct-3-yl)-2-(4,4-dimethyl-cyclohex-1-enyl)-pyridin-3-yl]-amide trifluoroacetic acid salt (235 mg, 0.479 mmol, as prepared in Example 18) in MeOH (20 mL) and water (2 mL) was treated with NaIO$_4$ (154 mg, 0.718 mmol) at RT for 20 min. NaBH$_4$ (54.3 mg, 1.44 mmol) was added, and the mixture stirred for 20 min. The mixture was quenched with NaOH (3 mL, 2M aqueous) and poured into EtOAc (75 mL). The organic layer were washed with 1M aq HCl, satd aq NaHCO$_3$, and brine (1×25 mL each). The combined aqueous layers were extracted with EtOAc (3×25 mL), and the combined organic layers were dried over MgSO$_4$ and concentrated in vacuo. The residue was purified on a 40-g Sepra Si 50 SPE column (Isco system: Flow rate=40 mL/min; Eluent=50% EtOAc-hexane for 0-5 min, then 50-100% EtOAc-hexane for 5-30 min, 100% EtOAc for 10 min, then 10% MeOH-EtOAc until all peaks eluted). The fractions containing the title compound were further purified by RP-HPLC (C18) with 10-80% CH$_3$CN in 0.1% TFA/H$_2$O over 25 min to afford the title compound (28.0 mg, 12%) as a white solid. $^1$H-NMR (CD$_3$OD; 400 MHz): δ 9.03 (d, 1H, J=8.8 Hz), 8.08 (s, 1H), 7.78 (d, 1H, J=8.8 Hz), 6.28-6.22 (m, 1H), 3.75-3.65 (m, 1H), 3.52-3.45 (m, 2H), 3.32-3.27 (m, 2H), 2.54-2.45 (m, 2H), 2.22-2.16 (m, 2H), 1.97-1.87 (m, 2H), 1.78-1.70 (m, 2H), 1.70-1.63 (m, 2H), 1.35 (s, 6H), 1.14 (s, 6H). Mass spectrum (ESI, m/z): Calcd. for $C_{27}H_{35}N_5O_4$, 494.3 (M+H), found 494.3.

Example 21

4-Cyano-1H-imidazole-2-carboxylic acid[2-(4,4-dimethyl-cyclohex-1-enyl)-6-(2,2,6,6-tetramethyl-1,1-dioxo-hexahydro-1$\lambda^6$-thiopyran-4-yl)-pyridin-3-yl]-amide

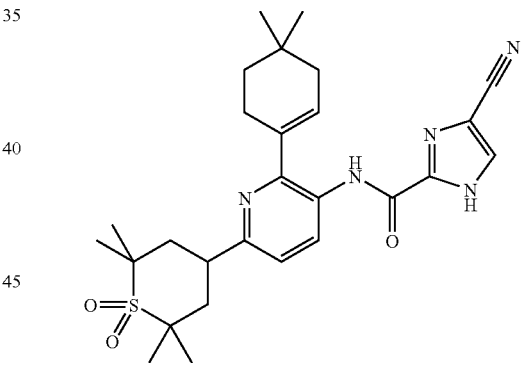

a) 1,1,2,2,3,3,4,4,4-Nonafluoro-butane-1-sulfonic acid 2,2,6,6-tetramethyl-3,6-dihydro-2H-thiopyran-4-yl ester

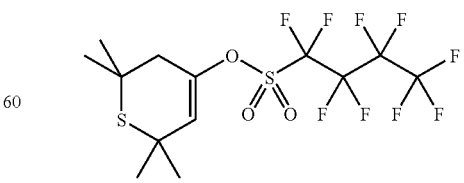

The title compound was prepared from 2,2,6,6-tetramethyl-tetrahydro-thiopyran-4-one (*J. Org. Chem.* (1970), 35(3), 592) according to the procedure of Example 15, step (a). ¹H-NMR (CDCl₃; 400 MHz): δ 5.81-5.76 (m, 1H), 2.49 (d, 2H, J=1.6 Hz), 1.47 (s, 6H), 1.43 (s, 6H).

b) 4,4,5,5-Tetramethyl-2-(2,2,6,6-tetramethyl-3,6-dihydro-2H-thiopyran-4-yl)-[1,3,2]dioxaborolane

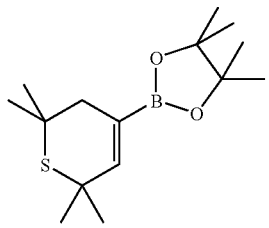

The title compound was prepared from 1,1,2,2,3,3,4,4,4-nonafluoro-butane-1-sulfonic acid 2,2,6,6-tetramethyl-3,6-dihydro-2H-thiopyran-4-yl ester (as prepared in the previous step) according to the procedure of Example 15, step (b). ¹H-NMR (CDCl₃; 400 MHz): δ 6.43-6.40 (m, 1H), 2.27 (d, 2H, J=2.0 Hz), 1.40 (s, 6H), 1.32 (s, 6H), 1.28 (s, 12H).

c) 5-Nitro-2-(2,2,6,6-tetramethyl-3,6-dihydro-2H-thiopyran-4-yl)-pyridine

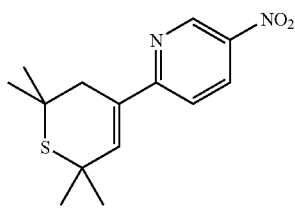 [SMILES: CC1(C)C=C(c2ccc([N+](=O)[O-])cn2)CC(C)(C)S1]

The title compound was prepared from 4,4,5,5-tetramethyl-2-(2,2,6,6-tetramethyl-3,6-dihydro-2H-thiopyran-4-yl)-[1,3,2]dioxaborolane (as prepared in the previous step) and 2-bromo-5-nitro-pyridine according to the procedure of Example 15, step (c). Mass spectrum (ESI, m/z): Calcd. for $C_{14}H_{18}N_2O_2S$, 279.1 (M+H), found 279.2.

d) 5-Nitro-2-(2,2,6,6-tetramethyl-1,1-dioxo-1,2,3,6-tetrahydro-1λ⁶-thiopyran-4-yl)-pyridine

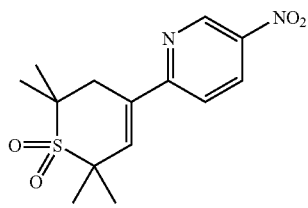 [SMILES: CC1(C)C=C(c2ccc([N+](=O)[O-])cn2)CC(C)(C)S1(=O)=O]

A solution of 5-nitro-2-(2,2,6,6-tetramethyl-3,6-dihydro-2H-thiopyran-4-yl)-pyridine (0.300 g, 1.08 mmol, as prepared in the previous step) in MeOH (15 mL) was cooled to 0° C. and treated with oxone (984 mg, 3.23 mmol based on KHSO₅ content) as a solution in water (1.5 mL). The ice bath was removed, and the mixture was allowed to stir at RT for 1 h. The mixture was diluted with water and extracted with CH₂Cl₂ (2×). The combined organic layers were dried over MgSO₄ and concentrated in vacuo. The residue was purified on a 25-g Sepra Si 50 SPE column (Isco system: Flow rate=20 mL/min; Eluent=5% EtOAc-hexane for 0-3 min, then 5-15% EtOAc-hexane for 5-30 min) to afford the title product (322 mg, 96%) as an off-white solid. Mass spectrum (ESI, m/z): Calcd. for $C_{14}H_{18}N_2O_4S$, 311.1 (M+H), found 311.0.

e) 6-(2,2,6,6-Tetramethyl-1,1-dioxo-hexahydro-1λ⁶-thiopyran-4-yl)-pyridin-3-ylamine

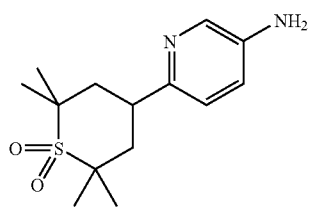 [SMILES: CC1(C)CC(c2ccc(N)cn2)CC(C)(C)S1(=O)=O]

A solution of 5-nitro-2-(2,2,6,6-tetramethyl-1,1-dioxo-1,2,3,6-tetrahydro-1λ⁶-thiopyran-4-yl)-pyridine (322 mg, 1.04 mmol, as prepared in the previous step) in MeOH (10 mL) was hydrogenated with 5% Pd/C and 1 atm H₂ at RT for 17 h. The mixture was filtered through Celite, and the filter cake was washed with MeOH. The solvents were evaporated in vacuo. The residue was purified on a 25-g Sepra Si 50 SPE column (Isco system: Flow rate=20 mL/min; Eluent=10% EtOAc-hexane for 0-3 min, then 10-50% EtOAc-hexane for 5-30 min, then 50-65% EtOAc-hexane over 40 min, then 65-100% EtOAc-hexane over 40 min) to afford the title compound (187 mg, 64%) as an off-white solid. Mass spectrum (ESI, m/z): Calcd. for $C_{14}H_{22}N_2O_2S$, 283.1 (M+H), found 283.1.

f) 2-Bromo-6-(2,2,6,6-tetramethyl-1,1-dioxo-hexahydro-1λ⁶-thiopyran-4-yl)-pyridin-3-ylamine

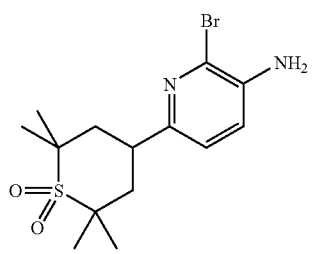 [SMILES: CC1(C)CC(c2ccc(N)c(Br)n2)CC(C)(C)S1(=O)=O]

The title compound was prepared from 6-(2,2,6,6-tetramethyl-1,1-dioxo-hexahydro-1λ⁶-thiopyran-4-yl)-pyridin-3-ylamine (as prepared in the previous step) according to the procedure of Example 17, step (d). Mass spectrum (ESI, m/z): Calcd. for $C_{14}H_{21}N_2O_2SBr$, 361.1/363.1 (M+H), found 361.1/363.1.

g) 2-(4,4-Dimethyl-cyclohex-1-enyl)-6-(2,2,6,6-tetramethyl-1,1-dioxo-hexahydro-1λ⁶-thiopyran-4-yl)-pyridin-3-ylamine

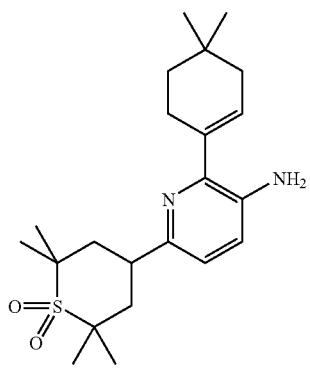 [SMILES: CC1(C)CC=C(c2nc(C3CC(C)(C)S(=O)(=O)C(C)(C)C3)ccc2N)CC1]

The title compound was prepared from 2-bromo-6-(2,2,6,6-tetramethyl-1,1-dioxo-hexahydro-1λ⁶-thiopyran-4-yl)-pyridin-3-ylamine (as prepared in the previous step) and 4,4-dimethyl-cyclohex-1-enyl-4,4,5,5-tetramethyl-[1,3,2]dioxaborolane according to the procedure of Example 15, step (f). Mass spectrum (APCI, m/z): Calcd. for $C_{22}H_{34}N_2O_2S$, 391.2 (M+H), found 391.3.

h) 4-Cyano-1-(2-trimethylsilanyl-ethoxymethyl)-1H-imidazole-2-carboxylic acid[2,(4,4-dimethyl-cyclohex-1-enyl)-6-(2,2,6,6-tetramethyl-1,1-dioxo-hexahydro-1λ⁶-thiopyran-4-yl)-pyridin-3-yl]-amide

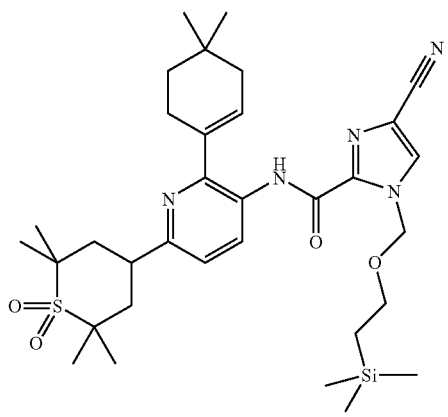 [SMILES: CC1(C)CC=C(c2nc(C3CC(C)(C)S(=O)(=O)C(C)(C)C3)ccc2NC(=O)c2nc(C#N)cn2COCC[Si](C)(C)C)CC1]

The title compound was prepared from 2-(4,4-dimethyl-cyclohex-1-enyl)-6-(2,2,6,6-tetramethyl-1,1-dioxo-hexahydro-1λ⁶-thiopyran-4-yl)-pyridin-3-ylamine (as prepared in the previous step) according to the procedure of Example 1, step (b). Mass spectrum (ESI, m/z): Calcd. for $C_{33}H_{49}N_5O_4SSi$, 640.3 (M+H), found 640.3.

i) 4-Cyano-1H-imidazole-2-carboxylic acid[2-(4,4-dimethyl-cyclohex-1-enyl)-6-(2,2,6,6-tetramethyl-1,1-dioxo-hexahydro-1λ⁶-thiopyran-4-yl)-pyridin-3-yl]-amide The title compound was prepared from 4-cyano-1-(2-trimethylsilanyl-ethoxymethyl)-1H-imidazole-2-carboxylic acid [2,(4,4-dimethyl-cyclohex-1-enyl)-6-(2,2,6,6-tetramethyl-1,1-dioxo-hexahydro-1λ⁶-thiopyran-4-yl)-pyridin-3-yl]-amide (as prepared in the previous step) according to the procedure of Example 1, step (c) followed by formation of the free base with NaHCO₃. ¹H-NMR (CDCl₃; 400 MHz): δ 9.76 (s, 1H), 8.77 (d, 1H, J=9.2 Hz), 7.74 (s, 1H), 7.40 (d, 1H, J=9.2 Hz), 6.02-5.95 (m, 1H), 3.48-3.37 (m, 1H), 2.60-2.42 (m, 4H), 2.20-2.13 (m, 2H), 2.03-1.95 (m, 2H), 1.68 (s, 6H), 1.67-1.62 (m, 2H), 1.43 (s, 6H), 1.13 (s, 6H). Mass spectrum (ESI, m/z): Calcd. for $C_{27}H_{35}N_5O_3S$, 510.3 (M+H), found 510.3.

Example 22

4-Cyano-1H-imidazole-2-carboxylic acid[2-(4,4-dimethyl-cyclohex-1-enyl)-4-(2,2,6,6-tetramethyl-1,1-dioxo-hexahydro-1λ⁶-thiopyran-4-yl)-phenyl]-amide

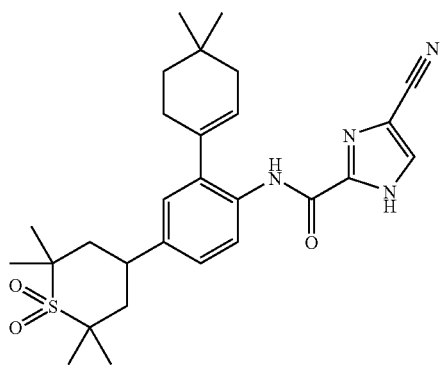 [SMILES: CC1(C)CC=C(c2cc(C3CC(C)(C)S(=O)(=O)C(C)(C)C3)ccc2NC(=O)c2nc(C#N)c[nH]2)CC1]

a) 4-(2,2,6,6-Tetramethyl-3,6-dihydro-2H-thiopyran-4-yl)-phenylamine

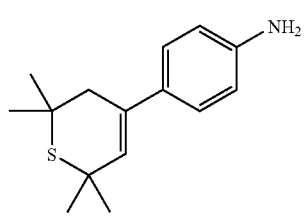 [SMILES: CC1(C)C=C(c2ccc(N)cc2)CC(C)(C)S1]

The title compound was prepared from 1,1,2,2,3,3,4,4,4-nonafluoro-butane-1-sulfonic acid 2,2,6,6-tetramethyl-3,6-dihydro-2H-thiopyran-4-yl ester (as prepared in Example 21, step (a)) and 4-(4,4,5,5-tetramethyl-[1,3,2]dioxaborolan-2-yl)-phenylamine according to the procedure of Example 15, step (c). Mass spectrum (ESI, m/z): Calcd. for $C_{15}H_{21}NS$, 248.1 (M+H), found 248.2.

b) 4-(2,2,6,6-Tetramethyl-1,1-dioxo-1,2,3,6-tetrahydro-1λ⁶-thiopyran-4-yl)-phenylamine

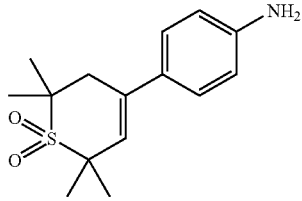 [SMILES: CC1(C)C=C(c2ccc(N)cc2)CC(C)(C)S1(=O)=O]

The title compound was prepared from 4-(2,2,6,6-tetramethyl-3,6-dihydro-2H-thiopyran-4-yl)-phenylamine (as prepared in the previous step) according to the procedure of Example 21, step (d). Mass spectrum (APCI, m/z): Calcd. for $C_{15}H_{21}NO_2S$, 280.1 (M+H), found 280.2.

c) 4-(2,2,6,6-Tetramethyl-1,1-dioxo-hexahydro-1λ⁶-thiopyran-4-yl)-phenylamine

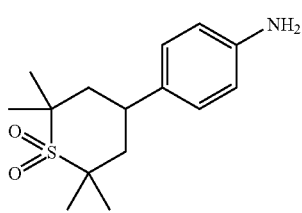 [SMILES: CC1(C)CC(c2ccc(N)cc2)CC(C)(C)S1(=O)=O]

The title compound was prepared from 4-(2,2,6,6-tetramethyl-1,1-dioxo-1,2,3,6-tetrahydro-1λ⁶-thiopyran-4-yl)-phenylamine (as prepared in the previous step) according to the procedure of Example 21, step (e). Mass spectrum (APCI, m/z): Calcd. for $C_{15}H_{23}NO_2S$, 282.1 (M+H), found 282.3.

d) 2-Bromo-4-(2,2,6,6-tetramethyl-1,1-dioxo-hexahydro-1λ⁶-thiopyran-4-yl)-phenylamine

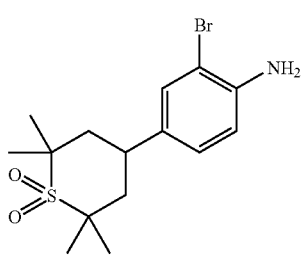 [SMILES: CC1(C)CC(c2ccc(N)c(Br)c2)CC(C)(C)S1(=O)=O]

The title compound was prepared from 4-(2,2,6,6-tetramethyl-1,1-dioxo-hexahydro-1λ⁶-thiopyran-4-yl)-phenylamine (as prepared in the previous step) according to the procedure of Example 17, step (d). Mass spectrum (ESI, m/z): Calcd. for $C_{15}H_{22}NO_2SBr$, 360.1/362.2 (M+H), found 360.2/362.2.

e) 2-(4,4-Dimethyl-cyclohex-1-enyl)-4-(2,2,6,6-tetramethyl-1,1-dioxo-hexahydro-1λ⁶-thiopyran-4-yl)-phenylamine

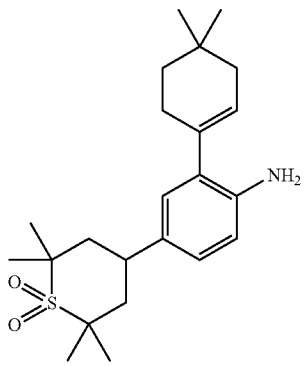 [SMILES: CC1(C)CC=C(c2cc(C3CC(C)(C)S(=O)(=O)C(C)(C)C3)ccc2N)CC1]

The title compound was prepared from 2-bromo-4-(2,2,6,6-tetramethyl-1,1-dioxo-hexahydro-1λ⁶-thiopyran-4-yl)-phenylamine (as prepared in the previous step) according to the procedure of Example 15, step (f). Mass spectrum (APCI, m/z): Calcd. for $C_{23}H_{35}NO_2S$, 390.2 (M+H), found 390.3.

f) 4-Cyano-1-(2-trimethylsilanyl-ethoxymethyl)-1H-imidazole-2-carboxylic acid[2-(4,4-dimethyl-cyclohex-1-enyl)-4-(2,2,6,6-tetramethyl-1,1-dioxo-hexahydro-1λ⁶-thiopyran-4-yl)-phenyl]-amide

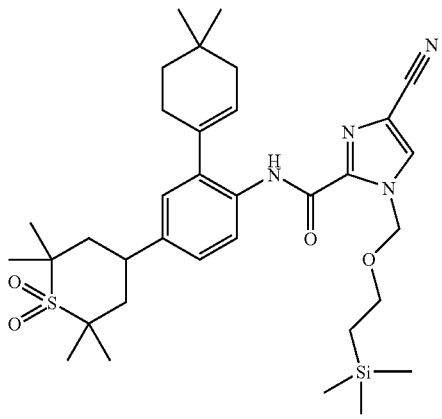 [SMILES: CC1(C)CC=C(c2cc(C3CC(C)(C)S(=O)(=O)C(C)(C)C3)ccc2NC(=O)c2nc(C#N)cn2COCC[Si](C)(C)C)CC1]

The title compound was prepared from 2-(4,4-dimethyl-cyclohex-1-enyl)-4-(2,2,6,6-tetramethyl-1,1-dioxo-hexahydro-1λ⁶-thiopyran-4-yl)-phenylamine (as prepared in the previous step) according to the procedure of Example 1, step (b). Mass spectrum (ESI, m/z): Calcd. for $C_{34}H_{50}N_4O_4SSi$, 639.3 (M+H), found 639.0.

g) 4-Cyano-1H-imidazole-2-carboxylic acid[2-(4,4-dimethyl-cyclohex-1-enyl)-4-(2,2,6,6-tetramethyl-1,1-dioxo-hexahydro-1λ⁶-thiopyran-4-yl)-phenyl]-amide The title compound was prepared from 4-cyano-1-(2-trimethylsilanyl-ethoxymethyl)-1H-imidazole-2-carboxylic acid

[2-(4,4-dimethyl-cyclohex-1-enyl)-4-(2,2,6,6-tetramethyl-1,1-dioxo-hexahydro-1λ⁶-thiopyran-4-yl)-phenyl]-amide (as prepared in the previous step) according to the procedure in Example 1, step (c). ¹H-NMR (CDCl₃; 400 MHz): δ 9.62 (s, 1H), 8.41 (d, 1H, J=8.0 Hz), 7.73 (s, 1H), 7.41 (d, 1H, J=8.0 Hz) 7.05 (d, 1H, J=2.4 Hz), 5.81-5.75 (m, 1H), 3.25-3.14 (m, 1H), 2.55-2.42 (m, 2H), 2.34-2.26 (m, 2H), 2.15-2.08 (m, 2H), 1.93-1.85 (m, 2H), 1.66 (s, 6H) 1.64-1.57 (m, 2H), 1.43 (s, 6H), 1.12 (s, 6H). Mass spectrum (APCI, m/z): Calcd. for $C_{28}H_{36}N_4O_3S$, 509.3 (M+H), found 509.1.

Example 23

4-Cyano-1H-imidazole-2-carboxylic acid[2-(4,4-dimethyl-cyclohex-1-enyl)-6-(2,2,6,6-tetramethyl-tetrahydro-pyran-4-yl)-pyridin-3-yl]-amide hydrochloride salt

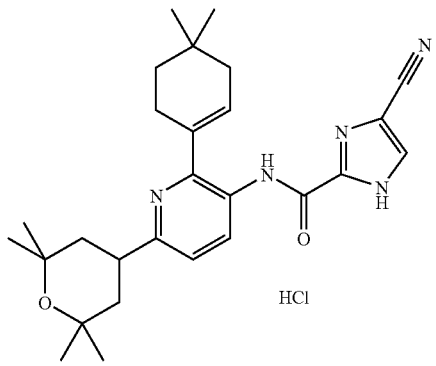 [SMILES: CC1(C)CC=C(c2nc(C3CC(C)(C)OC(C)(C)C3)ccc2NC(=O)c2nc(C#N)c[nH]2)CC1 ; Cl]

A solution of 4-cyano-1H-imidazole-2-carboxylic acid[2-(4,4-dimethyl-cyclohex-1-enyl)-6-(2,2,6,6-tetramethyl-tetrahydro-pyran-4-yl)-pyridin-3-yl]-amide (49.2 mg, 0.107 mmol, as prepared in Example 15, step (h)) in EtOH (2 mL) was treated with HCl (26.6 µL, 0.107 mmol, 4 M in dioxane) at room temperature for 1.5 h. The solvents were evaporated in vacuo, and the residue was dried under high vacuum overnight. The solid was dissolved in a minimum amount of EtOH (900 µL) with sonication and heating. While warm, the solution was slowly treated with hexanes (3 mL) to the cloud point. The mixture was heated again until clear, the sides of the vial were scratched, and the mixture was allowed to cool. The solid was filtered and air-dried to afford the title compound (20mg, 38%) as white crystals. ¹H-NMR (CD₃OD; 400 MHz): δ 9.17 (d, 1H, J=8.4 Hz), 8.10 (s, 1H), 7.95 (d, 1H, J=8.4 Hz), 6.38-6.32 (m, 1H), 3.76-3.65 (m, 1H), 2.54-2.46 (m, 2H), 2.25-2.19 (m, 2H), 1.98-1.91 (m, 2H), 1.76-1.65 (m, 4H), 1.43 (s, 6H), 1.30 (s, 6H), 1.15 (s, 6H). Mass spectrum (APCI, m/z): Calcd. for $C_{27}H_{35}N_5O_2$, 462.3 (M+H), found 462.3.

Example 24

4-Cyano-1H-imidazole-2-carboxylic acid[2-(4,4-dimethyl-cyclohex-1-enyl)-6-(2,2,6,6-tetramethyl-tetrahydro-pyran-4-yl)-pyridin-3-yl]-amide methanesulfonic acid salt

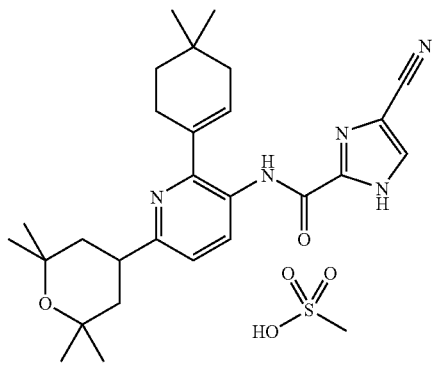

A solution of 4-cyano-1H-imidazole-2-carboxylic acid[2-(4,4-dimethyl-cyclohex-1-enyl)-6-(2,2,6,6-tetramethyl-tetrahydro-pyran-4-yl)-pyridin-3-yl]-amide (50.0 mg, 0.108 mmol, as prepared in Example 15, step (h)) in EtOH (2 mL) was treated with methanesulfonic acid (7.0 µL, 0.108 mmol) at room temperature for 1 h. The solvents were evaporated in vacuo, and the residue was dried under high vacuum overnight. The solid was dissolved in a minimum amount of EtOH (2 mL) with sonication and heating. While warm, the solution was slowly treated with hexanes (3 mL) to the cloud point. The mixture was heated again until clear, the sides of the vial were scratched, and the mixture was allowed to cool. The solid was filtered and air-dried to afford the title compound (24 mg, 40%) as white crystals. Mass spectrum (APCI, m/z): Calcd. for $C_{27}H_{35}N_5O_2$, 462.3 (M+H), found 462.3.

Example 25

4-Cyano-1H-imidazole-2-carboxylic acid[2-(4,4-dimethyl-cyclohex-1-enyl)-6-(2,2,6,6-tetramethyl-tetrahydro-pyran-4-yl)-pyridin-3-yl]-amide(1S)-(+)-10-camphorsulfonic acid salt

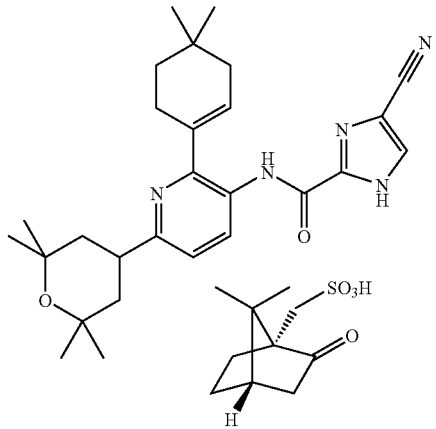

A solution of 4-cyano-1H-imidazole-2-carboxylic acid[2-(4,4-dimethyl-cyclohex-1-enyl)-6-(2,2,6,6-tetramethyl-tetrahydro-pyran-4-yl)-pyridin-3-yl]-amide (52.4 mg, 0.113 mmol, as prepared in Example 15, step (h)) in EtOH (2 mL) was treated with (1S)-(+)-10-camphorsulfonic acid (26.4 mg, 0.113 mmol) at room temperature for 1 h. The solvents were evaporated in vacuo, and the residue was dried under high vacuum overnight. The solid was dissolved in a minimum amount of EtOH (1 mL) with sonication and heating. While warm, the solution was slowly treated with hexanes until first precipitate was seen at the surface of the solution. The mixture was allowed to stir 30 min at room temperature while material continued to precipitate. The solid was filtered and air-dried to afford the title compound (66.2 mg, 84%) as white crystals. $^1$H-NMR (CD$_3$OD; 400 MHz): δ 9.17 (d, 1H, J=8.4 Hz), 8.10 (s, 1H), 7.95 (d, 1H, J=8.4 Hz), 6.39-6.32 (m, 1H), 3.76-3.64 (m, 1H), 3.38-3.34 (m, 2H), 2.80-2.75 (m, 1H), 2.75-2.65 (m, 1H), 2.54-2.45 (m, 2H), 2.40-2.30 (m, 1H), 2.25-2.18 (m, 2H), 2.10-2.00 (m, 2H), 1.98-1.86 (m, 3H), 1.76-1.66 (m, 4H), 1.65-1.56 (m, 1H), 1.47-1.38 (m, 7H), 1.30 (s, 6H), 1.15 (m, 9H), 0.87 (s, 3H). Mass spectrum (APCI, m/z): Calcd. for C$_{27}$H$_{35}$N$_5$O$_2$, 462.3 (M+H), found 462.3.

Example 26

N-(4-(8-oxabicyclo[3.2.1]octa-2,6-dien-3-yl)-2-(4,4-dimethylcyclohex-1-enyl)phenyl)-4-cyano-1H-imidazole-2-carboxamide (A) and N-(4-(8-oxabicyclo[3.2.1]octa-3,6-dien-3-yl)-2-(4,4dimethylcyclohex-1-enyl)phenyl)-4cyano-1H-imidazole-2-carboxamide (B)

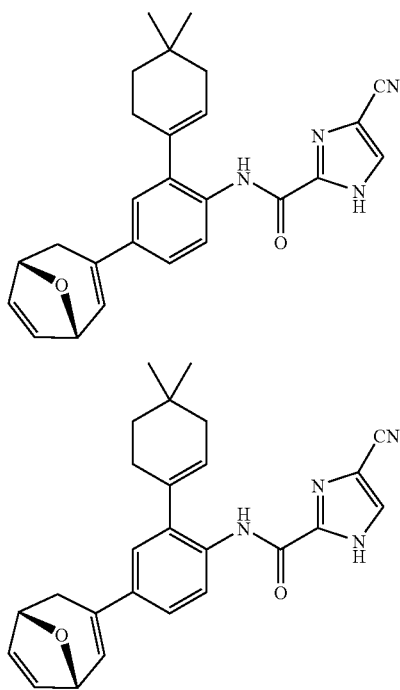

To a solution of 4-cyano-N-(2-(4,4-dimethylcyclohex-1-enyl)-4-(3-exo)-3-hydroxy-8-oxabicyclo[3.2.1]oct-6-en-3-yl)phenyl)-1H-imidazole-2-carboxamide (as prepared in Example 27, 37 mg, 0.083 mmol) in DCM (2 mL) at 0° C. was added thionyl chloride (20 mg, 0.16 mmol) in 0.5 mL of DCM. The reaction was allowed to warm to room temperature and then treated with MeLi-CuI complex (0.49 mmol) in 2 mL of THF. The reaction was stirred for 20 min and then quenched with saturated aqueous NH$_4$Cl (10 mL). The mixture was extracted with EtOAc (2×20 mL), dried (Na$_2$SO$_4$) and concentrated in vacuo. The crude product was purified by preparative thin layer chromatography (5% MeOH—CHCl$_3$) to afford 14 mg (40%) of the title compounds as a white solid. Mass spectrum (ESI, m/z): Calcd. for C$_{26}$H$_{26}$N$_4$O$_2$, 427.2 (M+H), found 427.1.

Example 27

4-Cyano-N-(2-(4,4-dimethylcyclohex-1-enyl)-4-((3-exo)-3-hydroxy-8-oxabicyclo[3.2.1]oct-6-en-3-yl)phenyl)-1H-imidazole-2-carboxamide

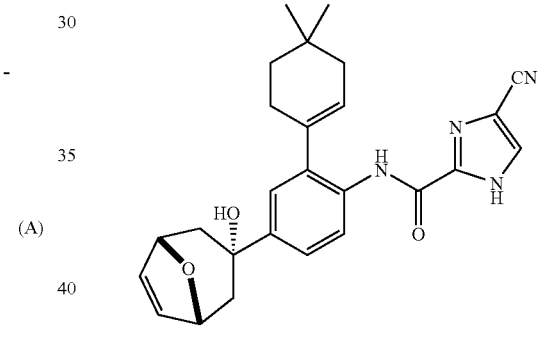

The title compound was prepared as described in Example 8, step b using 4-cyano-1H-imidazole-2-carboxylic acid[4-bromo-2-(4,4-dimethyl-cyclohex-1-enyl)-phenyl]-amide (as prepared in Example 1, step (c)) and 8-oxabicyclo[3.2.1]oct-6-en-3-one (*European Journal of Organic Chemistry* (2000), 12, 2195-2201); $^1$H NMR (400 MHz; DMSO-d$_6$) δ 9.72 (s, 1H), 8.22 (s, 1H), 7.93 (d, J=8.4 Hz, 1H) 7.30 (dd, J=8.4, 2.2 Hz, 1H) 7.22 (d, J=2.2 Hz, 1H), 6.27 (s, 2H), 5.65 (br s, 1H), 4.74 (d, J=4.0 Hz, 2 H), 4.49 (s, 1H), 2.16 (dd, J=14.2, 4.2 Hz, 4H), 1.96 (br s, 2 H), 1.68 (d, J=14.2 Hz, 2 H), 1.49 (t, J=6.2 Hz, 2H), 1.00 (s, 6H). Mass spectrum (ESI, m/z): Calcd. for C$_{26}$H$_{28}$N$_4$O$_3$, 445.2 (M+H), found 445.1.

Assignment of relative stereochemistry was made based on analogy to 4-cyano-1H-imidazole-2-carboxylic acid[2-(4,4-dimethyl-cyclohex-1-enyl)-4-[(3-exo)-3-hydroxy-1,5-bis-methoxymethyl-8-oxa-bicyclo[3.2.1]oct-6-en-3-yl]-phenyl]-amide (as prepared in Example 1, step (f)).

Example 28

4-Cyano-N-(2-(4,4dimethylcyclohex-1-enyl)-4-[(3-exo)-3-hydroxy-(2-endo-4-endo-dimethyl)-8-oxabicyclo[3.2.1]oct-6-en-3-yl)pheny])-1H-imidazole-2-carboxamide

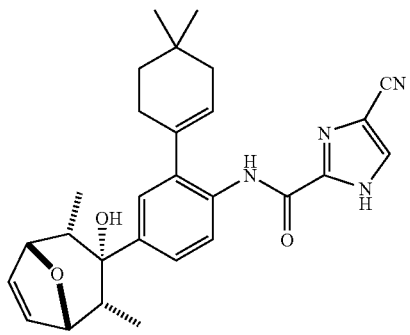

The title compound was prepared as described in Example 8, step b using 4-cyano-1H-imidazole-2-carboxylic acid[4-bromo-2-(4,4-dimethyl-cyclohex-1-enyl)-phenyl]-amide (as prepared in Example 1, step (c)) and 2-endo-4-endo-dimethyl-8-oxabicyclo[3.2.1]oct-6-en-3-one (*Tetrahedron* (1988), 44(16), 5151). $^1$H NMR (400 MHz; CD$_3$OD) δ 8.03 (d, J=8.3 Hz, 1H), 7.87 (s, 1H), 7.26 (dd, J=8.5, 2.2 Hz, 1H), 7.20 (d, J=2.2 Hz, 1H), 6.50 (s, 2H) 5.63 (dt, J=3.6, 1.8 Hz, 1H), 4.51 (d, J=3.5 Hz, 2H), 2.27-2.36 (m, 2H), 2.16-2.24 (m, 2H), 1.98 (d, J=3.5 Hz, 2H), 1.49 (t, J=6.3 Hz, 2H), 0.98 (s, 6H), 0.52-0.62 (m, 6H). Mass spectrum (ESI, m/z): Calcd. for C$_{28}$H$_{32}$N$_4$O$_3$, 473.2 (M+H), found 473.2.

Assignment of relative stereochemistry was made based on analogy to 4-cyano-1H-imidazole-2-carboxylic acid[2-(4,4-dimethyl-cyclohex-1-enyl)-4-[(3-exo)-3-hydroxy-1,5-bis-methoxymethyl-8-oxa-bicyclo[3.2.1]oct-6-en-3-yl]-phenyl]-amide (as prepared in Example 1, step (f)).

Example 29

4-Cyano-N-(2-(4,4dimethylcyclohex-1-enyl)-4-[(3-exo)-3-hydroxy-(2-endo,4endo-dimethyl)-1,5-dimethyl-8-oxabicyclo[3.2.1]octan-3-yl)pheny]-1H-imidazole-2-carboxamide

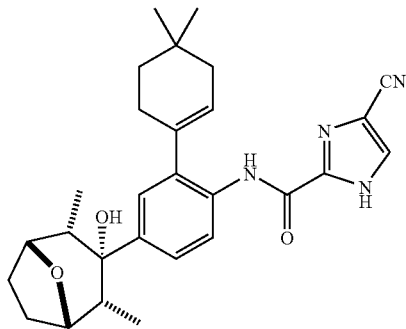

The title compound was prepared as described in Example 8, step b using 4-cyano-1H-imidazole-2-carboxylic acid[4-bromo-2-(4,4-dimethyl-cyclohex-1-enyl)-phenyl]-amide (as prepared in Example 1, step (c)) and 2-endo-4-endo-dimethyl-8-oxabicyclo[3.2.1]octan-3-one (*Tetrahedron* (1988), 44(16), 5151). $^1$H NMR (400 MHz; CD$_3$OD) δ 8.15 (d, J=8.59 Hz, 1 H), 8.00 (s, 1 H) 7.28-7.36 (m, 2 H) 5.76 (br s, 1 H), 4.18-4.22 (m, 2 H), 2.25-2.43 (m, 6 H), 2.10 (d, J=2.7 Hz, 2 H) 1.71-1.77 (m, 2 H), 1.62 (t, J=6.1 Hz, 2 H) 1.10 (s, 6 H) 0.68 (d, J=7.0 Hz, 6H). Mass spectrum (ESI, m/z): Calcd. for C$_{28}$H$_{34}$N$_4$O$_3$, 475.2 (M+H), found 475.2.

Assignment of relative stereochemistry was made based on analogy to 4-cyano-1H-imidazole-2-carboxylic acid[2-(4,4-dimethyl-cyclohex-1-enyl)-4-[(3-exo)-3-hydroxy-1,5-bis-methoxymethyl-8-oxa-bicyclo[3.2.1]oct-6-en-3-yl]-phenyl]-amide (as prepared in Example 1, step (f)).

Example 30

4-Cyano-N-(2-(4,4dimethylcyclohex-1-enyl)-4-[(3-exo)-3-hydroxy-(2-endo,4-endo-dimethyl)-1,5-dimethyl-8-oxabicyclo[3.2.1]oct-6-en-3-yl)phenyl)-1H-imidazole-2-carboxamide

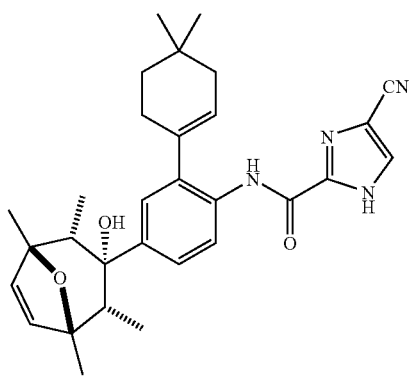

The title compound was prepared as described in Example 8, step b using 4-cyano-1H-imidazole-2-carboxylic acid[4-bromo-2-(4,4-dimethyl-cyclohex-1-enyl)-phenyl]-amide (as prepared in Example 1, step (c)) and 2-endo-4-endo-1,5-dimethyl-8-oxabicyclo[3.2.1]oct-6-en-3-one (*J Amer Chem Soc*, (1978), 100(6), 1765-77). $^1$H NMR (400 MHz; CD$_3$OD) δ 8.15 (d, J=8.5 Hz, 1H), 8.01 (s, 1H), 7.40 (dd, J=8.5, 2.2 Hz, 1H), 7.34 (d, J=2.2 Hz, 1H), 6.34 (s, 2H), 5.75 (m, 1H), 2.34 (d, J=1.7 Hz, 2H), 2.14-2.24 (m, 4H), 1.62 (t, J=6.3 Hz, 2H),1.39,(s, 6H),1.11 (s, 6H), 0.72 (d, J=7.3 Hz, 6H). Mass spectrum (ESI, m/z): Calcd. for C$_{30}$H$_{36}$N$_4$O$_3$, 501.2 (M+H), found 501.2.

Assignment of relative stereochemistry was made based on analogy to 4-cyano-1H-imidazole-2-carboxylic acid[2-(4,4-dimethyl-cyclohex-1-enyl)-4-[(3-exo)-3-hydroxy-1,5-bis-methoxymethyl-8-oxa-bicyclo[3.2.1]oct-6-en-3-yl]-phenyl]-amide (as prepared in Example 1, step (f)).

Example 31

4-Cyano-1H-imidazole-2-carboxylic acid[2-(4,4-dimethyl-cyclohex-1-enyl)-6-(2,2,6,6-tetramethyl-tetrahydro-pyran-4-yl)-pyridin-3-yl]-amide sulfate salt A suspension of 4-cyano-1H-imidazole-2-carboxylic acid [2-(4,4-dimethyl-cyclohex-1-enyl)-6-(2,2,6,6-tetramethyl-tetrahydro-pyran-4-yl)-pyridin-3-yl]-amide (24.8 mg, 0.0537 mmol), as prepared in Example 15, in acetonitrile (1.0 mL) was heated to yield a solution. To the solution was added a solution of concentrated sulfuric acid (0.0062 mL) in water (0.5 mL) at room temperature. The solution was reduced via evaporation with flowing nitrogen gas (approximately 1.0 mL). The solution was then allowed to sit overnight at room temperature in a sealed vial. The resulting crystals were then collected via filtration and air-dried. The white solid was characterized by Powder X-Ray Diffraction (PXRD), Differential Scanning Calorimetry (DSC), Thremogravimetric Analysis (TGA), and single-crystal X-ray diffraction. The DSC for the sulfate salt showed a 241 degree Celsius endotherm maximum. The PXRD of the sulfate salt product is shown in FIG. 1 and the prominent peaks are shown in the table below.

Peak Search Report (28 Peaks, Max P/N = 37.9)
[MT_1058_96_3.raw] rigaku_cu, comment line
PEAK: 21-pts/Parabolic Filter, Threshold = 0.0,
Cutoff = 0.0%, BG = 3/0.6, Peak-Top = Summit

| 2-Theta | d(Å) | BG | Height | I % | Area | I % | FWHM |
|---|---|---|---|---|---|---|---|
| 3.3108 | 26.6644 | 583 | 39 | 0.6 | 550 | 0.6 | 0.24 |
| 6.1903 | 14.266 | 926 | 1985 | 30.9 | 24961 | 29.2 | 0.214 |
| 6.5701 | 13.4421 | 744 | 6420 | 100 | 85576 | 100 | 0.227 |
| 9.2704 | 9.5319 | 666 | 343 | 5.3 | 7138 | 8.3 | 0.354 |
| 11.5099 | 7.6818 | 678 | 535 | 8.3 | 7650 | 8.9 | 0.243 |
| 12.4103 | 7.1264 | 723 | 454 | 7.1 | 5198 | 6.1 | 0.195 |
| 12.9899 | 6.8097 | 731 | 801 | 12.5 | 11747 | 13.7 | 0.249 |
| 14.0503 | 6.298 | 704 | 358 | 5.6 | 4649 | 5.4 | 0.221 |
| 14.7302 | 6.0088 | 710 | 316 | 4.9 | 4557 | 5.3 | 0.245 |
| 16.1501 | 5.4836 | 735 | 897 | 14 | 12087 | 14.1 | 0.229 |
| 16.8681 | 5.2518 | 842 | 117 | 1.8 | 890 | 1 | 0.129 |
| 17.3702 | 5.1011 | 816 | 1048 | 16.3 | 20457 | 23.9 | 0.332 |
| 18.5898 | 4.7691 | 809 | 1043 | 16.2 | 17554 | 20.5 | 0.286 |
| 19.8095 | 4.4781 | 829 | 1013 | 15.8 | 14571 | 17 | 0.245 |
| 20.8298 | 4.261 | 899 | 335 | 5.2 | 6464 | 7.6 | 0.328 |
| 21.1102 | 4.205 | 930 | 171 | 2.7 | 6551 | 7.7 | 0.651 |
| 21.6705 | 4.0975 | 978 | 537 | 8.4 | 10680 | 12.5 | 0.338 |
| 22.111 | 4.0169 | 982 | 236 | 3.7 | 4437 | 5.2 | 0.32 |
| 22.8897 | 3.882 | 889 | 95 | 1.5 | 1587 | 1.9 | 0.284 |
| 23.6107 | 3.765 | 867 | 615 | 9.6 | 12474 | 14.6 | 0.345 |
| 24.9701 | 3.5631 | 771 | 351 | 5.5 | 5360 | 6.3 | 0.26 |
| 25.6908 | 3.4647 | 746 | 33 | 0.5 | 422 | 0.5 | 0.217 |
| 26.4892 | 3.3621 | 722 | 85 | 1.3 | 1205 | 1.4 | 0.241 |
| 27.3297 | 3.2606 | 704 | 211 | 3.3 | 3384 | 4 | 0.273 |
| 28.3492 | 3.1456 | 729 | 169 | 2.6 | 3085 | 3.6 | 0.31 |
| 29.1107 | 3.065 | 736 | 98 | 1.5 | 1081 | 1.3 | 0.188 |
| 29.8104 | 2.9946 | 681 | 135 | 2.1 | 2593 | 3 | 0.327 |
| 31.1698 | 2.8671 | 654 | 50 | 0.8 | 815 | 1 | 0.277 |

Representative 2-Theta peaks of the sulfate salt product are shown below:

6.1903
6.5701
11.5099
12.4103
12.9899
14.0503
14.7302
16.1501
17.3702
18.5898
19.8095
21.6705
23.6107
24.9701

Example 32

4-Cyano-1H-imidazole-2-carboxylic acid[2-(4,4-dimethyl-cyclohex-1-enyl)-6-(2,2,6,6-tetramethyl-tetrahydro-pyran-4-yl)-pyridin-3-yl]-amide sodium salt (Form A)

Figure 2:
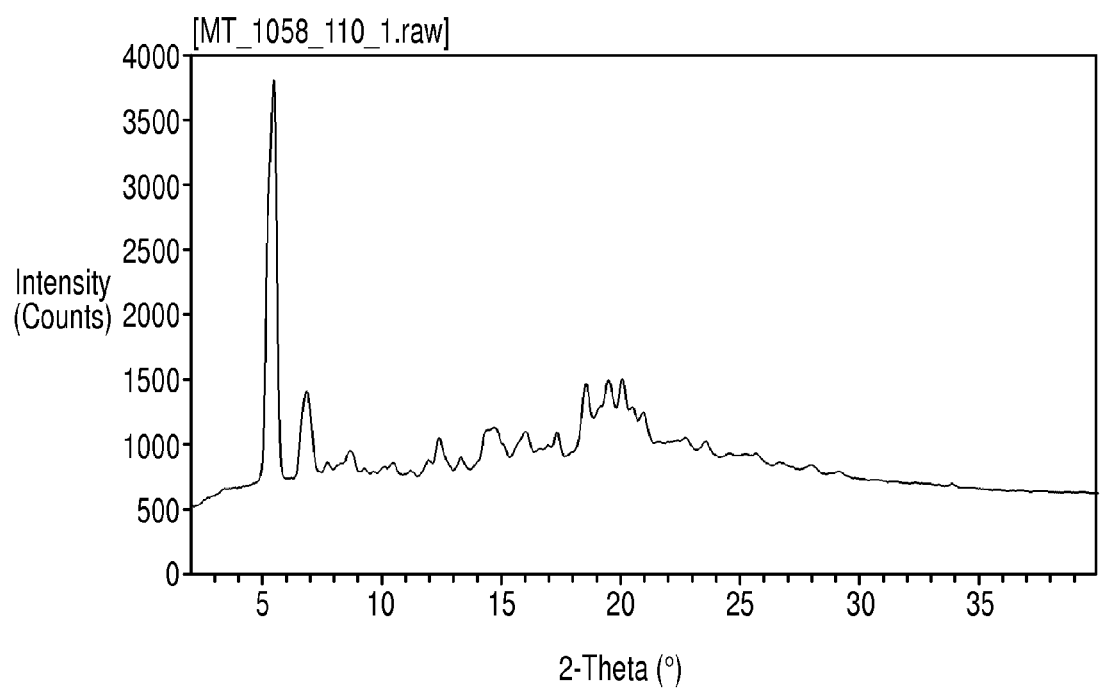
FIG. 2 is an X-ray powder diffraction pattern of the compound of Example 32 expressed in terms of °2θ.

To a suspension of 4-cyano-1H-imidazole-2-carboxylic acid[2-(4,4-dimethyl-cyclohex-1-enyl)-6-(2,2,6,6-tetramethyl-tetrahydro-pyran-4-yl)-pyridin-3-yl]-amide (23.1 mg, 0.0500 mmol), as prepared in Example 15, in ethanol (1.0 mL) was added a solution of sodium hydroxide (1.0N; 0.055 mL; 0.055 mmol). The solution was allowed to evaporate in an open vial at room temperature. A white crystalline solid resulted and was characterized by PXRD and TGA (6.1% loss of mass). The PXRD of Form A of the sodium salt is shown in FIG. 2 and the prominent peaks provided in the table below.

Peak Search Report (27 Peaks, Max P/N = 25.0)
[MT_1058_110_1.raw] rigaku_cu, comment line
PEAK: 23-pts/Parabolic Filter, Threshold = 1.0,
Cutoff = 0.0%, BG = 3/0.6, Peak-Top = Summit

| 2-Theta | d(Å) | BG | Height | I % | Area | I % | FWHM |
|---|---|---|---|---|---|---|---|
| 5.47 | 16.1427 | 731 | 3085 | 100 | 67721 | 100 | 0.373 |
| 6.8695 | 12.8569 | 761 | 648 | 21 | 15965 | 23.6 | 0.419 |
| 7.7112 | 11.4552 | 794 | 67 | 2.2 | 664 | 1 | 0.168 |
| 8.6899 | 10.1673 | 803 | 144 | 4.7 | 3133 | 4.6 | 0.37 |
| 9.2697 | 9.5325 | 780 | 32 | 1 | 302 | 0.4 | 0.16 |
| 10.0912 | 8.7583 | 775 | 49 | 1.6 | 2004 | 3 | 0.695 |
| 10.4306 | 8.4741 | 770 | 85 | 2.8 | 2056 | 3 | 0.411 |
| 11.208 | 7.888 | 758 | 36 | 1.2 | 483 | 0.7 | 0.228 |
| 11.9471 | 7.4016 | 832 | 49 | 1.6 | 419 | 0.6 | 0.145 |
| 12.3902 | 7.1379 | 808 | 241 | 7.8 | 5472 | 8.1 | 0.386 |
| 13.3096 | 6.6468 | 803 | 93 | 3 | 1324 | 2 | 0.242 |
| 14.3697 | 6.1588 | 914 | 191 | 6.2 | 6112 | 9 | 0.544 |
| 14.7099 | 6.0171 | 898 | 229 | 7.4 | 9027 | 13.3 | 0.67 |
| 16.0095 | 5.5314 | 927 | 171 | 5.5 | 4263 | 6.3 | 0.424 |
| 16.9507 | 5.2263 | 933 | 63 | 2 | 3406 | 5 | 0.919 |
| 17.3107 | 5.1185 | 927 | 169 | 5.5 | 2823 | 4.2 | 0.284 |
| 18.5489 | 4.7795 | 1117 | 351 | 11.4 | 5454 | 8.1 | 0.264 |
| 19.4892 | 4.551 | 1264 | 228 | 7.4 | 4366 | 6.4 | 0.326 |
| 20.0508 | 4.4247 | 1264 | 240 | 7.8 | 3965 | 5.9 | 0.281 |
| 20.491 | 4.3307 | 1241 | 46 | 1.5 | 1090 | 1.6 | 0.403 |
| 20.9324 | 4.2403 | 1128 | 119 | 3.9 | 1642 | 2.4 | 0.235 |
| 22.7096 | 3.9124 | 983 | 71 | 2.3 | 1451 | 2.1 | 0.347 |
| 23.5503 | 3.7746 | 932 | 90 | 2.9 | 1647 | 2.4 | 0.311 |
| 25.6499 | 3.4701 | 875 | 56 | 1.8 | 1475 | 2.2 | 0.448 |
| 26.6305 | 3.3446 | 829 | 32 | 1 | 732 | 1.1 | 0.389 |
| 28.0294 | 3.1807 | 786 | 50 | 1.6 | 1186 | 1.8 | 0.403 |
| 29.1306 | 3.063 | 753 | 38 | 1.2 | 895 | 1.3 | 0.4 |

Representative 2-Theta peaks of the Form A sodium salt product are shown below:

5.470
6.870
8.690
12.390
14.370
14.710
16.010
17.311
18.549
19.489
20.051

Example 33

4-Cyano-1H-imidazole-2-carboxylic acid[2-(4,4-dimethyl-cyclohex-1-enyl)-6-(2,2,6,6-tetramethyl-tetrahydro-pyran-4-yl)-pyridin-3-yl]-amide sodium salt (Form B)

Figure 3:
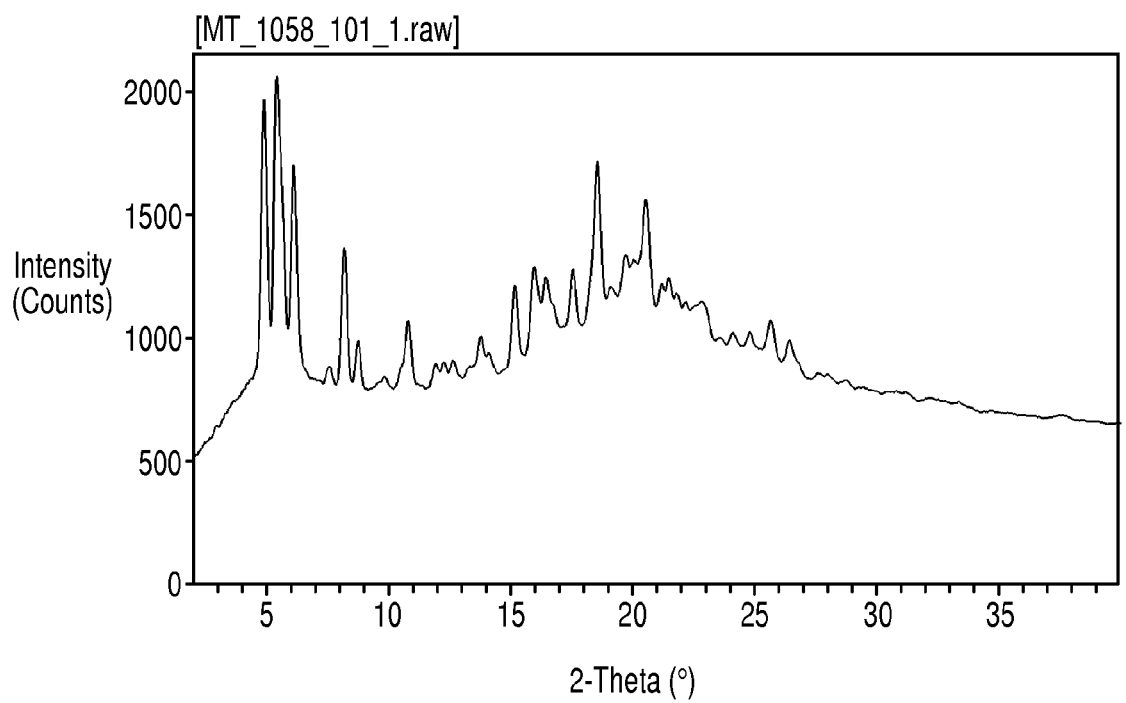
FIG. 3 is an X-ray powder diffraction pattern of the compound of Example 33 expressed in terms of °2θ.

To a suspension of 4-cyano- 1H-imidazole-2-carboxylic acid[2-(4,4-dimethyl-cyclohex-1-enyl)-6-(2,2,6,6-tetramethyl-tetrahydro-pyran-4-yl)-pyridin-3-yl]-amide (26.1 mg, 0.0556 mmol), as prepared in Example 15, in acetonitrile (1.0 mL) was added a solution of sodium hydroxide (1.0N; 0.062 mL; 0.062 mmol) to give a hazy solution. Water (0.44 mL) was then added causing the solution to become clear. The volatiles were then evaporated to give an amorphous solid. The solid was then dissolved in diethyl ether (1.0 mL) and propylene glycol (0.009 mL). Heptane (2.0 mL) was added causing the mixture to emulsify. The mixture was allowed to sit overnight in an open vial. A crystalline material formed which was collected and characterized by PXRD and TGA (31.0% loss of mass). The PXRD of Form B of the sodium salt is shown in FIG. 3 and the prominent peaks provided in the table below.

Peak Search Report (29 Peaks, Max P/N = 10.8)
[MT_1058_101_1.raw] rigaku_cu, comment line
PEAK: 21-pts/Parabolic Filter, Threshold = 1.0,
Cutoff = 0.0%, BG = 3/0.6, Peak-Top = Summit

| 2-Theta | d(Å) | BG | Height | I % | Area | I % | FWHM |
|---|---|---|---|---|---|---|---|
| 4.9097 | 17.9838 | 1004 | 952 | 97.5 | 11090 | 66.1 | 0.198 |
| 5.4497 | 16.2028 | 1074 | 976 | 100 | 16773 | 100 | 0.292 |
| 6.13 | 14.4062 | 995 | 698 | 71.5 | 8522 | 50.8 | 0.208 |
| 7.5895 | 11.6387 | 814 | 68 | 7 | 845 | 5 | 0.211 |
| 8.1899 | 10.7868 | 820 | 539 | 55.2 | 6957 | 41.5 | 0.219 |
| 8.7499 | 10.0976 | 813 | 171 | 17.5 | 1903 | 11.3 | 0.189 |
| 9.8485 | 8.9736 | 793 | 49 | 5 | 907 | 5.4 | 0.315 |
| 10.8097 | 8.1777 | 797 | 271 | 27.8 | 4977 | 29.7 | 0.312 |
| 11.9294 | 7.4126 | 825 | 68 | 7 | 1246 | 7.4 | 0.312 |
| 12.25 | 7.2193 | 823 | 75 | 7.7 | 2842 | 16.9 | 0.644 |
| 12.65 | 6.9919 | 853 | 51 | 5.2 | 526 | 3.1 | 0.175 |
| 13.7894 | 6.4166 | 860 | 142 | 14.5 | 3339 | 19.9 | 0.4 |
| 14.1102 | 6.2714 | 868 | 67 | 6.9 | 2452 | 14.6 | 0.622 |
| 15.1702 | 5.8355 | 901 | 307 | 31.5 | 4287 | 25.6 | 0.237 |
| 15.9882 | 5.5388 | 1060 | 224 | 23 | 3092 | 18.4 | 0.235 |
| 16.4312 | 5.3904 | 1068 | 172 | 17.6 | 5863 | 35 | 0.579 |
| 17.5691 | 5.0438 | 1047 | 223 | 22.8 | 2952 | 17.6 | 0.225 |
| 18.5695 | 4.7742 | 1121 | 586 | 60 | 10430 | 62.2 | 0.303 |
| 19.1098 | 4.6405 | 1164 | 37 | 3.8 | 373 | 2.2 | 0.171 |
| 19.7089 | 4.5007 | 1245 | 85 | 8.7 | 841 | 5 | 0.168 |
| 20.0485 | 4.4252 | 1272 | 40 | 4.1 | 1797 | 10.7 | 0.764 |
| 20.5504 | 4.3183 | 1190 | 361 | 37 | 6575 | 39.2 | 0.31 |
| 21.2081 | 4.1858 | 1139 | 74 | 7.6 | 1590 | 9.5 | 0.365 |
| 21.4894 | 4.1317 | 1125 | 112 | 11.5 | 2809 | 16.7 | 0.426 |
| 22.93 | 3.8752 | 1043 | 90 | 9.2 | 2236 | 13.3 | 0.422 |
| 24.1099 | 3.6882 | 967 | 51 | 5.2 | 665 | 4 | 0.222 |
| 24.7916 | 3.5883 | 958 | 61 | 6.3 | 747 | 4.5 | 0.208 |
| 25.6508 | 3.47 | 928 | 138 | 14.1 | 2247 | 13.4 | 0.277 |
| 26.4302 | 3.3694 | 879 | 105 | 10.8 | 2183 | 13 | 0.353 |

Representative 2-Theta peaks of the Form B sodium salt product are shown below:
4.910
5.450
6.130
8.190
8.750
10.810
15.170
15.988
16.431
17.569
18.570
20.550

The Powder X-ray diffraction patterns were performed using a D/Max Rapid, Contact (Rigaku/MSC, The Woodlands, Tex., U.S.A.), which uses as its control software RINT Rapid Control Software, Rigaku Rapid/XRD, version 1.0.0 ($^8$1999 Rigaku Co.). In addition, the analysis software used were RINT Rapid display software, version 1.18 (Rigaku/MSC), and JADE XRD Pattern Processing, versions 5.0 and 6.0 (($^8$1995-2002, Materials Data, Inc.).

For the PXRD analysis, the acquisition parameters were as follows: source was Cu with a K line at 1.5406 Å; x-y stage was manual; collimator size was 0.3 mm; capillary tube (Charles Supper Company, Natick, Mass., U.S.A.) was 0.3 mm ID; reflection mode was used; the power to the X-ray tube was 46 kV; the current to the X-ray tube was 40 mA; the omega-axis was oscillating in a range of 0-5 degrees at a speed of 1 degree/minute; the phi-axis was spinning at an angle of 360 degrees at a speed of 2 degrees/second; 0.3 mm collimator; the collection time was 60 minutes; the temperature was room temperature; and the heater was not used. The sample was presented to the X-ray source in a boron rich glass capillary.

In addition, the analysis parameters were as follows: the integration 2-theta range was 2-60 degrees; the integration chi range was 0-360 degrees; the number of chi segments was 1; the step size used was 0.02; the integration utility was cylint; normalization was used; dark counts were 8; omega offset was 180; and chi and phi offsets were 0.

DSC analysis was performed using a Q1000 Differential Scanning Calorimeter (TA Instruments, New Castle, Del., U.S.A.), which uses Advantage for QW-Series, version 1.0.0.78, Thermal Advantage Release 2.0 ($^8$2001 TA Instruments-Water LLC). In addition, the analysis software used was Universal Analysis 2000 for Windows 95/95/2000/NT, version 3.1E;Build 3.1.0.40 ($^8$2001 TA Instruments-Water LLC).

For the DSC analysis, the purge gas used was dry nitrogen, the reference material was an empty aluminum pan that was crimped, and the sample purge was 50 mL/minute.

TGA analysis was performed using a Q500 Thermogravimetric Analyzer (TA Instruments, New Castle, Del., U.S.A.), which uses Advantage for QW-Series, version 1.0.0.78, Thermal Advantage Release 2.0 ($^8$2001 TA Instruments-Water LLC). In addition, the analysis software used was Universal Analysis 2000 for Windows 95/95/2000/NT, version 3.1E; Build 3.1.0.40 ($^8$2001 TA Instruments-Water LLC).

For all of the TGA experiments, the purge gas used was dry nitrogen, the balance purge was 40 mL/minute $N_2$, and the sample purge was 60 mL/minute $N_2$.

IV. Biological Results

A. Fluorescence Polarization Competition Immunoassay

An autophosphorylation, fluorescence polarization competition immunoassay was used to determine the potency for c-fms inhibition exhibited by selected compounds of Formula I. The assay was performed in black 96-well microplates (LJL BioSystems). The assay buffer used was 100 mM 4-(2-hydroxyethyl)piperazine1-ethanesulfonic acid (HEPES), pH 7.5, 1 mM 1,4-dithio-DL-threitol (DTT), 0.01% (v/v) Tween-20. Compounds were diluted in assay buffer containing 4% dimethylsulfoxide (DMSO) just prior to the assay. To each well, 5 µL of compound were added followed by the addition of 3 µL of a mix containing 33 nM c-fms (Johnson & Johnson PRD) and 16.7 mM $MgCl_2$ (Sigma) in assay buffer. The kinase reaction was initiated by adding 2 µL of 5 mM ATP (Sigma) in assay buffer. The final concentrations in the assay were 10 nM c-fms, 1 mM ATP, 5 mM $MgCl_2$, 2% DMSO. Control reactions were ran in each plate: in positive and negative control wells, assay buffer (made 4% in DMSO) was substituted for the compound; in addition, positive control wells received 1.2 μL of 50 mM ethylenediaminetetraaceticacid (EDTA). The plates were incubated at room temperature for 45 min. At the end of the incubation, the reaction was quenched with 1.2 μL of 50 mM EDTA (EDTA was not added to the positive control wells at this point; see above). Following a 5-min incubation, each well received 10 μL of a 1:1:3 mixture of anti-phosphotyrosine antibody, 10×, PTK green tracer, 10× (vortexed), FP dilution buffer, respectively (all from PanVera, cat. # P2837). The plate was covered, incubated for 30 min at room temperature and the fluorescence polarization was read on the Analyst. The instrument settings were: 485 nm excitation filter; 530 nm emission filter; Z height: middle of well; G factor: 0.93. Under these conditions, the fluorescence polarization values for positive and negative controls were approximately 300 and 150, respectively, and were used to define the 100% and 0% inhibition of the c-fms reaction. The reported $IC_{50}$ values are averages of three independent measurements.

CSF-1-Driven Mouse Bone-Marrow Derived Macrophages Assay

Macrophages were derived by culturing mouse bone marrow in alpha-MEM supplemented with 10% FCS and 50 ng/ml recombinant mouse CSF-1 in bacteriologic dishes. On the sixth day, macrophages were detached from dishes, washed, and resuspended to 0.05 million cells/ml in alpha-MEM containing 10% FCS. One hundred ul of cell suspension were distributed per well into 96 well culture plates. Wells were further supplemented with the addition of 50 ul media containing 15 ng/ml CSF-1, 3 uM Indomethacin, and 3× of a dilution series of test compounds. The cells were cultured for 30 hrs at 37 degrees and 5% CO2. During the final six hours, cultures were supplemented with an additional 30 ul of media containing a 1:500 dilution of bromodeoxyuridine (BrDU). At the end of the culture period, the plates were spun at 1000 RPM for 1 minute and 130 ul of media was removed with a pipet and replaced with 150 ul of fixative solution for 1 hour@room temperature. The fixative was then dispelled from the plates and the plates allowed to air dry. Incorporation of BrDU into the fixed, dried cells was quantified using a specific ELISA.

Table 1 lists the assay results for representative compounds of the invention

TABLE 1

| Example No. | FMS $IC_{50}$ (μM) | BMDM $IC_{50}$ (μM) |
|---|---|---|
| 1 | 0.00086 | 0.0032 |
| 2 | 0.00043 | 0.037 |
| 3 | 0.00065 | 0.0093 |
| 4 | 0.00072 | 0.0066 |
| 5 | 0.00047 | 0.0047 |
| 6 | 0.0027 | 0.0050 |
| 7 | 0.0020 | 0.0033 |
| 8 | 0.00042 | 0.041 |
| 9 | 0.0011 | 0.0048 |
| 10 | 0.0035 | 0.040 |
| 11 | 0.0018 | 0.0025 |
| 12 | 0.00066 | 0.036 |
| 13 | 0.00081 | 0.0029 |
| 14 | 0.0011 | 0.0047 |
| 15 | 0.0029 | 0.0061 |
| 16 | 0.0014 | 0.0082 |
| 17 | 0.0046 | 0.037 |
| 18 | 0.00072 | 0.010 |
| 19 | 0.0029 | 0.027 |
| 20 | 0.00041 | 0.0065 |
| 21 | 0.0089 | 0.018 |
| 22 | 0.0020 | 0.0036 |

TABLE 1-continued

| Example No. | FMS $IC_{50}$ (μM) | BMDM $IC_{50}$ (μM) |
|---|---|---|
| 26 | 0.0071 | 0.059 |
| 27 | 0.00066 | 0.0069 |
| 28 | 0.016 | 0.069 |
| 29 | 0.014 | 0.088 |
| 30 | 0.099 | nd |

B. SCW Arthritis in Rats

Purpose: A polyarthritis occurs in female Lewis rats following i.p. administration of streptococcal cell wall (SCW) components. The model has an acute non-erosive phase (days 3-7) that is complement and neutrophil dependent and which resolves. A chronic erosive phase begins at about day ten and is dependent on the development of specific T cell immunity to SCW, and possibly to self-antigens. The SCW-induced model has been used less frequently for pharmaceutical testing than the adjuvant-induced or collagen-induced models of arthritis, but each model predicts accurately the anti-inflammatory potential of TNF-inhibitors. The chronic phase of the SCW model is macrophage dependent. Because the preponderance of data suggests a critical role for macrophages in RA, we selected the chronic phase of the SCW arthritis model to investigate the ability of select compounds of the present invention to reduce chronic joint inflammation and bone erosion.

Method: Female Lewis rats (80-100 gm each) were purchased from Charles River. Streptococcal cell wall peptidoglycan-polysaccharide polymers (PG-PS 10S) were purchased from BD (Cat#210866). PG-PS 10S was vortexed for 30 seconds to thoroughly mix the material and sonicated at low energy levels (level 6) for 3 min with a probe type sonicator prior to injection. On day 0, sixty rats were anesthetized using isoflurane, and injected i.p. with 15 μg of rhamnose/gram body weight (BW) in the lower left quadrant of the abdomen. Ten rats were treated in a similar manner with sterile saline.

On day 5, rats injected with PG-PS 10S that had a distinct acute phase arthritic response based on joint swelling were randomized into groups 2-5 listed in Table 2.

Chronic, T-cell dependent, erosive arthritis was severe by day 20 at which time twice daily oral dosing was commenced until sacrificed on day 32 to determine if the compound of Example 15 (hereinafter, Compound A) can reverse established disease.

Compound A was formulated in 5% solutol, 5% ethanol, 90% water. The dose volume was 5 ml/kg.

TABLE 2

| SCW-arthritis study design: IPD07-032 | | | | | |
|---|---|---|---|---|---|
| Gp | N | Induction (i.p., Day 0) | Treatment (b.i.d., oral) | Sacrifice | Sample Collection |
| 1 | 6 | Sterile Saline (ss) | Vehicle, Day 20-32 | Day 32 | Plasma, serum, hind limbs, weigh and fix liver, spleen & kidneys |
| 2 | 6 | PG-PS 10S in ss (15 ug/gramBW) | Vehicle, Day 20-32 | Day 32 | Plasma, serum, hind limbs, weigh and fix liver, spleen & kidneys |

TABLE 2-continued

SCW-arthritis study design: IPD07-032

| Gp | N | Induction (i.p., Day 0) | Treatment (b.i.d., oral) | Sacrifice | Sample Collection |
|---|---|---|---|---|---|
| 3 | 6 | PG-PS 10S in ss (15 ug/gramBW) | Compound A 3 mg/kg, Day 20-32 | Day 32 | Plasma, serum, hind limbs, weigh and fix liver, spleen & kidneys |
| 4 | 6 | PG-PS 10S in ss (15 ug/gramBW) | Compound A 10 mg/kg, Day 20-32 | Day 32 | Plasma, serum, hind limbs, weigh and fix liver, spleen & kidneys |
| 5 | 6 | PG-PS 10S in ss (15 ug/gramBW) | Compound A 20 mg/kg, Day 20-32 | Day 32 | Plasma, serum, hind limbs, weigh and fix liver, spleen & kidneys |

Left and right hind ankles of each rat were measured with calipers every day for the first six days (post-injection) and then at least every two or three days for the remainder of the study. Ankles were assigned a clinical score based on erythema and swelling as follows: 1=ankle only; 2=ankle and proximal half of tarsal joint; 3=ankle and entire tarsal joint; 4=involvement of the entire paw including digits. Animal scores represented the sum of the two hind paws.

Exposure: Two hours following the last dose of 3, 10 and 20 mpk, plasma levels of Compound A were 247±22, 802±35, and 1475±70 ng/ml, respectively (mean±SEM).

Figure 4:
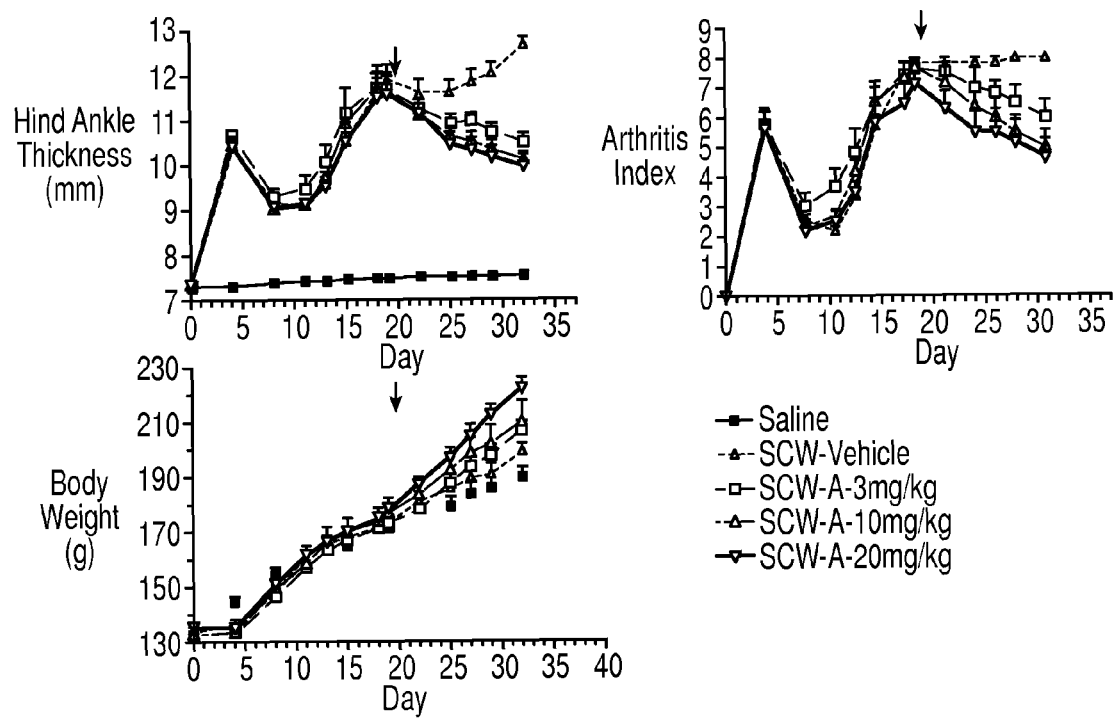
FIG. 4 shows the effect of Compound A on ankle and paw swelling in the streptococcal cell wall (SCW) model of arthritis in rats.

Results: When dosing was initiated on day 20, after disease was already severe, Compound A caused a reversal of paw swelling determined from caliper measurements of paw thickness and visual scores (see, FIG. 4. In FIG. 4, dosing p.o. b.i.d. was commenced on day 20. Ankle widths were determined by caliper measurements. Ankles were assigned a clinical score based on erythema and swelling as follows: 1=ankle only; 2=ankle and proximal half of tarsal joint; 3=ankle and entire tarsal join; 4=involvement of the entire paw including digits.). Reversal was not complete, presumably because of deposition of periarticular fibrosis prior to day 20. The therapeutic effect was dose-dependent, but already significant at the lowest dose of 3 mpk.

Disease reversal was accompanied by restoration of function. To assess function, three representative rats per group were videotaped for thirty seconds on days 19 and 32, and steps taken with hind limbs were counted and reported in Table 3. On day 19 following SCW, rats ambulated primarily using front paws. Hind paws were nearly immobilized. By day 32, rats treated with Compound A used hind limbs in a normal fashion, whereas the hind limbs of the vehicle-treated animals were immobilized.

TABLE 3

Ambulation of SCW-rats before and after treatment with Compound A

| | Disease free | Compound A, mg/kg, days 19-32 | | | |
|---|---|---|---|---|---|
| | | 0 (veh) | 3 | 10 | 20 |
| Day 19 | 19.3* (20, 16, 22) | 2.3* (3, 3, 1) | 1.7 (3, 0, 2) | 1.3 (0, 1, 3) | 1.3 (0, 3, 1) |

TABLE 3-continued

Ambulation of SCW-rats before and after treatment with Compound A

| | Disease free | Compound A, mg/kg, days 19-32 | | | |
|---|---|---|---|---|---|
| | | 0 (veh) | 3 | 10 | 20 |
| Day 32 | 10.6* (20, 2, 10) | 0 (0, 0, 0) | 7.7 (8, 10, 5) | 7.3 (8, 8, 6) | 6 (8, 3, 7) |

*Number of steps taken using hind limbs in a thirty second observation period. The value is the average of three rats. Numbers from individual rats are provided in parenthesis.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All publications disclosed in the above specification are hereby incorporated by reference in full.

The invention claimed is:

1. A compound of Formula I:

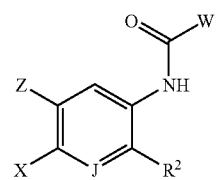

or a tautomer or pharmaceutically acceptable salt thereof, wherein:

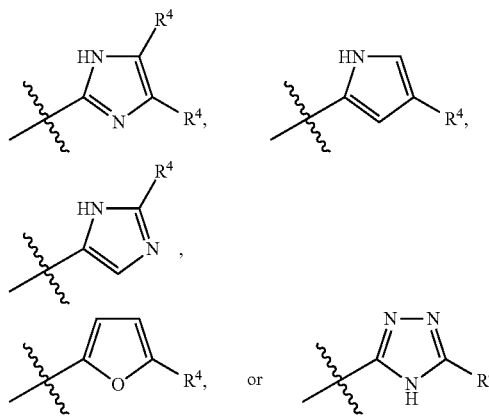

W is
wherein each $R^4$ is independently H, F, Cl, Br, I, OH, $OCH_3$, $OCH_2CH_3$, $SC_{(1-4)}$alkyl, $SOC_{(1-4)}$alkyl, $SO_2C_{(1-4)}$alkyl, —$C_{(1-3)}$alkyl, $CO_2R^d$, $CONR^eR^f$, $C\equiv CR^g$, or CN;
wherein $R^d$ is H, or —$C_{(1-3)}$alkyl;
$R^e$ is H, or —$C_{(1-3)}$alkyl;
$R^f$ is H, or —$C_{(1-3)}$alkyl; and
$R^g$ is H, —$CH_2OH$, or —$CH_2CH_2OH$;
$R^2$ is cycloalkyl, spiro-substituted cycloalkenyl, thiophenyl, dihydrosulfonopyranyl, phenyl, furanyl, tetrahydropyridyl, or dihydropyranyl, any of which may be independently substituted with one or two of each of the following: chloro, fluoro, hydroxy, $C_{(1-3)}$alkyl, and $C_{(1-4)}$alkyl;

Z is H, F, Cl, or CH₃;
J is CH, or N;
X is
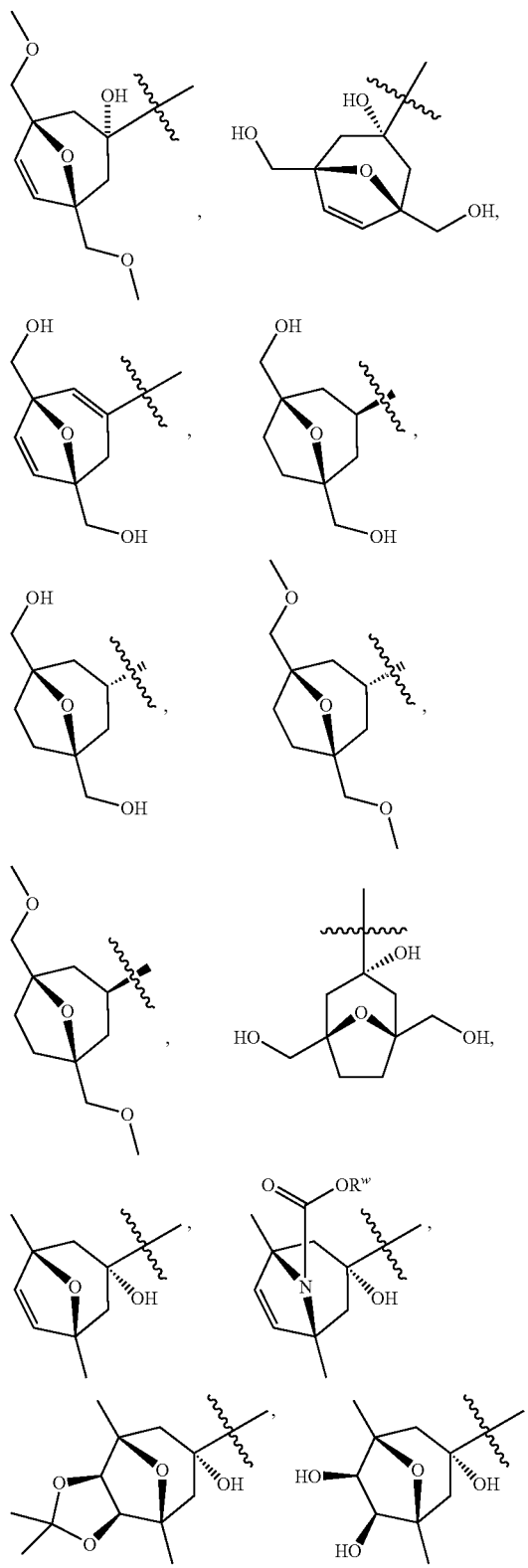
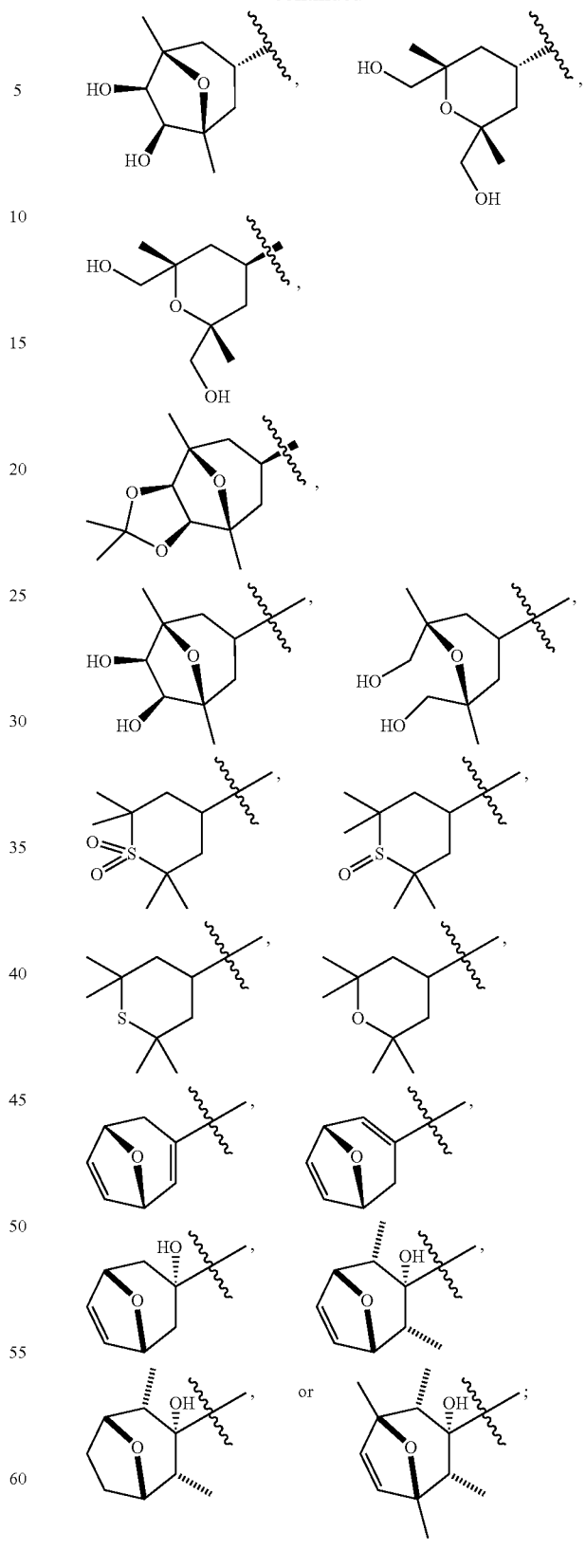
wherein $R^w$ is H, —$C_{(1-4)}$alkyl, —$CO_2C_{(1-4)}$alkyl, —$CONH_2$, —$CONHC_{(1-4)}$alkyl, —$CON(C_{(1-4)}$alkyl$)_2$, or —$COC_{(1-4)}$alkyl.

2. A compound of claim 1, wherein:
W is
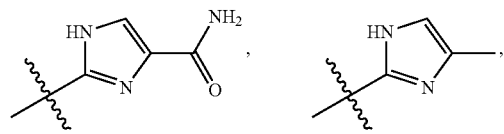
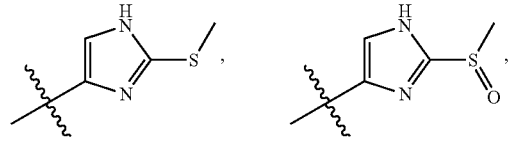
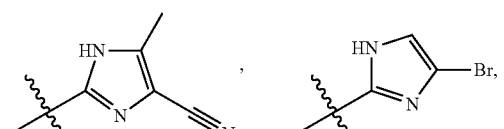
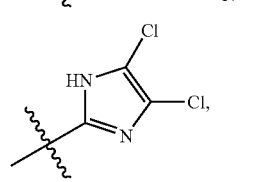
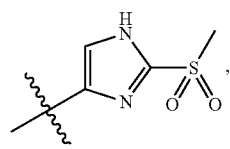
R² is
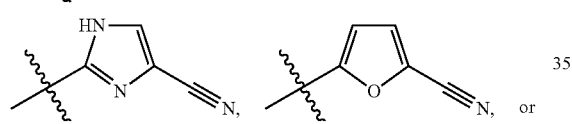
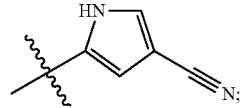
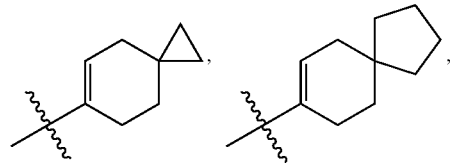
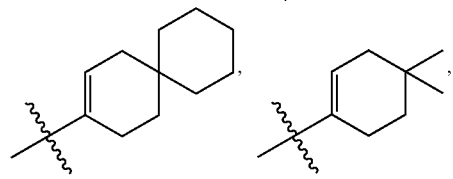
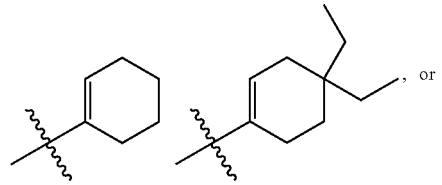
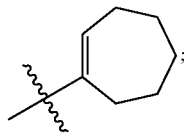
Z is H;
X is
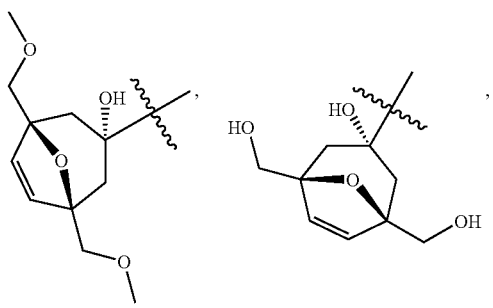
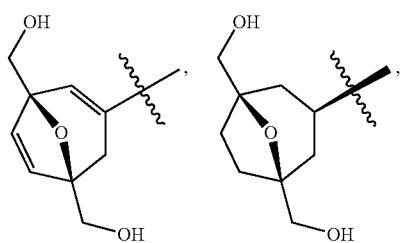
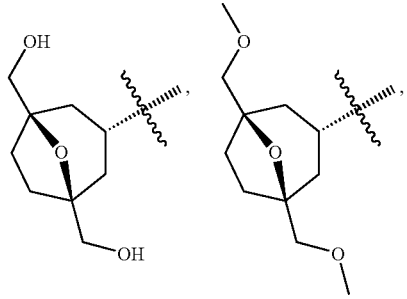
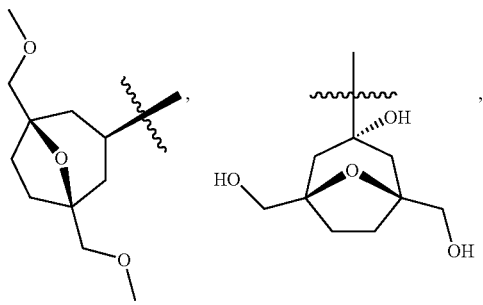
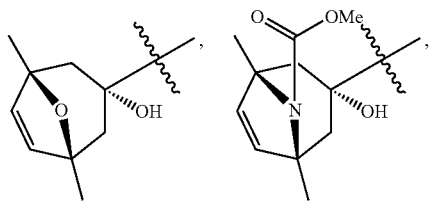

-continued
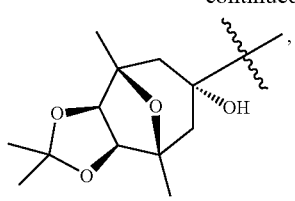,
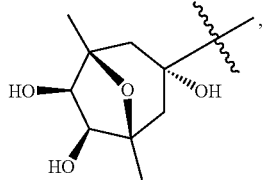,
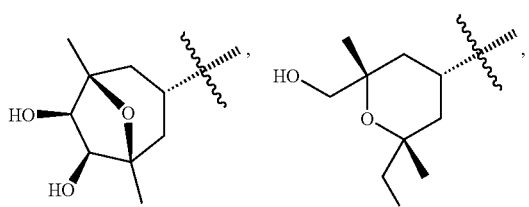,
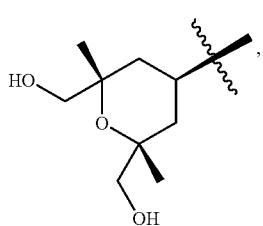,
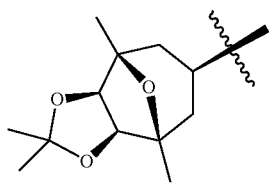,
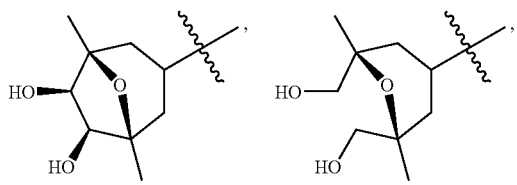,
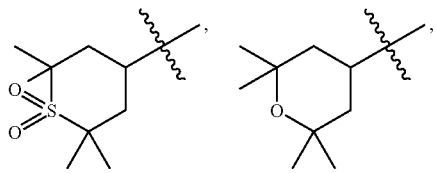,
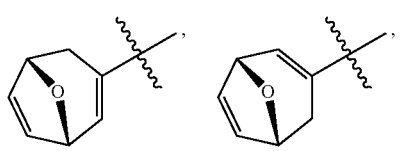,
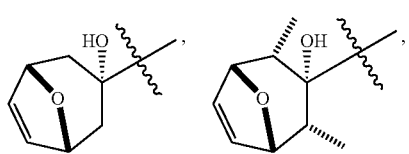,
-continued
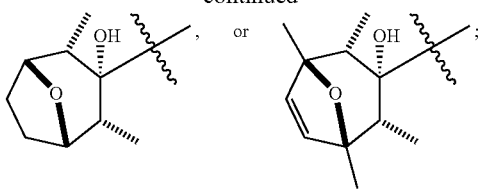
and tautomers and pharmaceutically acceptable salts thereof.
3. A compound of claim 2 wherein:
W is
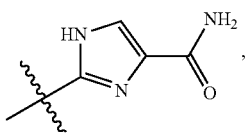, 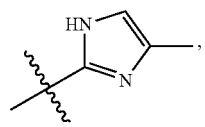,
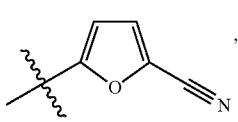, 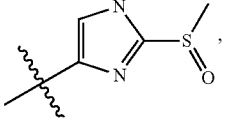,
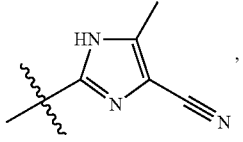, 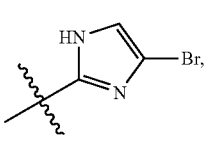,
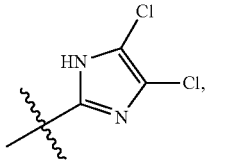,
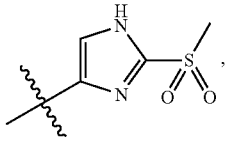,
$R^2$ is
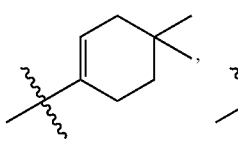,
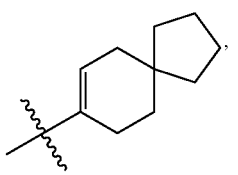;
and tautomers and pharmaceutically acceptable salts thereof.

4. A compound of claim 3 wherein:
W is
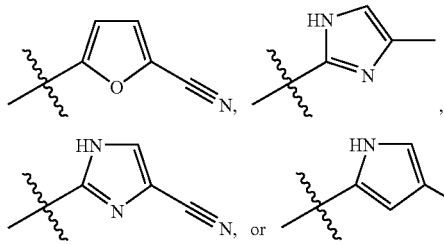
and tautomers and pharmaceutically acceptable salts thereof.
5. A compound of claim 4 wherein:
W is
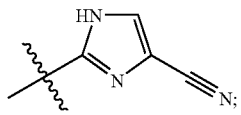
R² is
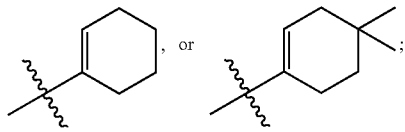
and tautomers and pharmaceutically acceptable salts thereof.
6. A compound of Formula Ia:
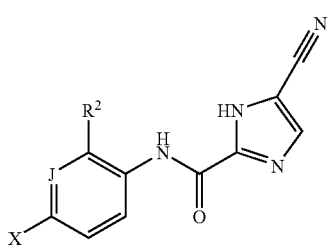
Ia
wherein:
R² is
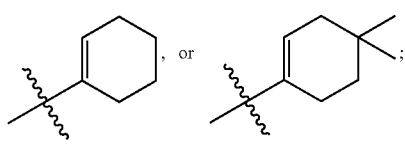
J is CH, or N; and
X is
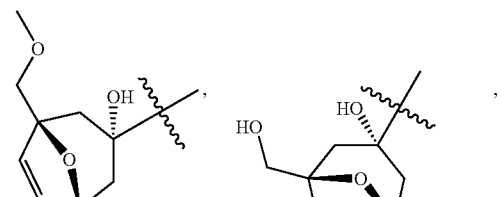
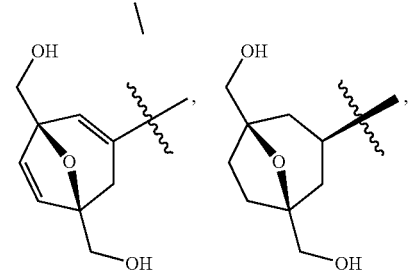
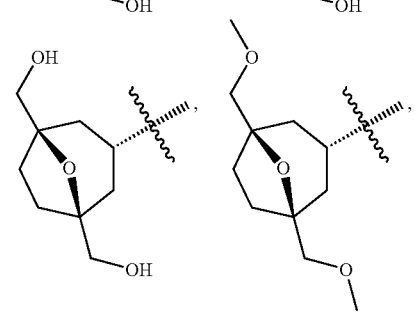
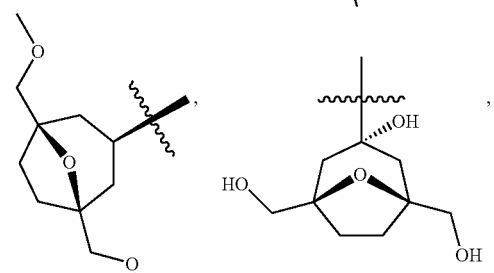
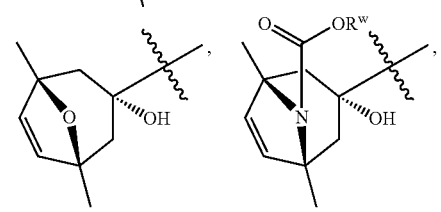
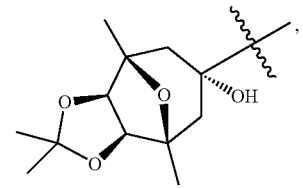
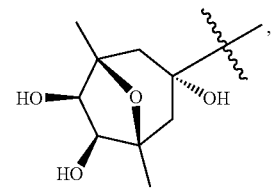

-continued
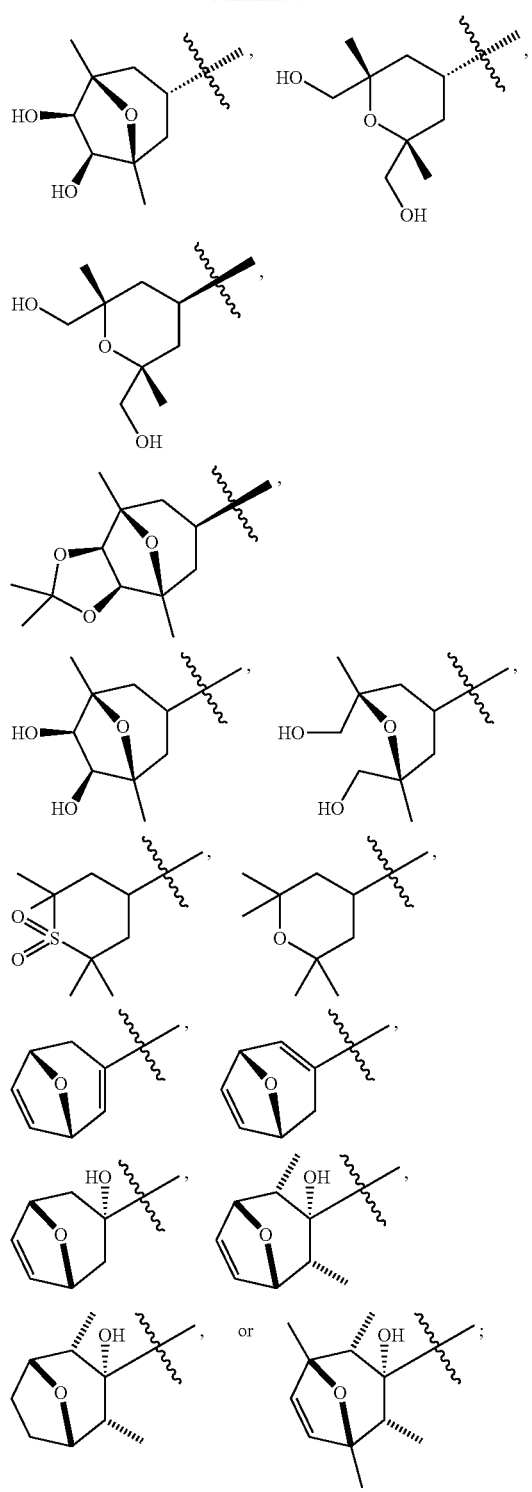
wherein $R^w$ is H, —$C_{(1-4)}$alkyl, —$CO_2C_{(1-4)}$alkyl, —$CONH_2$, —$CONHC_{(1-4)}$alkyl, —$CON(C_{(C1-4)}$alkyl$)_2$, or —$COC_{(1-4)}$alkyl;
and tautomers and pharmaceutically acceptable salts thereof.
7. A compound of claim 6, wherein X is
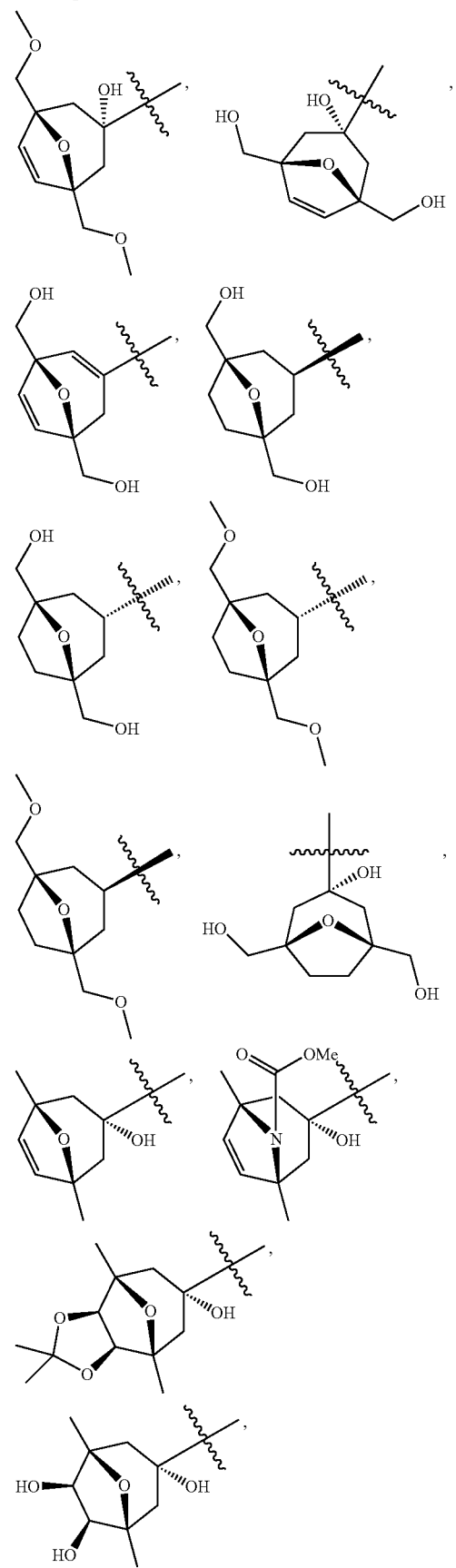

-continued
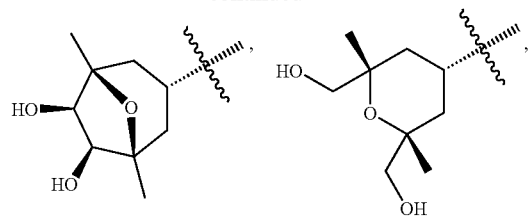
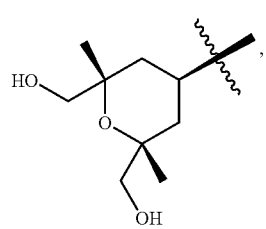
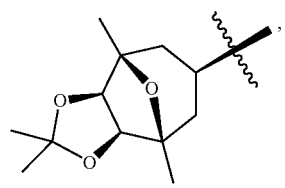
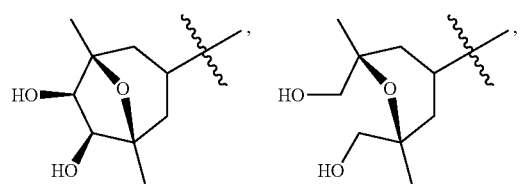
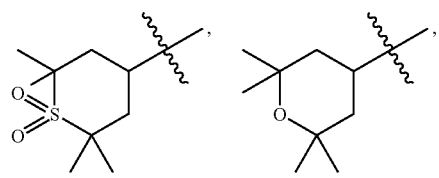
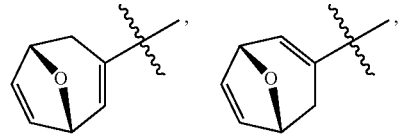
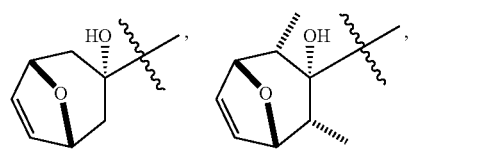
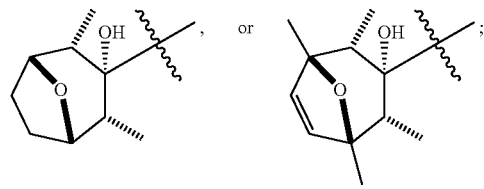 [SMILES: *[C@@]1(O)[C@H](C)[C@@H]2CC[C@@H](O2)[C@@H]1C ; *[C@]1(O)[C@@H](C)[C@@]2(C)C=C[C@](C)(O2)[C@H]1C]
and tautomers and pharmaceutically acceptable salts thereof.
8. A compound selected from the group consisting of:
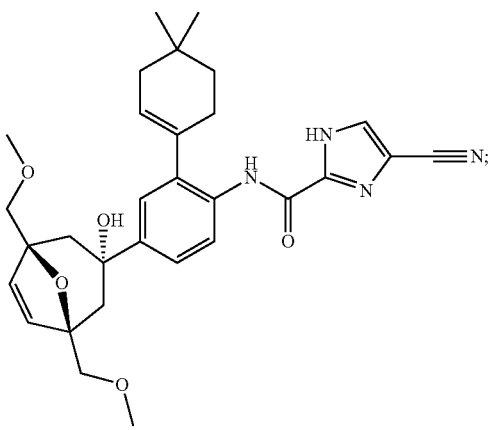
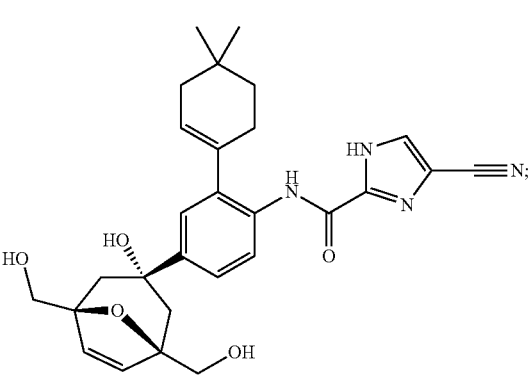
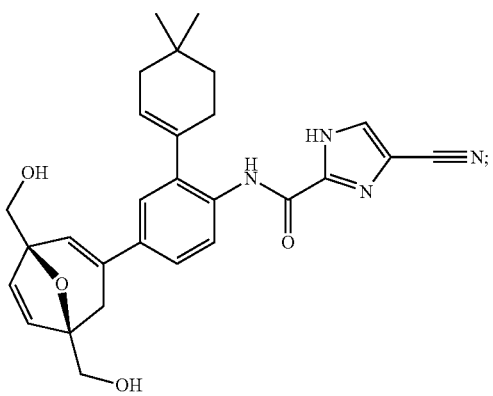
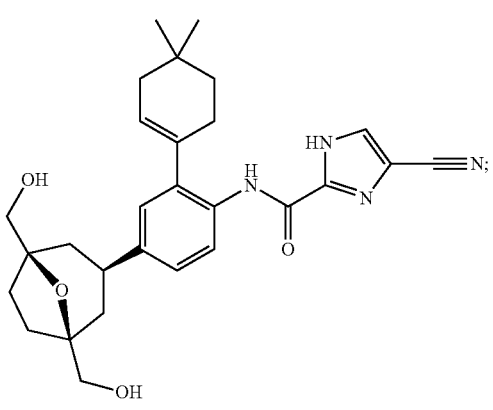

129
-continued
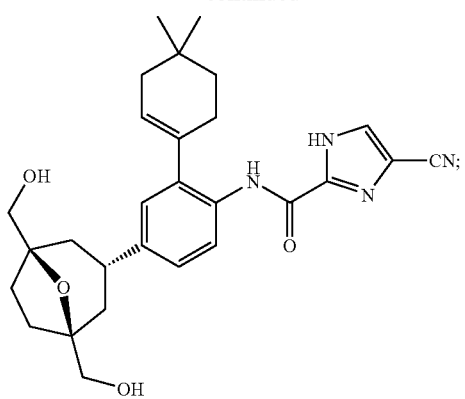
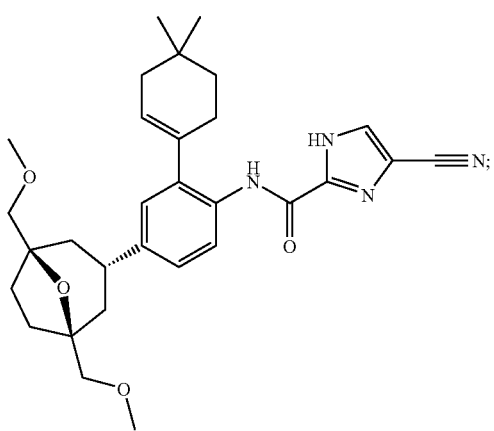
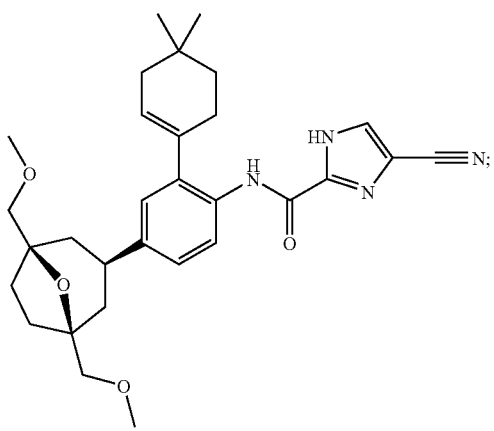
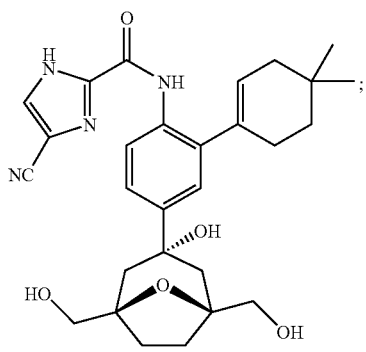
130
-continued
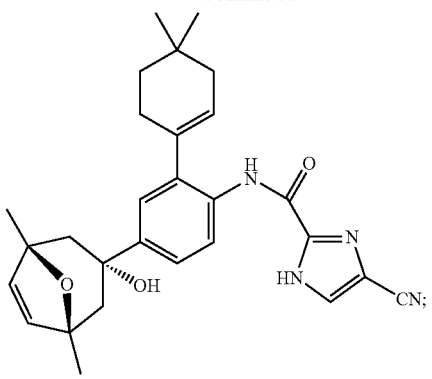
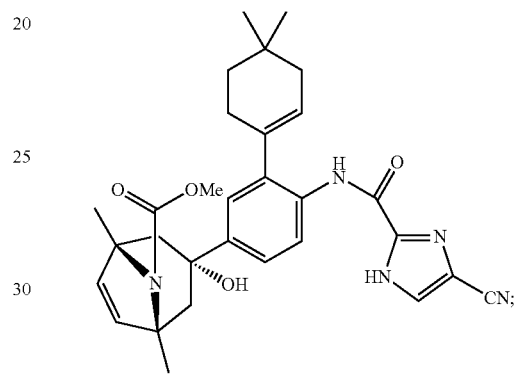
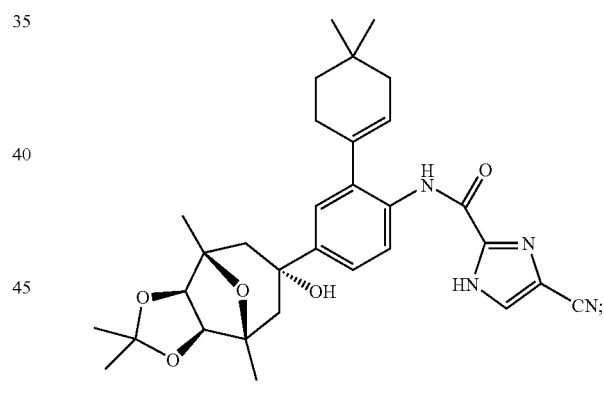
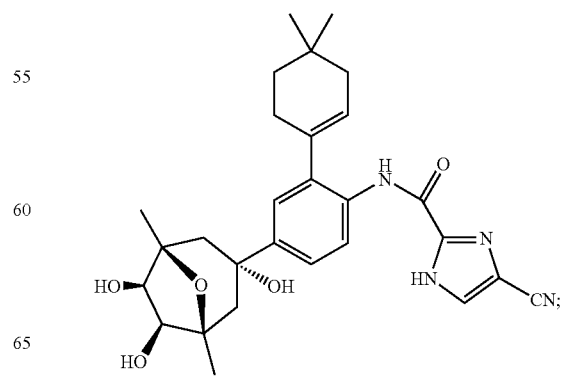

131
-continued
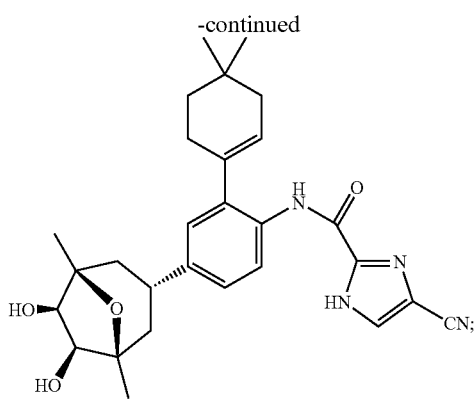
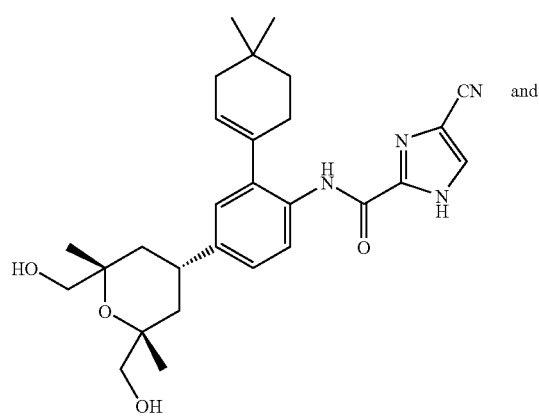
and
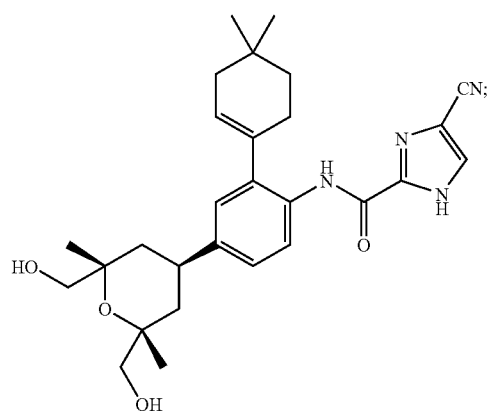
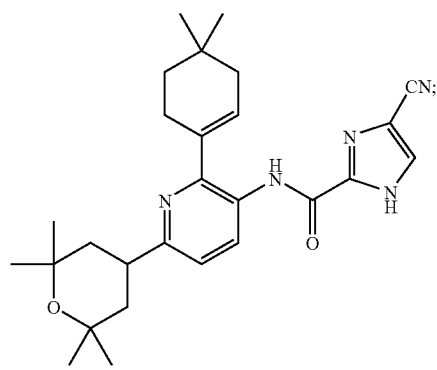 [SMILES: CC1(C)CC=C(c2nc(C3CC(C)(C)OC(C)(C)C3)ccc2NC(=O)c2nc(C#N)c[nH]2)CC1]
132
-continued
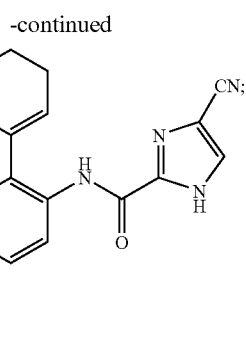
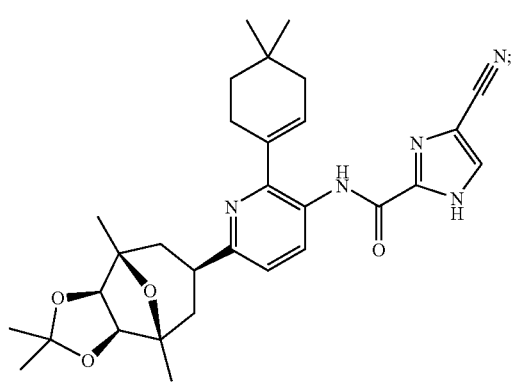
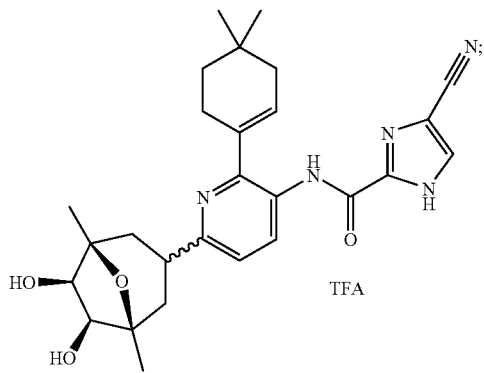
TFA
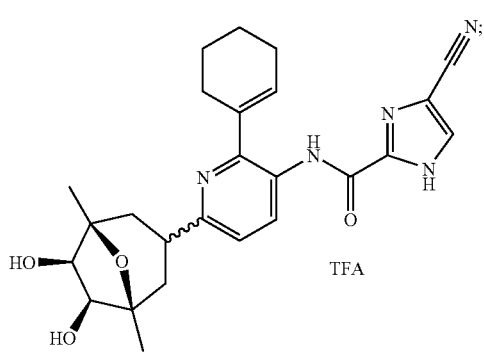
TFA 133
-continued
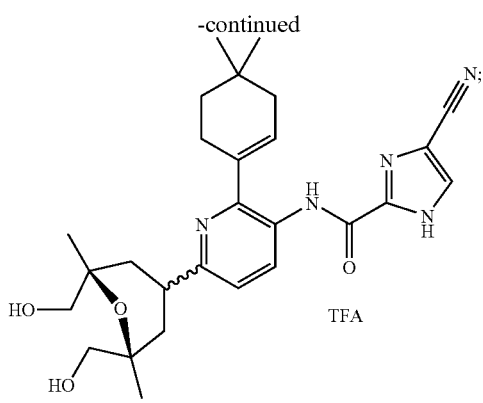
TFA
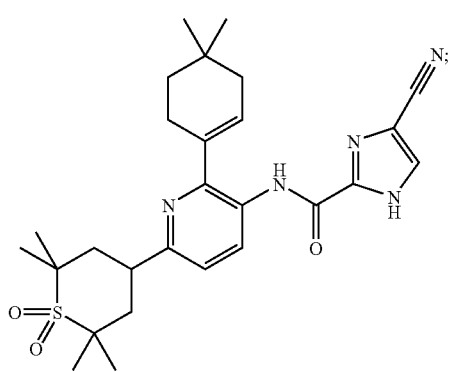
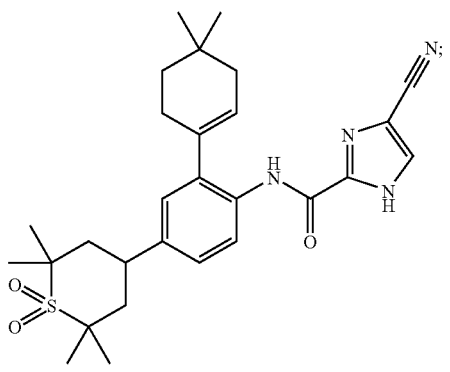
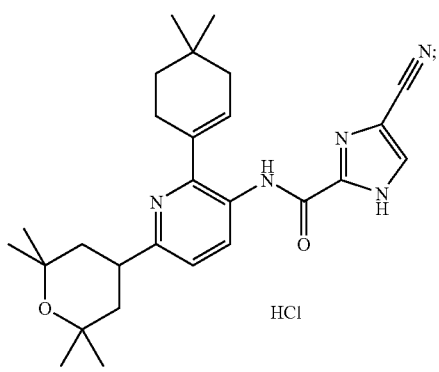
HCl
134
-continued
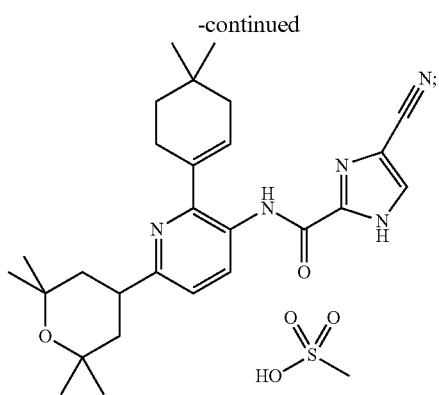
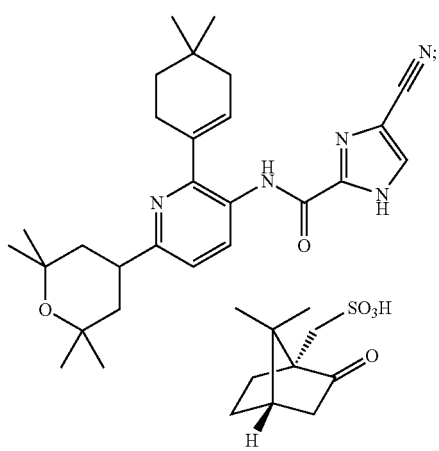
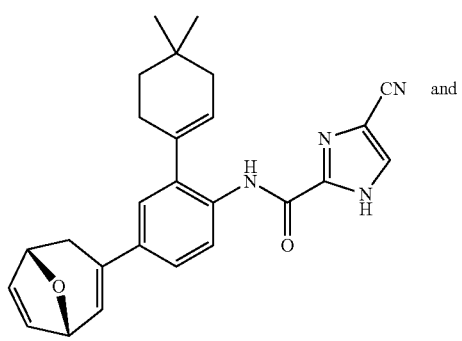
and
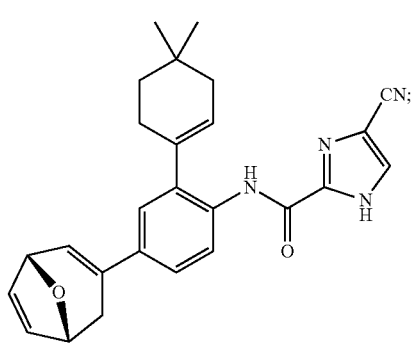

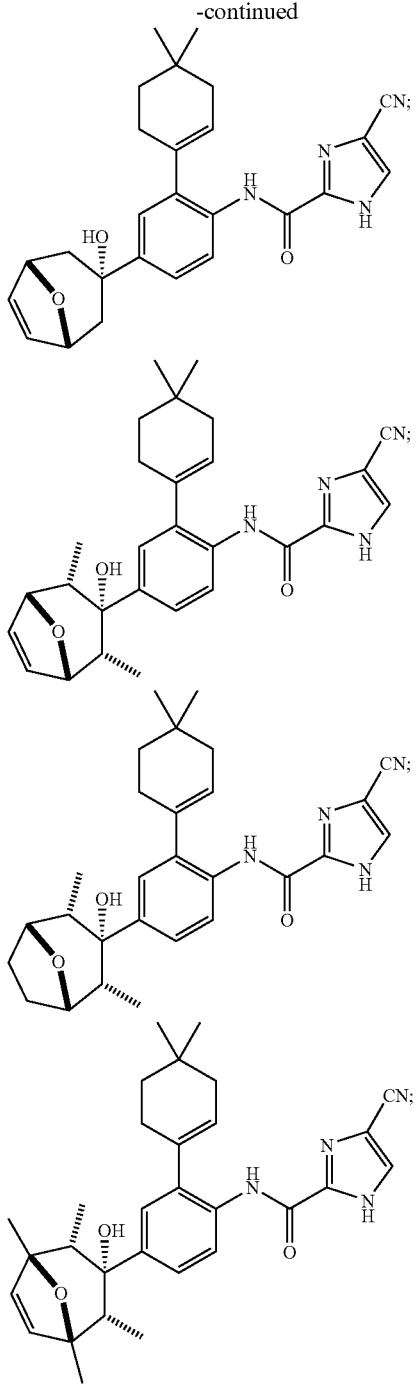

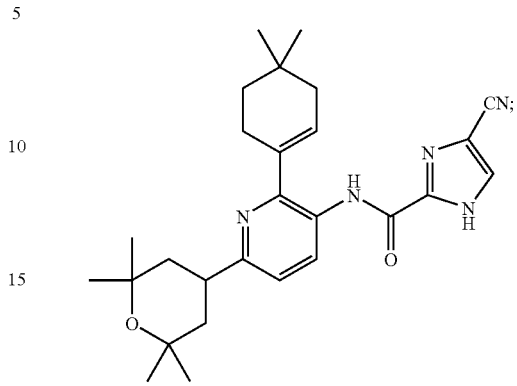

and tautomers, and pharmaceutically acceptable salts thereof.

9. A compound of the formula and tautomers, and pharmaceutically acceptable salts thereof.

10. The compound of claim 9 selected from the group consisting of:
  4-Cyano-1H-imidazole-2-carboxylic acid [2-cyclohex-1-enyl-6-(2,2,6,6-tetramethyl-tetrahydro-pyran-4-yl)-pyridin-3-yl]-amide;
  4-Cyano-1H-imidazole-2-carboxylic acid [2-(4,4-dimethyl-cyclohex-1-enyl)-6-(2,2,6,6-tetramethyl-tetrahydro-pyran-4-yl)-pyridin-3-yl]-amide hydrochloride salt;
  4-Cyano-1H-imidazole-2-carboxylic acid [2-(4,4-dimethyl-cyclohex-1-enyl)-6-(2,2,6,6-tetramethyl-tetrahydro-pyran-4-yl)-pyridin-3-yl]-amide methanesulfonic acid salt; and
  4-Cyano-1H-imidazole-2-carboxylic acid [2-(4,4-dimethyl-cyclohex-1-enyl)-6-(2,2,6,6-tetramethyl-tetrahydro-pyran-4-yl)-pyridin-3-yl]-amide (1S)-(+)-10-camphorsulfonic acid salt.

11. The compound of claim 9 which is 4-Cyano-1H-imidazole-2-carboxylic acid [2-(4,4-dimethyl-cyclohex-1-enyl)-6-(2,2,6,6-tetramethyl-tetrahydro-pyran-4-yl)-pyridin-3-yl]-amide hydrochloride salt.

12. A pharmaceutical composition, comprising a compound of claim 1 and a pharmaceutically acceptable carrier.

13. A pharmaceutical composition, comprising a compound of claim 6 and a pharmaceutically acceptable carrier.

14. A pharmaceutical composition, comprising a compound of claim 8 and a pharmaceutically acceptable carrier.

15. A pharmaceutical composition, comprising a compound of claim 9 and a pharmaceutically acceptable carrier.

16. A pharmaceutical composition made by mixing a compound of claim 9 with a pharmaceutically acceptable carrier.

\* \* \* \* \*